US012433296B2

(12) United States Patent
Shah et al.

(10) Patent No.: US 12,433,296 B2
(45) **Date of Patent: *Oct. 7, 2025**

(54) MODIFIED ANTIMICROBIAL PEPTIDES

(71) Applicant: Donald Danforth Plant Science Center, St. Louis, MO (US)

(72) Inventors: Dilip M. Shah, St. Louis, MO (US); Meenakshi Tetorya, St. Louis, MO (US)

(73) Assignee: DONALD DANFORTH PLANT SCIENCE CENTER, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/807,209

(22) Filed: Jun. 16, 2022

(65) Prior Publication Data

US 2022/0408731 A1 Dec. 29, 2022

Related U.S. Application Data

(60) Provisional application No. 63/365,928, filed on Jun. 6, 2022, provisional application No. 63/202,559, filed on Jun. 16, 2021.

(51) Int. Cl.

| | |
|---|---|
| ***A01N 63/50*** | (2020.01) |
| ***A01H 5/10*** | (2018.01) |
| ***A01N 37/46*** | (2006.01) |
| ***A01P 1/00*** | (2006.01) |
| ***A01P 3/00*** | (2006.01) |
| ***A61P 31/10*** | (2006.01) |
| ***C07K 14/47*** | (2006.01) |
| ***C12N 15/82*** | (2006.01) |
| *A61K 38/00* | (2006.01) |

(52) U.S. Cl.

CPC ............... *A01N 63/50* (2020.01); *A01H 5/10* (2013.01); *A01N 37/46* (2013.01); *A01P 1/00* (2021.08); *A01P 3/00* (2021.08); *A61P 31/10* (2018.01); *C07K 14/4723* (2013.01); *C12N 15/8282* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 5,421,839 A | 6/1995 | Ulbrich et al. | |
| 5,538,525 A | 7/1996 | Broekaert et al. | |
| 6,057,287 A * | 5/2000 | Markland | A61P 9/00 530/300 |
| 6,121,436 A | 9/2000 | Liang et al. | |
| 7,521,535 B2 | 4/2009 | Zhang et al. | |
| 7,825,297 B2 | 11/2010 | Shah et al. | |
| 10,253,328 B2 | 4/2019 | Shah | |
| 2002/0077284 A1 * | 6/2002 | Eckert | C07K 14/005 435/5 |
| 2003/0217382 A1 | 11/2003 | Anderson et al. | |
| 2004/0064850 A1 | 4/2004 | Liang et al. | |
| 2006/0026710 A1 | 2/2006 | Ali et al. | |
| 2010/0113342 A1 | 5/2010 | Yount et al. | |
| 2013/0117880 A1 | 5/2013 | Smith et al. | |
| 2015/0158918 A1 * | 6/2015 | Hulett | A61P 35/00 514/19.5 |
| 2015/0283204 A1 | 10/2015 | Van Der Weerden et al. | |
| 2015/0373995 A1 | 12/2015 | Smith et al. | |
| 2019/0185877 A1 | 6/2019 | Boyle et al. | |
| 2019/0194268 A1 | 6/2019 | Shah et al. | |
| 2020/0060286 A1 | 2/2020 | Martinez et al. | |
| 2022/0081475 A1 | 3/2022 | Li et al. | |
| 2022/0089661 A1 | 3/2022 | Li et al. | |
| 2022/0408731 A1 | 12/2022 | Shah et al. | |

FOREIGN PATENT DOCUMENTS

| | | |
|---|---|---|
| WO | 200011178 A2 | 3/2000 |
| WO | 2017156457 A1 | 9/2017 |
| WO | 2020146368 A1 | 7/2020 |
| WO | 2023004435 A1 | 1/2023 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home » Thesis Resources » Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Creighton, Thomas E. and Charles, Ian G.; "Sequences of the genes and polypeptide precursors for two bovine protease inhibitors." J. Mol. Biol. (1987) 194 p. 11-22.*

The Sigma-Aldrich Amino Acids reference chart, downloaded Nov. 15, 2023.*

Bauer, Finn et al; "Structure determination of humand and murine beta-defensins reveals structural conservation in the absence of significant sequence similarity." Prot. Sci. (2001) 10 p. 2470-2479.*

Zapadka, Karolina L. et al; "Factora affecting the physical stability (aggregation) of peptide therapeutics." Interface Focus (2017) 7 (0030).*

Allen et al., "Plant defensins and virally encoded fungal toxin KP4 inhibit plant root growth," Planta, Jan. 2008, vol. 227, Issue 2, pp. 331-339.

(Continued)

*Primary Examiner* — Fred H Reynolds

(74) *Attorney, Agent, or Firm* — McKee, Voorhees & Sease, PLC

(57) ABSTRACT

Antimicrobial defensin peptide variants comprising modified C-terminal fragments of a defensin and nucleic acids encoding the same are disclosed. Compositions comprising the defensin variant peptides and methods of their use to control microbial infections of plants and vertebrate subjects as well as contamination of feedstuffs and foodstuffs are also disclosed.

21 Claims, 11 Drawing Sheets
(4 of 11 Drawing Sheet(s) Filed in Color)

Specification includes a Sequence Listing.

(56) References Cited

OTHER PUBLICATIONS

Avitabile et al., "Antimicrobial peptides from plants: stabilization of the γ core of a tomato defensin by intramolecular disulfide bond," Journal of Peptide Science, Feb. 2013, vol. 19, Issue 4, 22 pages.
El-Mounadi et al., "Antifungal mechanisms of a plant defensin MtDef4 are not conserved between the ascomycete fungi *Neurospora crassa* and *Fusarium graminearum*," Molecular Microbiology, May 2016, vol. 100, No. 3, pp. 542-559.
International Search Report and Written Opinion in PCT/US2020/012565, mailed Jun. 9, 2020, 14 pages.
Kaur et al., "Subcellular targeting of an evolutionarily conserved plant defensin MtDef4.2 determines the outcome of blant-pathogen interaction in transgenic *Arabidopsis*," Molecular Plant Pathology, 2012, vol. 13, No. 9, pp. 1032-1046.
Kerenga et al., "Salt-Tolerant Antifungal and Antibacterial Activities of Corn Defensin ZmD32," Frontiers in Microbiology, Apr. 2019, vol. 10, Article 795, 13 pages.
Li et al., "Antifungal Potency and Modes of Action of a Novel Olive Tree Defensin Against Closely Related Ascomycete Fungal Pathogens," Molecular Plant-Microbe Interactions, 2019, vol. 32, No. 12, pp. 1649-1664.
Munoz et al., "Specific domains of plant defensins differentially disrupt colony initiation, cell fusion and calcium homeostasis in Neurospora crassa," Molecular Microbiology, 2014, vol. 92, No. 6, pp. 1357-1374.
Ramamoorthy et al., "Sphingolipid C-9 Methyltransferases Are Important for Growth and Virulence but Not for Sensitivity to Antifungal Plant Defensins in Fusarium graminearum," Eukaryotic Cell, Feb. 2009, vol. 8, No. 2, pp. 217-229.
Rigano et al., "A novel synthetic peptide from a tomato defensin exhibits antibacterial activities against Helicobacter pylori," Journal of Peptide Science, Dec. 2012, vol. 18, No. 12, 8 pages.
Sagaram et al., "Structural and Functional Studies of a Phosphatidic Acid-Binding Antifungal Plant Defensin MtDef4: Identification of an RGFRRR Motif Governing Fungal Cell Entry," PLoS One, Dec. 2013, vol. 8, Issue 12, 22 pages.
Sagaram et al., "Structure-Activity Determinants in Antifungal Plant Defensins MsDef1 and MtDef4 with Different Modes of Action against Fusarium graminearum," PLoS One, Apr. 2011, vol. 6, Issue 4, 13 pages.
Sathoff et al., "Plant Defensin Peptides have Antifungal and Antibacterial Activity Against Human and Plant Pathogens," Phytopathology, 2019, vol. 109, No. 3, pp. 402-408.
Shah et al., "Antifungal peptides come of age," Fungal Biology Reviews, 2013, vol. 26, pp. 107-108.
Spelbrink et al., "Differential Antifungal and Calcium Channel-Blocking Activity among Structurally Related Plant Defensins," Plant Physiology, Aug. 2004, vol. 135, pp. 2055-2067.
Velivelli et al., "Modes of Action of a Bi-domain Plant Defensin MtDef5 Against a Bacterial Pathogen Xanthomonas campestris," Frontiers in Microbiology, May 2018, vol. 9, Article 934, 9 pages.
Chan et al., "Tryptophan- and arginine-rich antimicrobial peptides: Structures and mechanisms of action," Biochimica et Biophysica Acta, Sep. 2006, vol. 1758, pp. 1184-1202.
Dathe et al., "Cyclization Increases the Antimicrobial Activity and Selectivity of Arginine- and Tryptophan-Containing Hexapeptides," Biochemistry, Jun. 2004, vol. 43, pp. 9140-9150.
Deslouches et al., "De Novo Generation of Cationic Antimicrobial Peptides: Influence of Length and Tryptophan Substitution on Antimicrobial Activity," Antimicrobial Agents and Chemotherapy, Jan. 2005, vol. 49, No. 1, pp. 316-322.
Falanga et al., "Cyclic Peptides as Novel Therapeutic Microbicides: Engineering of Human Defensin Mimetics," Molecules, Jul. 2017, vol. 22, No. 1217, pp. 1-15.
Munoz et al., "Concentration-dependent mechanisms of cell penetration and killing by the de novo designed antifungal hexapeptide PAF26," Molecular Microbiology, Jul. 2012, vol. 85, No. 1, pp. 89-106.
Schibli et al., "Tryptophan-rich antimicrobial peptides: comparative properties and membrane interactions," Biochemistry and Cell Biology, Oct. 2002, vol. 80, pp. 667-677.
Shi et al., "Cation-π Interaction in Model α-Helical Peptides," Journal of the American Chemical Society, Mar. 2002, vol. 124, pp. 3284-3291.
Tetorya et al., "Plant defensin MtDef4-derived antifungal peptide with multiple modes of action and potential as a bio-inspired fungicide," Molecular Plant Pathology, Apr. 2023, pp. 1-18.
Tucker et al., "Discovery of Next-Generation Antimicrobials through Bacterial Self-Screening of Surface-Displayed Peptide Libraries," Cell, Jan. 2018, vol. 172, pp. 618-628.
International Search Report and Written Opinion in PCT/US22/72971, mailed on Nov. 3, 2022, 16 pages.
Shah et al., "Defensin-like protein isoform 1 precursor [Glycine max]," NCBI Reference Sequence: NP_001336659.1, Apr. 26, 2021. Retrieved from the Internet: <URL:https://www.ncbi.nlm.nih.gov/protein/NP_001336659.1>, 2 pages.
Invitation to Pay Additional Fees in PCT/US22/72971, mailed on Sep. 15, 2022, 3 pages.
Shafee et al., "The Defensins Consist of Two Independent, Convergent Protein Superfamilies" Mol. Biol. Evol. 33(9) pp. 2345-2356 Jun. 2016.
Office Action in EA202393236, mailed Jun. 16, 2022, 3 pages.
Office Action in EG/P/2023/01933, mailed Apr. 7, 2025, 9 pages.
Office Action in EA202393236/28, mailed Apr. 1, 2025, 4 pages.
Partial Supplementary European Search Report in EP22826025.3, mailed Jun. 12, 2025, 15 pages.

* cited by examiner

| Source | Name | Peptide Sequence | SEQ ID NO |
|---|---|---|---|
| | | C1 C2 C3 C4 | |
| Medicago sativa | MsDef1 | GRCRDDFR------CWCTKN-C | 35 |
| Medicago truncatula | MtDef4 | GRCRGFRRR-----CFCTTH-C | 8 |
| Medicago truncatula | MtDef5A | GACHRQGFGFA--CFCYKK-C | 16 |
| Medicago truncatula | MtDef5B | GACHRQGIGFA--CFCKKK-C | **41** |
| Medicago truncatula | MtDef6 | GRCRGFRRR-----CFCTRP-C | 21 |
| Olea europaea | OeDef1 | GACLKNRHSKHYGCYCYYRHCY | **24** |
| Olea europaea | OeDef7 | GLCRGFRRR---CFCTKH-C | **27** |
| Sorghum bicolor | SbDef1 | GYCSSRRQI-----CKCTLQ-C | **30** |
| Nicotiana alata | NaD1 | GHCSKILRR-----CLCTKP-C | **37** |
| Raphanus sativum | RsAFP2 | GSCNYVFPAHK--CICYFP-C | **38** |
| Dahlia merckii | DmAMP1 | GACHVRNGKHM--CFCYFN-C | **39** |
| Heuchera sanguinea | HsAFP1 | GACHYQFPSVK--CFCTQN-C | **40** |

FIGURE 2

| Source | Name | Peptide Sequence (C1 C2 C3 C4) | SEQ ID NO |
|---|---|---|---|
| Medicago sativa | MsDef1 | GRCRDDFR-----CWCTKN-C | 35 |
| Medicago truncatula | MtDef4 | GRCRGFRRR----CFCTTH-C | 8 |
| Medicago truncatula | MtDef5A | GACHRQGFGFA--CFCYKK-C | 16 |
| Medicago truncatula | MtDef5B | GACHRQGIGFA--CFCKKK-C | 41 |
| Medicago truncatula | MtDef6 | GRCRGFRRR----CFCTRP-C | 21 |
| Olea europaea | OeDef1 | GACLKNRHSKHYGCYCYYRHCY | 24 |
| Olea europaea | OeDef7 | GLCRGFRRR----CFCTKH-C | 27 |
| Sorghum bicolor | SbDef1 | GYCSSRRQI----CKCTLQ-C | 30 |
| Nicotiana alata | NaD1 | GHCSKILRR----CLCTKP-C | 37 |
| Raphanus sativum | RsAFP2 | GSCNYVFPAHK--CICYFP-C | 38 |
| Dahlia merckii | DmAMP1 | GACHVRNGKHM--CFCYFN-C | 39 |
| Heuchera sanguinea | HsAFP1 | GACHYQFPSVK--CFCTQN-C | 40 |
| Malus baccata | | GKCSLLTRT----CMCTKK-C | 94 |
| Triticum dicoccoides | | GKCDHRR------CVCTKG-C | 96 |
| Pyrus sp. cross | | GHCSVLTRA----CVCTKK-C | 97 |
| Sesamum indicum | | GSCKGFLLR----CICFKD-C | 104 |
| Vanilla planifolia | | GHCSRREQHKIF CIC | 108 |
| Brachypodium distachyon | | GNCDGAVRR----CKCSRE-C | 112 |
| Setaria italica | | GFCKGFFHRE---CMCTKD-C | 121 |
| Setaria italica | | GECRFHGGLLRR-CFCNKL-C | 122 |
| Gamma-core consensus 1 | | GXCXXXXXXXXX-C | 9 |
| Gamma-core consensus 2 | | GXCXXXXXXXXXXC | 10 |
| Mod. Gamma-core consensus 5 | | GXCXXXXXXXX--X | 45 |
| Mod. Gamma-core consensus 6 | | GXCXXXXXXXXXXX | 46 |
| Mod. Gamma-core consensus 1 | | GXCXXXXXXXX--XXX | 33 |
| Mod. Gamma-core consensus 2 | | GXCXXXXXXXXX-XXX | 34 |
| Mod. Gamma-core consensus 11 | | GXCXXXXXXXX--XXX | 51 |
| Mod. Gamma-core consensus 12 | | GXCXXXXXXXXXXXXX | 52 |

FIGURE 3

| Species (isolate) | Isolate No. | GMA4C_V1A | GMA4C_V2A | GMA4C_V4A | GMA4C_V5A | Fluconazole | Voriconazole | Fluconazole | Voriconazole |
|---|---|---|---|---|---|---|---|---|---|
| | | 100% | 100% | 100% | 100% | 100% | 100% | 100% | 100% |
| *C. parapsilosis* | ATCC 22019 | 4 | 8 | 8 | 8 | 2 | --- | 4 | --- |
| *C. krusei* | ATCC 6258 | 8 | 16 | 8 | 8 | 64 | --- | 64 | --- |
| *P. variotii* | MYA-363 | 4 | 8 | 8 | 4 | 16 | 0.125 | 16 | 0.125 |
| *Candida albicans* | SC5314 | 8 | 16 | 8 | 16 | >64 | --- | >64 | --- |
| | ATCC 90028 | 8 | 16 | 8 | 16 | 4 | --- | >64 | --- |
| | CA3 | 8 | 16 | 8 | 8 | 1 | --- | >64 | --- |
| *Candida auris* | DI17-47 | 8 | 16 | 8 | 16 | >64 | --- | >64 | --- |
| | DI17-48 | 8 | 16 | 8 | 16 | 8 | --- | >64 | --- |
| | DI17-46 | 8 | 16 | 8 | 16 | >64 | --- | >64 | --- |
| *Aspergillus fumigatus* | AF293 | 32 | 32 | 16 | 32 | --- | 0.5 | --- | 0.5 |
| | DI15-106 | >32 | >32 | 16 | >32 | --- | >16 | --- | >16 |
| | DI15-116 | >32 | >32 | 32 | >32 | --- | 4 | --- | 4 |
| *Fusarium* | F1 (*F. oxysporum*) | 4 | 8 | 8 | 8 | --- | 4 | --- | 8 |
| | F2 (*F. oxysporum*) | 4 | 16 | 8 | 16 | --- | 4 | --- | 2 |
| | F4 (*F. solani*) | 4 | 8 | 8 | 8 | --- | >16 | --- | >16 |
| *Coccidioides* sp. | Cocci1 | 8 | 8 | 4 | 2 | 16 | --- | 16 | --- |
| | Cocci2 | 4 | 16 | 16 | 16 | 64 | --- | >64 | --- |
| | DI17-143 | 8 | 16 | 16 | 16 | 16 | --- | >64 | --- |

FIGURE 4

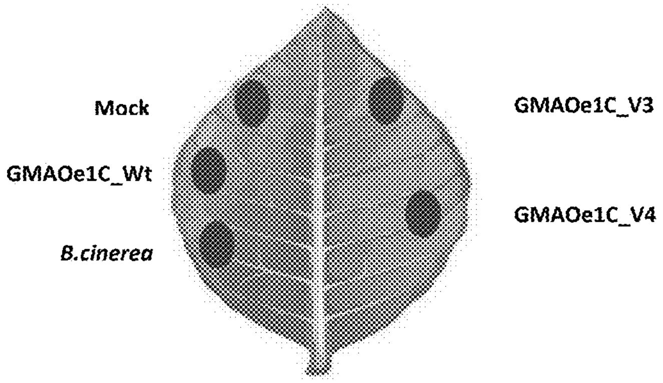
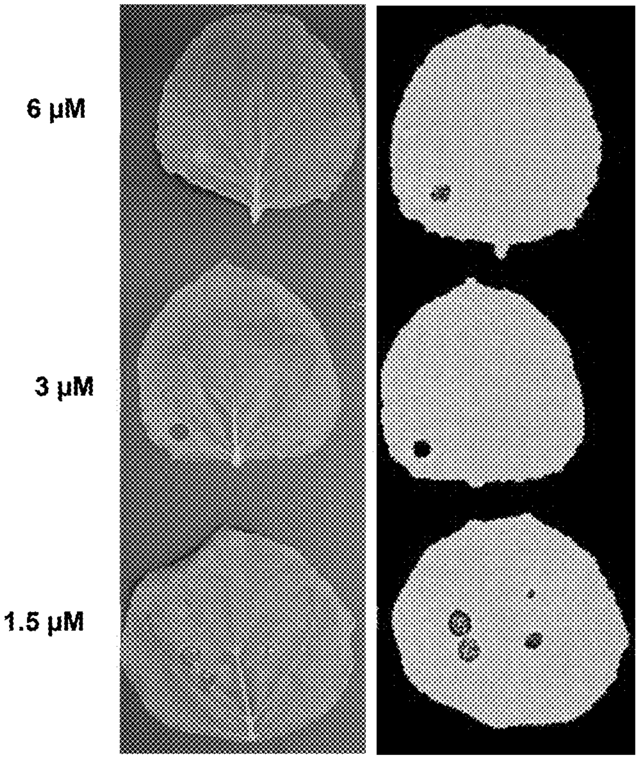
FIGURE 6A

SEQUENCE LISTING

```
<160> NUMBER OF SEQ ID NOS: 592

<210> SEQ ID NO 1
<211> LENGTH: 23
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is F, G, or absent
<220> FEATURE:
<221> NAME/KEY: VARIANT
<222> LOCATION: (3)..(3)
<223> OTHER INFORMATION: Xaa is A, G, Y, H, S, R or diaminobutyric acid
<220> FEATURE:
<221> NAME/KEY: VARIANT
<222> LOCATION: (5)..(5)
<223> OTHER INFORMATION: Xaa is H, L, S, N, R, K, or  diaminobutyric
      acid
<220> FEATURE:
<221> NAME/KEY: VARIANT
<222> LOCATION: (6)..(15)
<223> OTHER INFORMATION: Xaa is R, K, H, N, D, F, G, Q, P, A, I, L, V,
      Y, S, or diaminobutyric acid, , wherein one or more of Xaa 8, Xaa
      9, Xaa 10, Xaa 11, Xaa 12, Xaa 13, Xaa 14, and/or Xaa 15 may be
      absent
<220> FEATURE:
<221> NAME/KEY: VARIANT
<222> LOCATION: (16)..(16)
<223> OTHER INFORMATION: Xaa is C, V, W, Y, or F
<220> FEATURE:
<221> NAME/KEY: VARIANT
<222> LOCATION: (17)..(17)
<223> OTHER INFORMATION: Xaa is L, I, W, Y, or F
<220> FEATURE:
<221> NAME/KEY: VARIANT
<222> LOCATION: (18)..(18)
<223> OTHER INFORMATION: Xaa is C, V, W, Y, or F
<220> FEATURE:
<221> NAME/KEY: VARIANT
<222> LOCATION: (19)..(19)
<223> OTHER INFORMATION: Xaa is K, T, F, W, or Y
<220> FEATURE:
<221> NAME/KEY: VARIANT
<222> LOCATION: (20)..(20)
<223> OTHER INFORMATION: Xaa is R, K, T, L, F, Q, or diaminobutyric acid
<220> FEATURE:
<221> NAME/KEY: VARIANT
<222> LOCATION: (21)..(21)
<223> OTHER INFORMATION: Xaa is N, H, K, R, P, Q, I, F, W, or Y
<220> FEATURE:
<221> NAME/KEY: VARIANT
<222> LOCATION: (22)..(22)
<223> OTHER INFORMATION: Xaa is N, H, K, P, Q, I, F, W, Y, or absent
<220> FEATURE:
<221> NAME/KEY: MISC_FEATURE
<222> LOCATION: (23)..(23)
<223> OTHER INFORMATION: C is optionally amidated

<400> SEQUENCE: 1

Xaa Gly Xaa Cys Xaa Xaa Xaa Xaa Xaa Xaa Xaa Xaa Xaa Xaa Xaa Xaa
1               5                   10                  15
```

Xaa Xaa Xaa Xaa Xaa Xaa Cys
20

<210> SEQ ID NO 2
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 2

Gly Gly Arg Cys Arg Gly Phe Arg Arg Arg Cys Phe Cys Thr Thr His
1 5 10 15

Cys

<210> SEQ ID NO 3
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 3

Gly Gly Arg Cys Lys Gly Phe Arg Arg Arg Cys Phe Cys Thr Arg Ile
1 5 10 15

Cys

<210> SEQ ID NO 4
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 4

Gly Gly Arg Cys Arg Gly Phe Arg Arg Arg Cys Phe Cys Thr Arg Ile
1 5 10 15

Cys

<210> SEQ ID NO 5
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 5

Gly Gly Arg Cys Arg Gly Phe Arg Arg Arg Val Phe Val Thr Arg Ile
1 5 10 15

Cys

<210> SEQ ID NO 6
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 6

Phe Gly Arg Cys Arg Gly Phe Arg Arg Arg Cys Phe Cys Trp Arg Trp
1 5 10 15

Cys

<210> SEQ ID NO 7
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (3)..(3)
<223> OTHER INFORMATION: Xaa is diaminobutyric acid
<220> FEATURE:
<221> NAME/KEY: VARIANT
<222> LOCATION: (5)..(5)
<223> OTHER INFORMATION: Xaa is diaminobutyric acid
<220> FEATURE:
<221> NAME/KEY: VARIANT
<222> LOCATION: (8)..(10)
<223> OTHER INFORMATION: Xaa is diaminobutyric acid
<220> FEATURE:
<221> NAME/KEY: VARIANT
<222> LOCATION: (15)..(15)
<223> OTHER INFORMATION: Xaa is diaminobutyric acid
<220> FEATURE:
<221> NAME/KEY: MOD_RES
<222> LOCATION: (17)..(17)
<223> OTHER INFORMATION: AMIDATION

<400> SEQUENCE: 7

Phe Gly Xaa Cys Xaa Gly Phe Xaa Xaa Xaa Cys Phe Cys Trp Xaa Trp
1 5 10 15

Cys

<210> SEQ ID NO 8
<211> LENGTH: 16
<212> TYPE: PRT
<213> ORGANISM: Artificial
<220> FEATURE:
<223> OTHER INFORMATION: synthetic

<400> SEQUENCE: 8

Gly Arg Cys Arg Gly Phe Arg Arg Arg Cys Phe Cys Thr Thr His Cys
1 5 10 15

<210> SEQ ID NO 9
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid

```
<220> FEATURE:
<221> NAME/KEY: VARIANT
<222> LOCATION: (4)..(12)
<223> OTHER INFORMATION: Xaa is any amino acid, wherein Xaa 7 to Xaa 12
      are optionally present

<400> SEQUENCE: 9

Gly Xaa Cys Xaa Xaa Xaa Xaa Xaa Xaa Xaa Xaa Xaa Cys
1               5                   10


<210> SEQ ID NO 10
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(13)
<223> OTHER INFORMATION: Xaa is any amino acid, wherein Xaa 7 to Xaa 13
      are optionally present

<400> SEQUENCE: 10

Gly Xaa Cys Xaa Xaa Xaa Xaa Xaa Xaa Xaa Xaa Xaa Xaa Cys
1               5                   10


<210> SEQ ID NO 11
<211> LENGTH: 17
<212> TYPE: PRT
<213> ORGANISM: Artificial
<220> FEATURE:
<223> OTHER INFORMATION: synthetic

<400> SEQUENCE: 11

Phe Gly Arg Cys Arg Gly Phe Arg Arg Arg Cys Phe Cys Trp Arg Trp
1               5                   10                  15

Cys


<210> SEQ ID NO 12
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (3)..(3)
<223> OTHER INFORMATION: Xaa is diaminobutyric acid
<220> FEATURE:
<221> NAME/KEY: VARIANT
<222> LOCATION: (5)..(5)
<223> OTHER INFORMATION: Xaa is diaminobutyric acid
<220> FEATURE:
<221> NAME/KEY: VARIANT
<222> LOCATION: (8)..(10)
<223> OTHER INFORMATION: Xaa is diaminobutyric acid
<220> FEATURE:
<221> NAME/KEY: VARIANT
<222> LOCATION: (15)..(15)
<223> OTHER INFORMATION: Xaa is diaminobutyric acid

<400> SEQUENCE: 12

Phe Gly Xaa Cys Xaa Gly Phe Xaa Xaa Xaa Cys Phe Cys Trp Xaa Trp
1               5                   10                  15

Cys
```

<210> SEQ ID NO 13
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 13

Gly Gly Arg Cys Lys Gly Phe Arg Arg Arg Trp Phe Trp Thr Arg Ile
1 5 10 15

Cys

<210> SEQ ID NO 14
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa1 is F, G, or absent
<220> FEATURE:
<221> NAME/KEY: VARIANT
<222> LOCATION: (3)..(3)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is K or R
<220> FEATURE:
<221> NAME/KEY: VARIANT
<222> LOCATION: (11)..(13)
<223> OTHER INFORMATION: Xaa is F, W, or Y
<220> FEATURE:
<221> NAME/KEY: VARIANT
<222> LOCATION: (14)..(14)
<223> OTHER INFORMATION: Xaa is T, F, W, or Y
<220> FEATURE:
<221> NAME/KEY: VARIANT
<222> LOCATION: (15)..(15)
<223> OTHER INFORMATION: Xaa is R, K, or diaminobutyric acid
<220> FEATURE:
<221> NAME/KEY: VARIANT
<222> LOCATION: (16)..(16)
<223> OTHER INFORMATION: Xaa is is I, F, W, or Y
<220> FEATURE:
<221> NAME/KEY: MISC_FEATURE
<222> LOCATION: (17)..(17)
<223> OTHER INFORMATION: Cysteine is optionally amidated

<400> SEQUENCE: 14

Xaa Gly Arg Cys Xaa Gly Phe Arg Arg Arg Xaa Xaa Xaa Xaa Xaa Xaa
1 5 10 15

Cys

<210> SEQ ID NO 15
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 15

Gly Gly Arg Cys Lys Gly Phe Arg Arg Arg Trp Tyr Trp Thr Arg Ile
1 5 10 15

Cys

<210> SEQ ID NO 16
<211> LENGTH: 18
<212> TYPE: PRT
<213> ORGANISM: Artificial
<220> FEATURE:
<223> OTHER INFORMATION: synthetic

<400> SEQUENCE: 16

Gly Ala Cys His Arg Gln Gly Phe Gly Phe Ala Cys Phe Cys Tyr Lys
1 5 10 15

Lys Cys

<210> SEQ ID NO 17
<211> LENGTH: 19
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is F, G, or absent
<220> FEATURE:
<221> NAME/KEY: VARIANT
<222> LOCATION: (3)..(3)
<223> OTHER INFORMATION: Xaa is A, F, W, Y, or absent
<220> FEATURE:
<221> NAME/KEY: VARIANT
<222> LOCATION: (5)..(5)
<223> OTHER INFORMATION: Xaa is is H, R, or K
<220> FEATURE:
<221> NAME/KEY: VARIANT
<222> LOCATION: (6)..(6)
<223> OTHER INFORMATION: Xaa is R or K
<220> FEATURE:
<221> NAME/KEY: VARIANT
<222> LOCATION: (7)..(7)
<223> OTHER INFORMATION: Xaa is Q, R, or K
<220> FEATURE:
<221> NAME/KEY: VARIANT
<222> LOCATION: (10)..(10)
<223> OTHER INFORMATION: Xaa is G, R, or K
<220> FEATURE:
<221> NAME/KEY: VARIANT
<222> LOCATION: (11)..(11)
<223> OTHER INFORMATION: Xaa is F, W, Y, R, or K
<220> FEATURE:
<221> NAME/KEY: VARIANT
<222> LOCATION: (12)..(12)
<223> OTHER INFORMATION: Xaa is A, F, W, Y, R, or K
<220> FEATURE:
<221> NAME/KEY: VARIANT
<222> LOCATION: (13)..(15)
<223> OTHER INFORMATION: Xaa is F, W, or Y
<220> FEATURE:
<221> NAME/KEY: VARIANT
<222> LOCATION: (16)..(16)
<223> OTHER INFORMATION: Xaa is F, W, Y, R, or K
<220> FEATURE:
<221> NAME/KEY: VARIANT
<222> LOCATION: (17)..(18)
<223> OTHER INFORMATION: Xaa is R or K
<220> FEATURE:
<221> NAME/KEY: MISC_FEATURE
<222> LOCATION: (19)..(19)

<400> SEQUENCE: 17

```
Xaa Gly Xaa Cys Xaa Xaa Xaa Gly Phe Xaa Xaa Xaa Xaa Xaa Xaa Xaa
1               5                   10                  15

Xaa Xaa Cys
```

<210> SEQ ID NO 18
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (12)..(14)
<223> OTHER INFORMATION: Xaa is F, W, or Y
<220> FEATURE:
<221> NAME/KEY: MISC_FEATURE
<222> LOCATION: (18)..(18)
<223> OTHER INFORMATION: Cysteine is optionally amidated

<400> SEQUENCE: 18

```
Gly Ala Cys His Arg Gln Gly Phe Gly Phe Ala Xaa Xaa Xaa Tyr Lys
1               5                   10                  15

Lys Cys
```

<210> SEQ ID NO 19
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (18)..(18)
<223> OTHER INFORMATION: AMIDATION

<400> SEQUENCE: 19

```
Gly Ala Cys His Arg Gln Gly Phe Gly Phe Ala Trp Phe Trp Tyr Lys
1               5                   10                  15

Lys Cys
```

<210> SEQ ID NO 20
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (18)..(18)
<223> OTHER INFORMATION: AMIDATION

<400> SEQUENCE: 20

```
Gly Ala Cys His Arg Gln Gly Phe Gly Phe Ala Phe Phe Phe Tyr Lys
1               5                   10                  15

Lys Cys
```

<210> SEQ ID NO 21
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)

<223> OTHER INFORMATION: AMIDATION

<400> SEQUENCE: 21

Gly Gly Arg Cys Arg Gly Phe Arg Arg Arg Cys Phe Cys Thr Arg Pro
1 5 10 15

Cys

<210> SEQ ID NO 22
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (11)..(13)
<223> OTHER INFORMATION: Xaa is F, W, or Y
<220> FEATURE:
<221> NAME/KEY: MISC_FEATURE
<222> LOCATION: (17)..(17)
<223> OTHER INFORMATION: Cysteine is optionally amidated

<400> SEQUENCE: 22

Gly Gly Arg Cys Arg Gly Phe Arg Arg Arg Xaa Xaa Xaa Thr Arg Pro
1 5 10 15

Cys

<210> SEQ ID NO 23
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 23

Gly Gly Arg Cys Arg Gly Phe Arg Arg Arg Trp Phe Trp Thr Arg Pro
1 5 10 15

Cys

<210> SEQ ID NO 24
<211> LENGTH: 22
<212> TYPE: PRT
<213> ORGANISM: Artificial
<220> FEATURE:
<223> OTHER INFORMATION: synthetic

<400> SEQUENCE: 24

Gly Ala Cys Leu Lys Asn Arg His Ser Lys His Tyr Gly Cys Tyr Cys
1 5 10 15

Tyr Tyr Arg His Cys Tyr
20

<210> SEQ ID NO 25
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (14)..(16)
<223> OTHER INFORMATION: Xaa is F, W, or Y
<220> FEATURE:

```
<221> NAME/KEY: MISC_FEATURE
<222> LOCATION: (22)..(22)
<223> OTHER INFORMATION: Tyrosine is optionally amidated

<400> SEQUENCE: 25

Gly Ala Cys Leu Lys Asn Arg His Ser Lys His Tyr Gly Xaa Xaa Xaa
1               5                   10                  15

Tyr Tyr Arg His Cys Tyr
            20


<210> SEQ ID NO 26
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 26

Gly Ala Cys Leu Lys Asn Arg His Ser Lys His Tyr Gly Trp Phe Trp
1               5                   10                  15

Tyr Tyr Arg His Cys Tyr
            20


<210> SEQ ID NO 27
<211> LENGTH: 17
<212> TYPE: PRT
<213> ORGANISM: Artificial
<220> FEATURE:
<223> OTHER INFORMATION: synthetic

<400> SEQUENCE: 27

Gly Gly Leu Cys Arg Gly Phe Arg Arg Arg Cys Phe Cys Thr Lys His
1               5                   10                  15

Cys


<210> SEQ ID NO 28
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (11)..(13)
<223> OTHER INFORMATION: Xaa is F, W, or Y
<220> FEATURE:
<221> NAME/KEY: MISC_FEATURE
<222> LOCATION: (17)..(17)
<223> OTHER INFORMATION: Cysteine is optionally amidated

<400> SEQUENCE: 28

Gly Gly Leu Cys Arg Gly Phe Arg Arg Arg Xaa Xaa Xaa Thr Lys His
1               5                   10                  15

Cys


<210> SEQ ID NO 29
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
```

<222> LOCATION: (17)..(17)
<223> OTHER INFORMATION: AMIDATION

<400> SEQUENCE: 29

Gly Gly Leu Cys Arg Gly Phe Arg Arg Arg Trp Phe Trp Thr Lys His
1 5 10 15

Cys

<210> SEQ ID NO 30
<211> LENGTH: 17
<212> TYPE: PRT
<213> ORGANISM: Artificial
<220> FEATURE:
<223> OTHER INFORMATION: synthetic

<400> SEQUENCE: 30

Gly Gly Tyr Cys Ser Ser Arg Arg Gln Ile Cys Lys Cys Thr Leu Gln
1 5 10 15

Cys

<210> SEQ ID NO 31
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (11)..(13)
<223> OTHER INFORMATION: Xaa is F, W, or Y
<220> FEATURE:
<221> NAME/KEY: MISC_FEATURE
<222> LOCATION: (17)..(17)
<223> OTHER INFORMATION: Cysteine is optionally amidated

<400> SEQUENCE: 31

Gly Gly Tyr Cys Ser Ser Arg Arg Gln Ile Xaa Xaa Xaa Thr Leu Gln
1 5 10 15

Cys

<210> SEQ ID NO 32
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 32

Gly Gly Tyr Cys Ser Ser Arg Arg Gln Ile Trp Phe Trp Thr Leu Gln
1 5 10 15

Cys

<210> SEQ ID NO 33
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:

<221> NAME/KEY: VARIANT
<222> LOCATION: (4)..(11)
<223> OTHER INFORMATION: Xaa is any amino acid, Xaa7 to Xaa11 are optionally present
<220> FEATURE:
<221> NAME/KEY: VARIANT
<222> LOCATION: (12)..(14)
<223> OTHER INFORMATION: Xaa is F, W, or Y

<400> SEQUENCE: 33

Gly Xaa Cys Xaa Xaa Xaa Xaa Xaa Xaa Xaa Xaa Xaa Xaa Xaa
1 5 10

<210> SEQ ID NO 34
<211> LENGTH: 15
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(12)
<223> OTHER INFORMATION: Xaa is any amino acid, Xaa7 to Xaa12 are optionally present
<220> FEATURE:
<221> NAME/KEY: VARIANT
<222> LOCATION: (13)..(15)
<223> OTHER INFORMATION: Xaa is F, W, or Y

<400> SEQUENCE: 34

Gly Xaa Cys Xaa Xaa Xaa Xaa Xaa Xaa Xaa Xaa Xaa Xaa Xaa Xaa
1 5 10 15

<210> SEQ ID NO 35
<211> LENGTH: 15
<212> TYPE: PRT
<213> ORGANISM: Artificial
<220> FEATURE:
<223> OTHER INFORMATION: synthetic

<400> SEQUENCE: 35

Gly Arg Cys Arg Asp Asp Phe Arg Cys Trp Cys Thr Lys Asn Cys
1 5 10 15

<210> SEQ ID NO 36
<211> LENGTH: 15
<212> TYPE: PRT
<213> ORGANISM: Artificial
<220> FEATURE:
<223> OTHER INFORMATION: synthetic

<400> SEQUENCE: 36

Gly Arg Cys Arg Ile Leu Phe Arg Cys Phe Cys Thr Lys Asn Cys
1 5 10 15

<210> SEQ ID NO 37
<211> LENGTH: 16
<212> TYPE: PRT
<213> ORGANISM: Artificial
<220> FEATURE:
<223> OTHER INFORMATION: synthetic

<400> SEQUENCE: 37

Gly His Cys Ser Lys Ile Leu Arg Arg Cys Leu Cys Thr Lys Pro Cys
1 5 10 15

<210> SEQ ID NO 38
<211> LENGTH: 18
<212> TYPE: PRT
<213> ORGANISM: Artificial
<220> FEATURE:
<223> OTHER INFORMATION: synthetic

<400> SEQUENCE: 38

Gly Ser Cys Asn Tyr Val Phe Pro Ala His Lys Cys Ile Cys Tyr Phe
1 5 10 15

Pro Cys

<210> SEQ ID NO 39
<211> LENGTH: 18
<212> TYPE: PRT
<213> ORGANISM: Artificial
<220> FEATURE:
<223> OTHER INFORMATION: synthetic

<400> SEQUENCE: 39

Gly Ala Cys His Val Arg Asn Gly Lys His Met Cys Phe Cys Tyr Phe
1 5 10 15

Asn Cys

<210> SEQ ID NO 40
<211> LENGTH: 18
<212> TYPE: PRT
<213> ORGANISM: Artificial
<220> FEATURE:
<223> OTHER INFORMATION: synthetic

<400> SEQUENCE: 40

Gly Ala Cys His Tyr Gln Phe Pro Ser Val Lys Cys Phe Cys Thr Gln
1 5 10 15

Asn Cys

<210> SEQ ID NO 41
<211> LENGTH: 18
<212> TYPE: PRT
<213> ORGANISM: Artificial
<220> FEATURE:
<223> OTHER INFORMATION: synthetic

<400> SEQUENCE: 41

Gly Ala Cys His Arg Gln Gly Ile Gly Phe Ala Cys Phe Cys Lys Lys
1 5 10 15

Lys Cys

<210> SEQ ID NO 42
<211> LENGTH: 22
<212> TYPE: PRT
<213> ORGANISM: Artificial
<220> FEATURE:
<223> OTHER INFORMATION: synthetic

<400> SEQUENCE: 42

Gly Ala Cys Leu Lys Asn Arg His Ser Lys His Tyr Gly Phe Phe Trp
1 5 10 15

Tyr Tyr Arg His Cys Tyr
20

<210> SEQ ID NO 43
<211> LENGTH: 12

```
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(11)
<223> OTHER INFORMATION: Xaa is any amino acid, Xaa7 to Xaa11 are
      optionally present
<220> FEATURE:
<221> NAME/KEY: VARIANT
<222> LOCATION: (12)..(12)
<223> OTHER INFORMATION: Xaa is F, W, or Y

<400> SEQUENCE: 43

Gly Xaa Cys Xaa Xaa Xaa Xaa Xaa Xaa Xaa Xaa Xaa
1               5                   10


<210> SEQ ID NO 44
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(12)
<223> OTHER INFORMATION: Xaa is any amino acid, Xaa7 to Xaa12 are
      optionally present
<220> FEATURE:
<221> NAME/KEY: VARIANT
<222> LOCATION: (13)..(13)
<223> OTHER INFORMATION: Xaa is F, W, or Y

<400> SEQUENCE: 44

Gly Xaa Cys Xaa Xaa Xaa Xaa Xaa Xaa Xaa Xaa Xaa Xaa
1               5                   10


<210> SEQ ID NO 45
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(11)
<223> OTHER INFORMATION: Xaa is any amino acid, Xaa7 to Xaa11 are
      optionally present
<220> FEATURE:
<221> NAME/KEY: VARIANT
<222> LOCATION: (12)..(12)
<223> OTHER INFORMATION: Xaa is F, W, Y, L, V, I, or M

<400> SEQUENCE: 45

Gly Xaa Cys Xaa Xaa Xaa Xaa Xaa Xaa Xaa Xaa Xaa
1               5                   10


<210> SEQ ID NO 46
<211> LENGTH: 14
<212> TYPE: PRT
```

<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(13)
<223> OTHER INFORMATION: Xaa is any amino acid, Xaa7 to Xaa13 are optionally present
<220> FEATURE:
<221> NAME/KEY: VARIANT
<222> LOCATION: (14)..(14)
<223> OTHER INFORMATION: Xaa is F, W, Y, L, V, I, or M

<400> SEQUENCE: 46

Gly Xaa Cys Xaa Xaa Xaa Xaa Xaa Xaa Xaa Xaa Xaa Xaa Xaa
1               5                   10

<210> SEQ ID NO 47
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(11)
<223> OTHER INFORMATION: Xaa is any amino acid, Xaa7 to Xaa11 are optionally present
<220> FEATURE:
<221> NAME/KEY: VARIANT
<222> LOCATION: (12)..(12)
<223> OTHER INFORMATION: Xaa is  L, V, I, or M
<220> FEATURE:
<221> NAME/KEY: VARIANT
<222> LOCATION: (13)..(13)
<223> OTHER INFORMATION: Xaa is F, W, or Y
<220> FEATURE:
<221> NAME/KEY: VARIANT
<222> LOCATION: (14)..(14)
<223> OTHER INFORMATION: Xaa is  L, V, I, or M

<400> SEQUENCE: 47

Gly Xaa Cys Xaa Xaa Xaa Xaa Xaa Xaa Xaa Xaa Xaa Xaa Xaa
1               5                   10

<210> SEQ ID NO 48
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(13)
<223> OTHER INFORMATION: Xaa is any amino acid, Xaa7 to Xaa13 are optionally present
<220> FEATURE:
<221> NAME/KEY: VARIANT
<222> LOCATION: (14)..(14)
<223> OTHER INFORMATION: Xaa is  L, V, I, or M
<220> FEATURE:
<221> NAME/KEY: VARIANT
<222> LOCATION: (15)..(15)

```
<223> OTHER INFORMATION: Xaa is F, W, or Y
<220> FEATURE:
<221> NAME/KEY: VARIANT
<222> LOCATION: (16)..(16)
<223> OTHER INFORMATION: Xaa is  L, V, I, or M

<400> SEQUENCE: 48

Gly Xaa Cys Xaa Xaa Xaa Xaa Xaa Xaa Xaa Xaa Xaa Xaa Xaa Xaa Xaa
1               5                   10                  15


<210> SEQ ID NO 49
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(11)
<223> OTHER INFORMATION: Xaa is any amino acid, Xaa7 to Xaa11 are
      optionally present
<220> FEATURE:
<221> NAME/KEY: VARIANT
<222> LOCATION: (12)..(12)
<223> OTHER INFORMATION: Xaa is F, W, Y, L, V, I, or M
<220> FEATURE:
<221> NAME/KEY: VARIANT
<222> LOCATION: (13)..(13)
<223> OTHER INFORMATION: Xaa is F, W, or Y
<220> FEATURE:
<221> NAME/KEY: VARIANT
<222> LOCATION: (14)..(14)
<223> OTHER INFORMATION: Xaa is F, W, Y, L, V, I, or M

<400> SEQUENCE: 49

Gly Xaa Cys Xaa Xaa Xaa Xaa Xaa Xaa Xaa Xaa Xaa Xaa Xaa
1               5                   10


<210> SEQ ID NO 50
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(13)
<223> OTHER INFORMATION: Xaa is any amino acid, Xaa7 to Xaa13 are
      optionally present
<220> FEATURE:
<221> NAME/KEY: VARIANT
<222> LOCATION: (14)..(14)
<223> OTHER INFORMATION: Xaa is F, W, Y, L, V, I, or M
<220> FEATURE:
<221> NAME/KEY: VARIANT
<222> LOCATION: (15)..(15)
<223> OTHER INFORMATION: Xaa is F, W, or Y
<220> FEATURE:
<221> NAME/KEY: VARIANT
<222> LOCATION: (16)..(16)
<223> OTHER INFORMATION: Xaa is F, W, Y, L, V, I, or M

<400> SEQUENCE: 50

Gly Xaa Cys Xaa Xaa Xaa Xaa Xaa Xaa Xaa Xaa Xaa Xaa Xaa Xaa Xaa
1               5                   10                  15
```

```
<210> SEQ ID NO 51
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(11)
<223> OTHER INFORMATION: Xaa is any amino acid, Xaa7 to Xaa11 are
      optionally present
<220> FEATURE:
<221> NAME/KEY: VARIANT
<222> LOCATION: (12)..(14)
<223> OTHER INFORMATION: Xaa is F, W, Y, L, V, I, or M

<400> SEQUENCE: 51

Gly Xaa Cys Xaa Xaa Xaa Xaa Xaa Xaa Xaa Xaa Xaa Xaa Xaa
1               5                   10


<210> SEQ ID NO 52
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(13)
<223> OTHER INFORMATION: Xaa is any amino acid, Xaa7 to Xaa13 are
      optionally present
<220> FEATURE:
<221> NAME/KEY: VARIANT
<222> LOCATION: (14)..(16)
<223> OTHER INFORMATION: Xaa is F, W, Y, L, V, I, or M

<400> SEQUENCE: 52

Gly Xaa Cys Xaa Xaa Xaa Xaa Xaa Xaa Xaa Xaa Xaa Xaa Xaa Xaa Xaa
1               5                   10                  15


<210> SEQ ID NO 53
<211> LENGTH: 74
<212> TYPE: PRT
<213> ORGANISM: Arabidopsis thaliana

<400> SEQUENCE: 53

Cys Thr Ser Thr Leu Ile Asn Gly Ser Ser Asp Glu Glu Arg Thr Tyr
1               5                   10                  15

Ser Phe Ser Pro Thr Thr Ser Pro Phe Asp Pro Arg Ser Leu Asn Gln
            20                  25                  30

Glu Leu Lys Ile Gly Arg Ile Gly Tyr Cys Phe Asp Cys Ala Arg Ala
        35                  40                  45

Cys Met Arg Arg Gly Lys Tyr Ile Arg Thr Cys Ser Phe Glu Arg Lys
    50                  55                  60

Leu Cys Arg Cys Ser Ile Ser Asp Ile Lys
65                  70


<210> SEQ ID NO 54
<211> LENGTH: 57
<212> TYPE: PRT
```

<213> ORGANISM: Oryza sativa

<400> SEQUENCE: 54

Gly Thr Thr Lys Val Ala Glu Ala Arg His Cys Leu Ser Gln Ser His
1 5 10 15

Arg Phe Lys Gly Met Cys Val Ser Ser Asn Asn Cys Ala Asn Val Cys
20 25 30

Arg Thr Glu Ser Phe Pro Asp Gly Glu Cys Lys Ser His Gly Leu Glu
35 40 45

Arg Lys Cys Phe Cys Lys Lys Val Cys
50 55

<210> SEQ ID NO 55
<211> LENGTH: 108
<212> TYPE: PRT
<213> ORGANISM: Artemisia vulgaris

<400> SEQUENCE: 55

Ala Gly Ser Lys Leu Cys Glu Lys Thr Ser Lys Thr Tyr Ser Gly Lys
1 5 10 15

Cys Asp Asn Lys Lys Cys Asp Lys Lys Cys Ile Glu Trp Glu Lys Ala
20 25 30

Gln His Gly Ala Cys His Lys Arg Glu Ala Gly Lys Glu Ser Cys Phe
35 40 45

Cys Tyr Phe Asp Cys Ser Lys Ser Pro Pro Gly Ala Thr Pro Ala Pro
50 55 60

Pro Gly Ala Ala Pro Pro Pro Ala Ala Gly Gly Ser Pro Ser Pro Pro
65 70 75 80

Ala Asp Gly Gly Ser Pro Pro Pro Pro Ala Asp Gly Gly Ser Pro Pro
85 90 95

Val Asp Gly Gly Ser Pro Pro Pro Pro Ser Thr His
100 105

<210> SEQ ID NO 56
<211> LENGTH: 50
<212> TYPE: PRT
<213> ORGANISM: Arabidopsis thaliana

<400> SEQUENCE: 56

Arg Ile Cys Glu Arg Arg Ser Lys Thr Trp Thr Gly Phe Cys Gly Asn
1 5 10 15

Thr Arg Gly Cys Asp Ser Gln Cys Lys Arg Trp Glu Arg Ala Ser His
20 25 30

Gly Ala Cys His Ala Gln Phe Pro Gly Phe Ala Cys Phe Cys Tyr Phe
35 40 45

Asn Cys
50

<210> SEQ ID NO 57
<211> LENGTH: 96
<212> TYPE: PRT
<213> ORGANISM: Arabidopsis thaliana

<400> SEQUENCE: 57

Ser Ile Cys Asn Asp Arg Leu Gly Leu Cys Asp Gly Cys Asp Gln Arg
1 5 10 15

Cys Lys Ala Lys His Gly Pro Ser Cys Glu Ser Lys Cys Asp Gly Pro
20 25 30

```
Val Gly Met Leu Leu Cys Thr Cys Thr Tyr Glu Cys Gly Pro Thr Lys
        35                  40                  45

Leu Cys Asn Gly Gly Leu Gly Asn Cys Gly Glu Ser Cys Asn Glu Gln
    50                  55                  60

Cys Cys Asp Arg Asn Cys Ala Gln Arg Tyr Asn Gly Gly His Gly Tyr
65                  70                  75                  80

Cys Asn Thr Leu Asp Asp Phe Ser Leu Cys Leu Cys Lys Tyr Pro Cys
                85                  90                  95


<210> SEQ ID NO 58
<211> LENGTH: 46
<212> TYPE: PRT
<213> ORGANISM: Arachis duranensis

<400> SEQUENCE: 58

Lys Leu Cys Asn His Leu Ala Asp Thr Tyr Arg Gly Pro Cys Phe Thr
1               5                   10                  15

Asn Ala Ser Cys Asp Asp His Cys Lys Asn Lys Glu His Phe Val Ser
            20                  25                  30

Gly Thr Cys Met Lys Met Ala Cys Trp Cys Ala His Asn Cys
        35                  40                  45


<210> SEQ ID NO 59
<211> LENGTH: 57
<212> TYPE: PRT
<213> ORGANISM: Malus baccata

<400> SEQUENCE: 59

Arg Thr Glu Ser Ser Lys Ala Ile Glu Gly Lys Ile Cys Glu Phe Pro
1               5                   10                  15

Ser Thr Leu Phe Lys Gly Leu Cys Phe Ser Ser Asn Asn Cys Lys His
            20                  25                  30

Thr Cys Arg Lys Glu Gln Phe Thr Arg Gly Lys Cys Ser Leu Leu Thr
        35                  40                  45

Arg Thr Cys Met Cys Thr Lys Lys Cys
    50                  55


<210> SEQ ID NO 60
<211> LENGTH: 55
<212> TYPE: PRT
<213> ORGANISM: Oryza sativa

<400> SEQUENCE: 60

Leu Ala Pro Ala Gln Ser Ser Val Arg Pro Cys Glu Thr Lys Ser Leu
1               5                   10                  15

Arg Phe Glu Gly Phe Cys Met Val Glu Asp Asn Cys Ala Asn Val Cys
            20                  25                  30

Arg Thr Glu Gly Phe Val Asp Gly Arg Cys Ser Thr Phe Val Arg Asn
        35                  40                  45

Cys Ile Cys Ile Lys Pro Cys
    50                  55


<210> SEQ ID NO 61
<211> LENGTH: 45
<212> TYPE: PRT
<213> ORGANISM: Triticum dicoccoides

<400> SEQUENCE: 61

Arg Asp Cys Thr Ser Gln Ser His Lys Phe Val Gly Leu Cys Leu Ser
1               5                   10                  15
```

```
Asp Arg Asn Cys Ala Ser Val Cys Leu Thr Glu Tyr Phe Thr Gly Gly
            20                  25                  30

Lys Cys Asp His Arg Arg Cys Val Cys Thr Lys Gly Cys
        35                  40                  45


<210> SEQ ID NO 62
<211> LENGTH: 47
<212> TYPE: PRT
<213> ORGANISM: Pyrus ussuriensis x Pyrus communis

<400> SEQUENCE: 62

Lys Ile Cys Glu Val Pro Ser Thr Leu Phe Lys Gly Leu Cys Phe Ser
1               5                   10                  15

Ser Asn Asn Cys Lys His Thr Cys Arg Lys Glu Gln Phe Thr Arg Gly
            20                  25                  30

His Cys Ser Val Leu Thr Arg Ala Cys Val Cys Thr Lys Lys Cys
        35                  40                  45


<210> SEQ ID NO 63
<211> LENGTH: 46
<212> TYPE: PRT
<213> ORGANISM: Beta vulgaris subsp. vulgaris

<400> SEQUENCE: 63

Ala Ile Cys Lys Lys Pro Ser Lys Phe Phe Lys Gly Ala Cys Gly Arg
1               5                   10                  15

Asp Ala Asp Cys Glu Lys Ala Cys Asp Gln Glu Asn Trp Pro Gly Gly
            20                  25                  30

Val Cys Val Pro Phe Leu Arg Cys Glu Cys Gln Arg Ser Cys
        35                  40                  45


<210> SEQ ID NO 64
<211> LENGTH: 47
<212> TYPE: PRT
<213> ORGANISM: Miscanthus lutarioriparius

<400> SEQUENCE: 64

Arg Val Cys Arg Arg Arg Ile Ala Gly Phe Lys Gly Val Cys Met Ser
1               5                   10                  15

Asp His Asn Cys Ala Gln Val Cys Leu Gln Glu Gly Trp Gly Gly Gly
            20                  25                  30

Asn Cys Asp Gly Ile Leu Arg Gln Cys Lys Cys Ile Arg Gln Cys
        35                  40                  45


<210> SEQ ID NO 65
<211> LENGTH: 103
<212> TYPE: PRT
<213> ORGANISM: Lotus japonicus

<400> SEQUENCE: 65

Asn Thr Cys Ser Glu Ala Leu Asp Gln Cys Asp Ser Met Glu Ser Cys
1               5                   10                  15

Asp Gln Lys Cys Lys Gly Arg His Asn Gly Arg Arg Gly Ser Cys Asn
            20                  25                  30

Leu Gly Leu Cys Thr Cys Ser Tyr Ser Cys Gly Pro Pro Gly Pro Lys
        35                  40                  45

Ile Pro Ser Asn Leu Cys Thr Ala Gly Leu Gly Leu Cys Ser Thr Lys
    50                  55                  60
```

Cys Gly Asp Ser Tyr Cys Asn Ser Ile Cys Ala Ser Lys Tyr Asn Gln
65 70 75 80

Gly Val Gly Phe Cys Tyr Thr Ser Gly Pro Ser Ile Asn Leu Cys Thr
85 90 95

Cys Gln Tyr Pro Cys Ala Leu
100

<210> SEQ ID NO 66
<211> LENGTH: 49
<212> TYPE: PRT
<213> ORGANISM: Aquilegia formosa

<400> SEQUENCE: 66

Arg Asp Cys Glu Ser Gln Ser His Lys Phe Lys Gly Thr Cys Ile Arg
1 5 10 15

Lys Ser Asn Cys Ala Ser Val Cys Gln Ser Glu Gly Phe Asn Gly Gly
20 25 30

His Cys Arg Gly Val Thr Arg Arg Cys Tyr Cys Thr Ala Lys Cys His
35 40 45

Glu

<210> SEQ ID NO 67
<211> LENGTH: 49
<212> TYPE: PRT
<213> ORGANISM: Dichanthelium oligosanthes

<400> SEQUENCE: 67

Arg His Cys Leu Ser Pro Ser His His Phe Lys Gly Leu Cys Met Ser
1 5 10 15

Ser Asn Asn Cys Ala Asn Val Cys Arg Thr Glu Asn Phe Pro Gly Gly
20 25 30

Glu Cys Lys Thr Glu Gly Ala Thr Arg Lys Cys Met Cys Lys Lys Val
35 40 45

Cys

<210> SEQ ID NO 68
<211> LENGTH: 56
<212> TYPE: PRT
<213> ORGANISM: Arabis nemorensis

<400> SEQUENCE: 68

Cys Thr Thr Ser Ile Gly Pro Cys Glu Val Gly Lys Asn Cys Ser Pro
1 5 10 15

Lys Cys Asn Ala Met Phe Gly Glu Ile Val Thr Gly Phe Cys Asp Arg
20 25 30

Ser Gly Gly Gly Ile Gly Ile Cys Val Cys Val Thr Pro Cys Pro Pro
35 40 45

Pro Pro Pro Lys Ala Pro His Met
50 55

<210> SEQ ID NO 69
<211> LENGTH: 99
<212> TYPE: PRT
<213> ORGANISM: Sesamum indicum

<400> SEQUENCE: 69

Ala Val Cys Gln Thr Arg Ser Gln Gln Phe Arg Gly Leu Cys Phe Arg
1 5 10 15

```
Asn Asp Asn Cys Ala Ala Ile Cys Glu Lys Glu Gly Tyr Ile Ser Gly
            20                  25                  30

Ser Cys Lys Gly Phe Leu Leu Arg Cys Ile Cys Phe Lys Asp Cys Gly
        35                  40                  45

Ala Thr Gly Gly Gly Pro Pro Asp Gly Ser Pro Asp Gly Asp Gly Gly
    50                  55                  60

Thr Pro Glu Gly Leu Thr Gly Ser His Val Thr Ser Asn Ile Ser Ser
65                  70                  75                  80

Val Tyr Lys Tyr Gly Lys Asn Glu Ala Lys Pro Gly Asn Ala Glu Ile
                85                  90                  95

Lys Lys Gly


<210> SEQ ID NO 70
<211> LENGTH: 45
<212> TYPE: PRT
<213> ORGANISM: Brassica rapa

<400> SEQUENCE: 70

Arg Thr Cys Glu Ser Pro Ser Thr Lys Phe Gln Gly Val Cys Leu Asn
1               5                   10                  15

Ala Lys Asn Cys Ala Gly Val Cys Thr Gly Glu Gly Phe Thr Gly Gly
            20                  25                  30

Gln Cys Ser Ser Leu Lys Cys Tyr Cys Thr Lys Thr Cys
        35                  40                  45


<210> SEQ ID NO 71
<211> LENGTH: 49
<212> TYPE: PRT
<213> ORGANISM: Tetracentron sinense

<400> SEQUENCE: 71

Lys Thr Cys Thr Lys Arg Ser Arg Thr Trp Phe Gly Leu Cys Leu Asn
1               5                   10                  15

Ser Asn Gly Cys Asn Arg Gln Cys Lys Lys Trp Glu Gly Ala Lys His
            20                  25                  30

Gly Ala Cys His Ala Gln Phe Gln Gly Thr Ala Cys Phe Cys Tyr Tyr
        35                  40                  45

Cys


<210> SEQ ID NO 72
<211> LENGTH: 71
<212> TYPE: PRT
<213> ORGANISM: Microthlaspi erraticum

<400> SEQUENCE: 72

Arg Glu Thr Cys Asp Lys Pro Tyr Ser Ile Cys Trp Phe Trp Pro Phe
1               5                   10                  15

Phe Ser Asp Ser Asp Ala Tyr Cys Arg Glu Ser Cys Leu Lys Val Lys
            20                  25                  30

Asp Glu Lys Tyr Glu Tyr Tyr Asp Gly Gln Cys Arg Pro Ala Arg Ser
        35                  40                  45

Ala Leu Pro Leu Pro Pro Glu Cys Phe Cys Cys Val Arg Glu Arg Ser
    50                  55                  60

Arg Ala Glu Ile Glu Ser Ile
65                  70


<210> SEQ ID NO 73
<211> LENGTH: 62
```

<212> TYPE: PRT
<213> ORGANISM: Vanilla planifolia

<400> SEQUENCE: 73

```
Arg Arg Cys Arg Ala Gln Ser Phe Thr Phe Lys Gly Ile Cys Tyr Ser
1               5                   10                  15

Ser His Ser Cys Ala Leu Val Cys Lys Lys Glu Gly Tyr Glu Thr Gly
            20                  25                  30

His Cys Ser Arg Arg Glu Gln His Lys Ile Phe Cys Ile Cys Ala Phe
        35                  40                  45

Lys Ser Leu Asn Gln Thr Lys Asp Thr Leu Gln Glu Leu Asp
    50                  55                  60
```

<210> SEQ ID NO 74
<211> LENGTH: 47
<212> TYPE: PRT
<213> ORGANISM: Glycine max

<400> SEQUENCE: 74

```
Lys Asp Cys Leu Thr Arg Arg His Gly Phe Gln Gly Arg Cys Leu Phe
1               5                   10                  15

Asp Arg Gln Cys Ala His Val Cys Arg Ser Asp Gly Phe Ile Gly Gly
            20                  25                  30

Gln Cys Arg Gly Pro Leu Arg Lys Cys Phe Cys Ser Arg Pro Cys
        35                  40                  45
```

<210> SEQ ID NO 75
<211> LENGTH: 49
<212> TYPE: PRT
<213> ORGANISM: Brachypodium distachyon

<400> SEQUENCE: 75

```
Arg His Cys Leu Ser Gln Ser His Lys Phe Lys Gly Thr Cys Val Arg
1               5                   10                  15

Ser Gly Asn Cys Ala Asn Val Cys Lys Thr Glu Asn Phe Pro Asp Gly
            20                  25                  30

Glu Cys Lys Thr Gln Gly Leu Glu Arg Lys Cys Phe Cys Lys Arg Val
        35                  40                  45

Cys
```

<210> SEQ ID NO 76
<211> LENGTH: 49
<212> TYPE: PRT
<213> ORGANISM: Brachypodium distachyon

<400> SEQUENCE: 76

```
Lys Leu Cys Glu Glu Arg Ser Gln Lys Phe Arg Gly Pro Cys Lys Phe
1               5                   10                  15

Asn Thr Asn Cys Val Ala Val Cys Val Thr Glu Gly Tyr Thr Gly Gly
            20                  25                  30

Tyr Cys His Lys Thr Val Phe His Ser His Cys Met Cys Thr Lys Glu
        35                  40                  45

Cys
```

<210> SEQ ID NO 77
<211> LENGTH: 47
<212> TYPE: PRT
<213> ORGANISM: Brachypodium distachyon

<400> SEQUENCE: 77

```
Lys Ile Cys Arg Lys Arg Ser Ala Gly Tyr His Gly Met Cys Met Ser
1               5                   10                  15

Asp Arg Asn Cys Ala Gln Val Cys Gln Ala Glu Gly Trp Gly Gly Gly
            20                  25                  30

Asn Cys Asp Gly Ala Val Arg Arg Cys Lys Cys Ser Arg Glu Cys
        35                  40                  45
```

<210> SEQ ID NO 78
<211> LENGTH: 47
<212> TYPE: PRT
<213> ORGANISM: Brachypodium distachyon

<400> SEQUENCE: 78

```
Arg Glu Cys Glu Thr Glu Ser Thr Lys Phe Glu Gly Leu Cys Ile Met
1               5                   10                  15

His Ser His Cys Pro Asp Val Cys Val Thr Glu Gly Phe Thr Gly Gly
            20                  25                  30

Lys Cys Ser Thr Trp Lys Arg Lys Cys Met Cys Thr Lys Glu Cys
        35                  40                  45
```

<210> SEQ ID NO 79
<211> LENGTH: 48
<212> TYPE: PRT
<213> ORGANISM: Brachypodium distachyon

<400> SEQUENCE: 79

```
Lys Lys Cys Ser Lys Pro Ser Gly Arg Phe Lys Gly Pro Cys Phe Phe
1               5                   10                  15

Lys Val Asp Cys Glu Gln Gln Cys Lys Lys Glu Gly Trp Pro Arg Gly
            20                  25                  30

Val Cys Thr Gly Phe Ala Gly Arg Cys Val Cys Lys Asn Tyr Gly Cys
        35                  40                  45
```

<210> SEQ ID NO 80
<211> LENGTH: 146
<212> TYPE: PRT
<213> ORGANISM: Brachypodium distachyon

<400> SEQUENCE: 80

```
Tyr Val His Gly Phe Cys Asn Ser Pro Ser Gly Ser Phe Arg Gly Pro
1               5                   10                  15

Cys Phe Ser Asp Ser His Cys Lys Ala Ala Cys Glu His Glu Tyr Tyr
            20                  25                  30

Lys Gly Asp Lys Ser Lys Pro Phe Thr Asp Gly Lys Cys Ser Asp Ser
        35                  40                  45

Gly Ser Gln Arg Leu Asp Gly Val Gly Val Gly Ser Arg Trp Ser Leu
    50                  55                  60

Leu Pro Thr Cys Ile Cys Ser Ile Phe Cys Gly Ser Glu Lys Ile Thr
65                  70                  75                  80

Trp Arg Pro Ile Ile Thr Ile Arg Leu Arg Cys Gln Lys Thr Gln Asn
                85                  90                  95

Arg Arg Leu Arg Thr Thr Ile Thr Ile Arg Leu Arg Arg Gln Lys Ala
            100                 105                 110

Gln Asn Arg Arg Arg Arg Thr Ile Thr Ile Arg Leu Arg Arg Arg Asn
        115                 120                 125
```

```
Lys Ser Arg Gln His Lys Ala Ala Ser Arg Arg Gly Lys Cys Trp Glu
    130                 135                 140

Thr Ser
145


<210> SEQ ID NO 81
<211> LENGTH: 103
<212> TYPE: PRT
<213> ORGANISM: Brachypodium distachyon

<400> SEQUENCE: 81

Leu His Trp Phe Cys Asn Ile Pro Ser Gly Ser Phe His Gly Pro Cys
1               5                   10                  15

Met Ser Asn Asp His Cys Leu Ala Ala Cys Lys Ser Glu Tyr Tyr Asn
            20                  25                  30

Gly Asp Lys Ser Lys Pro Phe Thr Gly Gly Gln Cys Ser Leu Ser Gly
        35                  40                  45

Ser Ile Leu Pro Arg Cys Ile Cys Ser Ile Phe Cys Gly Pro Pro Met
    50                  55                  60

Ala Glu His Asp Asp Pro Glu Thr His Arg His His His Pro Pro Leu
65                  70                  75                  80

Pro Pro Pro Ser Glu Gly Pro Glu Leu Ser Pro Pro His His His Ala
                85                  90                  95

Pro Pro Pro Arg His His His
            100


<210> SEQ ID NO 82
<211> LENGTH: 47
<212> TYPE: PRT
<213> ORGANISM: Brachypodium distachyon

<400> SEQUENCE: 82

Arg Asp Cys Glu Ala Pro Ser His Lys Phe His Gly Ala Cys Val Arg
1               5                   10                  15

Asp Ser Asn Cys Ala Ser Val Cys Glu Thr Glu Gly Phe Ser Gly Asp
            20                  25                  30

Lys Arg Glu Gly Pro Leu Met Arg Cys Tyr Cys Thr Lys Gln Cys
        35                  40                  45


<210> SEQ ID NO 83
<211> LENGTH: 81
<212> TYPE: PRT
<213> ORGANISM: Brachypodium distachyon

<400> SEQUENCE: 83

Gly Asp Glu Leu Leu Cys Asp Val Arg Leu Thr Lys Cys Glu Asp Val
1               5                   10                  15

Cys Tyr Lys Ser Gly Lys Cys Ser Arg Cys Cys Lys Asn His Arg Phe
            20                  25                  30

Asn His Gly His Cys Asp Leu Lys Ser His Cys Tyr Cys Tyr Arg Gly
        35                  40                  45

Pro Asn Ser Gly Ala Gly Asp Gly Glu Gln Gln Arg Met Leu Arg Val
    50                  55                  60

Ile Pro Ala Ser Pro Pro Pro Pro Ala Ala Arg His Pro Pro Leu His
65                  70                  75                  80

Ala
```

```
<210> SEQ ID NO 84
<211> LENGTH: 49
<212> TYPE: PRT
<213> ORGANISM: Setaria italica

<400> SEQUENCE: 84

Thr Leu Cys Asn Leu Arg Ser Met Gly Phe Val Gly Val Cys Trp Ser
1               5                   10                  15

Asn Met Ser Cys Ala Asn Gln Cys Val Leu Glu Gly Arg Thr Ser Gly
            20                  25                  30

Tyr Cys Lys Gly Ile Pro Ala Ile Lys Tyr Cys Met Cys Thr Phe Glu
        35                  40                  45

Cys


<210> SEQ ID NO 85
<211> LENGTH: 47
<212> TYPE: PRT
<213> ORGANISM: Setaria italica

<400> SEQUENCE: 85

Asp Arg Cys Glu Thr His Ser Arg Thr Tyr Lys Gly Arg Cys Asn Asn
1               5                   10                  15

His Asn Cys Trp Ser Ile Cys Ile Thr Glu Gly Asn Thr Gly Gly Phe
            20                  25                  30

Cys Lys Gly Thr Leu Leu Leu Lys Cys Met Cys Thr Ser Glu Cys
        35                  40                  45


<210> SEQ ID NO 86
<211> LENGTH: 48
<212> TYPE: PRT
<213> ORGANISM: Setaria italica

<400> SEQUENCE: 86

Asp Met Cys Lys Lys Arg Ser Arg Thr Phe Glu Gly Arg Cys Gly Leu
1               5                   10                  15

Asn Met Asn Cys Ala Thr Val Cys Val Ala Glu His Tyr Thr Gly Gly
            20                  25                  30

Phe Cys Lys Gly Phe Phe His Arg Glu Cys Met Cys Thr Lys Asp Cys
        35                  40                  45


<210> SEQ ID NO 87
<211> LENGTH: 50
<212> TYPE: PRT
<213> ORGANISM: Setaria italica

<400> SEQUENCE: 87

Arg Arg Cys Val Ser Gln Ser His Lys Phe Val Gly Ser Cys Met Arg
1               5                   10                  15

Lys Ser Asn Cys Gln His Val Cys Gln Thr Glu Gly Phe Pro Trp Gly
            20                  25                  30

Glu Cys Arg Phe His Gly Gly Leu Leu Arg Arg Cys Phe Cys Asn Lys
        35                  40                  45

Leu Cys
    50


<210> SEQ ID NO 88
<211> LENGTH: 29
<212> TYPE: PRT
<213> ORGANISM: Arabidopsis thaliana
```

<400> SEQUENCE: 88

Gly Tyr Cys Phe Asp Cys Ala Arg Ala Cys Met Arg Arg Gly Lys Tyr
1 5 10 15

Ile Arg Thr Cys Ser Phe Glu Arg Lys Leu Cys Arg Cys
20 25

<210> SEQ ID NO 89
<211> LENGTH: 18
<212> TYPE: PRT
<213> ORGANISM: Oryza sativa Japonica

<400> SEQUENCE: 89

Gly Glu Cys Lys Ser His Gly Leu Glu Arg Lys Cys Phe Cys Lys Lys
1 5 10 15

Val Cys

<210> SEQ ID NO 90
<211> LENGTH: 19
<212> TYPE: PRT
<213> ORGANISM: Artemisia vulgaris

<400> SEQUENCE: 90

Gly Ala Cys His Lys Arg Glu Ala Gly Lys Glu Ser Cys Phe Cys Tyr
1 5 10 15

Phe Asp Cys

<210> SEQ ID NO 91
<211> LENGTH: 18
<212> TYPE: PRT
<213> ORGANISM: Arabidopsis thaliana

<400> SEQUENCE: 91

Gly Ala Cys His Ala Gln Phe Pro Gly Phe Ala Cys Phe Cys Tyr Phe
1 5 10 15

Asn Cys

<210> SEQ ID NO 92
<211> LENGTH: 18
<212> TYPE: PRT
<213> ORGANISM: Arabidopsis thaliana

<400> SEQUENCE: 92

Gly Tyr Cys Asn Thr Leu Asp Asp Phe Ser Leu Cys Leu Cys Lys Tyr
1 5 10 15

Pro Cys

<210> SEQ ID NO 93
<211> LENGTH: 14
<212> TYPE: PRT
<213> ORGANISM: Arachis duranensis

<400> SEQUENCE: 93

Gly Thr Cys Met Lys Met Ala Cys Trp Cys Ala His Asn Cys
1 5 10

<210> SEQ ID NO 94
<211> LENGTH: 16
<212> TYPE: PRT
<213> ORGANISM: Malus baccata

<400> SEQUENCE: 94

Gly Lys Cys Ser Leu Leu Thr Arg Thr Cys Met Cys Thr Lys Lys Cys
1 5 10 15

<210> SEQ ID NO 95
<211> LENGTH: 16
<212> TYPE: PRT
<213> ORGANISM: Oryza sativa

<400> SEQUENCE: 95

Gly Arg Cys Ser Thr Phe Val Arg Asn Cys Ile Cys Ile Lys Pro Cys
1 5 10 15

<210> SEQ ID NO 96
<211> LENGTH: 14
<212> TYPE: PRT
<213> ORGANISM: Triticum dicoccoides

<400> SEQUENCE: 96

Gly Lys Cys Asp His Arg Arg Cys Val Cys Thr Lys Gly Cys
1 5 10

<210> SEQ ID NO 97
<211> LENGTH: 16
<212> TYPE: PRT
<213> ORGANISM: Pyrus ussuriensis x Pyrus communis

<400> SEQUENCE: 97

Gly His Cys Ser Val Leu Thr Arg Ala Cys Val Cys Thr Lys Lys Cys
1 5 10 15

<210> SEQ ID NO 98
<211> LENGTH: 15
<212> TYPE: PRT
<213> ORGANISM: Beta vulgaris subsp. vulgaris

<400> SEQUENCE: 98

Gly Val Cys Val Pro Phe Leu Arg Cys Glu Cys Gln Arg Ser Cys
1 5 10 15

<210> SEQ ID NO 99
<211> LENGTH: 16
<212> TYPE: PRT
<213> ORGANISM: Miscanthus lutarioriparius

<400> SEQUENCE: 99

Gly Asn Cys Asp Gly Ile Leu Arg Gln Cys Lys Cys Ile Arg Gln Cys
1 5 10 15

<210> SEQ ID NO 100
<211> LENGTH: 21
<212> TYPE: PRT
<213> ORGANISM: Lotus japonicus

<400> SEQUENCE: 100

Gly Phe Cys Tyr Thr Ser Gly Pro Ser Ile Asn Leu Cys Thr Cys Gln
1 5 10 15

Tyr Pro Cys Ala Leu
20

<210> SEQ ID NO 101
<211> LENGTH: 18
<212> TYPE: PRT

<213> ORGANISM: Aquilegia formosa

<400> SEQUENCE: 101

Gly His Cys Arg Gly Val Thr Arg Arg Cys Tyr Cys Thr Ala Lys Cys
1               5                   10                  15

His Glu

<210> SEQ ID NO 102
<211> LENGTH: 18
<212> TYPE: PRT
<213> ORGANISM: Dichanthelium oligosanthes

<400> SEQUENCE: 102

Gly Glu Cys Lys Thr Glu Gly Ala Thr Arg Lys Cys Met Cys Lys Lys
1               5                   10                  15

Val Cys

<210> SEQ ID NO 103
<211> LENGTH: 29
<212> TYPE: PRT
<213> ORGANISM: Arabis nemorensis

<400> SEQUENCE: 103

Gly Phe Cys Asp Arg Ser Gly Gly Gly Ile Gly Ile Cys Val Cys Val
1               5                   10                  15

Thr Pro Cys Pro Pro Pro Pro Pro Lys Ala Pro His Met
            20                  25

<210> SEQ ID NO 104
<211> LENGTH: 16
<212> TYPE: PRT
<213> ORGANISM: Sesamum indicum

<400> SEQUENCE: 104

Gly Ser Cys Lys Gly Phe Leu Leu Arg Cys Ile Cys Phe Lys Asp Cys
1               5                   10                  15

<210> SEQ ID NO 105
<211> LENGTH: 14
<212> TYPE: PRT
<213> ORGANISM: Brassica rapa

<400> SEQUENCE: 105

Gly Gln Cys Ser Ser Leu Lys Cys Tyr Cys Thr Lys Thr Cys
1               5                   10

<210> SEQ ID NO 106
<211> LENGTH: 17
<212> TYPE: PRT
<213> ORGANISM: Tetracentron sinense

<400> SEQUENCE: 106

Gly Ala Cys His Ala Gln Phe Gln Gly Thr Ala Cys Phe Cys Tyr Tyr
1               5                   10                  15

Cys

<210> SEQ ID NO 107
<211> LENGTH: 18
<212> TYPE: PRT
<213> ORGANISM: Microthlaspi erraticum

<400> SEQUENCE: 107

Gly Gln Cys Arg Pro Ala Arg Ser Ala Leu Pro Leu Pro Pro Glu Cys
1 5 10 15

Phe Cys

<210> SEQ ID NO 108
<211> LENGTH: 15
<212> TYPE: PRT
<213> ORGANISM: Vanilla planifolia

<400> SEQUENCE: 108

Gly His Cys Ser Arg Arg Glu Gln His Lys Ile Phe Cys Ile Cys
1 5 10 15

<210> SEQ ID NO 109
<211> LENGTH: 17
<212> TYPE: PRT
<213> ORGANISM: Glycine max

<400> SEQUENCE: 109

Gly Gly Gln Cys Arg Gly Pro Leu Arg Lys Cys Phe Cys Ser Arg Pro
1 5 10 15

Cys

<210> SEQ ID NO 110
<211> LENGTH: 18
<212> TYPE: PRT
<213> ORGANISM: Brachypodium distachyon

<400> SEQUENCE: 110

Gly Glu Cys Lys Thr Gln Gly Leu Glu Arg Lys Cys Phe Cys Lys Arg
1 5 10 15

Val Cys

<210> SEQ ID NO 111
<211> LENGTH: 18
<212> TYPE: PRT
<213> ORGANISM: Brachypodium distachyon

<400> SEQUENCE: 111

Gly Tyr Cys His Lys Thr Val Phe His Ser His Cys Met Cys Thr Lys
1 5 10 15

Glu Cys

<210> SEQ ID NO 112
<211> LENGTH: 16
<212> TYPE: PRT
<213> ORGANISM: Brachypodium distachyon

<400> SEQUENCE: 112

Gly Asn Cys Asp Gly Ala Val Arg Arg Cys Lys Cys Ser Arg Glu Cys
1 5 10 15

<210> SEQ ID NO 113
<211> LENGTH: 16
<212> TYPE: PRT
<213> ORGANISM: Brachypodium distachyon

<400> SEQUENCE: 113

Gly Lys Cys Ser Thr Trp Lys Arg Lys Cys Met Cys Thr Lys Glu Cys
1 5 10 15

<210> SEQ ID NO 114
<211> LENGTH: 17
<212> TYPE: PRT
<213> ORGANISM: Brachypodium distachyon

<400> SEQUENCE: 114

```
Gly Val Cys Thr Gly Phe Ala Gly Arg Cys Val Cys Lys Asn Tyr Gly
1               5                   10                  15

Cys
```

<210> SEQ ID NO 115
<211> LENGTH: 32
<212> TYPE: PRT
<213> ORGANISM: Brachypodium distachyon

<400> SEQUENCE: 115

```
Gly Lys Cys Ser Asp Ser Gly Ser Gln Arg Leu Asp Gly Val Gly Val
1               5                   10                  15

Gly Ser Arg Trp Ser Leu Leu Pro Thr Cys Ile Cys Ser Ile Phe Cys
            20                  25                  30
```

<210> SEQ ID NO 116
<211> LENGTH: 19
<212> TYPE: PRT
<213> ORGANISM: Brachypodium distachyon

<400> SEQUENCE: 116

```
Gly Gln Cys Ser Leu Ser Gly Ser Ile Leu Pro Arg Cys Ile Cys Ser
1               5                   10                  15

Ile Phe Cys
```

<210> SEQ ID NO 117
<211> LENGTH: 26
<212> TYPE: PRT
<213> ORGANISM: Brachypodium distachyon

<400> SEQUENCE: 117

```
Ser Val Cys Glu Thr Glu Gly Phe Ser Gly Asp Lys Arg Glu Gly Pro
1               5                   10                  15

Leu Met Arg Cys Tyr Cys Thr Lys Gln Cys
            20                  25
```

<210> SEQ ID NO 118
<211> LENGTH: 25
<212> TYPE: PRT
<213> ORGANISM: Brachypodium distachyon

<400> SEQUENCE: 118

```
Gly Lys Cys Ser Arg Cys Cys Lys Asn His Arg Phe Asn His Gly His
1               5                   10                  15

Cys Asp Leu Lys Ser His Cys Tyr Cys
            20                  25
```

<210> SEQ ID NO 119
<211> LENGTH: 18
<212> TYPE: PRT
<213> ORGANISM: Setaria italica

<400> SEQUENCE: 119

```
Gly Tyr Cys Lys Gly Ile Pro Ala Ile Lys Tyr Cys Met Cys Thr Phe
1               5                   10                  15
```

Glu Cys

<210> SEQ ID NO 120
<211> LENGTH: 17
<212> TYPE: PRT
<213> ORGANISM: Setaria italica

<400> SEQUENCE: 120

Gly Phe Cys Lys Gly Thr Leu Leu Leu Lys Cys Met Cys Thr Ser Glu
1               5                   10                  15

Cys

<210> SEQ ID NO 121
<211> LENGTH: 17
<212> TYPE: PRT
<213> ORGANISM: Setaria italica

<400> SEQUENCE: 121

Gly Phe Cys Lys Gly Phe Phe His Arg Glu Cys Met Cys Thr Lys Asp
1               5                   10                  15

Cys

<210> SEQ ID NO 122
<211> LENGTH: 19
<212> TYPE: PRT
<213> ORGANISM: Setaria italica

<400> SEQUENCE: 122

Gly Glu Cys Arg Phe His Gly Gly Leu Leu Arg Arg Cys Phe Cys Asn
1               5                   10                  15

Lys Leu Cys

<210> SEQ ID NO 123
<211> LENGTH: 75
<212> TYPE: PRT
<213> ORGANISM: Capsicum annuum

<400> SEQUENCE: 123

Asp Ile Cys Thr Thr Pro Pro Arg Arg Tyr Ile Gly Val Cys Trp Ser
1               5                   10                  15

Asp Thr Ser Cys Arg Lys Val Cys Val Glu Met Glu Asn Phe Glu Asp
            20                  25                  30

Gly Tyr Cys Ser Lys Ile Gln Arg Lys Cys Leu Cys Thr Trp Thr Cys
        35                  40                  45

Val Leu Asp Asn Ile Pro Asn Asp Ala Gly Thr Ile Met Leu Gln Asp
    50                  55                  60

Ala Lys Thr Met Gln Leu Leu Glu Glu Lys Phe
65                  70                  75

<210> SEQ ID NO 124
<211> LENGTH: 75
<212> TYPE: PRT
<213> ORGANISM: Capsicum annuum

<400> SEQUENCE: 124

Tyr Asn Ile Cys Lys Thr Lys Ser Lys Tyr Phe Glu Gly Leu Cys Trp
1               5                   10                  15

Val Asp Ser Ser Cys Arg Lys Val Cys Ile Glu Lys Asp Lys Phe Glu
            20                  25                  30

```
Asp Gly His Cys Ser Lys Leu Leu Arg Asn Cys Leu Cys Thr Lys Ile
        35                  40                  45

Cys Ala Phe Asp Asn Ile Pro Asn Asp Ala Gly Thr Ile Leu Val Gln
    50                  55                  60

Asp Ala Lys Ser Leu Glu Ala Gln Leu Leu Glu
65                  70                  75


<210> SEQ ID NO 125
<211> LENGTH: 75
<212> TYPE: PRT
<213> ORGANISM: Capsicum annuum

<400> SEQUENCE: 125

Gln Asn Asn Ile Cys Lys Thr Thr Ser Lys His Phe Lys Gly Leu Cys
1               5                   10                  15

Phe Ala Asp Ser Lys Cys Arg Lys Val Cys Ile Gln Glu Asp Lys Phe
            20                  25                  30

Glu Asp Gly His Cys Ser Lys Leu Gln Arg Lys Cys Leu Cys Thr Lys
        35                  40                  45

Asn Cys Val Phe Asp Asn Ile Pro Asn Asp Val Gly Thr Ile Leu Val
    50                  55                  60

Glu Asp Ala Lys Thr Leu Glu Ala Gln Leu Leu
65                  70                  75


<210> SEQ ID NO 126
<211> LENGTH: 75
<212> TYPE: PRT
<213> ORGANISM: Capsicum annuum

<400> SEQUENCE: 126

Gln Gln Thr Cys Lys Thr Glu Ser Gln Lys Phe Lys Gly Leu Cys Ile
1               5                   10                  15

Thr Lys Ser Ser Cys Arg Lys Ala Cys Leu Lys Glu Lys Phe Thr Asp
            20                  25                  30

Gly His Cys Ser Lys Leu Gln Arg Arg Cys Leu Cys Thr Lys Pro Cys
        35                  40                  45

Val Phe Glu Asn Asn Pro Asn Glu Val Glu Thr Lys Leu Val Gly Lys
    50                  55                  60

Thr Lys Thr Leu Arg Glu Ala Met Leu Glu Glu
65                  70                  75


<210> SEQ ID NO 127
<211> LENGTH: 79
<212> TYPE: PRT
<213> ORGANISM: Capsicum annuum

<400> SEQUENCE: 127

Arg Gln Thr Cys Lys Thr Glu Ser Gln Lys Phe Lys Gly Leu Cys Ile
1               5                   10                  15

Thr Lys Ser Ser Cys Arg Lys Ala Cys Leu Lys Glu Lys Phe Thr Asp
            20                  25                  30

Gly His Cys Ser Lys Leu Gln Arg Arg Cys Leu Cys Thr Lys Pro Cys
        35                  40                  45

Val Phe Glu Asn Asn Pro Asn Glu Asp Glu Thr Asn Leu Val Gly Lys
    50                  55                  60

Thr Lys Thr Leu Arg Glu Ala Met Leu Glu Glu Gln Ile Met Glu
65                  70                  75
```

<210> SEQ ID NO 128
<211> LENGTH: 75
<212> TYPE: PRT
<213> ORGANISM: Capsicum annuum

<400> SEQUENCE: 128

```
Tyr Asn Ile Cys Lys Thr Lys Ser Lys Lys Phe Glu Gly Leu Cys Phe
1               5                   10                  15

Leu Asp Ser Ser Cys Arg Lys Val Cys Val Glu Gln Glu Asn Phe Glu
            20                  25                  30

Asp Gly His Cys Ser Lys Leu Arg Arg Leu Cys Leu Cys Thr Lys Leu
        35                  40                  45

Cys Val Phe Asp Asn Ile Pro Asn Asp Val Gly Thr Ile Leu Val Gln
    50                  55                  60

Asp Ala Lys Thr Leu Glu Ala Gln Leu Leu Glu
65                  70                  75
```

<210> SEQ ID NO 129
<211> LENGTH: 75
<212> TYPE: PRT
<213> ORGANISM: Capsicum annuum

<400> SEQUENCE: 129

```
Gln Asn Ile Cys Lys Thr Lys Ser Lys Tyr Phe Thr Gly Leu Cys Trp
1               5                   10                  15

Thr Asp Ser Ser Cys Arg Lys Val Cys Ile Glu Lys Asp Lys Phe Gln
            20                  25                  30

Asp Gly His Cys Ser Lys Leu Gln Arg Asn Cys Leu Cys Thr Lys Ile
        35                  40                  45

Cys Val Phe Asp Asn Ile Pro Asn Asp Ala Gly Thr Ile Leu Val Gln
    50                  55                  60

Asp Ala Lys Thr Asn Glu Ala Gln Leu Leu Glu
65                  70                  75
```

<210> SEQ ID NO 130
<211> LENGTH: 75
<212> TYPE: PRT
<213> ORGANISM: Capsicum annuum

<400> SEQUENCE: 130

```
Tyr Asn Ile Cys Lys Thr Lys Ser Lys Tyr Phe Glu Gly Leu Cys Trp
1               5                   10                  15

Val Asp Ser Ser Cys Arg Lys Val Cys Ile Glu Lys Asp Lys Phe Glu
            20                  25                  30

Asp Gly His Cys Ser Lys Leu Leu Arg Asn Cys Leu Cys Thr Lys Ile
        35                  40                  45

Cys Ala Phe Asp Asn Ile Pro Asn Asp Ala Gly Thr Ile Leu Val Gln
    50                  55                  60

Asp Ala Lys Ser Leu Glu Ala Gln Leu Leu Glu
65                  70                  75
```

<210> SEQ ID NO 131
<211> LENGTH: 75
<212> TYPE: PRT
<213> ORGANISM: Nicotiana tabacum

<400> SEQUENCE: 131

```
Arg Glu Cys Lys Thr Glu Ser Asn Thr Phe Pro Gly Leu Cys Ile Thr
1               5                   10                  15
```

Lys Pro Pro Cys Arg Lys Ala Cys Ile Ser Glu Gly Phe Thr Asp Gly
20 25 30

His Cys Ser Lys Ile Leu Arg Arg Cys Leu Cys Thr Lys Pro Cys Val
35 40 45

Phe Asp Glu Lys Met Ile Lys Thr Gly Ala Glu Thr Leu Ala Glu Glu
50 55 60

Ala Lys Thr Leu Ala Ala Ala Leu Phe Glu Glu
65 70 75

<210> SEQ ID NO 132
<211> LENGTH: 75
<212> TYPE: PRT
<213> ORGANISM: Nicotiana tabacum

<400> SEQUENCE: 132

Arg Glu Cys Lys Thr Glu Ser Asn Thr Phe Pro Gly Leu Cys Ile Thr
1 5 10 15

Lys Pro Pro Cys Arg Lys Ala Cys Ile Ser Glu Gly Phe Thr Asp Gly
20 25 30

His Cys Ser Lys Ile Leu Arg Arg Cys Leu Cys Thr Lys Pro Cys Val
35 40 45

Phe Asp Glu Lys Met Ile Lys Thr Gly Ala Glu Thr Phe Ala Glu Glu
50 55 60

Ala Lys Thr Leu Ala Ala Ala Leu Leu Glu Glu
65 70 75

<210> SEQ ID NO 133
<211> LENGTH: 75
<212> TYPE: PRT
<213> ORGANISM: Nicotiana tabacum

<400> SEQUENCE: 133

Arg Glu Cys Lys Ala Val Ser Asn Thr Leu Ser Gly Leu Cys Ile Thr
1 5 10 15

Lys Pro Pro Cys Arg Glu Ala Cys Ile Ser Glu Gly Phe Thr Asp Gly
20 25 30

Lys Cys Ser Lys Ile Leu Lys Arg Cys Ile Cys His Lys Pro Cys Val
35 40 45

Phe Asp Glu Lys Met Val Lys Thr Gly Ala Glu Thr Leu Ala Glu Glu
50 55 60

Val Lys Thr Leu Ala Ala Ala Phe Leu Glu Glu
65 70 75

<210> SEQ ID NO 134
<211> LENGTH: 75
<212> TYPE: PRT
<213> ORGANISM: Nicotiana tabacum

<400> SEQUENCE: 134

Arg Glu Cys Lys Ala Glu Ser Ile Thr Phe Ser Gly Leu Cys Val Ser
1 5 10 15

Lys Pro Pro Cys Arg Lys Ala Cys Ile Cys Glu Gly Phe Thr Asn Gly
20 25 30

His Cys Ser Lys Ile Leu Arg Arg Cys Leu Cys Thr Thr Pro Ser Val
35 40 45

Phe Asp Glu Lys Met Ile Lys Thr Gly Ala Glu Thr Leu Gly Glu Glu
50 55 60

Ala Lys Thr Leu Ala Ala Thr Leu Leu Glu Glu
65 70 75

<210> SEQ ID NO 135
<211> LENGTH: 75
<212> TYPE: PRT
<213> ORGANISM: Nicotiana tabacum

<400> SEQUENCE: 135

Gln Ser Thr Cys Lys Ala Glu Ser Asn Thr Phe Pro Gly Ile Cys Ile
1 5 10 15

Thr Lys Pro Pro Cys Arg Lys Ala Cys Leu Ser Glu Gly Phe Thr Asp
20 25 30

Gly Lys Cys Ser Lys Ile Leu Arg Arg Cys Ile Cys Tyr Lys Pro Cys
35 40 45

Val Phe Asp Glu Lys Met Thr Lys Thr Gly Ala Glu Thr Leu Ala Glu
50 55 60

Glu Ala Lys Thr Leu Ala Ala Ala Leu Leu Glu
65 70 75

<210> SEQ ID NO 136
<211> LENGTH: 75
<212> TYPE: PRT
<213> ORGANISM: Nicotiana tabacum

<400> SEQUENCE: 136

Arg Glu Cys Lys Thr Glu Ser Asn Thr Phe Pro Gly Ile Cys Ile Thr
1 5 10 15

Lys Pro Pro Cys Arg Lys Ala Cys Ile Ser Glu Lys Phe Thr Asp Gly
20 25 30

His Cys Ser Lys Leu Leu Arg Arg Cys Leu Cys Thr Lys Pro Cys Val
35 40 45

Phe Asp Glu Lys Met Ile Lys Thr Gly Ala Glu Thr Leu Val Glu Glu
50 55 60

Ala Lys Thr Leu Ala Ala Ala Leu Leu Glu Glu
65 70 75

<210> SEQ ID NO 137
<211> LENGTH: 75
<212> TYPE: PRT
<213> ORGANISM: Petunia hybrida

<400> SEQUENCE: 137

Ala Thr Cys Lys Ala Glu Cys Ala Thr Trp Glu Gly Ile Cys Ile Asn
1 5 10 15

Lys Ala Pro Cys Val Lys Cys Cys Lys Glu Gln Pro Glu Asn Phe Thr
20 25 30

Asp Gly His Cys Ser Lys Ile Leu Arg Arg Cys Leu Cys Thr Lys Pro
35 40 45

Cys Ala Thr Ala Glu Ala Thr Ala Thr Leu Ala Asn Glu Val Lys Thr
50 55 60

Met Gly Glu Ala Leu Val Glu Val Asp Met Met
65 70 75

<210> SEQ ID NO 138
<211> LENGTH: 75
<212> TYPE: PRT
<213> ORGANISM: Petunia hybrida

<400> SEQUENCE: 138

Ala Thr Cys Lys Ala Glu Cys Pro Thr Trp Asp Gly Ile Cys Ile Asn
1 5 10 15

Lys Gly Pro Cys Val Lys Cys Cys Lys Ala Gln Pro Glu Lys Phe Thr
20 25 30

Asp Gly His Cys Ser Lys Val Leu Arg Arg Cys Leu Cys Thr Lys Pro
35 40 45

Cys Ala Thr Glu Glu Ala Thr Ala Thr Leu Ala Asn Glu Val Lys Thr
50 55 60

Met Ala Glu Ala Leu Val Glu Glu Asp Met Met
65 70 75

<210> SEQ ID NO 139
<211> LENGTH: 75
<212> TYPE: PRT
<213> ORGANISM: Petunia hybrida

<400> SEQUENCE: 139

Ala Thr Cys Lys Ala Glu Cys Pro Thr Trp Asp Ser Val Cys Ile Asn
1 5 10 15

Lys Lys Pro Cys Val Ala Cys Cys Lys Lys Ala Lys Phe Ser Asp Gly
20 25 30

His Cys Ser Lys Ile Leu Arg Arg Cys Leu Cys Thr Lys Glu Cys Val
35 40 45

Phe Glu Lys Thr Glu Ala Thr Gln Thr Glu Thr Phe Thr Lys Asp Val
50 55 60

Asn Thr Leu Ala Glu Ala Leu Leu Glu Ala Asp
65 70 75

<210> SEQ ID NO 140
<211> LENGTH: 75
<212> TYPE: PRT
<213> ORGANISM: Solanum lycopersicum

<400> SEQUENCE: 140

Gln Gln Ile Cys Lys Ala Pro Ser Gln Thr Phe Pro Gly Leu Cys Phe
1 5 10 15

Met Asp Ser Ser Cys Arg Lys Tyr Cys Ile Lys Glu Lys Phe Thr Gly
20 25 30

Gly His Cys Ser Lys Leu Gln Arg Lys Cys Leu Cys Thr Lys Pro Cys
35 40 45

Val Phe Asp Lys Ile Ser Ser Glu Val Lys Ala Thr Leu Gly Glu Glu
50 55 60

Ala Lys Thr Leu Ser Glu Val Val Leu Glu Glu
65 70 75

<210> SEQ ID NO 141
<211> LENGTH: 68
<212> TYPE: PRT
<213> ORGANISM: Solanum lycopersicum

<400> SEQUENCE: 141

Gln Pro Met Cys Lys Ser Thr Ser Gln Thr Phe Lys Gly Leu Cys Phe
1 5 10 15

Thr Asp Ser Ser Cys Arg Lys Ser Cys Leu Lys Glu Glu Phe Glu Gly
20 25 30

Gly His Cys Ser Lys Leu Gln Arg Lys Cys Leu Cys Thr Lys Ile Cys
35 40 45

```
Val Phe Asp Lys Ile Ser Asn Glu Val Arg Thr Asn Phe Gly Trp Gly
    50                  55                  60

Ser Lys Asn Ser
65


<210> SEQ ID NO 142
<211> LENGTH: 78
<212> TYPE: PRT
<213> ORGANISM: Solanum lycopersicum

<400> SEQUENCE: 142

Ala Ser Ser Thr Arg Ala Asn Gln Gln Ala Lys Ser Ser Lys Asp Tyr
1               5                   10                  15

Val Leu Pro Thr His His Val Glu Lys Leu Val Ser Lys Arg Ser Leu
            20                  25                  30

Lys Val Asp Ile Ile Phe Lys Leu Gln Ser Lys Cys Leu Cys Thr Lys
        35                  40                  45

Ile Cys Val Phe Glu Lys Asn Pro Asn Glu Val Lys Pro Thr Leu Gly
    50                  55                  60

Gly Glu Ala Lys Thr Leu Ser Glu Thr Met Leu Glu Asp Asp
65                  70                  75


<210> SEQ ID NO 143
<211> LENGTH: 62
<212> TYPE: PRT
<213> ORGANISM: Solanum lycopersicum

<400> SEQUENCE: 143

Gln His Met Cys Lys Ser Thr Ser Gln Thr Phe Lys Gly Leu Cys Phe
1               5                   10                  15

Thr Tyr Ser Ser Cys Arg Lys Gly Cys Leu Lys Glu Lys Phe Glu Gly
            20                  25                  30

Gly His Tyr Ile Val Ala Asn Ser Lys Gly Ser Ala Tyr Ala Leu Arg
        35                  40                  45

Phe Val Tyr Leu Thr Lys Phe Gln Met Lys Leu Asn Gln Leu
    50                  55                  60


<210> SEQ ID NO 144
<211> LENGTH: 75
<212> TYPE: PRT
<213> ORGANISM: Solanum lycopersicum

<400> SEQUENCE: 144

Gln Tyr Met Cys Lys Ser Thr Ser Gln Thr Phe Lys Gly Leu Cys Phe
1               5                   10                  15

Thr Asp Ser Ser Cys Arg Lys Ala Cys Val Thr Glu Glu Phe Thr Gly
            20                  25                  30

Gly His Cys Ser Lys Leu Gln Arg Lys Cys Leu Cys Thr Lys Val Cys
        35                  40                  45

Val Leu Glu Lys Asp Ser Asn Glu Val Lys Thr Thr Leu Val Gly Glu
    50                  55                  60

Ala Lys Thr Leu Ser Glu Thr Val Leu Glu Glu
65                  70                  75


<210> SEQ ID NO 145
<211> LENGTH: 75
<212> TYPE: PRT
<213> ORGANISM: Solanum lycopersicum
```

<400> SEQUENCE: 145

```
Gln Gln Met Cys Lys Ser Thr Ser Gln Thr Phe Lys Gly Leu Cys Phe
1               5                   10                  15

Thr Asp Ser Ser Cys Arg Lys Ala Cys Val Thr Glu Glu Phe Thr Gly
            20                  25                  30

Gly His Cys Ser Lys Leu Gln Arg Lys Cys Leu Cys Thr Lys Val Cys
        35                  40                  45

Val Phe Glu Lys Asp Ser Asn Glu Val Lys Thr Thr Leu Val Gly Glu
    50                  55                  60

Ala Lys Thr Leu Ser Glu Thr Val Leu Glu Glu
65                  70                  75
```

<210> SEQ ID NO 146
<211> LENGTH: 75
<212> TYPE: PRT
<213> ORGANISM: Solanum pennellii

<400> SEQUENCE: 146

```
Arg Gln Ile Cys Lys Ala Pro Ser Gln Thr Phe Pro Gly Leu Cys Phe
1               5                   10                  15

Met Asp Ser Ser Cys Arg Lys Tyr Cys Ile Lys Glu Lys Phe Thr Gly
            20                  25                  30

Gly His Cys Ser Thr Leu Gln Arg Arg Cys Leu Cys Thr Lys Pro Cys
        35                  40                  45

Val Phe Asp Ile Ile Ser Asn Glu Val Lys Ala Thr Leu Gly Glu Glu
    50                  55                  60

Ala Lys Thr Leu Ser Glu Val Val Leu Glu Glu
65                  70                  75
```

<210> SEQ ID NO 147
<211> LENGTH: 75
<212> TYPE: PRT
<213> ORGANISM: Solanum pennellii

<400> SEQUENCE: 147

```
Gln Gln Met Cys Lys Ser Thr Ser Gln Thr Phe Lys Gly Leu Cys Phe
1               5                   10                  15

Ile Asp Ser Ser Cys Arg Lys Ala Cys Val Thr Glu Glu Phe Thr Gly
            20                  25                  30

Gly His Cys Ser Lys Leu Gln Arg Lys Cys Leu Cys Thr Lys Val Cys
        35                  40                  45

Val Phe Glu Lys Asp Ser Asn Glu Val Lys Thr Thr Leu Val Gly Glu
    50                  55                  60

Ala Lys Thr Leu Ser Glu Thr Val Leu Glu Glu
65                  70                  75
```

<210> SEQ ID NO 148
<211> LENGTH: 49
<212> TYPE: PRT
<213> ORGANISM: Cajanus cajus

<400> SEQUENCE: 148

```
Ala Val Cys Ser Lys Pro Ser Thr Tyr Phe Phe Gly Pro Cys Val Arg
1               5                   10                  15

Arg Ser Thr Cys Arg Arg Ala Cys Ser His Glu Asn Tyr Pro Asp Gly
            20                  25                  30
```

Lys Cys Ser Arg Phe Leu Gly Lys Cys Ile Cys Tyr Lys Pro Cys Thr
35 40 45

Thr

<210> SEQ ID NO 149
<211> LENGTH: 46
<212> TYPE: PRT
<213> ORGANISM: Eucalyptus grandis

<400> SEQUENCE: 149

Ala Thr Cys Arg Lys Pro Ser Met Tyr Phe Ser Gly Ala Cys Phe Ser
1 5 10 15

Asp Thr Asn Cys Gln Lys Ala Cys Asn Arg Glu Asp Trp Pro Asn Gly
20 25 30

Lys Cys Leu Val Gly Phe Lys Cys Glu Cys Gln Arg Pro Cys
35 40 45

<210> SEQ ID NO 150
<211> LENGTH: 55
<212> TYPE: PRT
<213> ORGANISM: Eucalyptus grandis

<400> SEQUENCE: 150

Met Asn Ile Val Thr Lys Val Asp Gly Ala Ile Cys Lys Lys Pro Ser
1 5 10 15

Lys Phe Phe Lys Gly Ala Cys Gly Arg Asp Ala Asp Cys Glu Lys Ala
20 25 30

Cys Asp Gln Glu Asn Trp Pro Gly Gly Val Cys Val Pro Phe Leu Arg
35 40 45

Cys Glu Cys Gln Arg Ser Cys
50 55

<210> SEQ ID NO 151
<211> LENGTH: 49
<212> TYPE: PRT
<213> ORGANISM: Eucalyptus grandis

<400> SEQUENCE: 151

Ala Thr Cys Ala Lys Pro Ser Lys Tyr Tyr Lys Gly Gly Cys Phe Ala
1 5 10 15

Thr Ile Ser Val Ser Ala Cys Lys Lys Thr Cys Ser Arg Glu Asn Trp
20 25 30

Pro Asp Gly Ala Cys Val Tyr Pro Phe Arg Cys Glu Cys Arg Arg Pro
35 40 45

Cys

<210> SEQ ID NO 152
<211> LENGTH: 49
<212> TYPE: PRT
<213> ORGANISM: Eucalyptus grandis

<400> SEQUENCE: 152

Lys Thr Cys Ala Lys Pro Ser Lys Tyr Tyr Lys Gly Gly Cys Phe Ser
1 5 10 15

Thr Ile Ser Val Ser Ala Cys Lys Lys Thr Cys Ser Arg Glu Asn Trp
20 25 30

Pro Asp Gly Asp Cys Val Phe Pro Tyr Arg Cys Glu Cys Arg Arg Pro
35 40 45

Cys

<210> SEQ ID NO 153
<211> LENGTH: 49
<212> TYPE: PRT
<213> ORGANISM: Eucalyptus grandis

<400> SEQUENCE: 153

Ala Asn Cys Ala Lys Pro Ser Lys Phe Tyr Arg Gly Pro Cys Phe Asn
1               5                   10                  15

Ser Ile Ser Val Lys Pro Cys Thr Gln Arg Cys Ser Gln Glu Asn Trp
            20                  25                  30

Pro Ile Gly Val Cys Thr Lys Asp Leu Arg Cys Glu Cys Gln Arg Pro
        35                  40                  45

Cys

<210> SEQ ID NO 154
<211> LENGTH: 49
<212> TYPE: PRT
<213> ORGANISM: Eucalyptus grandis

<400> SEQUENCE: 154

Phe Ser Val Ile Ser Asp Ser Ala Cys Lys Lys Ala Cys Asn Gln Glu
1               5                   10                  15

Asn Trp Pro Ile Gly Ile Cys Val Pro Val Phe Arg Cys Glu Cys Arg
            20                  25                  30

Arg Ser Cys Gln Ala Met Phe Ser Pro Glu Ser Ser Ser Ile Lys Tyr
        35                  40                  45

Glu

<210> SEQ ID NO 155
<211> LENGTH: 49
<212> TYPE: PRT
<213> ORGANISM: Brassica napus

<400> SEQUENCE: 155

Lys Ala Arg Met Cys Glu Thr Ser Ser Gln Leu Phe Asn Gly Pro Cys
1               5                   10                  15

Leu Ser Thr Thr Asn Cys Ala Asn Ile Cys Gln Asn Glu Gly Phe Pro
            20                  25                  30

Asp Gly Asp Cys Lys Gly Phe Arg Leu Arg Cys Ile Cys Asn Arg Pro
        35                  40                  45

Cys

<210> SEQ ID NO 156
<211> LENGTH: 47
<212> TYPE: PRT
<213> ORGANISM: Brassica rapa

<400> SEQUENCE: 156

Arg Thr Cys Glu Ser Gln Ser His Arg Phe Lys Gly Pro Cys Val Ser
1               5                   10                  15

Glu Asn Asn Cys Ala Asn Val Cys His Asn Glu Gly Phe Gly Gly Gly
            20                  25                  30

Lys Cys Arg Gly Leu Arg Arg Arg Cys Phe Cys Thr Arg His Cys
        35                  40                  45

<210> SEQ ID NO 157
<211> LENGTH: 50

<212> TYPE: PRT
<213> ORGANISM: Brassica napus

<400> SEQUENCE: 157

Ile Glu Gly Arg Met Cys Gln Ser Arg Ser His His Phe Arg Ser Ile
1               5                   10                  15

Cys Leu Ser Asn His Asn Cys Ala Asn Ile Cys Arg Gly Glu Arg Phe
            20                  25                  30

Ser Gly Gly Arg Cys His Gly Leu His Arg Lys Cys Tyr Cys Thr Arg
        35                  40                  45

Leu Cys
    50

<210> SEQ ID NO 158
<211> LENGTH: 45
<212> TYPE: PRT
<213> ORGANISM: Brassica rapa

<400> SEQUENCE: 158

Arg Thr Cys Glu Ser Pro Ser Thr Lys Phe Gln Gly Val Cys Leu Asn
1               5                   10                  15

Ala Lys Asn Cys Ala Gly Val Cys Thr Gly Glu Gly Phe Thr Gly Gly
            20                  25                  30

Gln Cys Ser Ser Leu Lys Cys Tyr Cys Thr Lys Thr Cys
        35                  40                  45

<210> SEQ ID NO 159
<211> LENGTH: 47
<212> TYPE: PRT
<213> ORGANISM: Brassica cretica

<400> SEQUENCE: 159

Arg Thr Cys Glu Ser Lys Ser His Arg Phe Lys Gly Thr Cys Val Ser
1               5                   10                  15

Ser Thr Asn Cys Gly Asn Val Cys His Asn Glu Gly Phe Gly Gly Gly
            20                  25                  30

Lys Cys Arg Gly Phe Arg Arg Arg Cys Tyr Cys Thr Arg His Cys
        35                  40                  45

<210> SEQ ID NO 160
<211> LENGTH: 47
<212> TYPE: PRT
<213> ORGANISM: Brassica napus

<400> SEQUENCE: 160

Arg Thr Cys Glu Ser Lys Ser His Lys Phe Arg Gly Pro Cys Val Ser
1               5                   10                  15

Arg His Asn Cys Ala Asn Val Cys His Asn Glu Gly Phe His Gly Gly
            20                  25                  30

Lys Cys Arg Gly Phe Arg Arg Arg Cys Tyr Cys Thr Arg His Cys
        35                  40                  45

<210> SEQ ID NO 161
<211> LENGTH: 48
<212> TYPE: PRT
<213> ORGANISM: Zostera marina

<400> SEQUENCE: 161

Arg Thr Cys Val Ser Lys Ser Glu Lys Phe Lys Gly Val Cys Leu Ile
1               5                   10                  15

Asn Thr Asn Cys Ala His Val Cys Gln Thr Glu Gly Phe Pro Asp Gly
            20                  25                  30

Asp Cys Arg Gly Ser Val Arg Arg Arg Cys Phe Cys Ile Arg Pro Cys
        35                  40                  45

<210> SEQ ID NO 162
<211> LENGTH: 47
<212> TYPE: PRT
<213> ORGANISM: Microthlaspi erraticum

<400> SEQUENCE: 162

Arg Thr Cys Glu Ser Lys Ser His Arg Phe Lys Gly Pro Cys Val Ser
1               5                   10                  15

Thr His Asn Cys Gly Asn Val Cys His Asn Glu Gly Phe Gly Gly Gly
            20                  25                  30

Lys Cys Arg Gly Phe Arg Arg Arg Cys Tyr Cys Thr Arg His Cys
        35                  40                  45

<210> SEQ ID NO 163
<211> LENGTH: 47
<212> TYPE: PRT
<213> ORGANISM: Arabidopsis lyrata

<400> SEQUENCE: 163

Arg Thr Cys Ala Ser Lys Ser Glu Lys Phe Lys Gly Ser Cys Val Ser
1               5                   10                  15

Asn Thr Asn Cys Ala Asn Ile Cys His Thr Glu Gly Phe Pro Glu Gly
            20                  25                  30

Ala Cys Arg Gly Leu Arg His His Cys Phe Cys Thr Arg Pro Cys
        35                  40                  45

<210> SEQ ID NO 164
<211> LENGTH: 53
<212> TYPE: PRT
<213> ORGANISM: Thalspi arvense

<400> SEQUENCE: 164

Gln Val Arg Met Cys Glu Ser Lys Ser His Glu Phe Lys Gly Phe Cys
1               5                   10                  15

Thr Lys Trp Arg Ile Cys Arg Asp Val Cys Ile Thr Glu Gly Phe Thr
            20                  25                  30

Asp Gly Gly Cys His Gly Val Leu Arg His Cys Val Cys Lys Lys Pro
        35                  40                  45

Cys Leu Leu Ser Asn
    50

<210> SEQ ID NO 165
<211> LENGTH: 54
<212> TYPE: PRT
<213> ORGANISM: Actinidia chinensis

<400> SEQUENCE: 165

Met Ile Lys Gln Gly Glu Ala Arg Val Cys Glu Ser Lys Ser His Gly
1               5                   10                  15

Phe Lys Gly Ala Cys Leu Ile Asp His Asn Cys Ala Leu Val Cys Arg
            20                  25                  30

Asn Glu Gly Phe Ser Gly Gly Lys Cys Arg Gly Phe Arg His Arg Cys
        35                  40                  45

Phe Cys Thr Lys Ile Cys
    50

<210> SEQ ID NO 166
<211> LENGTH: 63
<212> TYPE: PRT
<213> ORGANISM: Actinidia chinensis

<400> SEQUENCE: 166

```
Lys Leu Cys Thr Ala Pro Ser Ser Thr Phe Lys Tyr Leu Cys Ile Ser
1               5                   10                  15

Asp Gln Asn Cys Ser Ser Ala Cys Glu Gln Glu Gly Phe Thr Ser Gly
            20                  25                  30

Glu Cys Glu Gly Leu Arg Arg Arg Cys Ile Cys Gly Lys Pro Cys Gly
        35                  40                  45

Met Glu Val Ser Lys Thr Lys Phe Asp Asn Gly Ile Gly Gly Glu
    50                  55                  60
```

<210> SEQ ID NO 167
<211> LENGTH: 47
<212> TYPE: PRT
<213> ORGANISM: Arabidopsis lyrata

<400> SEQUENCE: 167

```
Arg Thr Cys Glu Thr Ser Ser Asn Leu Phe Asn Gly Pro Cys Leu Ser
1               5                   10                  15

Ser Ser Asn Cys Ala Asn Val Cys His Asn Glu Gly Phe Ser Asp Gly
            20                  25                  30

Asp Cys Arg Gly Phe Arg Arg Arg Cys Leu Cys Thr Arg Pro Cys
        35                  40                  45
```

<210> SEQ ID NO 168
<211> LENGTH: 54
<212> TYPE: PRT
<213> ORGANISM: Arabidopsis lyrata

<400> SEQUENCE: 168

```
Gln Pro Gln Leu Cys Glu Thr Lys Ser Leu Asn Tyr Arg Gly Leu Cys
1               5                   10                  15

Met Lys Trp Arg Asn Cys Lys Arg Val Cys Ile Ser Glu Gly Phe Pro
            20                  25                  30

Asp Gly Arg Cys Lys Gly Phe Phe Asn Asn Lys Cys Val Cys Arg Lys
        35                  40                  45

Pro Cys Ala Leu Ser Thr
    50
```

<210> SEQ ID NO 169
<211> LENGTH: 47
<212> TYPE: PRT
<213> ORGANISM: Arabidopsis lyrata

<400> SEQUENCE: 169

```
Arg Thr Cys Ala Ser Gln Ser Gln Arg Phe Lys Gly Lys Cys Val Ser
1               5                   10                  15

Asp Thr Asn Cys Ala Asn Val Cys His Asn Glu Gly Phe Pro Gly Gly
            20                  25                  30

Asp Cys Arg Gly Phe Arg Arg Arg Cys Phe Cys Thr Arg Asn Cys
        35                  40                  45
```

<210> SEQ ID NO 170
<211> LENGTH: 47
<212> TYPE: PRT

<213> ORGANISM: Arabidopsis lyrata

<400> SEQUENCE: 170

Arg Thr Cys Glu Ser Lys Ser His Arg Phe Lys Gly Pro Cys Val Ser
1 5 10 15

Thr His Asn Cys Ala Asn Val Cys His Asn Glu Gly Phe Gly Gly Gly
20 25 30

Lys Cys Arg Gly Phe Arg Arg Arg Cys Tyr Cys Thr Arg His Cys
35 40 45

<210> SEQ ID NO 171
<211> LENGTH: 45
<212> TYPE: PRT
<213> ORGANISM: Arabidopsis lyrata

<400> SEQUENCE: 171

Arg Thr Cys Glu Ser Pro Ser Asn Lys Phe Gln Gly Val Cys Leu Asn
1 5 10 15

Ser Gln Ser Cys Ala Lys Ala Cys Pro Ser Glu Gly Phe Ser Gly Gly
20 25 30

Arg Cys Ser Ser Leu Arg Cys Tyr Cys Ser Lys Ala Cys
35 40 45

<210> SEQ ID NO 172
<211> LENGTH: 59
<212> TYPE: PRT
<213> ORGANISM: Arabidopsis lyrata

<400> SEQUENCE: 172

Glu Val Ser Pro Val Asp Asn Lys Ile Cys Lys Thr Arg Ser Asp Arg
1 5 10 15

Phe Ser Gly Val Cys Leu Ser Thr Asn Asn Cys Ala Ile Ile Cys Gln
20 25 30

Gln Phe Glu His Phe Asp Gly Gly His Cys Glu Phe Asp Gly Ala Leu
35 40 45

Arg Arg Cys Met Cys Thr Lys Gln Cys Asn Asn
50 55

<210> SEQ ID NO 173
<211> LENGTH: 54
<212> TYPE: PRT
<213> ORGANISM: Arabidopsis lyrata

<400> SEQUENCE: 173

Gln Pro Gln Leu Cys Glu Thr Lys Ser Leu Asn Tyr Arg Gly Leu Cys
1 5 10 15

Met Lys Trp Arg Asn Cys Lys Arg Val Cys Ile Ser Glu Gly Phe Pro
20 25 30

Asp Gly Arg Cys Lys Gly Phe Phe Asn Asn Lys Cys Val Cys Arg Lys
35 40 45

Pro Cys Ala Leu Ser Thr
50

<210> SEQ ID NO 174
<211> LENGTH: 52
<212> TYPE: PRT
<213> ORGANISM: Arabidopsis lyrata

<400> SEQUENCE: 174

Gln Gln Met Cys Glu Thr Gln Ser Ile Asn Phe Arg Gly Met Cys Thr
1               5                   10                  15

Lys Trp Arg Asn Cys Gln Arg Val Cys Met Ser Glu Gly Phe Pro Asp
            20                  25                  30

Gly Arg Cys Lys Gly Phe Ile Arg Lys Cys Ile Cys Thr Lys Pro Cys
        35                  40                  45

Pro Val Ser Thr
    50

<210> SEQ ID NO 175
<211> LENGTH: 53
<212> TYPE: PRT
<213> ORGANISM: Arabidopsis lyrata

<400> SEQUENCE: 175

Ile Ile Gly Ser Asp Gly Arg Thr Cys Gln Ser Lys Ser His His Phe
1               5                   10                  15

Lys Tyr Met Cys Thr Ser Ser His Asn Cys Ala Ile Val Cys Arg Asn
            20                  25                  30

Glu Gly Phe Ser Gly Gly Arg Cys His Gly Phe His Arg Arg Cys Tyr
        35                  40                  45

Cys Thr Arg Leu Cys
    50

<210> SEQ ID NO 176
<211> LENGTH: 49
<212> TYPE: PRT
<213> ORGANISM: Aquilegia oxysepala

<400> SEQUENCE: 176

Arg Asp Cys Glu Ser Gln Ser His Lys Phe Lys Gly Thr Cys Ile Arg
1               5                   10                  15

Lys Ser Asn Cys Ala Ser Val Cys Gln Ser Glu Gly Phe Asn Gly Gly
            20                  25                  30

His Cys Arg Gly Val Thr Arg Arg Cys Tyr Cys Thr Ala Lys Cys His
        35                  40                  45

Glu

<210> SEQ ID NO 177
<211> LENGTH: 49
<212> TYPE: PRT
<213> ORGANISM: Arachis hypogaea

<400> SEQUENCE: 177

Gly Gly Arg His Cys Glu Ser Lys Ser His Arg Phe Lys Gly Met Cys
1               5                   10                  15

Val His Glu Arg Asn Cys Ala Ser Val Cys Asn Leu Glu Gly Phe Ser
            20                  25                  30

Gly Gly Lys Cys Arg Gly Phe Arg Arg Arg Cys Phe Cys Thr Arg His
        35                  40                  45

Cys

<210> SEQ ID NO 178
<211> LENGTH: 63
<212> TYPE: PRT
<213> ORGANISM: Arachis hypogaea

<400> SEQUENCE: 178

Glu Gly Arg Lys Cys Asp Ser Gln Ser His His Phe Lys Gly Lys Cys
1               5                   10                  15

Phe Ser Asp Thr Asn Cys Ala Ser Val Cys His Gly Ser Phe Ile His
            20                  25                  30

Val Phe Val Glu Leu Asp Leu Gln Ser Phe Glu Phe Thr Ser Cys Phe
        35                  40                  45

Ser Leu Glu Ile Lys Lys Phe Ser Ser Arg Ser Gly Gln Leu Phe
    50                  55                  60

<210> SEQ ID NO 179
<211> LENGTH: 48
<212> TYPE: PRT
<213> ORGANISM: Arachis hypogaea

<400> SEQUENCE: 179

Arg Thr Cys Ala Ser Gln Ser His Arg Phe Lys Gly Val Cys Leu Ser
1               5                   10                  15

Asp Thr Asn Cys Ala Ser Val Cys Lys Thr Glu Gly Phe Pro Ser Gly
            20                  25                  30

Asp Cys His Gly Phe Arg Arg Arg Cys Phe Cys Thr Lys His Cys Ala
        35                  40                  45

<210> SEQ ID NO 180
<211> LENGTH: 55
<212> TYPE: PRT
<213> ORGANISM: Arachis hypogaea

<400> SEQUENCE: 180

Arg Thr Cys Ala Ser Gln Ser His Arg Phe Lys Gly Val Cys Leu Ser
1               5                   10                  15

Asp Thr Asn Cys Ala Ser Val Cys Lys Thr Glu Gly Phe Pro Ser Gly
            20                  25                  30

Asp Cys His Gly Phe Arg Arg Arg Cys Phe Cys Thr Lys His Tyr Arg
        35                  40                  45

Lys Ile Arg Ser Gln Asp Ser
    50                  55

<210> SEQ ID NO 181
<211> LENGTH: 49
<212> TYPE: PRT
<213> ORGANISM: Arachis hypogaea

<400> SEQUENCE: 181

Glu Gly Arg His Cys Glu Ser Lys Ser His Arg Phe Lys Gly Met Cys
1               5                   10                  15

Val His Glu Arg Asn Cys Ala Ser Val Cys Asn Leu Glu Gly Phe Ser
            20                  25                  30

Gly Gly Lys Cys Arg Gly Phe Arg Arg Arg Cys Phe Cys Thr Arg His
        35                  40                  45

Cys

<210> SEQ ID NO 182
<211> LENGTH: 47
<212> TYPE: PRT
<213> ORGANISM: Arachis hypogaea

<400> SEQUENCE: 182

```
Arg Val Cys Gln Ser Lys Ser His Met Phe Lys Gly Gly Cys Trp Gly
1               5                   10                  15

Asp His Asn Cys Ala Leu Val Cys Arg Asn Glu Gly Phe Ser Gly Gly
            20                  25                  30

Arg Cys Arg Gly Phe Arg Arg Arg Cys Phe Cys Thr Lys Leu Cys
        35                  40                  45
```

<210> SEQ ID NO 183
<211> LENGTH: 47
<212> TYPE: PRT
<213> ORGANISM: Arabidopsis thaliana

<400> SEQUENCE: 183

```
Arg Thr Cys Glu Thr Ser Ser Asn Leu Phe Asn Gly Pro Cys Leu Ser
1               5                   10                  15

Ser Ser Asn Cys Ala Asn Val Cys His Asn Glu Gly Phe Ser Asp Gly
            20                  25                  30

Asp Cys Arg Gly Phe Arg Arg Arg Cys Leu Cys Thr Arg Pro Cys
        35                  40                  45
```

<210> SEQ ID NO 184
<211> LENGTH: 47
<212> TYPE: PRT
<213> ORGANISM: Arabidopsis thaliana

<400> SEQUENCE: 184

```
Arg Thr Cys Glu Ser Gln Ser His Arg Phe Lys Gly Thr Cys Val Ser
1               5                   10                  15

Ala Ser Asn Cys Ala Asn Val Cys His Asn Glu Gly Phe Val Gly Gly
            20                  25                  30

Asn Cys Arg Gly Phe Arg Arg Arg Cys Phe Cys Thr Arg His Cys
        35                  40                  45
```

<210> SEQ ID NO 185
<211> LENGTH: 47
<212> TYPE: PRT
<213> ORGANISM: Arabidopsis thaliana

<400> SEQUENCE: 185

```
Arg Thr Cys Ala Ser Gln Ser Gln Arg Phe Lys Gly Lys Cys Val Ser
1               5                   10                  15

Asp Thr Asn Cys Glu Asn Val Cys His Asn Glu Gly Phe Pro Gly Gly
            20                  25                  30

Asp Cys Arg Gly Phe Arg Arg Arg Cys Phe Cys Thr Arg Asn Cys
        35                  40                  45
```

<210> SEQ ID NO 186
<211> LENGTH: 47
<212> TYPE: PRT
<213> ORGANISM: Arabidopsis thaliana

<400> SEQUENCE: 186

```
Arg Thr Cys Glu Ser Lys Ser His Arg Phe Lys Gly Pro Cys Val Ser
1               5                   10                  15

Thr His Asn Cys Ala Asn Val Cys His Asn Glu Gly Phe Gly Gly Gly
            20                  25                  30

Lys Cys Arg Gly Phe Arg Arg Arg Cys Tyr Cys Thr Arg His Cys
        35                  40                  45
```

<210> SEQ ID NO 187
<211> LENGTH: 45
<212> TYPE: PRT
<213> ORGANISM: Arabidopsis thaliana

<400> SEQUENCE: 187

```
Arg Thr Cys Glu Ser Pro Ser Asn Lys Phe Gln Gly Val Cys Leu Asn
1               5                   10                  15

Ser Gln Ser Cys Ala Lys Ala Cys Pro Ser Glu Gly Phe Ser Gly Gly
            20                  25                  30

Arg Cys Ser Ser Leu Arg Cys Tyr Cys Ser Lys Ala Cys
        35                  40                  45
```

<210> SEQ ID NO 188
<211> LENGTH: 57
<212> TYPE: PRT
<213> ORGANISM: Arabidopsis thaliana

<400> SEQUENCE: 188

```
Glu Val Ser Pro Leu Asp Asn Lys Ile Cys Lys Thr Arg Ser Asp Arg
1               5                   10                  15

Phe Ser Gly Val Cys Ile Ser Thr Asn Asn Cys Ala Ile Ile Cys Gln
            20                  25                  30

Gln Phe Glu His Phe Asp Gly Gly His Cys Glu Phe Asp Gly Ala Phe
        35                  40                  45

Arg Arg Cys Met Cys Thr Lys Gln Cys
    50                  55
```

<210> SEQ ID NO 189
<211> LENGTH: 57
<212> TYPE: PRT
<213> ORGANISM: Arabidopsis thaliana

<400> SEQUENCE: 189

```
Gln Pro Gln Leu Cys Glu Thr Lys Ser Leu Asn Tyr Arg Gly Leu Cys
1               5                   10                  15

Leu Lys Trp Arg Ser Cys Lys Arg Val Cys Ile Ser Glu Gly Phe Pro
            20                  25                  30

Asp Gly Arg Cys Lys Gly Phe Phe Asn Asn Lys Cys Val Cys Arg Lys
        35                  40                  45

Pro Cys Ala Leu Leu Ser Thr Glu Asn
    50                  55
```

<210> SEQ ID NO 190
<211> LENGTH: 53
<212> TYPE: PRT
<213> ORGANISM: Arabidopsis thaliana

<400> SEQUENCE: 190

```
Gln Gln Met Cys Glu Ala Lys Ser Leu Asp Trp Lys Gly Met Cys Leu
1               5                   10                  15

Lys Trp Arg Asn Cys Arg Gln Val Cys Ile Ser Glu Gly Phe Thr Asp
            20                  25                  30

Gly Arg Cys Lys Gly Phe Thr Arg Lys Cys Ile Cys Ser Lys Pro Cys
        35                  40                  45

Phe Val Leu Pro Asn
    50
```

<210> SEQ ID NO 191
<211> LENGTH: 47
<212> TYPE: PRT
<213> ORGANISM: Arabidopsis thaliana

<400> SEQUENCE: 191

Arg Thr Cys Gln Ser Lys Ser His His Phe Lys Tyr Met Cys Thr Ser
1 5 10 15

Asn His Asn Cys Ala Ile Val Cys Arg Asn Glu Gly Phe Ser Gly Gly
20 25 30

Arg Cys His Gly Phe His Arg Arg Cys Tyr Cys Thr Arg Leu Cys
35 40 45

<210> SEQ ID NO 192
<211> LENGTH: 58
<212> TYPE: PRT
<213> ORGANISM: Acer truncatum

<400> SEQUENCE: 192

Glu Met Gly Gln Asn Gln Met Val Ala Glu Ala Arg Thr Cys Glu Ser
1 5 10 15

Gln Ser His Lys Phe Lys Gly Thr Cys Val Ser Lys Ser Asn Cys Ala
20 25 30

His Val Cys Gln Thr Glu Gly Phe Pro Gly Gly His Cys Arg Gly Phe
35 40 45

Arg Arg Arg Cys Phe Cys Ala Lys Asn Cys
50 55

<210> SEQ ID NO 193
<211> LENGTH: 55
<212> TYPE: PRT
<213> ORGANISM: Acer truncatum

<400> SEQUENCE: 193

Gln Asn Glu Met Val Ala Glu Ala Arg Thr Cys Glu Ser Gln Ser His
1 5 10 15

Lys Phe Lys Gly Thr Cys Leu Ser Lys Ser Asn Cys Ala Asn Val Cys
20 25 30

Lys Thr Glu Gly Phe Pro Gly Gly His Cys Arg Gly Phe Arg Arg Arg
35 40 45

Cys Phe Cys Thr Lys Lys Cys
50 55

<210> SEQ ID NO 194
<211> LENGTH: 49
<212> TYPE: PRT
<213> ORGANISM: Brassica carinata

<400> SEQUENCE: 194

Lys Ala Arg Met Cys Glu Thr Ser Ser Gln Leu Phe Asn Gly Pro Cys
1 5 10 15

Leu Ser Thr Thr Asn Cys Ala Asn Ile Cys Gln Asn Glu Gly Phe Pro
20 25 30

Asp Gly Asp Cys His Gly Phe Arg Leu Arg Cys Ile Cys Asn Arg Pro
35 40 45

Cys

<210> SEQ ID NO 195
<211> LENGTH: 47
<212> TYPE: PRT

<213> ORGANISM: Brassica carinata

<400> SEQUENCE: 195

Arg Thr Cys Glu Ser Gln Ser His Arg Phe Lys Gly Thr Cys Val Ser
1 5 10 15

Glu Asn Asn Cys Ala Asn Val Cys His Asn Glu Gly Phe Gly Gly Gly
20 25 30

Lys Cys Arg Gly Phe Arg Arg Arg Cys Phe Cys Thr Arg Asn Cys
35 40 45

<210> SEQ ID NO 196
<211> LENGTH: 75
<212> TYPE: PRT
<213> ORGANISM: Brassica carinata

<400> SEQUENCE: 196

Met Asp Pro Val Thr Val Glu Ala Arg Thr Cys Glu Ser Lys Ser His
1 5 10 15

Lys Phe Arg Gly Leu Cys Val Ser Thr His Asn Cys Ala Asn Val Cys
20 25 30

His Thr Lys Val Lys Arg Ser Lys Glu Cys Val Ser Thr Asp Arg Thr
35 40 45

Val Pro Leu Leu Val Pro Lys Lys Val Pro Gln Ala Val Val Ala Val
50 55 60

Val Ser Val Ala Pro Ala Pro Asn Pro Ala Ser
65 70 75

<210> SEQ ID NO 197
<211> LENGTH: 47
<212> TYPE: PRT
<213> ORGANISM: Brassica carinata

<400> SEQUENCE: 197

Arg Thr Cys Glu Ser Lys Ser His Lys Phe Arg Gly Pro Cys Val Ser
1 5 10 15

Arg His Asn Cys Ala Asn Val Cys His Asn Glu Gly Phe His Gly Gly
20 25 30

Lys Cys Arg Gly Phe Arg Arg Arg Cys Tyr Cys Thr Arg His Cys
35 40 45

<210> SEQ ID NO 198
<211> LENGTH: 47
<212> TYPE: PRT
<213> ORGANISM: Brassica carinata

<400> SEQUENCE: 198

Arg Thr Cys Glu Ser Gln Ser His Arg Phe Lys Gly Pro Cys Val Ser
1 5 10 15

Asp Asn Asn Cys Ala Asn Val Cys His Asn Glu Gly Phe Gly Gly Gly
20 25 30

Lys Cys Arg Gly Leu Arg Arg Arg Cys Phe Cys Thr Thr His Cys
35 40 45

<210> SEQ ID NO 199
<211> LENGTH: 47
<212> TYPE: PRT
<213> ORGANISM: Brassica carinata

<400> SEQUENCE: 199

Arg Thr Cys Glu Ser Lys Ser His Lys Phe Arg Gly Leu Cys Val Ser
1 5 10 15

Arg His Asn Cys Ala Asn Val Cys His Asn Glu Gly Phe His Gly Gly
20 25 30

Lys Cys Arg Gly Phe Arg Arg Arg Cys Tyr Cys Thr Arg His Cys
35 40 45

<210> SEQ ID NO 200
<211> LENGTH: 47
<212> TYPE: PRT
<213> ORGANISM: Brassica carinata

<400> SEQUENCE: 200

Arg Thr Cys Glu Ser Lys Ser His Arg Phe Lys Gly Thr Cys Val Ser
1 5 10 15

Thr Thr Asn Cys Ala Asn Val Cys His Asn Glu Gly Phe Pro Gly Gly
20 25 30

Lys Cys Arg Gly Phe Arg Arg Arg Cys Phe Cys Thr Arg His Cys
35 40 45

<210> SEQ ID NO 201
<211> LENGTH: 47
<212> TYPE: PRT
<213> ORGANISM: Brassica carinata

<400> SEQUENCE: 201

Arg Thr Cys Glu Ser Lys Ser His Arg Phe Lys Gly Thr Cys Val Ser
1 5 10 15

Ser Thr Asn Cys Gly Asn Val Cys His Asn Glu Gly Phe Gly Gly Gly
20 25 30

Lys Cys Arg Gly Phe Arg Arg Arg Cys Tyr Cys Thr Arg His Cys
35 40 45

<210> SEQ ID NO 202
<211> LENGTH: 49
<212> TYPE: PRT
<213> ORGANISM: Brassica carinata

<400> SEQUENCE: 202

Lys Ala Arg Met Cys Glu Thr Ser Ser Gln Leu Phe Asn Gly Pro Cys
1 5 10 15

Leu Ser Thr Thr Asn Cys Ala Asn Ile Cys Gln Asn Glu Gly Phe Pro
20 25 30

Asp Gly Asp Cys Lys Gly Phe Arg Leu Arg Cys Ile Cys Asn Arg Pro
35 40 45

Cys

<210> SEQ ID NO 203
<211> LENGTH: 49
<212> TYPE: PRT
<213> ORGANISM: Brassica oleracea

<400> SEQUENCE: 203

Lys Ala Arg Met Cys Glu Thr Ser Ser Gln Leu Phe Asn Gly Pro Cys
1 5 10 15

Leu Ser Thr Thr Asn Cys Ala Asn Ile Cys Gln Asn Glu Gly Phe Pro
20 25 30

Asp Gly Asp Cys Lys Gly Phe Arg Leu Arg Cys Ile Cys Asn Arg Pro
35 40 45

Cys

<210> SEQ ID NO 204
<211> LENGTH: 47
<212> TYPE: PRT
<213> ORGANISM: Brassica oleracea

<400> SEQUENCE: 204

Arg Thr Cys Glu Ser Gln Ser His Arg Phe Lys Gly Pro Cys Val Ser
1 5 10 15

Asp Asn Asn Cys Ala Asn Val Cys His Asn Glu Gly Phe Gly Gly Gly
20 25 30

Lys Cys Arg Gly Leu Arg Arg Arg Cys Phe Cys Thr Arg His Cys
35 40 45

<210> SEQ ID NO 205
<211> LENGTH: 50
<212> TYPE: PRT
<213> ORGANISM: Brassica oleracea

<400> SEQUENCE: 205

Ile Glu Gly Arg Met Cys Gln Ser Arg Ser His His Phe Arg Ser Ile
1 5 10 15

Cys Leu Ser Asn His Asn Cys Ala Asn Ile Cys Arg Gly Glu Arg Phe
20 25 30

Ser Gly Gly Arg Cys His Gly Leu His Arg Lys Cys Tyr Cys Thr Arg
35 40 45

Leu Cys
50

<210> SEQ ID NO 206
<211> LENGTH: 72
<212> TYPE: PRT
<213> ORGANISM: Brassica oleracea

<400> SEQUENCE: 206

Gln Gln Met Cys Glu Ala Lys Ser Leu Asn Phe Lys Gly Met Cys Leu
1 5 10 15

Lys Trp Lys Asn Cys Lys His Val Phe Phe Thr Arg Lys Gln Leu Ile
20 25 30

Lys Leu Ser Lys Lys Asp Val Ala Ala Ala Glu Glu Glu Lys Ile Leu
35 40 45

Lys Glu Thr Cys Met Lys Leu Val Gln Gly Gln Gln Met Cys Glu Ala
50 55 60

Lys Ser Ile Asn Phe Lys Gly Met
65 70

<210> SEQ ID NO 207
<211> LENGTH: 47
<212> TYPE: PRT
<213> ORGANISM: Brassica oleracea

<400> SEQUENCE: 207

Arg Thr Cys Glu Ser Lys Ser His Arg Phe Lys Gly Thr Cys Val Ser
1 5 10 15

Ser Thr Asn Cys Gly Asn Val Cys His Asn Glu Gly Phe Gly Gly Gly
20 25 30

Lys Cys Arg Gly Phe Arg Arg Arg Cys Tyr Cys Thr Arg His Cys
35 40 45

<210> SEQ ID NO 208
<211> LENGTH: 47
<212> TYPE: PRT
<213> ORGANISM: Brassica oleracea

<400> SEQUENCE: 208

Arg Thr Cys Glu Ser Lys Ser His Lys Phe Arg Gly Leu Cys Val Ser
1 5 10 15

Arg His Asn Cys Ala Asn Val Cys His Asn Glu Gly Phe His Gly Gly
20 25 30

Lys Cys Arg Gly Phe Arg Arg Arg Cys Tyr Cys Thr Arg His Cys
35 40 45

<210> SEQ ID NO 209
<211> LENGTH: 49
<212> TYPE: PRT
<213> ORGANISM: Brassica rapa

<400> SEQUENCE: 209

Lys Ala Arg Met Cys Glu Thr Ser Ser Gln Leu Phe Asn Gly Pro Cys
1 5 10 15

Leu Ser Thr Thr Asn Cys Ala Asn Ile Cys Gln Asn Glu Gly Phe Pro
20 25 30

Asp Gly Asp Cys Lys Gly Phe Arg Leu Arg Cys Ile Cys Asn Arg Pro
35 40 45

Cys

<210> SEQ ID NO 210
<211> LENGTH: 47
<212> TYPE: PRT
<213> ORGANISM: Brassica rapa

<400> SEQUENCE: 210

Arg Thr Cys Glu Ser Gln Ser His Arg Phe Lys Gly Pro Cys Val Ser
1 5 10 15

Glu Asn Asn Cys Ala Asn Val Cys His Asn Glu Gly Phe Gly Gly Gly
20 25 30

Lys Cys Arg Gly Leu Arg Arg Arg Cys Phe Cys Thr Arg His Cys
35 40 45

<210> SEQ ID NO 211
<211> LENGTH: 47
<212> TYPE: PRT
<213> ORGANISM: Brassica rapa

<400> SEQUENCE: 211

Arg Met Cys Gln Ser Arg Ser His His Phe Arg Ser Ile Cys Leu Ser
1 5 10 15

Asn His Asn Cys Ala Asn Ile Cys Arg Gly Glu Arg Phe Ser Gly Gly
20 25 30

Arg Cys His Gly Leu His Arg Lys Cys Tyr Cys Thr Arg Leu Cys
35 40 45

<210> SEQ ID NO 212
<211> LENGTH: 47
<212> TYPE: PRT
<213> ORGANISM: Brassica rapa

<400> SEQUENCE: 212

Arg Thr Cys Glu Ser Lys Ser His Arg Phe Lys Gly Thr Cys Val Ser
1 5 10 15

Ser Thr Asn Cys Gly Asn Val Cys His Asn Glu Gly Phe Gly Gly Gly
20 25 30

Lys Cys Arg Gly Phe Arg Arg Arg Cys Tyr Cys Thr Arg His Cys
35 40 45

<210> SEQ ID NO 213
<211> LENGTH: 47
<212> TYPE: PRT
<213> ORGANISM: Brassica rapa

<400> SEQUENCE: 213

Arg Thr Cys Glu Ser Lys Ser His Lys Phe Arg Gly Pro Cys Val Ser
1 5 10 15

Arg His Asn Cys Ala Asn Val Cys His Asn Glu Gly Phe His Gly Gly
20 25 30

Lys Cys Arg Gly Phe Arg Arg Arg Cys Tyr Cys Thr Arg His Cys
35 40 45

<210> SEQ ID NO 214
<211> LENGTH: 49
<212> TYPE: PRT
<213> ORGANISM: Corchorus olitorius

<400> SEQUENCE: 214

Lys Ala Arg Met Cys Glu Thr Ser Ser Gln Leu Phe Asn Gly Pro Cys
1 5 10 15

Leu Ser Thr Thr Asn Cys Ala Asn Ile Cys Gln Asn Glu Gly Phe Pro
20 25 30

Asp Gly Asp Cys Lys Gly Phe Arg Leu Arg Cys Ile Cys Asn Arg Pro
35 40 45

Cys

<210> SEQ ID NO 215
<211> LENGTH: 47
<212> TYPE: PRT
<213> ORGANISM: Corchorus olitorius

<400> SEQUENCE: 215

Arg Thr Cys Glu Ser Gln Ser His Arg Phe Lys Gly Pro Cys Val Ser
1 5 10 15

Asp Asn Asn Cys Ala Asn Val Cys His Asn Glu Gly Phe Gly Gly Gly
20 25 30

Lys Cys Arg Gly Leu Arg Arg Arg Cys Phe Cys Thr Arg His Cys
35 40 45

<210> SEQ ID NO 216
<211> LENGTH: 50
<212> TYPE: PRT
<213> ORGANISM: Corchorus olitorius

<400> SEQUENCE: 216

Ile Glu Gly Arg Met Cys Gln Ser Arg Ser His His Phe Arg Ser Ile
1 5 10 15

Cys Leu Ser Asn His Asn Cys Ala Asn Ile Cys Arg Gly Glu Arg Phe
20 25 30

```
Ser Gly Gly Arg Cys His Gly Leu His Arg Lys Cys Tyr Cys Thr Arg
        35                  40                  45

Leu Cys
    50


<210> SEQ ID NO 217
<211> LENGTH: 72
<212> TYPE: PRT
<213> ORGANISM: Corchorus olitorius

<400> SEQUENCE: 217

Gln Gln Met Cys Glu Ala Lys Ser Ile Asn Phe Lys Gly Met Ser Leu
1               5                   10                  15

Lys Trp Lys Asn Cys Lys His Phe Ile His Glu Asn Glu Leu Ile Lys
            20                  25                  30

Leu Ser Arg Lys Glu Val Ala Ala Ala Glu Glu Glu Lys Phe Leu Lys
        35                  40                  45

Glu Thr Cys Met Lys Leu Val Gln Gly Gln Gln Met Cys Glu Ala Lys
    50                  55                  60

Ser Ile Asn Phe Lys Gly Ile Cys
65                  70


<210> SEQ ID NO 218
<211> LENGTH: 47
<212> TYPE: PRT
<213> ORGANISM: Corchorus olitorius

<400> SEQUENCE: 218

Arg Thr Cys Glu Ser Lys Ser His Arg Phe Lys Gly Thr Cys Val Ser
1               5                   10                  15

Ser Thr Asn Cys Gly Asn Val Cys His Asn Glu Gly Phe Gly Gly Gly
            20                  25                  30

Lys Cys Arg Gly Phe Arg Arg Arg Cys Tyr Cys Thr Arg His Cys
        35                  40                  45


<210> SEQ ID NO 219
<211> LENGTH: 45
<212> TYPE: PRT
<213> ORGANISM: Corchorus olitorius

<400> SEQUENCE: 219

Arg Thr Cys Glu Ser Pro Ser Thr Lys Phe Gln Gly Val Cys Leu Asn
1               5                   10                  15

Ala Lys Asn Cys Ala Gly Val Cys Thr Gly Glu Gly Phe Thr Gly Gly
            20                  25                  30

Gln Cys Ser Ser Leu Lys Cys Tyr Cys Thr Lys Thr Cys
        35                  40                  45


<210> SEQ ID NO 220
<211> LENGTH: 47
<212> TYPE: PRT
<213> ORGANISM: Corchorus olitorius

<400> SEQUENCE: 220

Arg Thr Cys Glu Ser Lys Ser His Lys Phe Arg Gly Leu Cys Val Ser
1               5                   10                  15

Arg His Asn Cys Ala Asn Val Cys His Asn Glu Gly Phe His Gly Gly
            20                  25                  30
```

Lys Cys Arg Gly Phe Arg Arg Arg Cys Tyr Cys Thr Arg His Cys
35 40 45

<210> SEQ ID NO 221
<211> LENGTH: 48
<212> TYPE: PRT
<213> ORGANISM: Capsicum annuum

<400> SEQUENCE: 221

Arg Ser Cys Glu Ser Ala Ser Gln Arg Phe Asn Gly Tyr Cys Val Arg
1 5 10 15

Ser Ser Asn Cys Ala Ser Ile Cys Ser Thr Glu Gly Phe Thr Asp Gly
20 25 30

Lys Cys Lys Gly Thr Ile Arg Arg His Cys Thr Cys Ile Arg Asn Cys
35 40 45

<210> SEQ ID NO 222
<211> LENGTH: 48
<212> TYPE: PRT
<213> ORGANISM: Capsicum annuum

<400> SEQUENCE: 222

Arg Val Cys Ile Ser Gln Ser His Gly Phe Lys Gly Pro Cys Gly His
1 5 10 15

Asp His Asn Cys Ala Leu Val Cys Arg Asn Glu Gly Phe Ser Gly Gly
20 25 30

Asp Cys Ile Gly Val Phe Ile Arg Lys Cys Tyr Cys Thr Lys Asn Cys
35 40 45

<210> SEQ ID NO 223
<211> LENGTH: 48
<212> TYPE: PRT
<213> ORGANISM: Capsicum annuum

<400> SEQUENCE: 223

Lys Ile Cys Glu Ala Leu Ser Gly Asn Phe Lys Gly Leu Cys Leu Ser
1 5 10 15

Ser Arg Asp Cys Gly Asn Val Cys Arg Arg Glu Gly Phe Thr Asp Gly
20 25 30

Ser Cys Ile Gly Phe Arg Leu Gln Cys Phe Cys Thr Lys Pro Cys Ala
35 40 45

<210> SEQ ID NO 224
<211> LENGTH: 47
<212> TYPE: PRT
<213> ORGANISM: Capsicum annuum

<400> SEQUENCE: 224

Arg Lys Cys Glu Ser Gln Ser His Arg Phe Lys Gly Pro Cys Val Arg
1 5 10 15

Lys Ser Asn Cys Ala Ser Val Cys Gln Thr Glu Gly Phe Thr Gly Gly
20 25 30

His Cys Arg Gly Phe Arg Arg Arg Cys Phe Cys Thr Lys His Cys
35 40 45

<210> SEQ ID NO 225
<211> LENGTH: 47
<212> TYPE: PRT
<213> ORGANISM: Capsicum annuum

<400> SEQUENCE: 225

Arg His Cys Glu Ser Lys Ser Gln Arg Phe Lys Gly Pro Cys Val Arg
1 5 10 15

Gln Lys Asn Cys Ala Ala Val Cys Glu Thr Glu Gly Phe Pro Gly Gly
20 25 30

Asp Cys Arg Gly Phe Arg Arg Arg Cys Phe Cys Thr Arg Pro Cys
35 40 45

<210> SEQ ID NO 226
<211> LENGTH: 47
<212> TYPE: PRT
<213> ORGANISM: Capsicum annuum

<400> SEQUENCE: 226

Arg Thr Cys Glu Ser Gln Ser His Arg Phe Lys Gly Val Cys Ala Ser
1 5 10 15

Glu Thr Asn Cys Ala Ser Val Cys Gln Thr Glu Gly Phe Ser Gly Gly
20 25 30

Asp Cys Arg Gly Phe Arg Arg Arg Cys Phe Cys Thr Arg Pro Cys
35 40 45

<210> SEQ ID NO 227
<211> LENGTH: 51
<212> TYPE: PRT
<213> ORGANISM: Capsicum annuum

<400> SEQUENCE: 227

Lys Thr Cys Asp Thr Leu Ser Glu Asn Phe Lys Gly Ile Cys Phe Ser
1 5 10 15

Ser Thr Asn Cys Ala Thr Thr Cys Gln Asn Glu Asp Glu Glu Tyr Thr
20 25 30

Gly Gly His Cys Arg Gly Leu His Arg Arg Cys Phe Cys Thr Thr Glu
35 40 45

Cys Glu Leu
50

<210> SEQ ID NO 228
<211> LENGTH: 49
<212> TYPE: PRT
<213> ORGANISM: Capsicum annuum

<400> SEQUENCE: 228

Lys Thr Cys Glu Arg Leu Ser Gly Thr Phe Lys Gly Ile Cys Phe Ser
1 5 10 15

Ser Lys Asn Cys Ala Ser Val Cys Glu Asn Glu Asp Glu Glu Phe Thr
20 25 30

Gly Gly His Cys Ser Gly Leu Arg Arg Arg Cys Tyr Cys Thr Ala Asp
35 40 45

Cys

<210> SEQ ID NO 229
<211> LENGTH: 47
<212> TYPE: PRT
<213> ORGANISM: Cannabis sativa

<400> SEQUENCE: 229

Arg Val Cys Glu Ser Lys Ser His His Phe Lys Gly Leu Cys Val Ile
1 5 10 15

```
Asp His Asn Cys Ala Thr Ile Cys Arg Thr Glu Gly Phe Ser Gly Gly
            20                  25                  30

Asn Cys Gln Gly Phe Arg Gln Arg Cys Phe Cys Thr Arg His Cys
        35                  40                  45


<210> SEQ ID NO 230
<211> LENGTH: 47
<212> TYPE: PRT
<213> ORGANISM: Cannabis sativa

<400> SEQUENCE: 230

Arg Thr Cys Glu Ala Gln Ser His His Phe Lys Gly Pro Cys Val Arg
1               5                   10                  15

Lys Ser Asn Cys Ala Asn Val Cys Arg Thr Glu Gly Phe Pro Ser Gly
            20                  25                  30

His Cys Arg Gly Phe Arg Arg Arg Cys Phe Cys Thr Lys His Cys
        35                  40                  45


<210> SEQ ID NO 231
<211> LENGTH: 47
<212> TYPE: PRT
<213> ORGANISM: Cannabis sativa

<400> SEQUENCE: 231

Lys Thr Cys Glu Ala Arg Ser Gln Ser His Arg Gly Ile Cys Val Thr
1               5                   10                  15

Asn His Thr Cys Asp Asn Val Cys Lys Ile Glu Arg Phe Ser Ser Gly
            20                  25                  30

Tyr Cys Ser Gly Ile Asp Arg Arg Cys Leu Cys Thr Lys His Cys
        35                  40                  45


<210> SEQ ID NO 232
<211> LENGTH: 47
<212> TYPE: PRT
<213> ORGANISM: Cardamine hirsuta

<400> SEQUENCE: 232

Arg Thr Cys Gln Ser Ser Ser Gln Leu Phe Ser Gly Pro Arg Leu Ser
1               5                   10                  15

Thr Ser Asn Cys Ala Asn Val Cys Gln Asn Glu Gly Phe Thr Asp Gly
            20                  25                  30

Asp Cys Arg Gly Phe Arg Arg Arg Cys Phe Cys Asn Lys Gln Cys
        35                  40                  45


<210> SEQ ID NO 233
<211> LENGTH: 54
<212> TYPE: PRT
<213> ORGANISM: Cardamine hirsuta

<400> SEQUENCE: 233

Gln Gln Leu Cys Glu Thr Lys Ser Thr Asn Tyr Arg Gly Leu Cys Leu
1               5                   10                  15

Arg Trp Arg Asn Cys Lys Arg Val Cys Met Ser Glu Gly Phe Pro Asp
            20                  25                  30

Gly Arg Cys Arg Gly Ile Phe Asp Asn Lys Cys Val Cys Arg Lys Pro
        35                  40                  45

Cys Ala Leu Ser Thr Ala
    50


<210> SEQ ID NO 234
```

```
<211> LENGTH: 47
<212> TYPE: PRT
<213> ORGANISM: Cardamine hirsuta

<400> SEQUENCE: 234

Arg Thr Cys Glu Ser Gln Ser His Arg Phe Lys Gly Thr Cys Val Ser
1               5                   10                  15

Ala Ser Asn Cys Gly Asn Val Cys His Asn Glu Gly Phe Asn Gly Gly
            20                  25                  30

Asn Cys Arg Gly Phe Arg Arg Arg Cys Phe Cys Thr Arg His Cys
        35                  40                  45


<210> SEQ ID NO 235
<211> LENGTH: 47
<212> TYPE: PRT
<213> ORGANISM: Cardamine hirsuta

<400> SEQUENCE: 235

Arg Thr Cys Glu Ser Gln Ser His Arg Phe Lys Gly Thr Cys Thr Asn
1               5                   10                  15

Glu Gln Asn Cys Arg Asn Ile Cys His Asn Glu Gly Phe Phe Gly Gly
            20                  25                  30

Lys Cys Arg Gly Phe Arg Arg Arg Cys Phe Cys Thr Arg Asn Cys
        35                  40                  45


<210> SEQ ID NO 236
<211> LENGTH: 47
<212> TYPE: PRT
<213> ORGANISM: Cardamine hirsuta

<400> SEQUENCE: 236

Arg Met Cys Glu Ser Lys Ser Gln Gln Phe Arg Gly Leu Cys Met Ser
1               5                   10                  15

Ser Thr Asn Cys Ala Thr Val Cys His Asn Glu Gly Phe Pro Gly Gly
            20                  25                  30

Glu Cys Arg Gly Phe Arg Arg Arg Cys Phe Cys Thr Arg Pro Cys
        35                  40                  45


<210> SEQ ID NO 237
<211> LENGTH: 100
<212> TYPE: PRT
<213> ORGANISM: Cardamine hirsuta

<400> SEQUENCE: 237

Lys Pro Arg Arg Cys Glu Ser Gln Ser Asn Lys Phe Lys Gly Lys Cys
1               5                   10                  15

Val Ser Glu Thr Asn Cys Gly Asn Val Cys Arg Thr Glu Gly Phe Thr
            20                  25                  30

Gly Gly Asp Cys Arg Gly Phe Arg Arg Arg Cys Phe Cys Thr Arg Asn
        35                  40                  45

Cys Cys Ala Arg His Arg Met Lys Leu Ser Met Arg Leu Ile Ser Ala
    50                  55                  60

Ala Leu Leu Leu Leu Met Leu Phe Val Ala Thr Gly Met Gly Pro Val
65                  70                  75                  80

Met Val Asp Ala Arg Thr Cys Glu Ser Lys Ser His Arg Phe Lys Gly
                85                  90                  95

Pro Cys Val Ser
            100
```

<210> SEQ ID NO 238
<211> LENGTH: 47
<212> TYPE: PRT
<213> ORGANISM: Cardamine hirsuta

<400> SEQUENCE: 238

Arg Val Cys Glu Thr Arg Ser Gln Lys Phe Lys Gly Pro Cys Val Ser
1 5 10 15

Glu Asn Asn Cys Ala Asn Val Cys Gln Thr Glu Gly Phe Pro Asp Gly
20 25 30

Asp Cys Asn Gly Ile Leu Arg Arg Cys Tyr Cys Asn Ser Pro Cys
35 40 45

<210> SEQ ID NO 239
<211> LENGTH: 45
<212> TYPE: PRT
<213> ORGANISM: Cardamine hirsuta

<400> SEQUENCE: 239

Lys Thr Cys Glu Thr Pro Ser Thr Lys Phe Gln Gly Val Cys Leu Asn
1 5 10 15

Ser Gln Asn Cys Ala Lys Val Cys Pro Thr Glu Gly Ala Ser Gly Gly
20 25 30

Arg Cys Asn Ser Leu Arg Cys Val Cys Ser Lys Thr Cys
35 40 45

<210> SEQ ID NO 240
<211> LENGTH: 47
<212> TYPE: PRT
<213> ORGANISM: Cardamine hirsuta

<400> SEQUENCE: 240

Arg Ile Cys Gln Ser Lys Ser His His Tyr Lys Tyr Met Cys Thr Ser
1 5 10 15

Asn His Asn Cys Ala Met Val Cys Arg Asn Glu Gly Phe Ser Gly Gly
20 25 30

Gln Cys His Gly Phe His Arg Arg Cys Tyr Cys Thr Arg Leu Cys
35 40 45

<210> SEQ ID NO 241
<211> LENGTH: 47
<212> TYPE: PRT
<213> ORGANISM: Capsella rubela

<400> SEQUENCE: 241

Arg Thr Cys Glu Ser Ser Ser Asn Leu Phe Ser Gly Pro Cys Leu Ser
1 5 10 15

Glu Ser Asn Cys Ala Asn Val Cys Asn Thr Glu Gly Phe Pro Asp Gly
20 25 30

Asp Cys Arg Gly Phe Arg Arg Arg Cys Met Cys Thr Arg Pro Cys
35 40 45

<210> SEQ ID NO 242
<211> LENGTH: 47
<212> TYPE: PRT
<213> ORGANISM: Capsella rubela

<400> SEQUENCE: 242

Arg Thr Cys Glu Ser Lys Ser His Arg Phe Lys Gly Pro Cys Val Ser
1 5 10 15

```
Gly Asn Asn Cys Lys Asn Val Cys His Asn Glu Gly Phe Pro Gly Gly
            20                  25                  30

Arg Cys Arg Gly Phe Arg Arg Arg Cys Tyr Cys Thr Arg His Cys
        35                  40                  45


<210> SEQ ID NO 243
<211> LENGTH: 45
<212> TYPE: PRT
<213> ORGANISM: Capsella rubela

<400> SEQUENCE: 243

Arg Thr Cys Glu Ser Pro Ser Ser Lys Phe Ser Gly Val Cys Leu Asn
1               5                   10                  15

Ser Gln Thr Cys Ala Lys Ala Cys Pro Ser Glu Gly Phe Thr Gly Gly
            20                  25                  30

Arg Cys Asn Ser Leu Arg Cys Tyr Cys Ser Lys Pro Cys
        35                  40                  45


<210> SEQ ID NO 244
<211> LENGTH: 57
<212> TYPE: PRT
<213> ORGANISM: Capsella rubela

<400> SEQUENCE: 244

Glu Met Gly Leu Ala Ala Asp Lys Val Cys Lys Thr Arg Ser Asp Arg
1               5                   10                  15

Phe Ser Gly Val Cys Leu Ser Asn Asn Asn Cys Ala Ile Ile Cys Gln
            20                  25                  30

Gln Phe Glu Asn Phe Asp Ser Gly His Cys Glu Phe Asp Gly Ala Phe
        35                  40                  45

Arg Arg Cys Leu Cys Thr Lys Asn Cys
    50                  55


<210> SEQ ID NO 245
<211> LENGTH: 47
<212> TYPE: PRT
<213> ORGANISM: Capsella rubela

<400> SEQUENCE: 245

Arg Met Cys Gln Ser Lys Ser His His Phe Arg Arg Met Cys Trp Ser
1               5                   10                  15

Asp His Asn Cys Ala Met Ile Cys Arg Ser Glu Arg Phe Ser Gly Gly
            20                  25                  30

His Cys His Gly Phe His Arg Arg Cys Tyr Cys Thr Arg Leu Cys
        35                  40                  45


<210> SEQ ID NO 246
<211> LENGTH: 47
<212> TYPE: PRT
<213> ORGANISM: Cicer arientinum

<400> SEQUENCE: 246

Arg Val Cys Ala Ser Gln Ser His Ala Phe Lys Gly Pro Cys Val Gly
1               5                   10                  15

Asp His Asn Cys Ala Leu Val Cys Arg Asn Glu Gly Phe Ser Gly Gly
            20                  25                  30

Asn Cys Gln Gly Phe Arg Arg Arg Cys Phe Cys Thr Lys Leu Cys
        35                  40                  45
```

```
<210> SEQ ID NO 247
<211> LENGTH: 47
<212> TYPE: PRT
<213> ORGANISM: Citrus clementina

<400> SEQUENCE: 247

Arg Thr Cys Glu Ser Leu Ser His Arg Phe Lys Gly Thr Cys Val Arg
1               5                   10                  15

Gly Ser Asn Cys Ala Ala Val Cys Gln Thr Glu Gly Phe Pro Gly Gly
            20                  25                  30

Gln Cys Ser Gly Leu Arg Arg Arg Cys Phe Cys Ser Lys Pro Cys
        35                  40                  45


<210> SEQ ID NO 248
<211> LENGTH: 77
<212> TYPE: PRT
<213> ORGANISM: Citrus clementina

<400> SEQUENCE: 248

His Asp Thr Glu Met Gly Pro Val Leu Cys Gly Asp Thr Gly Asn Glu
1               5                   10                  15

Lys Gly Pro Ser Arg Arg Lys Ala Ala Ala Val Ala Ala Ile Glu Arg
            20                  25                  30

Thr Cys Glu Thr Pro Ser Lys Arg Phe Lys Gly Pro Cys Val Lys Glu
        35                  40                  45

Ser Asn Cys Ala Ala Val Cys Gln Thr Glu Gly Phe Gln Gly Gly Lys
    50                  55                  60

Cys Arg Gly Leu Arg Arg Arg Cys Phe Cys Thr Arg Pro
65                  70                  75


<210> SEQ ID NO 249
<211> LENGTH: 47
<212> TYPE: PRT
<213> ORGANISM: Citrus clementina

<400> SEQUENCE: 249

Arg Ile Cys Glu Ser Gln Ser His Arg Phe Lys Gly Pro Cys Ile Arg
1               5                   10                  15

Lys Asp Asn Cys Ala Ala Val Cys Gln Thr Glu Gly Phe His Gly Gly
            20                  25                  30

Arg Cys Arg Gly Phe Arg Arg Arg Cys Phe Cys Thr Lys His Cys
        35                  40                  45


<210> SEQ ID NO 250
<211> LENGTH: 47
<212> TYPE: PRT
<213> ORGANISM: Ceratophyllum demensis

<400> SEQUENCE: 250

Arg Met Cys Glu Ser Pro Ser Arg His Tyr Lys Gly Leu Cys Phe Arg
1               5                   10                  15

Ser Ser Asn Cys Ala Ser Ile Cys His Ile Glu His Phe Ser His Gly
            20                  25                  30

His Cys His Gly Phe Arg Arg Arg Cys Ile Cys Ser Arg Pro Cys
        35                  40                  45


<210> SEQ ID NO 251
<211> LENGTH: 47
<212> TYPE: PRT
<213> ORGANISM: Ceratophyllum demensis
```

<400> SEQUENCE: 251

Arg Met Cys Glu Ser Pro Ser Arg His Tyr Lys Gly Leu Cys Phe Arg
1 5 10 15

Ser Ser Asn Cys Ala Ser Ile Cys His Ile Glu His Phe Ser His Gly
20 25 30

Tyr Cys His Gly Phe Arg Arg Arg Cys Ile Cys Ser Arg Pro Cys
35 40 45

<210> SEQ ID NO 252
<211> LENGTH: 47
<212> TYPE: PRT
<213> ORGANISM: Carpinus fangiana

<400> SEQUENCE: 252

Arg Val Cys Glu Ser Gln Ser His Lys Phe His Gly Pro Cys Leu Gly
1 5 10 15

Asp His Asn Cys Ala Leu Val Cys Arg Asn Glu Gly Phe Ser Gly Gly
20 25 30

Asp Cys Lys Gly Leu Arg Arg Arg Cys Phe Cys Thr Arg Leu Cys
35 40 45

<210> SEQ ID NO 253
<211> LENGTH: 50
<212> TYPE: PRT
<213> ORGANISM: Citrullus lanatus

<400> SEQUENCE: 253

Ala Glu Ala Arg Ile Cys Glu Ser Gln Ser His Arg Phe Lys Gly Pro
1 5 10 15

Cys Val Ser Lys Ser Asn Cys Ala Ala Val Cys Gln Thr Glu Gly Phe
20 25 30

His Gly Gly His Cys Arg Gly Phe Arg Arg Arg Cys Phe Cys Thr Lys
35 40 45

Arg Cys
50

<210> SEQ ID NO 254
<211> LENGTH: 47
<212> TYPE: PRT
<213> ORGANISM: Citrullus lanatus

<400> SEQUENCE: 254

Arg Val Cys Gln Ser Gln Ser His His Phe His Gly Ala Cys Phe Ser
1 5 10 15

His His Asn Cys Ala Phe Val Cys Arg Asn Glu Gly Phe Ser Gly Gly
20 25 30

Lys Cys Arg Gly Ala Arg Arg Arg Cys Phe Cys Ser Lys Leu Cys
35 40 45

<210> SEQ ID NO 255
<211> LENGTH: 47
<212> TYPE: PRT
<213> ORGANISM: Carya illinoinensis

<400> SEQUENCE: 255

Arg Val Cys Glu Ser Lys Ser His Gly Phe Gln Gly Met Cys Thr Arg
1 5 10 15

Asp His Asn Cys Ala Leu Val Cys Arg Asn Glu Gly Phe Ser Gly Gly
20 25 30

Lys Cys Arg Gly Phe Arg His Arg Cys Phe Cys Thr Lys Leu Cys
35 40 45

<210> SEQ ID NO 256
<211> LENGTH: 47
<212> TYPE: PRT
<213> ORGANISM: Carya illinoinensis

<400> SEQUENCE: 256

Arg Val Cys Glu Ser Lys Ser His Lys Phe Gln Gly Pro Cys Val Arg
1 5 10 15

Asp Asn Asn Cys Gly Leu Val Cys Lys Asn Glu Gly Phe Thr Gly Gly
20 25 30

Lys Cys Arg Gly Phe Arg Arg Arg Cys Phe Cys Thr Lys Ile Cys
35 40 45

<210> SEQ ID NO 257
<211> LENGTH: 58
<212> TYPE: PRT
<213> ORGANISM: Citrullus lanatus

<400> SEQUENCE: 257

Glu Glu Met Met Gly Gly Gly Arg Ala Glu Gly Arg Val Cys Lys Ser
1 5 10 15

Gln Ser His Ser Phe His Gly Pro Cys Met Arg Asp His Asn Cys Ala
20 25 30

Val Val Cys Arg Thr Glu Gly Phe Ser Gly Gly Asp Cys Val Gly Phe
35 40 45

Arg Arg Arg Cys Phe Cys Thr Arg Leu Cys
50 55

<210> SEQ ID NO 258
<211> LENGTH: 47
<212> TYPE: PRT
<213> ORGANISM: Corchorus olitorius

<400> SEQUENCE: 258

Arg Val Cys Glu Ser Lys Ser His Trp Phe Lys Gly Pro Cys Trp Gly
1 5 10 15

Asp His Asn Cys Ala Leu Val Cys Arg Asn Glu Gly Phe Ser Gly Gly
20 25 30

Arg Cys Arg Gly Phe Arg His Arg Cys Phe Cys Thr Lys Leu Cys
35 40 45

<210> SEQ ID NO 259
<211> LENGTH: 47
<212> TYPE: PRT
<213> ORGANISM: Corchorus olitorius

<400> SEQUENCE: 259

Arg Leu Cys Gln Ser Gln Ser His Gly Phe Lys Gly Gly Cys Leu Ser
1 5 10 15

Asn His Asn Cys Ala Leu Val Cys Arg Asn Glu Gly Phe Ser Gly Gly
20 25 30

Gln Cys Arg Gly Leu Arg His Arg Cys Phe Cys Thr Arg Arg Cys
35 40 45

<210> SEQ ID NO 260
<211> LENGTH: 32
<212> TYPE: PRT
<213> ORGANISM: Carica papaya

```
<220> FEATURE:
<221> NAME/KEY: misc_feature
<222> LOCATION: (32)..(32)
<223> OTHER INFORMATION: Xaa can be any naturally occurring amino acid

<400> SEQUENCE: 260

Arg Thr Cys Gln Ser Gln Ser His Gly Phe His Gly Ala Cys Leu Ser
1               5                   10                  15

His His Asn Cys Ala Val Val Cys Gln Lys Glu Gly Phe Ser Gly Xaa
            20                  25                  30


<210> SEQ ID NO 261
<211> LENGTH: 47
<212> TYPE: PRT
<213> ORGANISM: Carica papaya

<400> SEQUENCE: 261

Arg Thr Cys Glu Ser Gln Ser His Arg Phe Lys Gly Ala Cys Gly Ser
1               5                   10                  15

Arg Ser Asn Cys Ala Ala Val Cys Gln Thr Glu Gly Phe His Gly Gly
            20                  25                  30

His Cys Arg Gly Phe Arg Arg Arg Cys Phe Cys Thr Lys His Cys
        35                  40                  45


<210> SEQ ID NO 262
<211> LENGTH: 50
<212> TYPE: PRT
<213> ORGANISM: Cucumis sativus

<400> SEQUENCE: 262

Val Glu Gly Arg Ile Cys Glu Ser Lys Ser His Gly Phe Lys Gly Pro
1               5                   10                  15

Cys Met Thr Asp His Asn Cys Ala Leu Val Cys Arg Asn Glu Gly Phe
            20                  25                  30

Ser Gly Gly Lys Cys Arg Gly Val Arg His Arg Cys Phe Cys Thr Lys
        35                  40                  45

Leu Cys
    50


<210> SEQ ID NO 263
<211> LENGTH: 50
<212> TYPE: PRT
<213> ORGANISM: Cucumis sativus

<400> SEQUENCE: 263

Val Glu Gly Arg Ile Cys Glu Ser Lys Ser His Gly Phe Lys Gly Pro
1               5                   10                  15

Cys Met Thr Asp His Asn Cys Ala Leu Val Cys Arg Asn Glu Gly Phe
            20                  25                  30

Ser Gly Gly Lys Cys Arg Gly Val Arg His Arg Cys Phe Cys Thr Lys
        35                  40                  45

Leu Cys
    50


<210> SEQ ID NO 264
<211> LENGTH: 73
<212> TYPE: PRT
<213> ORGANISM: Daucus carota
```

<400> SEQUENCE: 264

Thr Asp Thr Cys Glu Val Arg Ser Ala Tyr Phe Val Ser Leu Cys Leu
1               5                   10                  15

Ile Asp His His Cys Glu Met Val Cys Lys Val Glu Gly Phe Pro Thr
            20                  25                  30

Gly Lys Cys Leu Gly Leu Val Pro His Cys Ile Cys Leu Gly Thr Cys
        35                  40                  45

Lys Gln Pro Ser Pro Pro Ser Pro Pro Pro Ala Asn Pro Pro Glu Ser
    50                  55                  60

Pro Pro Pro Val Pro Pro Pro Thr Pro
65                  70

<210> SEQ ID NO 265
<211> LENGTH: 47
<212> TYPE: PRT
<213> ORGANISM: Daucus carota

<400> SEQUENCE: 265

Arg Thr Cys Glu Ser Gln Ser His Lys Phe Lys Gly Thr Cys Leu Ser
1               5                   10                  15

Glu Thr Asn Cys Gly Asn Val Cys Lys Asn Glu Gly Phe Ser Gly Gly
            20                  25                  30

Asn Cys Arg Gly Leu Arg Arg Arg Cys Phe Cys Thr Arg His Cys
        35                  40                  45

<210> SEQ ID NO 266
<211> LENGTH: 47
<212> TYPE: PRT
<213> ORGANISM: Daucus carota

<400> SEQUENCE: 266

Arg Thr Cys Glu Ser Gln Ser His Lys Phe Lys Gly Thr Cys Val Ser
1               5                   10                  15

Arg Ser Asn Cys Ala Asn Val Cys Lys Asn Glu Gly Phe Pro Gly Gly
            20                  25                  30

His Cys Arg Gly Phe Arg Arg Arg Cys Phe Cys Ile Lys His Cys
        35                  40                  45

<210> SEQ ID NO 267
<211> LENGTH: 47
<212> TYPE: PRT
<213> ORGANISM: Davidia involucrata

<400> SEQUENCE: 267

Arg Val Cys Glu Ala Gln Ser His Gly Phe Lys Gly Ala Cys Met Ser
1               5                   10                  15

Asn His Asn Cys Ala Leu Val Cys Arg Asn Glu Gly Phe Ser Gly Gly
            20                  25                  30

Lys Cys Arg Gly Phe Arg His Arg Cys Phe Cys Thr Lys Gln Cys
        35                  40                  45

<210> SEQ ID NO 268
<211> LENGTH: 47
<212> TYPE: PRT
<213> ORGANISM: Durio zibethin

<400> SEQUENCE: 268

Arg Val Cys Glu Ser Lys Ser His Arg Phe Lys Gly Pro Cys Leu Ser
1               5                   10                  15

```
His His Asn Cys Gly Met Val Cys Lys Asn Glu Gly Phe Ser Gly Gly
            20                  25                  30

Lys Cys Arg Gly Val Arg Arg Arg Cys Phe Cys Thr Arg Arg Cys
        35                  40                  45


<210> SEQ ID NO 269
<211> LENGTH: 52
<212> TYPE: PRT
<213> ORGANISM: Durio zibethin

<400> SEQUENCE: 269

Ile Ser Val Glu Gly Arg Thr Cys Glu Ser Gln Ser His Arg Phe Lys
1               5                   10                  15

Gly Ala Cys Val Ser Glu Asn Asn Cys Ala Ala Val Cys Gln Thr Glu
            20                  25                  30

Gly Phe Leu Gly Gly Asn Cys Arg Gly Phe Arg Arg Arg Cys Phe Cys
        35                  40                  45

Thr Lys Gln Cys
    50


<210> SEQ ID NO 270
<211> LENGTH: 52
<212> TYPE: PRT
<213> ORGANISM: Durio zibethin

<400> SEQUENCE: 270

Ile Pro Leu Glu Gly Arg Thr Cys Glu Ser Gln Ser His Arg Phe Lys
1               5                   10                  15

Gly Met Cys Val Arg Glu Ser Asn Cys Ala Thr Val Cys Gln Thr Glu
            20                  25                  30

Gly Phe Gln Gly Gly His Cys Arg Gly Phe His Arg Arg Cys Phe Cys
        35                  40                  45

Thr Lys His Cys
    50


<210> SEQ ID NO 271
<211> LENGTH: 47
<212> TYPE: PRT
<213> ORGANISM: Durio zibethin

<400> SEQUENCE: 271

Arg Thr Cys Glu Ser Gln Ser His Arg Phe Lys Gly Thr Cys Leu Arg
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys His Cys
        35                  40                  45


<210> SEQ ID NO 272
<211> LENGTH: 50
<212> TYPE: PRT
<213> ORGANISM: Durio zibethin

<400> SEQUENCE: 272

Gly Glu Ala Arg Val Cys Glu Ser Lys Ser His Lys Tyr Lys Gly Ala
1               5                   10                  15

Cys Phe His Asp His Asn Cys Ala Tyr Val Cys Arg Asn Glu Gly Phe
            20                  25                  30
```

```
Ser Gly Gly Lys Cys His Gly Leu His His His Cys Phe Cys Thr Lys
        35                  40                  45

Ile Cys
    50


<210> SEQ ID NO 273
<211> LENGTH: 47
<212> TYPE: PRT
<213> ORGANISM: Durio zibethin

<400> SEQUENCE: 273

Arg Val Cys Glu Ser Lys Ser His Lys Phe Lys Gly Pro Cys Met Gly
1               5                   10                  15

Asp His Asn Cys Ala Tyr Val Cys Arg Asn Glu Gly Phe Ser Gly Gly
            20                  25                  30

Lys Cys Arg Gly Leu Arg His Arg Cys Phe Cys Thr Lys Ile Cys
        35                  40                  45


<210> SEQ ID NO 274
<211> LENGTH: 47
<212> TYPE: PRT
<213> ORGANISM: Erigeron canadensis

<400> SEQUENCE: 274

Arg Met Cys Gln Ser Gln Ser His Met Tyr His Gly Ala Cys Leu Arg
1               5                   10                  15

Asp His Asn Cys Ala Leu Val Cys Arg Asn Glu Gly Phe Ser Gly Gly
            20                  25                  30

Arg Cys Arg Gly Phe Arg Arg Arg Cys Phe Cys Thr Arg Leu Cys
        35                  40                  45


<210> SEQ ID NO 275
<211> LENGTH: 71
<212> TYPE: PRT
<213> ORGANISM: Erigeron canadensis

<400> SEQUENCE: 275

Asn Glu Met Gly Gly Pro Met Val Val Glu Gly Arg Thr Leu Ala Val
1               5                   10                  15

Val Thr Val Ile Gly Ala Gly Gly Val Gln Arg Trp Trp Arg Trp Trp
            20                  25                  30

Gln Cys Asn Gly Asp Ser Gly Gly Asp Gly Gly Thr Arg Ala Met Val
        35                  40                  45

Ala Val Thr Asn Ser Gly Gly Ser Ser Ser Asn Gly Gly Gly Gly Asp
    50                  55                  60

Asp Trp Trp Trp Trp Trp Gln
65                  70


<210> SEQ ID NO 276
<211> LENGTH: 48
<212> TYPE: PRT
<213> ORGANISM: Eutrema salsugenium

<400> SEQUENCE: 276

Arg Met Cys Thr Asn Pro Ser Lys Thr Tyr Lys Gly Pro Cys Val Ser
1               5                   10                  15

Asp Thr Asn Cys Glu Ser Val Cys Gln Ser Glu Gly Phe Pro Gln Gly
            20                  25                  30
```

```
Asn Cys His Gly Phe Arg Arg Arg Cys Ile Cys Gly Lys Pro Cys Ala
        35                  40                  45


<210> SEQ ID NO 277
<211> LENGTH: 47
<212> TYPE: PRT
<213> ORGANISM: Eutrema salsugenium

<400> SEQUENCE: 277

Arg Thr Cys Glu Thr Ala Ser His Lys Phe Lys Gly Pro Cys Leu Gly
1               5                   10                  15

Asp Arg Asn Cys Ala Asn Val Cys Gln Thr Glu Gly Phe Pro Gly Gly
            20                  25                  30

Asp Cys Gln Gly Leu Arg Arg Arg Cys Phe Cys Thr Arg Pro Cys
        35                  40                  45


<210> SEQ ID NO 278
<211> LENGTH: 48
<212> TYPE: PRT
<213> ORGANISM: Eutrema salsugenium

<400> SEQUENCE: 278

Arg Thr Cys Asp Ala Pro Ser His Ser Phe Lys Gly Ile Cys Thr Arg
1               5                   10                  15

Lys Arg Asn Cys Glu Ser Val Cys Asn Ser Glu Gly Phe Ala Asp Gly
            20                  25                  30

Asp Cys Lys Gly Phe Arg Arg Arg Cys Ile Cys Asn Arg Pro Cys Ala
        35                  40                  45


<210> SEQ ID NO 279
<211> LENGTH: 49
<212> TYPE: PRT
<213> ORGANISM: Eutrema salsugenium

<400> SEQUENCE: 279

Arg Thr Cys Val Thr Pro Ser His Arg Phe Arg Gly Ile Cys Val Ser
1               5                   10                  15

Lys Arg Asn Cys Glu Ser Ala Cys Asn Ser Glu Gly Phe Pro Asp Gly
            20                  25                  30

Asn Cys Lys Gly Phe Arg Arg Arg Cys Ile Cys Asn Arg Pro Cys Ala
        35                  40                  45

Lys


<210> SEQ ID NO 280
<211> LENGTH: 51
<212> TYPE: PRT
<213> ORGANISM: Eutrema salsugenium

<400> SEQUENCE: 280

Leu Phe Gly Arg Cys Lys Lys Val Pro Ser Arg Thr Tyr Lys Gly Pro
1               5                   10                  15

Cys Ala Arg Asp Ala Asn Cys Arg Ser Val Cys Ile Ser Glu Gly Tyr
            20                  25                  30

Asn Gly Gly Asp Cys His Gly Phe Arg Arg Arg Cys Met Cys Thr Asp
        35                  40                  45

Lys Cys Ser
    50


<210> SEQ ID NO 281
```

<211> LENGTH: 47
<212> TYPE: PRT
<213> ORGANISM: Eucalyptus grandis

<400> SEQUENCE: 281

```
Arg Thr Cys Glu Ser Gln Ser Gln Arg Phe Lys Gly Ala Cys Val Ser
1               5                   10                  15

Lys Thr Asn Cys Ala Ser Val Cys Gln Thr Glu Gly Phe His Gly Gly
            20                  25                  30

His Cys Arg Gly Phe Arg Arg Arg Cys Phe Cys Thr Lys His Cys
        35                  40                  45
```

<210> SEQ ID NO 282
<211> LENGTH: 50
<212> TYPE: PRT
<213> ORGANISM: Eucalyptus grandis

<400> SEQUENCE: 282

```
Ile Glu Gly Arg Met Cys Glu Ser Gln Ser His Lys Phe His Gly Leu
1               5                   10                  15

Cys Met Ser Asp Arg Thr Cys Val Val Val Cys Lys Glu Glu Asp Phe
            20                  25                  30

Asp Asp Gly Lys Cys Arg Gly Phe Arg His Arg Cys Phe Cys Arg Lys
        35                  40                  45

Pro Cys
    50
```

<210> SEQ ID NO 283
<211> LENGTH: 47
<212> TYPE: PRT
<213> ORGANISM: Eucalyptus grandis

<400> SEQUENCE: 283

```
Arg Val Cys Glu Ser Gln Ser His Gly Phe His Gly Ser Cys Val Ser
1               5                   10                  15

Gly His Asn Cys Ala Leu Val Cys Arg Asn Glu Gly Phe Ser Gly Gly
            20                  25                  30

Arg Cys Arg Gly Phe Arg Arg Arg Cys Phe Cys Thr Lys Leu Cys
        35                  40                  45
```

<210> SEQ ID NO 284
<211> LENGTH: 47
<212> TYPE: PRT
<213> ORGANISM: Fragaraia x ananassa

<400> SEQUENCE: 284

```
Arg Val Cys Glu Ser Gln Ser His Gly Phe His Gly Thr Cys Ile Arg
1               5                   10                  15

Ala His Asn Cys Ala Leu Val Cys Arg His Glu Gly Phe Ser Gly Gly
            20                  25                  30

Arg Cys Arg Gly Phe Arg Arg Arg Cys Phe Cys Thr Arg Arg Cys
        35                  40                  45
```

<210> SEQ ID NO 285
<211> LENGTH: 47
<212> TYPE: PRT
<213> ORGANISM: Fragaraia x ananassa

<400> SEQUENCE: 285

```
Arg Thr Cys Glu Thr Leu Ser His Lys Phe Lys Gly Thr Cys Leu Arg
1               5                   10                  15
```

Glu Ser Asn Cys Ala Ser Val Cys Gln Thr Glu Gly Phe Thr Gly Gly
20 25 30

Asp Cys Arg Gly Leu Arg Arg Arg Cys Phe Cys Thr Lys His Cys
35 40 45

<210> SEQ ID NO 286
<211> LENGTH: 47
<212> TYPE: PRT
<213> ORGANISM: Fragaraia x ananassa

<400> SEQUENCE: 286

Arg Val Cys Glu Ser Gln Ser His Gly Phe Tyr Gly Thr Cys Ile His
1 5 10 15

Ala His Asn Cys Ala Leu Val Cys Arg His Glu Gly Phe Ser Gly Gly
20 25 30

Arg Cys Arg Gly Phe Arg Arg Arg Cys Phe Cys Thr Arg Arg Cys
35 40 45

<210> SEQ ID NO 287
<211> LENGTH: 47
<212> TYPE: PRT
<213> ORGANISM: Fragaraia x ananassa

<400> SEQUENCE: 287

Ala Ile Cys Lys Val Pro Ser Lys Thr Phe Lys Gly Met Cys Phe Ser
1 5 10 15

Gln Lys Asn Cys Ile Val Arg Cys His Ser Glu Gly Tyr Gly Trp Gly
20 25 30

Glu Cys Ser His Leu Arg Arg Arg Cys Met Cys Tyr Lys Pro Cys
35 40 45

<210> SEQ ID NO 288
<211> LENGTH: 47
<212> TYPE: PRT
<213> ORGANISM: Fragaraia x ananassa

<400> SEQUENCE: 288

Arg Val Cys Glu Val Pro Ser Lys Thr Phe Thr Gly Leu Cys Phe Arg
1 5 10 15

Asp Thr His Cys Ile Val Arg Cys His Ser Glu Gly Tyr Gly Tyr Gly
20 25 30

Lys Cys Ser His Val Leu Arg Arg Cys Arg Cys Leu Lys Ala Cys
35 40 45

<210> SEQ ID NO 289
<211> LENGTH: 47
<212> TYPE: PRT
<213> ORGANISM: Fragaraia x ananassa

<400> SEQUENCE: 289

Ala Ile Cys Lys Val Pro Ser Lys Thr Phe Lys Gly Met Cys Phe Ser
1 5 10 15

Gln Lys Asn Cys Ile Val Arg Cys His Ser Glu Gly Tyr Gly Trp Gly
20 25 30

Glu Cys Ser His Leu Arg Arg Arg Cys Met Cys Tyr Lys Pro Cys
35 40 45

<210> SEQ ID NO 290
<211> LENGTH: 47
<212> TYPE: PRT

<213> ORGANISM: Fragaraia x ananassa

<400> SEQUENCE: 290

```
Arg Val Cys Glu Ser Gln Ser His Gly Phe His Gly Thr Cys Ile Arg
1               5                   10                  15

Ala His Asn Cys Ala Leu Val Cys Arg His Glu Gly Phe Ser Gly Gly
            20                  25                  30

Arg Cys Arg Gly Phe Arg Arg Arg Cys Phe Cys Thr Arg Arg Cys
        35                  40                  45
```

<210> SEQ ID NO 291
<211> LENGTH: 53
<212> TYPE: PRT
<213> ORGANISM: Fragaraia x ananassa

<400> SEQUENCE: 291

```
Gly Arg Pro Asp Pro Lys Thr Cys Glu Ser Pro Ser Ala Lys Phe Glu
1               5                   10                  15

Gly Pro Cys Ile Met Gly Ser Asn Cys Ala Leu Thr Cys Gln Lys Glu
            20                  25                  30

Gly His Asp Gly Gly Phe Cys Arg Asp Phe Trp Leu Pro Lys Cys Phe
        35                  40                  45

Cys Thr Lys Pro Cys
    50
```

<210> SEQ ID NO 292
<211> LENGTH: 47
<212> TYPE: PRT
<213> ORGANISM: Fragaraia x ananassa

<400> SEQUENCE: 292

```
Arg Thr Cys Glu Ser Leu Ser His Lys Phe Gln Gly Thr Cys Leu Arg
1               5                   10                  15

Glu Ser Asn Cys Ala Ser Val Cys Gln Thr Glu Gly Phe Thr Gly Gly
            20                  25                  30

Asp Cys Arg Gly Leu Arg Arg Arg Cys Phe Cys Thr Lys His Cys
        35                  40                  45
```

<210> SEQ ID NO 293
<211> LENGTH: 53
<212> TYPE: PRT
<213> ORGANISM: Fragaraia x ananassa

<400> SEQUENCE: 293

```
Gly Arg Pro Asp Pro Lys Thr Cys Glu Pro Pro Ser Ala Lys Phe Glu
1               5                   10                  15

Glu Pro Cys Ile Met Gly Ser Asn Cys Ala Leu Thr Cys Gln Lys Glu
            20                  25                  30

Gly His Asp Gly Gly Phe Cys His Asp Phe Trp Leu Pro Lys Cys Phe
        35                  40                  45

Cys Thr Lys Pro Cys
    50
```

<210> SEQ ID NO 294
<211> LENGTH: 75
<212> TYPE: PRT
<213> ORGANISM: Fragaraia x ananassa

<400> SEQUENCE: 294

Leu Gly Pro Lys Val Met Val Ala His Glu Ala Ile Thr Cys Glu Thr
1               5                   10                  15

Gln Ser Ile Lys Tyr Glu Gly Met Cys Ser Arg Glu Lys Pro Cys Ala
            20                  25                  30

Ser Leu Cys Gln Thr Lys Gly Tyr Ser Arg Gly Glu Cys His Glu Val
        35                  40                  45

Ile Thr Leu Arg Leu Leu Tyr Arg Pro Gly Lys Thr Asp Pro Ile Gly
    50                  55                  60

Gln Ser Lys Arg Arg Thr Tyr Pro Leu Thr Asn
65                  70                  75

<210> SEQ ID NO 295
<211> LENGTH: 47
<212> TYPE: PRT
<213> ORGANISM: Fragaraia x ananassa

<400> SEQUENCE: 295

Arg Val Cys Glu Val Pro Ser Lys Thr Phe Thr Gly Leu Cys Phe Arg
1               5                   10                  15

Asp Thr His Cys Ile Val Arg Cys His Ser Glu Gly Tyr Gly Tyr Gly
            20                  25                  30

Lys Cys Ser His Val Leu Arg Arg Cys Arg Cys Leu Lys Ala Cys
        35                  40                  45

<210> SEQ ID NO 296
<211> LENGTH: 53
<212> TYPE: PRT
<213> ORGANISM: Fragaraia x ananassa

<400> SEQUENCE: 296

Gly Arg Pro Asp Pro Lys Thr Cys Glu Ser Pro Ser Ala Lys Phe Glu
1               5                   10                  15

Gly Pro Cys Ile Met Gly Ser Asn Cys Ala Leu Thr Cys Gln Lys Glu
            20                  25                  30

Gly His Asn Gly Gly Phe Cys Arg Asp Phe Trp Leu Pro Lys Cys Phe
        35                  40                  45

Cys Thr Lys Pro Cys
    50

<210> SEQ ID NO 297
<211> LENGTH: 53
<212> TYPE: PRT
<213> ORGANISM: Fragaraia x ananassa

<400> SEQUENCE: 297

Gly Arg Pro Asp Pro Lys Thr Cys Glu Ser Pro Ser Gly Lys Phe Glu
1               5                   10                  15

Gly Pro Cys Ile Met Gly Ser Asn Cys Ala Leu Thr Cys Gln Lys Glu
            20                  25                  30

Gly His Asp Gly Gly Phe Cys Arg Asp Phe Trp Leu Pro Lys Cys Phe
        35                  40                  45

Cys Thr Lys Pro Cys
    50

<210> SEQ ID NO 298
<211> LENGTH: 53
<212> TYPE: PRT

<213> ORGANISM: Fragaraia vesca

<400> SEQUENCE: 298

Gly Arg Pro Asp Pro Lys Thr Cys Glu Ser Pro Ser Ala Lys Phe Glu
1               5                   10                  15

Gly Pro Cys Ile Met Gly Ser Asn Cys Ala Leu Thr Cys Gln Lys Glu
            20                  25                  30

Gly His Asp Gly Gly Phe Cys Arg Asp Phe Trp Leu Pro Lys Cys Phe
        35                  40                  45

Cys Thr Lys Pro Cys
    50

<210> SEQ ID NO 299
<211> LENGTH: 58
<212> TYPE: PRT
<213> ORGANISM: Fragaraia vesca

<400> SEQUENCE: 299

Leu Gly Pro Lys Val Met Val Ala His Glu Ala Ile Thr Cys Glu Thr
1               5                   10                  15

Gln Ser Ile Lys Tyr Glu Gly Met Cys Ser Arg Glu Lys Pro Cys Ala
            20                  25                  30

Ser Leu Cys Gln Thr Lys Gly Tyr Ser Arg Gly Glu Cys His Gly Val
        35                  40                  45

Tyr Lys Ile Cys Val Cys Ala Thr Gln Cys
    50                  55

<210> SEQ ID NO 300
<211> LENGTH: 47
<212> TYPE: PRT
<213> ORGANISM: Fragaraia vesca

<400> SEQUENCE: 300

Ala Ile Cys Lys Val Pro Ser Lys Thr Phe Lys Gly Met Cys Phe Ser
1               5                   10                  15

Gln Lys Asn Cys Ile Val Arg Cys His Ser Glu Gly Tyr Gly Trp Gly
            20                  25                  30

Glu Cys Ser His Leu Arg Arg Arg Cys Met Cys Tyr Lys Pro Cys
        35                  40                  45

<210> SEQ ID NO 301
<211> LENGTH: 48
<212> TYPE: PRT
<213> ORGANISM: Fragaraia vesca

<400> SEQUENCE: 301

Ser Ile Cys Glu Ile Pro Ser Lys Lys Phe Lys Gly Leu Cys Ile Arg
1               5                   10                  15

Asp Arg Lys Cys Ile Val Ile Cys His Ser Glu Gly Tyr Gly Tyr Gly
            20                  25                  30

Lys Cys Ser His Ile Gly Arg Arg Cys Met Cys Leu Lys Thr Cys Asp
        35                  40                  45

<210> SEQ ID NO 302
<211> LENGTH: 54
<212> TYPE: PRT
<213> ORGANISM: Fragaraia vesca

<400> SEQUENCE: 302

```
Met Val Ala Ala Asp Asp Ala Arg Lys Cys Glu Ser Leu Ser His Asn
1               5                   10                  15

Phe Asn Gly Leu Cys Leu Ser Glu Ser Asn Cys Ala Ser Val Cys Ala
            20                  25                  30

Thr Glu Gly Phe Thr Gly Gly Asp Cys Arg Gly Leu Arg Arg Arg Cys
        35                  40                  45

Phe Cys Thr Lys Gln Cys
    50
```

<210> SEQ ID NO 303
<211> LENGTH: 47
<212> TYPE: PRT
<213> ORGANISM: Fragaraia vesca

<400> SEQUENCE: 303

```
Arg Thr Cys Glu Thr Leu Ser His Lys Phe Lys Gly Thr Cys Leu Arg
1               5                   10                  15

Glu Ser Asn Cys Ala Ser Val Cys Gln Thr Glu Gly Phe Thr Gly Gly
            20                  25                  30

Asp Cys Arg Gly Leu Arg Arg Arg Cys Phe Cys Thr Lys His Cys
        35                  40                  45
```

<210> SEQ ID NO 304
<211> LENGTH: 47
<212> TYPE: PRT
<213> ORGANISM: Fragaraia vesca

<400> SEQUENCE: 304

```
Arg Thr Cys Glu Ser Leu Ser His Lys Phe Lys Gly Thr Cys Leu Ser
1               5                   10                  15

Glu Thr Asn Cys Ala Ser Val Cys Lys Thr Glu Gly Phe Ser Gly Gly
            20                  25                  30

Asp Cys Arg Gly Leu Arg Arg Arg Cys Phe Cys Thr Lys His Cys
        35                  40                  45
```

<210> SEQ ID NO 305
<211> LENGTH: 47
<212> TYPE: PRT
<213> ORGANISM: Fragaraia vesca

<400> SEQUENCE: 305

```
Arg Val Cys Glu Ser Gln Ser His Gly Phe His Gly Thr Cys Ile Arg
1               5                   10                  15

Ala His Asn Cys Ala Leu Val Cys Arg His Glu Gly Phe Ser Gly Gly
            20                  25                  30

Arg Cys Arg Gly Phe Arg Arg Arg Cys Phe Cys Thr Arg Arg Cys
        35                  40                  45
```

<210> SEQ ID NO 306
<211> LENGTH: 45
<212> TYPE: PRT
<213> ORGANISM: Glycine max

<400> SEQUENCE: 306

```
Met His Leu Arg Ser His Arg Phe Lys Gly Met Cys Leu Ser Glu His
1               5                   10                  15

Asn Cys Ala Ser Val Ser His Leu Glu Gly Phe Thr Gly Gly Lys Cys
            20                  25                  30
```

```
Trp Gly Phe Arg Arg Arg Cys Phe Cys Ser Lys His Cys
        35                  40                  45


<210> SEQ ID NO 307
<211> LENGTH: 47
<212> TYPE: PRT
<213> ORGANISM: Glycine max

<400> SEQUENCE: 307

Lys Asp Cys Leu Thr Arg Arg His Gly Phe Gln Gly Arg Cys Leu Phe
1               5                   10                  15

Asp Arg Gln Cys Ala His Val Cys Arg Ser Asp Gly Phe Ile Gly Gly
            20                  25                  30

Gln Cys Arg Gly Pro Leu Arg Lys Cys Phe Cys Ser Arg Pro Cys
        35                  40                  45


<210> SEQ ID NO 308
<211> LENGTH: 47
<212> TYPE: PRT
<213> ORGANISM: Glycine max

<400> SEQUENCE: 308

Arg Val Cys Glu Ser Gln Ser His Gly Phe His Gly Leu Cys Asn Arg
1               5                   10                  15

Asp His Asn Cys Ala Leu Val Cys Arg Asn Glu Gly Phe Ser Gly Gly
            20                  25                  30

Arg Cys Lys Gly Phe Arg Arg Arg Cys Phe Cys Thr Arg Ile Cys
        35                  40                  45


<210> SEQ ID NO 309
<211> LENGTH: 47
<212> TYPE: PRT
<213> ORGANISM: Glycine max

<400> SEQUENCE: 309

Arg His Cys Glu Ser Lys Ser His Arg Phe Lys Gly Met Cys Leu Ser
1               5                   10                  15

Lys His Asn Cys Ala Ser Val Cys His Leu Glu Gly Phe Thr Gly Gly
            20                  25                  30

Lys Cys Arg Gly Phe Arg Arg Arg Cys Phe Cys Thr Arg His Cys
        35                  40                  45


<210> SEQ ID NO 310
<211> LENGTH: 63
<212> TYPE: PRT
<213> ORGANISM: Glycine max

<400> SEQUENCE: 310

Arg Tyr Ile Tyr Ile Ile Pro Tyr Val Ala Val Lys Arg Ala Glu Gly
1               5                   10                  15

Arg Asp Cys Ser Ser Lys Ser His Gly Phe Lys Gly Leu Cys Phe Ser
            20                  25                  30

Asp Thr Asn Cys Ala His Val Cys Arg Thr Glu Gly Phe Thr Gly Gly
        35                  40                  45

Asp Cys Gly Gly Phe Arg Arg Arg Cys Phe Cys Thr Arg Ile Cys
    50                  55                  60


<210> SEQ ID NO 311
<211> LENGTH: 69
<212> TYPE: PRT
```

<213> ORGANISM: Glycine max

<400> SEQUENCE: 311

Arg Thr Cys Glu Ser Gln Ser His Arg Phe Lys Gly Pro Cys Leu Ser
1               5                   10                  15

Asp Thr Asn Cys Gly Ser Val Cys Arg Thr Glu Gly Phe Ser Gly Gly
            20                  25                  30

His Cys Arg Gly Phe Ser Arg Arg Cys Phe Cys Thr Lys Glu Tyr Asp
        35                  40                  45

Asn Tyr Tyr Lys Ser Ser Asp Val Ile Arg Cys Lys Asp Gly Ser Gly
    50                  55                  60

Lys Phe Thr Lys Ala
65

<210> SEQ ID NO 312
<211> LENGTH: 47
<212> TYPE: PRT
<213> ORGANISM: Glycine max

<400> SEQUENCE: 312

Arg Thr Cys Glu Ser Gln Ser His Arg Phe Lys Gly Pro Cys Leu Ser
1               5                   10                  15

Asp Thr Asn Cys Gly Ser Val Cys Arg Thr Glu Arg Phe Thr Gly Gly
            20                  25                  30

His Cys Arg Gly Phe Arg Arg Arg Cys Phe Cys Thr Lys His Cys
        35                  40                  45

<210> SEQ ID NO 313
<211> LENGTH: 48
<212> TYPE: PRT
<213> ORGANISM: Gossypium hirsutum

<400> SEQUENCE: 313

Gly Pro Ile Cys Lys Ala Thr Ser Asn Val Tyr Lys Gly Leu Cys Leu
1               5                   10                  15

Ile Asp Asp Ser Cys Asp Ile Val Cys Lys Arg Glu Gly Phe His Lys
            20                  25                  30

Gly Asn Cys Lys Gly Phe Leu Arg Lys Cys Val Cys Thr Asn Pro Cys
        35                  40                  45

<210> SEQ ID NO 314
<211> LENGTH: 48
<212> TYPE: PRT
<213> ORGANISM: Gossypium hirsutum

<400> SEQUENCE: 314

Lys Thr Cys Glu Thr Lys Ser Gly Lys Phe Lys Gly Met Cys Met Ser
1               5                   10                  15

Ser Thr Asn Cys Ala Ser Val Cys Lys Ser Glu Pro Gly Phe Asp Gly
            20                  25                  30

Gly His Cys Arg Gly Phe Arg Arg Gln Cys Val Cys Thr Lys Pro Cys
        35                  40                  45

<210> SEQ ID NO 315
<211> LENGTH: 48
<212> TYPE: PRT
<213> ORGANISM: Gossypium hirsutum

<400> SEQUENCE: 315

```
Thr Thr Cys Glu Thr Gln Ser Gly Lys Phe Lys Gly Met Cys Met Ser
1               5                   10                  15

Ser Thr Asn Cys Ala Ser Val Cys Lys Ser Glu Pro Gly Phe Asp Gly
            20                  25                  30

Gly Tyr Cys Arg Gly Phe Arg Arg Gln Cys Phe Cys Thr Lys Pro Cys
        35                  40                  45
```

<210> SEQ ID NO 316
<211> LENGTH: 48
<212> TYPE: PRT
<213> ORGANISM: Gossypium hirsutum

<400> SEQUENCE: 316

```
Arg Thr Cys Glu Thr Lys Ser Ser Glu Tyr Lys Gly Ile Cys Leu Phe
1               5                   10                  15

Asp Ala Asn Cys Asp Ser Ile Cys Lys Val Glu Pro Ser Phe Asp Gly
            20                  25                  30

Gly His Cys His Gly Phe Phe Arg Arg Cys Tyr Cys Thr Lys Pro Cys
        35                  40                  45
```

<210> SEQ ID NO 317
<211> LENGTH: 48
<212> TYPE: PRT
<213> ORGANISM: Gossypium hirsutum

<400> SEQUENCE: 317

```
Arg Thr Cys Glu Thr Lys Ser Ser Glu Tyr Lys Gly Ile Cys Leu Phe
1               5                   10                  15

Asp Ala Asn Cys Asp Ser Val Cys Lys Val Glu Pro Gly Phe Asp Gly
            20                  25                  30

Gly His Cys His Gly Phe Phe Arg Arg Cys Tyr Cys Thr Lys Pro Ser
        35                  40                  45
```

<210> SEQ ID NO 318
<211> LENGTH: 51
<212> TYPE: PRT
<213> ORGANISM: Gossypium hirsutum

<400> SEQUENCE: 318

```
Met Glu Asp Arg Ile Cys Gln Ser Arg Ser Thr Glu Tyr Arg Gly Met
1               5                   10                  15

Cys Leu Phe Asp Val Asn Cys Asp Asn Ile Cys Lys Thr Glu Pro Gly
            20                  25                  30

Phe Thr Gly Gly His Cys His Ser Phe Phe Arg Ser Cys Tyr Cys Thr
        35                  40                  45

Lys Pro Cys
    50
```

<210> SEQ ID NO 319
<211> LENGTH: 48
<212> TYPE: PRT
<213> ORGANISM: Gossypium hirsutum

<400> SEQUENCE: 319

```
Arg Lys Cys Glu Ser Pro Ser His Lys Phe Lys Gly Met Cys Met Asn
1               5                   10                  15

Arg Asp Asn Cys Ala Ile Val Cys Gln Thr Glu Gly Tyr Glu Asp Gly
            20                  25                  30
```

Lys Cys Glu Gly Phe Arg Arg Arg Cys Ile Cys Ile Lys Pro Cys Phe
35 40 45

<210> SEQ ID NO 320
<211> LENGTH: 55
<212> TYPE: PRT
<213> ORGANISM: Gossypium hirsutum

<400> SEQUENCE: 320

Gly Pro Thr Ile Val Gly Gly Arg Lys Cys Asp Ser Pro Ser Lys Lys
1 5 10 15

Phe Asn Gly Met Cys Met Asn His Asp Asn Cys Ala Thr Val Cys Gln
20 25 30

Thr Glu Ser His Glu Asp Gly Lys Cys Glu Gly Phe Tyr Arg Arg Cys
35 40 45

Ile Cys Ile Lys Pro Cys Phe
50 55

<210> SEQ ID NO 321
<211> LENGTH: 52
<212> TYPE: PRT
<213> ORGANISM: Gossypium hirsutum

<400> SEQUENCE: 321

Gly Val Val Glu Gly Arg Ile Cys Glu Ser Lys Ser His Arg Phe Lys
1 5 10 15

Gly Val Cys Leu Ser Asp His Asn Cys Gly Leu Val Cys Arg Asn Glu
20 25 30

Gly Phe Leu Asp Gly Trp Cys Arg Gly Phe Arg His Arg Cys Phe Cys
35 40 45

Thr Arg Asn Cys
50

<210> SEQ ID NO 322
<211> LENGTH: 47
<212> TYPE: PRT
<213> ORGANISM: Gossypium hirsutum

<400> SEQUENCE: 322

Arg Val Cys Gln Ser Gln Ser His Lys Phe His Gly Ala Cys Val Ser
1 5 10 15

Ser His Asn Cys Ala Met Val Cys Arg Asp Glu Gly Phe Ser Gly Gly
20 25 30

Arg Cys Arg Gly Phe Arg Arg Arg Cys Phe Cys Thr Lys Leu Cys
35 40 45

<210> SEQ ID NO 323
<211> LENGTH: 50
<212> TYPE: PRT
<213> ORGANISM: Gossypium hirsutum

<400> SEQUENCE: 323

Asp Gly Asp Lys Ile Cys Glu Ser Pro Ser Asn Ala Phe Lys Gly Leu
1 5 10 15

Cys Leu Arg Asp Asp Asn Cys Asp Ile Val Cys Lys Thr Glu Gly Phe
20 25 30

Pro Asn Gly Asp Cys Lys Gly Phe Leu Arg Lys Cys Val Cys Thr Lys
35 40 45

Pro Cys
50

<210> SEQ ID NO 324
<211> LENGTH: 48
<212> TYPE: PRT
<213> ORGANISM: Gossypium hirsutum

<400> SEQUENCE: 324

Lys Thr Cys Glu Thr Gln Ser Gly Lys Phe Lys Gly Met Cys Met Ser
1 5 10 15

Ser Thr Asn Cys Ala Ser Val Cys Lys Ser Glu Pro Gly Phe Asp Gly
20 25 30

Gly His Cys Gln Gly Phe Arg Arg Gln Cys Val Cys Thr Lys Pro Cys
35 40 45

<210> SEQ ID NO 325
<211> LENGTH: 48
<212> TYPE: PRT
<213> ORGANISM: Gossypium hirsutum

<400> SEQUENCE: 325

Lys Thr Cys Val Ala Glu Ser Gly Lys Phe Lys Gly Met Cys Met Ser
1 5 10 15

Ser Thr Asn Cys Ala Ser Val Cys Lys Ser Glu Pro Gly Phe Asp Gly
20 25 30

Gly His Cys Gln Gly Phe Arg Arg Arg Cys Leu Cys Thr Lys Pro Cys
35 40 45

<210> SEQ ID NO 326
<211> LENGTH: 48
<212> TYPE: PRT
<213> ORGANISM: Gossypium hirsutum

<400> SEQUENCE: 326

Arg Thr Cys Glu Thr Lys Ser Ser Glu Tyr Lys Gly Ile Cys Leu Phe
1 5 10 15

Asp Ala Asn Cys Asp Ser Ile Cys Lys Val Glu Pro Gly Phe Asp Gly
20 25 30

Gly His Cys His Gly Phe Phe Arg Arg Cys Tyr Cys Thr Lys Pro Cys
35 40 45

<210> SEQ ID NO 327
<211> LENGTH: 48
<212> TYPE: PRT
<213> ORGANISM: Gossypium hirsutum

<400> SEQUENCE: 327

Lys Thr Cys Val Ala Glu Ser Gly Lys Phe Lys Gly Met Cys Met Ser
1 5 10 15

Ser Thr Asn Cys Ala Ser Val Cys Lys Ser Glu Pro Asp Phe Asp Gly
20 25 30

Gly His Cys Gln Gly Phe Arg Arg Arg Cys Leu Cys Thr Lys Pro Cys
35 40 45

<210> SEQ ID NO 328
<211> LENGTH: 48
<212> TYPE: PRT

<213> ORGANISM: Gossypium hirsutum

<400> SEQUENCE: 328

Arg Thr Cys Glu Thr Lys Ser Ser Glu Tyr Lys Gly Ile Cys Leu Phe
1               5                   10                  15

Asp Ala Asn Cys Asp Ser Ile Cys Lys Ile Glu Ser Gly Phe Asp Gly
            20                  25                  30

Gly His Cys His Gly Phe Phe Arg Arg Cys Tyr Cys Thr Lys Pro Cys
        35                  40                  45

<210> SEQ ID NO 329
<211> LENGTH: 65
<212> TYPE: PRT
<213> ORGANISM: Gossypium hirsutum

<400> SEQUENCE: 329

Asp Glu Glu His Lys Glu Ile Glu Ile Gly Thr Met Ala Glu Glu Glu
1               5                   10                  15

His Lys Ile Cys Glu Ser Lys Ser Gly Lys Phe Lys Gly Met Cys Phe
            20                  25                  30

Leu Asp Ala Asn Cys Asp Ser Ile Cys Lys Ala Glu Pro Gly Ser Thr
        35                  40                  45

Gly Gly His Cys His Gly Ile Phe Arg Ile Cys Tyr Cys Thr Lys Pro
    50                  55                  60

Cys
65

<210> SEQ ID NO 330
<211> LENGTH: 48
<212> TYPE: PRT
<213> ORGANISM: Gossypium hirsutum

<400> SEQUENCE: 330

Arg Lys Cys Glu Ser Pro Ser His Lys Phe Lys Gly Met Cys Met Asn
1               5                   10                  15

Arg Asp Asn Cys Ala Thr Val Cys Gln Thr Glu Gly Tyr Glu Asp Gly
            20                  25                  30

Lys Cys Glu Gly Phe Arg Arg Arg Cys Ile Cys Ile Lys Pro Cys Phe
        35                  40                  45

<210> SEQ ID NO 331
<211> LENGTH: 52
<212> TYPE: PRT
<213> ORGANISM: Gossypium hirsutum

<400> SEQUENCE: 331

Gly Met Val Glu Gly Arg Ile Cys Glu Ser Lys Ser His Arg Phe Lys
1               5                   10                  15

Gly Val Cys Leu Ser Asp His Asn Cys Gly Leu Val Cys Arg Asn Glu
            20                  25                  30

Gly Phe Leu Asp Gly Trp Cys Arg Gly Phe Arg His Arg Cys Phe Cys
        35                  40                  45

Thr Arg Asn Cys
    50

<210> SEQ ID NO 332
<211> LENGTH: 47
<212> TYPE: PRT
<213> ORGANISM: Gossypium hirsutum

<400> SEQUENCE: 332

Arg Val Cys Gln Ser Gln Ser His Lys Phe His Gly Ala Cys Leu Ser
1               5                   10                  15

Ser His Asn Cys Ala Met Val Cys Arg Asn Glu Gly Phe Ser Gly Gly
            20                  25                  30

Arg Cys Arg Gly Phe Arg Arg Arg Cys Phe Cys Thr Lys Leu Cys
        35                  40                  45

<210> SEQ ID NO 333
<211> LENGTH: 50
<212> TYPE: PRT
<213> ORGANISM: Gossypium raimondii

<400> SEQUENCE: 333

Asp Gly Asp Lys Ile Cys Glu Ser Arg Ser Asn Ala Phe Lys Gly Leu
1               5                   10                  15

Cys Leu Arg Asp Asn Asn Cys Asp Ile Val Cys Lys Thr Glu Gly Phe
            20                  25                  30

Pro Asn Gly Gly Cys Lys Gly Phe Ile Arg Lys Cys Val Cys Thr Lys
        35                  40                  45

Pro Cys
    50

<210> SEQ ID NO 334
<211> LENGTH: 48
<212> TYPE: PRT
<213> ORGANISM: Gossypium raimondii

<400> SEQUENCE: 334

Gly Thr Thr Cys Lys Ala Thr Ser Asn Ile Tyr Lys Gly Leu Cys Leu
1               5                   10                  15

Leu Asp Asp Ser Cys Asp Ile Val Cys Lys Arg Glu Gly Phe His Ser
            20                  25                  30

Gly Asn Cys Lys Gly Phe Leu Arg Lys Cys Val Cys Thr Asn Pro Cys
        35                  40                  45

<210> SEQ ID NO 335
<211> LENGTH: 50
<212> TYPE: PRT
<213> ORGANISM: Gossypium raimondii

<400> SEQUENCE: 335

Asp Gly Asp Lys Ile Cys Glu Ser Pro Ser Asn Ala Phe Lys Gly Leu
1               5                   10                  15

Cys Leu Arg Asp Asp Asn Cys Asp Ile Val Cys Lys Thr Glu Gly Phe
            20                  25                  30

Pro Asn Gly Asp Cys Lys Gly Phe Leu Arg Lys Cys Val Cys Thr Lys
        35                  40                  45

Pro Cys
    50

<210> SEQ ID NO 336
<211> LENGTH: 48
<212> TYPE: PRT
<213> ORGANISM: Gossypium raimondii

<400> SEQUENCE: 336

Lys Thr Cys Glu Val Glu Ser Gly Lys Phe Lys Gly Met Cys Met Ser
1               5                   10                  15

```
Ser Thr Asn Cys Ala Ser Val Cys Lys Ser Glu Pro Gly Phe Asp Gly
            20                  25                  30

Gly His Cys Gln Gly Phe Arg Arg Arg Cys Leu Cys Thr Lys Pro Cys
        35                  40                  45


<210> SEQ ID NO 337
<211> LENGTH: 48
<212> TYPE: PRT
<213> ORGANISM: Gossypium raimondii

<400> SEQUENCE: 337

Lys Thr Cys Glu Val Glu Ser Gly Lys Phe Lys Gly Met Cys Met Ser
1               5                   10                  15

Ser Thr Asn Cys Ala Ser Val Cys Lys Ser Glu Pro Gly Phe Asp Gly
            20                  25                  30

Gly His Cys Gln Gly Phe Arg Arg Arg Cys Leu Cys Thr Lys Pro Cys
        35                  40                  45


<210> SEQ ID NO 338
<211> LENGTH: 48
<212> TYPE: PRT
<213> ORGANISM: Gossypium raimondii

<400> SEQUENCE: 338

Arg Thr Cys Glu Thr Lys Ser Ser Glu Tyr Lys Gly Ile Cys Leu Phe
1               5                   10                  15

Asp Ala Asn Cys Asp Ser Ile Cys Lys Ile Glu Pro Gly Phe Asp Gly
            20                  25                  30

Gly His Cys His Gly Phe Phe Arg Arg Cys Tyr Cys Thr Lys Pro Cys
        35                  40                  45


<210> SEQ ID NO 339
<211> LENGTH: 48
<212> TYPE: PRT
<213> ORGANISM: Gossypium raimondii

<400> SEQUENCE: 339

Arg Lys Cys Glu Ser Pro Ser His Lys Phe Lys Gly Met Cys Met Asn
1               5                   10                  15

Arg Asp Asn Cys Ala Thr Val Cys Gln Thr Glu Gly Tyr Glu Asp Gly
            20                  25                  30

Lys Cys Glu Gly Phe Arg Arg Arg Cys Ile Cys Ile Lys Pro Cys Phe
        35                  40                  45


<210> SEQ ID NO 340
<211> LENGTH: 47
<212> TYPE: PRT
<213> ORGANISM: Vitis vinifera

<400> SEQUENCE: 340

Arg Val Cys Glu Ser Gln Ser His Lys Phe Glu Gly Ala Cys Met Gly
1               5                   10                  15

Asp His Asn Cys Ala Leu Val Cys Arg Asn Glu Gly Phe Ser Gly Gly
            20                  25                  30

Lys Cys Lys Gly Leu Arg Arg Arg Cys Phe Cys Thr Lys Leu Cys
        35                  40                  45


<210> SEQ ID NO 341
<211> LENGTH: 47
<212> TYPE: PRT
<213> ORGANISM: Vitis vinifera
```

<400> SEQUENCE: 341

```
Arg Thr Cys Glu Ser Gln Ser His Arg Phe Lys Gly Thr Cys Val Arg
1               5                   10                  15

Gln Ser Asn Cys Ala Ala Val Cys Gln Thr Glu Gly Phe His Gly Gly
            20                  25                  30

Asn Cys Arg Gly Phe Arg Arg Arg Cys Phe Cys Thr Lys His Cys
        35                  40                  45
```

<210> SEQ ID NO 342
<211> LENGTH: 47
<212> TYPE: PRT
<213> ORGANISM: Helianthus annuus

<400> SEQUENCE: 342

```
Arg Ile Cys Glu Ser Pro Ser His Lys Phe Lys Gly Ile Cys Leu Ser
1               5                   10                  15

Asp Thr Asn Cys Ser Ser Val Cys Gln Ser Glu Gly Phe Pro Trp Gly
            20                  25                  30

Lys Cys Ile Gly Phe Arg Arg Arg Cys Phe Cys Leu Arg Glu Cys
        35                  40                  45
```

<210> SEQ ID NO 343
<211> LENGTH: 47
<212> TYPE: PRT
<213> ORGANISM: Helianthus annuus

<400> SEQUENCE: 343

```
Arg Thr Cys Glu Ser Gln Ser His Lys Phe Lys Gly Thr Cys Leu Ser
1               5                   10                  15

Asp Thr Asn Cys Ala Asn Val Cys His Ser Glu Arg Phe Ser Gly Gly
            20                  25                  30

Lys Cys Arg Gly Phe Arg Arg Arg Cys Phe Cys Thr Thr His Cys
        35                  40                  45
```

<210> SEQ ID NO 344
<211> LENGTH: 47
<212> TYPE: PRT
<213> ORGANISM: Helianthus annuus

<400> SEQUENCE: 344

```
Arg Met Cys Gln Ser Gln Ser His Met Phe His Gly Thr Cys Met Arg
1               5                   10                  15

Asp His Asn Cys Ala Leu Val Cys Arg Asn Glu Gly Phe Ser Gly Gly
            20                  25                  30

Lys Cys Arg Gly Phe Arg Arg Arg Cys Phe Cys Thr Arg Leu Cys
        35                  40                  45
```

<210> SEQ ID NO 345
<211> LENGTH: 47
<212> TYPE: PRT
<213> ORGANISM: Helianthus annuus

<400> SEQUENCE: 345

```
Arg Ile Cys Glu Ser Gln Ser Gln Glu Phe His Gly Ser Cys Met Ser
1               5                   10                  15

Asn His Asn Cys Gly Leu Val Cys Arg Thr Glu Gly Phe Ser Ala Gly
            20                  25                  30

Ile Cys Arg Gly Val Arg Gly Arg Cys Phe Cys Leu Lys Thr Cys
        35                  40                  45
```

<210> SEQ ID NO 346
<211> LENGTH: 47
<212> TYPE: PRT
<213> ORGANISM: Hydrangea macrophylla

<400> SEQUENCE: 346

Arg Thr Cys Glu Ser Lys Ser Asn Arg Phe Lys Gly Pro Cys Ala Arg
1 5 10 15

Asp Ser Asn Cys Ala Thr Val Cys Gln Thr Glu Gly Phe Tyr Gly Gly
20 25 30

Asn Cys Lys Gly Phe Arg Arg Arg Cys Phe Cys Thr Lys Asn Cys
35 40 45

<210> SEQ ID NO 347
<211> LENGTH: 47
<212> TYPE: PRT
<213> ORGANISM: Hydrangea macrophylla

<400> SEQUENCE: 347

Arg Thr Cys Glu Ser Lys Ser His Arg Phe Lys Gly Pro Cys Val Ser
1 5 10 15

Ala Thr Asn Cys Gly Ser Val Cys Gln Thr Glu Gly Phe His Gly Gly
20 25 30

Asn Cys Arg Gly Phe Arg Arg Arg Cys Phe Cys Thr Lys His Cys
35 40 45

<210> SEQ ID NO 348
<211> LENGTH: 71
<212> TYPE: PRT
<213> ORGANISM: Vanilla planifolia

<400> SEQUENCE: 348

Arg Arg Cys Arg Ala Gln Ser Phe Thr Phe Lys Gly Ile Cys Tyr Ser
1 5 10 15

Ser His Ser Cys Ala Leu Val Cys Lys Lys Glu Gly Tyr Glu Thr Gly
20 25 30

His Cys Ser Arg Gly Phe Cys Thr Leu Leu Lys Pro Ala Asn Ala Glu
35 40 45

Gln Arg Ala Gln Ser Leu Gln Val Phe Ala Ser Val Pro Thr Pro Ala
50 55 60

Leu Leu Cys Val Ser Lys Lys
65 70

<210> SEQ ID NO 349
<211> LENGTH: 58
<212> TYPE: PRT
<213> ORGANISM: Cicer arietinum

<400> SEQUENCE: 349

Ser Glu Val Thr Ile Arg Val Ala Glu Gly Arg Glu Cys Arg Asp Leu
1 5 10 15

Ser His Lys Phe Lys Gly Phe Cys Val Arg Asp Arg Asn Cys Ala Asn
20 25 30

Val Cys Ser Thr Glu Gly Phe Thr Asn Gly His Cys Asp Gly Phe Arg
35 40 45

Arg Arg Cys Phe Cys Ser Arg Pro Cys Ala
50 55

```
<210> SEQ ID NO 350
<211> LENGTH: 49
<212> TYPE: PRT
<213> ORGANISM: Beta vulgaris subsp. vulgaris

<400> SEQUENCE: 350

Arg Val Cys Glu Thr Pro Ser His Lys Phe Gln Gly Ile Cys Ile Ser
1               5                   10                  15

Ser Arg Asn Cys Ala Ser Thr Cys Ala Ser Glu His Phe Pro Gly Gly
            20                  25                  30

Tyr Cys Arg Gly Leu Arg Arg Arg Cys Met Cys Thr Arg Pro Cys Val
        35                  40                  45

Asn


<210> SEQ ID NO 351
<211> LENGTH: 47
<212> TYPE: PRT
<213> ORGANISM: Beta vulgaris subsp. vulgaris

<400> SEQUENCE: 351

Arg Thr Cys Glu Thr Pro Ser Arg Lys Phe Arg Gly Ile Cys Val Ser
1               5                   10                  15

Arg Thr Asn Cys Ala Asn Val Cys Lys Thr Glu Gly Phe Pro Gly Gly
            20                  25                  30

Arg Cys Arg Gly Phe Arg Arg Arg Cys Phe Cys Leu Glu His Cys
        35                  40                  45


<210> SEQ ID NO 352
<211> LENGTH: 47
<212> TYPE: PRT
<213> ORGANISM: Beta vulgaris subsp. vulgaris

<400> SEQUENCE: 352

Arg Ile Cys Glu Ser Pro Ser Tyr Ser Phe Lys Gly Ile Cys Val Ser
1               5                   10                  15

Arg Thr Asn Cys Ala Asn Val Cys Lys Thr Glu Gly Phe Pro Gly Gly
            20                  25                  30

Arg Cys Arg Gly Leu Arg Arg Arg Cys Phe Cys Leu Lys His Cys
        35                  40                  45


<210> SEQ ID NO 353
<211> LENGTH: 47
<212> TYPE: PRT
<213> ORGANISM: Spinacea oleracea

<400> SEQUENCE: 353

Arg Thr Cys Glu Ser Arg Ser Tyr Arg Phe Lys Gly Ile Cys Val Ser
1               5                   10                  15

Arg Thr Asn Cys Ala Asn Val Cys Lys Thr Glu Gly Phe Pro Gly Gly
            20                  25                  30

Arg Cys Arg Gly Val Arg Arg Arg Cys Phe Cys Leu Lys His Cys
        35                  40                  45


<210> SEQ ID NO 354
<211> LENGTH: 47
<212> TYPE: PRT
<213> ORGANISM: Beta vulgaris subsp. vulgaris

<400> SEQUENCE: 354

Arg Thr Cys Glu Thr Pro Ser His Lys Phe Lys Gly Ile Cys Val Ser
1               5                   10                  15
```

```
Arg Thr Asn Cys Ala Asn Val Cys Lys Thr Glu Gly Phe Pro Ala Gly
            20                  25                  30

Arg Cys Arg Gly Phe Arg Arg Arg Cys Phe Cys Leu Thr His Cys
        35                  40                  45


<210> SEQ ID NO 355
<211> LENGTH: 47
<212> TYPE: PRT
<213> ORGANISM: Ipomoea triloba

<400> SEQUENCE: 355

Arg Ile Cys Glu Ser Lys Ser His His Tyr Lys Gly Met Cys Leu Arg
1               5                   10                  15

Asp His Asn Cys Ala Met Val Cys Arg Thr Glu Gly Phe Ser Gly Gly
            20                  25                  30

His Cys Ile Gly Ala Arg Arg Arg Cys Phe Cys Thr Arg Gly Cys
        35                  40                  45


<210> SEQ ID NO 356
<211> LENGTH: 47
<212> TYPE: PRT
<213> ORGANISM: Lupinus albus

<400> SEQUENCE: 356

Arg Thr Cys Glu Ser Gln Ser His Arg Phe Lys Gly Ala Cys Leu Ser
1               5                   10                  15

Asp Thr Asn Cys Gly Ser Val Cys His Asn Glu Gly Phe Asn Gly Gly
            20                  25                  30

His Cys Arg Gly Phe Arg Arg Arg Cys Phe Cys Thr Lys His Cys
        35                  40                  45


<210> SEQ ID NO 357
<211> LENGTH: 52
<212> TYPE: PRT
<213> ORGANISM: Lupinus albus

<400> SEQUENCE: 357

Phe Leu Gly Ser His Arg Cys Gly Lys Val Leu Ser Ser Arg Phe Lys
1               5                   10                  15

Gly Lys Cys Leu Thr Asp His Asn Cys Asp Ser Val Cys Gln Leu Glu
            20                  25                  30

Gly Tyr Val Gly Gly Asp Cys His Gly Val Arg Arg Arg Cys Phe Cys
        35                  40                  45

Asn Lys Lys Cys
    50


<210> SEQ ID NO 358
<211> LENGTH: 47
<212> TYPE: PRT
<213> ORGANISM: Lupinus albus

<400> SEQUENCE: 358

Arg His Cys Glu Ser Lys Ser His Arg Phe Lys Gly Leu Cys His Ser
1               5                   10                  15

Asp His Asn Cys Ala Ser Ile Cys Leu Val Glu Gly Phe Thr Ser Gly
            20                  25                  30

Lys Cys His Gly Phe Arg Gln Arg Cys Phe Cys Thr Lys Val Cys
        35                  40                  45
```

<210> SEQ ID NO 359
<211> LENGTH: 49
<212> TYPE: PRT
<213> ORGANISM: Lupinus albus

<400> SEQUENCE: 359

```
Arg Thr Arg Val Cys Glu Ser Gln Ser His Leu Phe Lys Gly Pro Cys
1               5                   10                  15

Ser Arg Asp His Asn Cys Ala Leu Val Cys Arg Asn Glu Ala Phe Ser
            20                  25                  30

Gly Gly Arg Cys Lys Gly Phe Arg Arg Arg Cys Phe Cys Thr Lys Leu
        35                  40                  45

Cys
```

<210> SEQ ID NO 360
<211> LENGTH: 59
<212> TYPE: PRT
<213> ORGANISM: Lupinus albus

<400> SEQUENCE: 360

```
Met Val Ile Glu Thr Glu Gly Val Leu Gly Arg Asn Arg Cys Asp Pro
1               5                   10                  15

Val Leu Ser Ser Arg Phe Lys Gly Lys Cys Phe Ser Asp His Asn Cys
            20                  25                  30

Asn Ser Val Cys Gln Leu Glu Gly Tyr Thr Asp Gly Asn Cys His Gly
        35                  40                  45

Leu Arg Gln Arg Cys Phe Cys Asn Arg Lys Cys
    50                  55
```

<210> SEQ ID NO 361
<211> LENGTH: 59
<212> TYPE: PRT
<213> ORGANISM: Lupinus albus

<400> SEQUENCE: 361

```
Ser Asp Asn Asn Val Gly Leu Lys Arg Ala Glu Gly Arg Val Cys Gln
1               5                   10                  15

Ser Lys Ser His Arg Phe Lys Gly Pro Cys Leu Ser Tyr Ser Asn Cys
            20                  25                  30

Gly His Val Cys Arg Asn Glu Gly Phe Ser Gly Gly Arg Cys Arg Gly
        35                  40                  45

Leu Arg Arg Arg Cys Phe Cys Thr Lys Asn Cys
    50                  55
```

<210> SEQ ID NO 362
<211> LENGTH: 59
<212> TYPE: PRT
<213> ORGANISM: Lupinus albus

<400> SEQUENCE: 362

```
Glu Met Gly Pro Thr Met Met Glu Glu Ala Arg Thr Cys Lys Ser Lys
1               5                   10                  15

Ser Gln Arg Tyr Lys Gly Ser Cys Tyr Ser Asp Asn Asn Cys Ala Ile
            20                  25                  30

Ile Cys Glu Gly Glu Gly Phe Thr Gly Gly Lys Cys His Gly Phe Phe
        35                  40                  45

Cys Lys Cys Trp Cys Lys Arg Pro Cys Leu Asp
    50                  55
```

<210> SEQ ID NO 363
<211> LENGTH: 69
<212> TYPE: PRT
<213> ORGANISM: Lupinus albus

<400> SEQUENCE: 363

```
Lys Glu Cys Ser Thr Lys Ser Asp Arg Phe Arg Gly Thr Cys Phe Arg
1               5                   10                  15

Ser Ser Asn Cys Ala Ala Val Cys Asn Ser Glu Asn Phe Pro Ser Gly
            20                  25                  30

Thr Cys Arg Gly Phe Pro Gly Thr Cys Tyr Cys Thr Ser Asn Cys Ala
        35                  40                  45

Ile Asn Ala Pro Ile Thr Asn Pro Pro Pro Glu Val Val Glu Pro Pro
    50                  55                  60

Pro Glu Val Val Glu
65
```

<210> SEQ ID NO 364
<211> LENGTH: 48
<212> TYPE: PRT
<213> ORGANISM: Lupinus albus

<400> SEQUENCE: 364

```
Lys Thr Cys Glu Ser Arg Ser His Lys Leu Lys Gly Phe Cys Tyr Ser
1               5                   10                  15

Ser Lys Arg Cys Ala His Val Cys Thr Ser His His Asn Phe Ile Gly
            20                  25                  30

Gly His Cys Arg Gly Phe Ile Arg Arg Cys His Cys Thr Lys Pro Cys
        35                  40                  45
```

<210> SEQ ID NO 365
<211> LENGTH: 48
<212> TYPE: PRT
<213> ORGANISM: Lupinus albus

<400> SEQUENCE: 365

```
Asn Asn Cys Lys Tyr Glu Ser Asn Lys Phe His Gly Val Cys Leu Ser
1               5                   10                  15

Asp Thr Asn Cys Glu Ser Val Cys Gln Thr Glu Gly Phe Pro Phe Gly
            20                  25                  30

Lys Cys Asp Gly Val Leu Pro Arg Thr Cys Val Cys Lys Lys Pro Cys
        35                  40                  45
```

<210> SEQ ID NO 366
<211> LENGTH: 47
<212> TYPE: PRT
<213> ORGANISM: Lotus japonica

<400> SEQUENCE: 366

```
Arg His Cys Glu Ser Lys Ser His Arg Phe His Gly Leu Cys Leu Ser
1               5                   10                  15

His His Asn Cys Ala Ser Val Cys His Leu Glu Gly Phe Thr Gly Gly
            20                  25                  30

Lys Cys Arg Gly Phe Arg Lys Arg Cys Phe Cys Lys Lys Arg Cys
        35                  40                  45
```

<210> SEQ ID NO 367
<211> LENGTH: 48
<212> TYPE: PRT
<213> ORGANISM: Lotus japonica

<400> SEQUENCE: 367

Arg Val Cys Gln Ser Gln Ser His Arg Phe Arg Gly Gly Cys Trp Gly
1 5 10 15

Asp His Asn Cys Ala Leu Val Cys Arg Asn Glu Gly Phe Ser Gly Gly
20 25 30

Arg Cys Arg Gly Phe Arg Arg Arg Cys Phe Cys Thr Arg Leu Cys Asn
35 40 45

<210> SEQ ID NO 368
<211> LENGTH: 47
<212> TYPE: PRT
<213> ORGANISM: Lotus japonica

<400> SEQUENCE: 368

Arg Val Cys Glu Thr Lys Ser His Thr Phe His His Ser Cys Val Ser
1 5 10 15

Gly His Asn Cys Ala Gln Val Cys Lys Thr Glu Gly Phe Thr Gly Gly
20 25 30

Lys Cys Arg Gly Phe Arg Arg Arg Cys Phe Cys Thr Lys Arg Cys
35 40 45

<210> SEQ ID NO 369
<211> LENGTH: 47
<212> TYPE: PRT
<213> ORGANISM: Lotus japonica

<400> SEQUENCE: 369

Arg Asp Cys Glu Ser Gln Ser His Arg Phe Lys Gly Pro Cys Val Ser
1 5 10 15

Asp Thr Asn Cys Ala Ser Val Cys His Gly Glu Lys Phe Ser Gly Gly
20 25 30

His Cys Arg Gly Phe Arg Arg Arg Cys Phe Cys Thr Lys His Cys
35 40 45

<210> SEQ ID NO 370
<211> LENGTH: 55
<212> TYPE: PRT
<213> ORGANISM: Lactuca sativa

<400> SEQUENCE: 370

Met Gly Val Glu Thr Lys Ser Cys Arg Tyr Ser Ser Lys Thr Tyr Lys
1 5 10 15

Gly Leu Cys Phe Tyr Ser Arg Asn Cys Asp Ile Ile Cys Lys Ala Glu
20 25 30

Gly Ala Pro Gly Gly Gly His Cys Gln Ile Leu Thr Leu Arg Cys Phe
35 40 45

Cys Asn Val Cys Asp Pro Asp
50 55

<210> SEQ ID NO 371
<211> LENGTH: 47
<212> TYPE: PRT
<213> ORGANISM: Manihot esculenta

<400> SEQUENCE: 371

Arg Ile Cys Glu Ser Gln Ser His Arg Phe Lys Gly Val Cys Val Arg
1 5 10 15

Lys Ser Asn Cys Ala Ala Ile Cys Gln Thr Glu Gly Phe His Gly Gly
20 25 30

```
His Cys Arg Gly Leu Arg Arg Arg Cys Phe Cys Thr Lys His Cys
        35                  40                  45


<210> SEQ ID NO 372
<211> LENGTH: 47
<212> TYPE: PRT
<213> ORGANISM: Manihot esculenta

<400> SEQUENCE: 372

Arg Val Cys Glu Ser Lys Ser His His Phe Arg Gly Leu Cys Thr Ile
1               5                   10                  15

Ala His Asn Cys Ala Met Val Cys Arg Asn Glu Gly Phe Ser Gly Gly
            20                  25                  30

Lys Cys Arg Gly Phe Arg Arg Arg Cys Phe Cys Thr Arg Leu Cys
        35                  40                  45


<210> SEQ ID NO 373
<211> LENGTH: 47
<212> TYPE: PRT
<213> ORGANISM: Manihot esculenta

<400> SEQUENCE: 373

Arg Val Cys Glu Ser Lys Ser His His Phe Arg Gly Val Cys Thr Ile
1               5                   10                  15

Ala His Asn Cys Ala Ile Val Cys Arg Asn Glu Gly Phe Ser Gly Gly
            20                  25                  30

Lys Cys Lys Gly Phe Arg Arg Arg Cys Phe Cys Thr Arg Leu Cys
        35                  40                  45


<210> SEQ ID NO 374
<211> LENGTH: 47
<212> TYPE: PRT
<213> ORGANISM: Manihot esculenta

<400> SEQUENCE: 374

Arg Lys Cys Glu Ser Gln Ser His Lys Phe Lys Gly Ile Cys Leu Ser
1               5                   10                  15

Asp Thr Asn Cys Ala Ser Val Cys Lys Thr Glu Gly Phe Thr Gly Gly
            20                  25                  30

Asp Cys Lys Gly Ala Arg Arg Arg Cys Phe Cys Thr Arg Gln Cys
        35                  40                  45


<210> SEQ ID NO 375
<211> LENGTH: 47
<212> TYPE: PRT
<213> ORGANISM: Manihot esculenta

<400> SEQUENCE: 375

Arg Lys Cys Glu Ser Gln Ser His Arg Phe Lys Gly Met Cys Thr Arg
1               5                   10                  15

His Ser Asn Cys Ala Ala Ile Cys Gln Thr Glu Gly Phe His Ala Gly
            20                  25                  30

His Cys Arg Gly Leu Arg Arg Arg Cys Phe Cys Thr Lys His Cys
        35                  40                  45


<210> SEQ ID NO 376
<211> LENGTH: 47
<212> TYPE: PRT
<213> ORGANISM: Malus domestica
```

<400> SEQUENCE: 376

Arg Val Cys Gln Ser Gln Ser His Gly Phe His Gly Thr Cys Leu Arg
1 5 10 15

His His Asn Cys Ala Leu Val Cys Arg Asn Glu Gly Phe Ser Gly Gly
20 25 30

Arg Cys Arg Gly Leu Arg Arg Arg Cys Phe Cys Thr Arg Leu Cys
35 40 45

<210> SEQ ID NO 377
<211> LENGTH: 57
<212> TYPE: PRT
<213> ORGANISM: Malus domestica

<400> SEQUENCE: 377

Arg Thr Glu Ser Ser Lys Ala Val Glu Gly Lys Ile Cys Glu Phe Pro
1 5 10 15

Ser Thr Leu Phe Lys Gly Leu Cys Phe Ser Ser Asn Asn Cys Lys His
20 25 30

Thr Cys Arg Lys Glu Gln Phe Thr Arg Gly Lys Cys Ser Leu Leu Thr
35 40 45

Arg Thr Cys Met Cys Thr Lys Lys Cys
50 55

<210> SEQ ID NO 378
<211> LENGTH: 47
<212> TYPE: PRT
<213> ORGANISM: Malus domestica

<400> SEQUENCE: 378

Arg Thr Cys Glu Ser Gln Ser Asn Arg Phe Lys Gly Thr Cys Val Ser
1 5 10 15

Lys Ser Asn Cys Ala Ala Val Cys Gln Thr Glu Gly Phe Pro Gly Gly
20 25 30

Asn Cys Arg Gly Leu Arg Arg Arg Cys Phe Cys Thr Lys His Cys
35 40 45

<210> SEQ ID NO 379
<211> LENGTH: 47
<212> TYPE: PRT
<213> ORGANISM: Malus domestica

<400> SEQUENCE: 379

Arg Thr Cys Glu Ser His Ser Arg Lys Tyr Lys Gly Thr Cys Leu Gly
1 5 10 15

Lys Ser Asn Cys Ala Ser Val Cys Gln Thr Glu Gly Phe His Gly Gly
20 25 30

His Cys Arg Gly Phe Arg Arg Arg Cys Phe Cys Thr Lys His Cys
35 40 45

<210> SEQ ID NO 380
<211> LENGTH: 63
<212> TYPE: PRT
<213> ORGANISM: Malus domestica

<400> SEQUENCE: 380

Arg Val Cys Glu Val Pro Ser Lys Thr Phe Arg Gly Leu Cys Phe Ser
1 5 10 15

Asp Thr His Cys Ile Val Lys Cys His Ser Glu Gly Phe Gly Tyr Gly
20 25 30

Lys Cys Ser His Val Leu Arg Gln Cys Arg Cys Leu Lys Ala Cys Gly
35 40 45

Arg Leu Ala Glu Ser Glu Thr Thr His Gly Thr Glu Thr Ser Pro
50 55 60

<210> SEQ ID NO 381
<211> LENGTH: 57
<212> TYPE: PRT
<213> ORGANISM: Malus domestica

<400> SEQUENCE: 381

Arg Thr Glu Pro Ser Lys Ala Val Glu Gly Lys Ile Cys Glu Val Pro
1 5 10 15

Ser Thr Leu Phe Lys Gly Leu Cys Ile Ser Ser Asn Asn Cys Lys His
20 25 30

Thr Cys Arg Lys Glu Gln Phe Thr Arg Gly His Cys Ser Val Phe Thr
35 40 45

Arg Ala Cys Val Cys Thr Lys Lys Cys
50 55

<210> SEQ ID NO 382
<211> LENGTH: 57
<212> TYPE: PRT
<213> ORGANISM: Malus domestica

<400> SEQUENCE: 382

Arg Val Glu Ser Ser Lys Ala Val Glu Gly Lys Ile Cys Glu Val Pro
1 5 10 15

Cys Thr Leu Phe Lys Gly Leu Cys Phe Ser Ser Asn Asn Cys Lys His
20 25 30

Thr Cys Arg Lys Glu Gln Phe Thr Arg Gly His Cys Ser Val Phe Thr
35 40 45

Arg Ala Cys Val Cys Thr Lys Lys Cys
50 55

<210> SEQ ID NO 383
<211> LENGTH: 57
<212> TYPE: PRT
<213> ORGANISM: Malus domestica

<400> SEQUENCE: 383

Arg Thr Glu Ser Asn Lys Ala Val Glu Gly Lys Ile Cys Glu Tyr Pro
1 5 10 15

Ser Thr Leu Phe Lys Gly Leu Cys Phe Ser Ser Asn Asn Cys Lys His
20 25 30

Thr Cys Arg Lys Glu Gln Phe Thr Arg Gly His Cys Ser Val Phe Thr
35 40 45

Arg Ala Cys Val Cys Thr Lys Lys Cys
50 55

<210> SEQ ID NO 384
<211> LENGTH: 60
<212> TYPE: PRT
<213> ORGANISM: Malus domestica

<400> SEQUENCE: 384

Lys Thr Asn Glu Asn Ser Ser Lys Asn Glu Lys Ser Ser Lys Ile Cys
1 5 10 15

```
Glu Ser Pro Ser His Lys Tyr Arg Gly Ile Cys Phe Arg Ser Ser Asn
            20                  25                  30

Cys Ala Thr Thr Cys Lys Lys Glu Gly Phe Met Gly Gly Lys Cys Ala
        35                  40                  45

Gly Phe Arg Met Arg Cys Val Cys Thr Lys Lys Cys
    50                  55                  60


<210> SEQ ID NO 385
<211> LENGTH: 60
<212> TYPE: PRT
<213> ORGANISM: Malus domestica

<400> SEQUENCE: 385

Lys Thr Lys Glu Glu Ser Ser Lys Asn Glu Lys Ser Ser Lys Ile Cys
1               5                   10                  15

Glu Ser Pro Ser His Lys Tyr Arg Gly Ile Cys Phe Arg Ser Ser Asn
            20                  25                  30

Cys Ala Thr Thr Cys Lys Lys Glu Gly Phe Met Gly Gly Lys Cys Ala
        35                  40                  45

Gly Phe Arg Met Arg Cys Val Cys Thr Lys Lys Cys
    50                  55                  60


<210> SEQ ID NO 386
<211> LENGTH: 59
<212> TYPE: PRT
<213> ORGANISM: Malus domestica

<400> SEQUENCE: 386

Lys Thr Glu Ser Ser Lys Ala Val Glu Gly Lys Ile Cys Glu Val Pro
1               5                   10                  15

Ser Thr Leu Phe Lys Gly Leu Cys Ile Ser Ser Asn Asn Cys Lys His
            20                  25                  30

Thr Cys Arg Lys Glu Gln Phe Thr Arg Gly Lys Cys Ile Gly Asp Gly
        35                  40                  45

Phe Thr Arg Lys Cys Val Cys Thr Lys Lys Cys
    50                  55


<210> SEQ ID NO 387
<211> LENGTH: 57
<212> TYPE: PRT
<213> ORGANISM: Malus domestica

<400> SEQUENCE: 387

Arg Ser Lys Ser Ser Lys Glu Val Gln Glu Arg Thr Cys Glu Ala Ala
1               5                   10                  15

Ser Gly Lys Phe Lys Gly Leu Cys Phe Ser Ser Thr Asn Cys Lys Asn
            20                  25                  30

Thr Cys Lys Arg Glu Gln Phe Thr Gly Gly Lys Cys Arg Gly Phe Arg
        35                  40                  45

Arg Arg Cys Met Cys Asn Lys Lys Cys
    50                  55


<210> SEQ ID NO 388
<211> LENGTH: 57
<212> TYPE: PRT
<213> ORGANISM: Malus domestica
```

```
<400> SEQUENCE: 388

Arg Ser Lys Ser Asp Lys Val Ala Lys Glu Arg Thr Cys Glu Ala Ala
1               5                   10                  15

Ser Gly Lys Phe Lys Gly Leu Cys Phe Ser Ser Thr Asn Cys Lys Asn
            20                  25                  30

Thr Cys Lys Val Glu Lys Phe Thr Gly Gly Gln Cys Gln Gly Phe Arg
        35                  40                  45

Arg Arg Cys Met Cys Asn Lys Lys Cys
    50                  55


<210> SEQ ID NO 389
<211> LENGTH: 57
<212> TYPE: PRT
<213> ORGANISM: Malus domestica

<400> SEQUENCE: 389

Arg Ser Lys Ser Gly Lys Ala Val Lys Glu Arg Thr Cys Glu Ala Thr
1               5                   10                  15

Ser Gly Lys Phe Lys Gly Met Cys Phe Ser Ser Thr Asn Cys Lys Asn
            20                  25                  30

Thr Cys Lys Thr Glu Lys Phe Ile Gly Gly Glu Cys His Gly Phe Arg
        35                  40                  45

Arg Arg Cys Ile Cys Asn Lys Lys Cys
    50                  55


<210> SEQ ID NO 390
<211> LENGTH: 57
<212> TYPE: PRT
<213> ORGANISM: Malus domestica

<400> SEQUENCE: 390

Arg Thr Glu Ser Ser Lys Ala Ile Glu Gly Lys Ile Cys Glu Val Pro
1               5                   10                  15

Ser Thr Leu Phe Lys Gly Leu Cys Phe Ser Ser Asn Asn Cys Lys His
            20                  25                  30

Thr Cys Arg Lys Glu Gln Phe Thr Arg Gly Lys Cys Ser Gly Leu Thr
        35                  40                  45

Arg Thr Cys Val Cys Thr Lys Lys Cys
    50                  55


<210> SEQ ID NO 391
<211> LENGTH: 57
<212> TYPE: PRT
<213> ORGANISM: Malus domestica

<400> SEQUENCE: 391

Arg Thr Glu Ser Ser Lys Ala Val Glu Gly Lys Ile Cys Glu Val Pro
1               5                   10                  15

Ser Thr Leu Phe Lys Gly Leu Cys Phe Ser Ser Asn Asn Cys Lys His
            20                  25                  30

Thr Cys Arg Lys Glu Gln Phe Thr Arg Gly Lys Cys Ser Gly Leu Thr
        35                  40                  45

Arg Thr Cys Met Cys Thr Lys Lys Cys
    50                  55


<210> SEQ ID NO 392
<211> LENGTH: 57
<212> TYPE: PRT
```

<213> ORGANISM: Malus domestica

<400> SEQUENCE: 392

Met Thr Glu Ser Asn Lys Ala Val Glu Gly Lys Ile Cys Glu Val Pro
1 5 10 15

Ser Thr Leu Phe Lys Gly Leu Cys Phe Ser Ser Asn Asn Cys Lys His
20 25 30

Thr Cys Arg Lys Glu Gln Phe Thr Arg Gly Lys Cys Ser Gly Leu Thr
35 40 45

Arg Thr Cys Met Cys Thr Lys Lys Cys
50 55

<210> SEQ ID NO 393
<211> LENGTH: 60
<212> TYPE: PRT
<213> ORGANISM: Malus domestica

<400> SEQUENCE: 393

Val Glu Ala Arg Ser Lys Ser Ser Lys Val Val Glu Glu Arg Thr Cys
1 5 10 15

Glu Ala Ala Ser Gly Lys Phe Lys Gly Leu Cys Phe Ser Ser Asn Asn
20 25 30

Cys Lys His Thr Cys Lys Arg Glu Gln Phe Thr Gly Gly Lys Cys Arg
35 40 45

Gly Phe Arg Arg Arg Cys Met Cys Asn Lys Lys Cys
50 55 60

<210> SEQ ID NO 394
<211> LENGTH: 47
<212> TYPE: PRT
<213> ORGANISM: Malus domestica

<400> SEQUENCE: 394

Arg Thr Cys Asp Ser Gln Ser His Arg Phe Lys Gly Ser Cys Val Ser
1 5 10 15

Lys Ser Asn Cys Ala Thr Val Cys Gln Thr Glu Gly Phe Arg Gly Gly
20 25 30

His Cys Arg Gly Phe Arg Arg Arg Cys Phe Cys Thr Lys His Cys
35 40 45

<210> SEQ ID NO 395
<211> LENGTH: 60
<212> TYPE: PRT
<213> ORGANISM: Malus domestica

<400> SEQUENCE: 395

Lys Thr Lys Glu Lys Ser Ser Lys Asn Glu Lys Ser Ser Lys Thr Cys
1 5 10 15

Glu Ser Pro Ser His Lys Tyr His Gly Ile Cys Phe Arg Ser Ser Asn
20 25 30

Cys Ala Thr Thr Cys Lys Lys Glu Gly Phe Met Gly Gly Lys Cys Thr
35 40 45

Gly Phe Trp Met Arg Cys Val Cys Thr Lys Lys Cys
50 55 60

<210> SEQ ID NO 396
<211> LENGTH: 60
<212> TYPE: PRT
<213> ORGANISM: Malus domestica

<400> SEQUENCE: 396

Lys Thr Lys Glu Lys Ser Ser Lys Asn Glu Lys Ser Ser Lys Ile Cys
1               5                   10                  15

Glu Ser Pro Ser His Lys Phe His Gly Ile Cys Phe Arg Ser Ser Asn
            20                  25                  30

Cys Ala Thr Thr Cys Lys Lys Glu Gly Phe Met Gly Gly Lys Cys Thr
        35                  40                  45

Gly Phe Arg Met Arg Cys Val Cys Thr Lys Lys Cys
    50                  55                  60

<210> SEQ ID NO 397
<211> LENGTH: 61
<212> TYPE: PRT
<213> ORGANISM: Malus domestica

<400> SEQUENCE: 397

Lys Ile Arg His Met Ser Lys Asp Glu Asn Ser Leu Thr Cys Glu Ser
1               5                   10                  15

Arg Ser His Lys Tyr His Gly Pro Cys Phe Arg Phe Ile Phe Ser Ser
            20                  25                  30

Asn Cys Ala Val Thr Cys Lys Gly Glu Gly Phe Thr Gly Gly Lys Cys
        35                  40                  45

Lys Gly Phe His Met Arg Cys Ile Cys Thr Lys Gln Cys
    50                  55                  60

<210> SEQ ID NO 398
<211> LENGTH: 59
<212> TYPE: PRT
<213> ORGANISM: Malus domestica

<400> SEQUENCE: 398

Lys Thr Lys Gly Lys Pro Ser Lys Asn Val Lys Leu Ser Lys Thr Cys
1               5                   10                  15

Glu Ser Pro Ser Gln Lys Tyr Pro Gly Ile Cys Arg Ser Ser Tyr Cys
            20                  25                  30

Ala Ala Ile Cys Lys Gln Gln Gly Leu Met Gly Gly Lys Cys Thr Gly
        35                  40                  45

Phe Arg Arg Lys Cys Val Cys Thr Lys Lys Cys
    50                  55

<210> SEQ ID NO 399
<211> LENGTH: 57
<212> TYPE: PRT
<213> ORGANISM: Malus domestica

<400> SEQUENCE: 399

Arg Thr Glu Ser Ser Lys Ala Ile Glu Gly Lys Ile Cys Glu Phe Pro
1               5                   10                  15

Ser Thr Leu Phe Lys Gly Leu Cys Phe Ser Ser Asn Asn Cys Lys His
            20                  25                  30

Thr Cys Arg Lys Glu Gln Phe Thr Arg Gly Lys Cys Ser Leu Leu Thr
        35                  40                  45

Arg Thr Cys Met Cys Thr Lys Lys Cys
    50                  55

<210> SEQ ID NO 400
<211> LENGTH: 60
<212> TYPE: PRT
<213> ORGANISM: Malus domestica

<400> SEQUENCE: 400

Arg Ser Gly Met Thr Ser Lys Gly Ala Ala Glu Lys Lys Lys Cys Asp
1 5 10 15

Ser His Pro Ser Ser Lys Phe Lys Gly Val Cys Phe Phe Thr Asn Asn
20 25 30

Cys Val Asp Thr Cys Lys Leu Glu Gly Ser Ser Gly Gly Gln Cys Arg
35 40 45

Gly Phe Arg Arg Arg Cys Ile Cys Thr Lys Gln Cys
50 55 60

<210> SEQ ID NO 401
<211> LENGTH: 57
<212> TYPE: PRT
<213> ORGANISM: Malus domestica

<400> SEQUENCE: 401

Lys Ser Lys Ser Ser Lys Glu Val Glu Lys Arg Thr Cys Glu Ala Ala
1 5 10 15

Ser Gly Lys Phe Lys Gly Met Cys Phe Ser Ser Asn Asn Cys Ala Asn
20 25 30

Thr Cys Ala Arg Glu Lys Phe Asp Gly Gly Lys Cys Lys Gly Phe Arg
35 40 45

Arg Arg Cys Met Cys Thr Lys Lys Cys
50 55

<210> SEQ ID NO 402
<211> LENGTH: 47
<212> TYPE: PRT
<213> ORGANISM: Malus domestica

<400> SEQUENCE: 402

Arg Thr Cys Glu Ser Gln Ser Asn Arg Phe Lys Gly Ser Cys Val Ser
1 5 10 15

Lys Ser Asn Cys Ala Ala Val Cys Gln Thr Glu Gly Phe Pro Gly Gly
20 25 30

Asn Cys Arg Gly Leu Arg Arg Arg Cys Phe Cys Thr Lys His Cys
35 40 45

<210> SEQ ID NO 403
<211> LENGTH: 47
<212> TYPE: PRT
<213> ORGANISM: Malus domestica

<400> SEQUENCE: 403

Arg Thr Cys Glu Ser Gln Ser Arg Lys Phe Lys Gly Thr Cys Leu Ser
1 5 10 15

Lys Thr Asn Cys Ala Ser Val Cys Gln Thr Glu Gly Phe Pro Gly Gly
20 25 30

Asn Cys Arg Gly Phe Arg Arg Arg Cys Phe Cys Thr Lys His Cys
35 40 45

<210> SEQ ID NO 404
<211> LENGTH: 57
<212> TYPE: PRT
<213> ORGANISM: Medicago truncatula

<400> SEQUENCE: 404

Gln Pro Thr His Val Glu Glu Pro Glu Ala Arg Thr Cys Asp Ser Gln
1 5 10 15

Ser His Ser Phe Lys Gly Val Cys Trp Ile Lys His Asn Cys Ala Asn
            20                  25                  30

Val Cys Lys Thr Glu Gly Phe Thr Gly Gly His Cys His Gly Phe Arg
        35                  40                  45

Arg Arg Cys Phe Cys Ser Lys Pro Cys
    50                  55

<210> SEQ ID NO 405
<211> LENGTH: 76
<212> TYPE: PRT
<213> ORGANISM: Medicago truncatula

<400> SEQUENCE: 405

Glu Glu Phe Asn Phe Ala Pro Phe Thr Pro Leu His Phe Arg Val Glu
1               5                   10                  15

Ser Cys Phe Thr Arg Ser Arg Arg Tyr Asn Gly Ile Cys Leu Ser Asp
            20                  25                  30

Glu Ser Cys Phe Lys Ala Cys Ser Leu Glu Gly Tyr Ala Cys Gly Arg
        35                  40                  45

Cys Glu Lys Arg Arg Pro Tyr Leu Gly Asp His Cys Cys Cys Lys Lys
    50                  55                  60

Ser Cys Gln Leu Lys Leu Val Leu Ala Val Leu Cys
65                  70                  75

<210> SEQ ID NO 406
<211> LENGTH: 50
<212> TYPE: PRT
<213> ORGANISM: Medicago truncatula

<400> SEQUENCE: 406

Arg Lys His Cys Arg Glu Lys Ser Arg Leu Phe Glu Glu Leu Cys Phe
1               5                   10                  15

Asn Ser Glu Asp Cys Ala Asn Thr Cys Arg Tyr Glu Gly Phe His Leu
            20                  25                  30

Gly Gly Lys Cys Trp Gly Leu Phe Arg Thr Cys Tyr Cys Lys Lys Lys
        35                  40                  45

Cys Arg
    50

<210> SEQ ID NO 407
<211> LENGTH: 47
<212> TYPE: PRT
<213> ORGANISM: Medicago truncatula

<400> SEQUENCE: 407

Arg His Cys Glu Ser Lys Ser His Arg Phe Lys Gly Met Cys Met Ser
1               5                   10                  15

Asp His Asn Cys Ala Ser Val Cys His Val Glu Gly Phe Pro Gly Gly
            20                  25                  30

Asn Cys Arg Gly Phe Arg Arg Arg Cys Phe Cys Lys Lys Arg Cys
        35                  40                  45

<210> SEQ ID NO 408
<211> LENGTH: 47
<212> TYPE: PRT
<213> ORGANISM: Medicago truncatula

<400> SEQUENCE: 408

Arg Thr Cys Glu Ser Gln Ser His Lys Phe Lys Gly Pro Cys Ala Ser
1 5 10 15

Asp His Asn Cys Ala Ser Val Cys Gln Thr Glu Arg Phe Ser Gly Gly
20 25 30

His Cys Arg Gly Phe Arg Arg Arg Cys Phe Cys Thr Thr His Cys
35 40 45

<210> SEQ ID NO 409
<211> LENGTH: 47
<212> TYPE: PRT
<213> ORGANISM: Medicago truncatula

<400> SEQUENCE: 409

Arg Thr Cys Glu Thr Pro Ser Asn Ser Phe Lys Gly Ala Cys Phe Ser
1 5 10 15

Asp Thr Asn Cys Ala Ser Val Cys Gln Thr Glu Gly Phe Pro Gly Gly
20 25 30

His Cys Lys Gly Phe Arg Gln Arg Cys Phe Cys Thr Lys Pro Cys
35 40 45

<210> SEQ ID NO 410
<211> LENGTH: 47
<212> TYPE: PRT
<213> ORGANISM: Medicago truncatula

<400> SEQUENCE: 410

Arg Thr Cys Glu Thr Pro Ser Asn Asn Phe Lys Gly Leu Cys Val Ser
1 5 10 15

Asp Thr Asn Cys Ala Ser Val Cys Gln Thr Glu Gly Phe Pro Gly Gly
20 25 30

His Cys Glu Gly Phe Arg Gln Arg Cys Phe Cys Thr Lys Pro Cys
35 40 45

<210> SEQ ID NO 411
<211> LENGTH: 50
<212> TYPE: PRT
<213> ORGANISM: Medicago truncatula

<400> SEQUENCE: 411

Arg Lys Cys Leu Ser Gln Ser His Ser Phe Lys Gly Leu Cys Leu Ser
1 5 10 15

Asp Gln Asn Cys Ala Thr Val Cys Leu Thr Glu Gly Phe Thr Asp Gly
20 25 30

Arg Cys Arg Gly Phe Arg Gln Arg Cys Phe Cys Ser Lys Pro Cys Leu
35 40 45

Lys Val
50

<210> SEQ ID NO 412
<211> LENGTH: 47
<212> TYPE: PRT
<213> ORGANISM: Medicago truncatula

<400> SEQUENCE: 412

Arg Arg Cys Glu Ser Lys Ser His Lys Phe Lys Gly Pro Cys Ser Arg
1 5 10 15

Asp Ser Asn Cys Ala Ser Val Cys Arg Gly Glu Gly Phe Thr Gly Gly
20 25 30

Asp Cys Arg Gly Phe Arg Arg Arg Cys Phe Cys Thr Arg Asn Cys
35 40 45

<210> SEQ ID NO 413
<211> LENGTH: 47
<212> TYPE: PRT
<213> ORGANISM: Medicago truncatula

<400> SEQUENCE: 413

Arg Arg Cys Glu Ser Gln Ser His Lys Phe Lys Gly Pro Cys Val Ser
1 5 10 15

Asp Ser Asn Cys Gly Ser Val Cys Arg Gly Glu Gly Phe Ile Gly Gly
20 25 30

Asp Cys Arg Gly Val Arg His Arg Cys Phe Cys Thr Arg Asn Cys
35 40 45

<210> SEQ ID NO 414
<211> LENGTH: 48
<212> TYPE: PRT
<213> ORGANISM: Cucumis melo

<400> SEQUENCE: 414

Arg Val Cys Glu Ser Pro Ser His Asn Phe Lys Gly Leu Cys Phe Ser
1 5 10 15

Asp Thr Asn Cys Gly Asn Ile Cys Lys Thr Glu Gly Phe Ser Gly Gly
20 25 30

Leu Cys Arg Gly Phe Arg Arg Arg Cys Phe Cys Thr Lys His Cys Val
35 40 45

<210> SEQ ID NO 415
<211> LENGTH: 47
<212> TYPE: PRT
<213> ORGANISM: Cucumis melo

<400> SEQUENCE: 415

Arg Met Cys Gln Ser Gln Ser His His Phe His Gly Thr Cys Ile Arg
1 5 10 15

Asp His Asn Cys Ala Leu Val Cys Arg Thr Glu Gly Phe Ser Gly Gly
20 25 30

Glu Cys Val Gly Phe Arg Arg Arg Cys Phe Cys Thr His Arg Cys
35 40 45

<210> SEQ ID NO 416
<211> LENGTH: 58
<212> TYPE: PRT
<213> ORGANISM: Mimulus guttatus

<400> SEQUENCE: 416

Val Lys Glu Val Gly Thr Val Glu Asp Glu Lys Lys Val Cys Lys Tyr
1 5 10 15

Lys Ser Lys Lys Phe Trp Gly Val Cys Leu Ser Asp Ile Arg Cys Thr
20 25 30

Asp Val Cys Lys Arg Glu Gly Phe Gln Gly Gly Asp Cys Gln Gly Ile
35 40 45

Arg Arg Arg Cys Leu Cys Tyr Asn Arg Cys
50 55

<210> SEQ ID NO 417
<211> LENGTH: 48
<212> TYPE: PRT

<213> ORGANISM: Mimulus guttatus

<400> SEQUENCE: 417

Thr Arg Thr Cys Glu Ala Lys Ser His Arg Phe Lys Gly Ile Cys Ala
1               5                   10                  15

Arg Lys Ala Asn Cys Ala Ala Val Cys Gln Thr Glu Gly Phe His Gly
            20                  25                  30

Gly His Cys Arg Gly Phe Arg Arg Arg Cys Phe Cys Thr Lys His Cys
        35                  40                  45

<210> SEQ ID NO 418
<211> LENGTH: 47
<212> TYPE: PRT
<213> ORGANISM: Mimulus guttatus

<400> SEQUENCE: 418

Arg Val Cys Glu Ser Lys Ser Ala Ser Tyr Lys Gly Val Cys Val Leu
1               5                   10                  15

Asp Val Thr Cys Lys Leu Ala Cys Leu Asn Glu Gly Phe Ala Asp Gly
            20                  25                  30

Asp Cys Glu Gly Val Arg Arg Arg Cys Met Cys Arg Arg Pro Cys
        35                  40                  45

<210> SEQ ID NO 419
<211> LENGTH: 39
<212> TYPE: PRT
<213> ORGANISM: Mimulus guttatus

<400> SEQUENCE: 419

Phe Lys Gly Ile Cys Val Leu Asp Glu Thr Cys Arg Leu Ala Cys Leu
1               5                   10                  15

Asn Glu Gly Phe Ser Asp Gly Asp Cys Glu Gly Leu Arg Arg Arg Cys
            20                  25                  30

Leu Cys Arg Lys Pro Cys Lys
        35

<210> SEQ ID NO 420
<211> LENGTH: 72
<212> TYPE: PRT
<213> ORGANISM: Mimulus guttatus

<400> SEQUENCE: 420

Ala Leu Cys Glu Thr Lys Ser Ser Ile Phe Thr Gly Ala Cys Phe Ser
1               5                   10                  15

Asp Arg Asn Cys Glu Thr Ile Cys Glu Lys Glu Gly Phe Leu Asn Gly
            20                  25                  30

Arg Cys Lys Leu Trp Lys Cys Ile Cys Ser Lys Asp Cys Gly Ile Gly
        35                  40                  45

Gly Gly Gly Gly Val Val Val Pro Pro Gly Gly Gly Gly Asp Val Pro
    50                  55                  60

Pro Gly Gly Gly Asp Asp Val Pro
65                  70

<210> SEQ ID NO 421
<211> LENGTH: 48
<212> TYPE: PRT
<213> ORGANISM: Mimulus guttatus

<400> SEQUENCE: 421

```
Arg Met Cys Glu Thr Gln Ser His Gly Phe Lys Gly Gln Cys Trp Ser
1               5                   10                  15

Glu His Asn Cys Arg Leu Val Cys Ala His Glu Gly Phe Arg Gly Gly
            20                  25                  30

Lys Cys Arg Gly Phe Arg Lys Arg Cys Phe Cys Thr Arg Pro Cys His
        35                  40                  45
```

<210> SEQ ID NO 422
<211> LENGTH: 47
<212> TYPE: PRT
<213> ORGANISM: Mimulus guttatus

<400> SEQUENCE: 422

```
Arg Thr Cys Leu Ser Gln Ser Gln Arg Phe Arg Gly Pro Cys Val Ser
1               5                   10                  15

Asp Thr Asn Cys Arg Leu Val Cys His Asn Glu Gly Phe Ser Gly Gly
            20                  25                  30

Asp Cys Gln Gly Phe Arg Arg Arg Cys Phe Cys Thr Lys His Cys
        35                  40                  45
```

<210> SEQ ID NO 423
<211> LENGTH: 64
<212> TYPE: PRT
<213> ORGANISM: Mimulus guttatus

<400> SEQUENCE: 423

```
Gln Ser Asn Val Asp Gly Glu Ile Ala Asp Tyr Leu Lys Ile Glu Glu
1               5                   10                  15

Lys Lys Arg Cys Asn Tyr Glu Ser Lys Lys Phe Trp Gly Ile Cys Leu
            20                  25                  30

Ser Asp Ser Lys Cys Gly Glu Val Cys Thr Lys Glu Gly Phe Glu Gly
        35                  40                  45

Gly Asp Cys Lys Gly Leu Arg Arg Arg Cys Tyr Cys Phe Asn Asn Cys
    50                  55                  60
```

<210> SEQ ID NO 424
<211> LENGTH: 71
<212> TYPE: PRT
<213> ORGANISM: Mimulus guttatus

<400> SEQUENCE: 424

```
Ser Leu Cys Glu Thr Pro Ser Arg Tyr Phe Asn Gly Ile Cys Phe Ser
1               5                   10                  15

Arg Arg Asn Cys Gly Ala Ile Cys Glu Lys Glu Gly Phe Ser Ser Gly
            20                  25                  30

Arg Cys Lys Ala Phe Lys Cys Val Cys Gly Lys Asp Cys Asn Ala Ala
        35                  40                  45

Gly Gly Gly Gly Gly Gly Gly Gly Gly Asp Pro Gly Leu Gly Pro Pro
    50                  55                  60

Val Glu Gly Pro Pro Asp Gln
65                  70
```

<210> SEQ ID NO 425
<211> LENGTH: 47
<212> TYPE: PRT
<213> ORGANISM: Mimulus guttatus

<400> SEQUENCE: 425

Arg Thr Cys Glu Ser Gln Ser His Gly Phe Lys Gly Arg Cys Leu Ser
1               5                   10                  15

Asp His Asn Cys Gly Met Val Cys Lys Asn Glu Gly Phe Ser Asn Gly
            20                  25                  30

Trp Cys Arg Gly Phe Arg Gln Arg Cys Phe Cys Thr Arg Ala Cys
        35                  40                  45

<210> SEQ ID NO 426
<211> LENGTH: 47
<212> TYPE: PRT
<213> ORGANISM: Mimulus guttatus

<400> SEQUENCE: 426

Arg Thr Cys Thr Ser Lys Ser Ser Asn Phe Lys Gly Leu Cys Phe Ser
1               5                   10                  15

Ser His Asn Cys Lys Ala Val Cys Asn Gly Glu Asn Phe Pro Asp Gly
            20                  25                  30

Lys Cys His Gly Phe Lys Arg Arg Cys Phe Cys Gln Lys Pro Cys
        35                  40                  45

<210> SEQ ID NO 427
<211> LENGTH: 47
<212> TYPE: PRT
<213> ORGANISM: Mimulus guttatus

<400> SEQUENCE: 427

Arg Thr Cys Glu Ser Gln Ser Phe Asn Phe Arg Gly Pro Cys Val Ile
1               5                   10                  15

Asp His Asn Cys Lys Ala Val Cys Glu Ser Glu Gly Phe Thr Asp Gly
            20                  25                  30

Asp Cys Gln Gly Phe Arg Arg Arg Cys Phe Cys Arg Lys Pro Cys
        35                  40                  45

<210> SEQ ID NO 428
<211> LENGTH: 62
<212> TYPE: PRT
<213> ORGANISM: Handroanthus impetiginosus

<400> SEQUENCE: 428

Ala Leu Cys Glu Lys Pro Ser Arg Leu Tyr Asn Gly Ser Cys Thr Glu
1               5                   10                  15

Glu Arg Leu Cys Ile Glu Ile Cys Gln Lys Glu Ala Tyr Pro Ser Gly
            20                  25                  30

Arg Cys Asp Leu Leu Lys Cys Met Cys Ile Asn Lys Cys Pro Pro Val
        35                  40                  45

Gly Ala Gly Gln Gly Ala Gly Ser Asp Gly Gln Arg Gly Ile
    50                  55                  60

<210> SEQ ID NO 429
<211> LENGTH: 47
<212> TYPE: PRT
<213> ORGANISM: Nicotiana tabacum

<400> SEQUENCE: 429

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

```
Asp Cys Arg Gly Phe Arg Arg Arg Cys Phe Cys Thr Arg Pro Cys
        35                  40                  45


<210> SEQ ID NO 430
<211> LENGTH: 47
<212> TYPE: PRT
<213> ORGANISM: Nicotiana tabacum

<400> SEQUENCE: 430

Arg His Cys Glu Ser Gln Ser Gln Arg Phe Arg Gly Leu Cys Val Arg
1               5                   10                  15

Glu Lys Asn Cys Ala Ala Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45


<210> SEQ ID NO 431
<211> LENGTH: 47
<212> TYPE: PRT
<213> ORGANISM: Nicotiana tabacum

<400> SEQUENCE: 431

Arg Val Cys Met Ser Pro Ser His Gly Tyr His Gly Pro Cys Trp His
1               5                   10                  15

Asp His Asn Cys Ala Leu Val Cys Arg Asn Glu Gly Phe Ser Gly Gly
            20                  25                  30

Asp Cys Val Gly Ile Gln Arg Lys Cys Tyr Cys Thr Lys Leu Cys
        35                  40                  45


<210> SEQ ID NO 432
<211> LENGTH: 47
<212> TYPE: PRT
<213> ORGANISM: Nicotiana tabacum

<400> SEQUENCE: 432

Arg Thr Cys Glu Ser Gln Ser His Arg Phe His Gly Thr Cys Val Arg
1               5                   10                  15

Gly Ser Asn Cys Ala Ser Val Cys Gln Thr Glu Gly Phe Ile Gly Gly
            20                  25                  30

Asn Cys Arg Gly Leu Arg Arg Arg Cys Phe Cys Thr Arg Asn Cys
        35                  40                  45


<210> SEQ ID NO 433
<211> LENGTH: 58
<212> TYPE: PRT
<213> ORGANISM: Nicotiana tabacum

<400> SEQUENCE: 433

Thr Glu Met Gly Pro Met Thr Ile Ala Glu Ala Arg Arg Cys Glu Ser
1               5                   10                  15

Lys Ser Gln Arg Phe Arg Gly Pro Cys Val Arg Glu Lys Asn Cys Ala
            20                  25                  30

Ala Val Cys Glu Thr Glu Gly Phe Ser Gly Gly Asp Cys Arg Gly Leu
        35                  40                  45

Arg Arg Arg Cys Phe Cys Thr Arg Pro Cys
    50                  55


<210> SEQ ID NO 434
<211> LENGTH: 48
<212> TYPE: PRT
```

<213> ORGANISM: Nelumbo nucifera

<400> SEQUENCE: 434

```
Arg Thr Cys Glu Ser Gln Ser His Arg Phe Lys Gly Ile Cys Val Arg
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys His Cys Ala
        35                  40                  45
```

<210> SEQ ID NO 435
<211> LENGTH: 13
<212> TYPE: PRT
<213> ORGANISM: Nelumbo nucifera

<400> SEQUENCE: 435

```
Cys Arg Asp Gly Ala Lys Ser Ser Arg Gly Lys Asp Leu
1               5                   10
```

<210> SEQ ID NO 436
<211> LENGTH: 49
<212> TYPE: PRT
<213> ORGANISM: Nelumbo nucifera

<400> SEQUENCE: 436

```
Lys Met Cys Lys Thr Pro Ser Arg Gln Phe Arg Gly Leu Cys Leu Ile
1               5                   10                  15

Gly Arg Asn Cys Asp Asn Val Cys Arg Gly Glu Gly Phe Pro Asp Gly
            20                  25                  30

Asp Cys Asp Gly Phe Arg Arg Arg Cys Ile Cys Ser Arg Pro Cys Arg
        35                  40                  45

Pro
```

<210> SEQ ID NO 437
<211> LENGTH: 100
<212> TYPE: PRT
<213> ORGANISM: Nelumbo nucifera

<400> SEQUENCE: 437

```
Arg Met Cys Asp Thr Pro Ser Gln Lys Phe Val Gly Leu Cys Leu Ile
1               5                   10                  15

Asp Arg Asn Cys Glu Asn Val Cys Lys Thr Glu Gly Phe Pro Ala Gly
            20                  25                  30

His Cys Glu Gly Leu Arg Arg Arg Cys Phe Cys Ser Glu Pro Cys Pro
        35                  40                  45

Pro Asn Asn Gly Met Glu Arg Lys Phe Leu Cys Gly Val Leu Leu Phe
    50                  55                  60

Leu Thr Leu Leu Tyr Ala Ser Leu Gly Glu Glu Met Val Val Asn Glu
65                  70                  75                  80

Gly Pro Ala Asp Gly Gly Arg Val Cys Ser Thr Pro Ser Leu Asn Tyr
                85                  90                  95

Arg Gly Pro Cys
            100
```

<210> SEQ ID NO 438
<211> LENGTH: 49
<212> TYPE: PRT
<213> ORGANISM: Nelumbo nucifera

<400> SEQUENCE: 438

```
Arg Met Cys Asp Thr Pro Ser Arg Leu Phe Arg Gly Leu Cys Leu Ile
1               5                   10                  15

Asn Arg Asn Cys Asp Asn Thr Cys Arg Val Glu Gly Phe Pro Asp Gly
            20                  25                  30

His Cys Lys Gly Leu Arg Arg Arg Cys Phe Cys Ser Arg Pro Cys Arg
        35                  40                  45

Pro
```

<210> SEQ ID NO 439
<211> LENGTH: 49
<212> TYPE: PRT
<213> ORGANISM: Olea europea

<400> SEQUENCE: 439

```
Arg Ile Cys Glu Ser Leu Ser His Arg Phe Lys Gly Pro Cys Val Arg
1               5                   10                  15

Asn Ala Asn Cys Ala Ala Val Cys Gln Thr Glu Gly Phe Pro Gly Gly
            20                  25                  30

His Cys Arg Gly Phe Arg Arg Arg Cys Phe Cys Thr Lys Pro Cys Ser
        35                  40                  45

Asp
```

<210> SEQ ID NO 440
<211> LENGTH: 47
<212> TYPE: PRT
<213> ORGANISM: Olea europea

<400> SEQUENCE: 440

```
Arg Ile Cys Glu Ser Leu Ser His Arg Phe Lys Gly Pro Cys Val Arg
1               5                   10                  15

Arg Gly Asn Cys Ala Ala Val Cys Gln Thr Glu Gly Phe Pro Gly Gly
            20                  25                  30

Leu Cys Arg Gly Phe Arg Arg Arg Cys Phe Cys Thr Lys His Cys
        35                  40                  45
```

<210> SEQ ID NO 441
<211> LENGTH: 70
<212> TYPE: PRT
<213> ORGANISM: Oryza sativa

<400> SEQUENCE: 441

```
Ile Ile Cys Lys Ala Arg Ser Lys Met Tyr Arg Gly Lys Cys Arg Gly
1               5                   10                  15

Asn Arg Asn Cys Ala Met Ile Cys Val His Glu Glu Tyr Thr Gly Gly
            20                  25                  30

Tyr Cys Ser Lys Gly Val Phe Ser Lys Cys Met Cys Thr Lys Arg Cys
        35                  40                  45

Gly Gly Gly Gly Gly Gly Gly Gly Gly Gly Gly Gly Gly Gly Gly Asp
    50                  55                  60

Glu Pro Pro Leu Arg Glu
65                  70
```

<210> SEQ ID NO 442
<211> LENGTH: 70
<212> TYPE: PRT
<213> ORGANISM: Oryza sativa

<400> SEQUENCE: 442

```
Ile Cys His Asp His Ser Gln Thr Phe Lys Gly Met Cys Phe His Thr
1               5                   10                  15

Ser Asn Cys Ile Ala Cys Cys Thr Asn Glu Gly Tyr Thr Gly Gly Tyr
            20                  25                  30

Cys Lys Pro Phe Thr Tyr Arg Cys Met Cys Thr Lys Asp Cys Gly Gly
        35                  40                  45

Asp Ser Pro Pro Asp Asp Pro Pro Pro Ala Met Pro Thr Ser Pro Ala
    50                  55                  60

Ala Thr Thr Thr Val Ala
65                  70
```

<210> SEQ ID NO 443
<211> LENGTH: 59
<212> TYPE: PRT
<213> ORGANISM: Oryza sativa

<400> SEQUENCE: 443

```
Arg Leu Cys Glu Lys Pro Ser Ser His Phe Lys Gly Leu Cys Leu Arg
1               5                   10                  15

Ser Gln Asn Cys Asp Asn Glu Cys Met Leu Glu Gly Tyr Met Asp Gly
            20                  25                  30

Lys Cys Lys Tyr Leu Thr Arg Arg Cys Ile Cys Ser Met Glu Cys Ala
        35                  40                  45

Thr Met Ser Asn Val Gly Leu Thr Pro Thr Lys
    50                  55
```

<210> SEQ ID NO 444
<211> LENGTH: 49
<212> TYPE: PRT
<213> ORGANISM: Oryza sativa

<400> SEQUENCE: 444

```
Arg His Cys Leu Ser Gln Ser His Arg Phe Lys Gly Met Cys Val Ser
1               5                   10                  15

Ser Asn Asn Cys Ala Asn Val Cys Arg Thr Glu Ser Phe Pro Asp Gly
            20                  25                  30

Glu Cys Lys Ser His Gly Leu Glu Arg Lys Cys Phe Cys Lys Lys Val
        35                  40                  45

Cys
```

<210> SEQ ID NO 445
<211> LENGTH: 48
<212> TYPE: PRT
<213> ORGANISM: Oryza sativa

<400> SEQUENCE: 445

```
Arg Thr Cys Glu Ser Gln Ser His Arg Phe Lys Gly Pro Cys Ala Arg
1               5                   10                  15

Lys Ala Asn Cys Ala Ser Val Cys Asn Thr Glu Gly Phe Pro Asp Gly
            20                  25                  30

Tyr Cys His Gly Val Arg Arg Arg Cys Met Cys Thr Lys Pro Cys Pro
        35                  40                  45
```

<210> SEQ ID NO 446
<211> LENGTH: 49
<212> TYPE: PRT
<213> ORGANISM: Oryza sativa

<400> SEQUENCE: 446

Arg His Cys Val Ser Gln Ser His Arg Phe Val Gly Ala Cys Met Arg
1               5                   10                  15

Lys Ser Asn Cys Glu His Val Cys Met Thr Glu Gly Phe Pro Trp Gly
            20                  25                  30

Glu Cys Arg Phe His Gly Ile Glu Arg Lys Cys Phe Cys Lys Lys Arg
        35                  40                  45

Cys

<210> SEQ ID NO 447
<211> LENGTH: 47
<212> TYPE: PRT
<213> ORGANISM: Petunia axillaris

<400> SEQUENCE: 447

Arg Thr Cys Glu Ser Gln Ser His Arg Phe Lys Gly Pro Cys Val Ser
1               5                   10                  15

Lys Ser Asn Cys Ala Ser Val Cys Gln Thr Glu Gly Phe His Gly Gly
            20                  25                  30

His Cys Arg Gly Leu Arg Arg Arg Cys Phe Cys Thr Lys His Cys
        35                  40                  45

<210> SEQ ID NO 448
<211> LENGTH: 49
<212> TYPE: PRT
<213> ORGANISM: Petunia axillaris

<400> SEQUENCE: 448

Arg Tyr Arg Val Cys Leu Ser Pro Ser His Arg Tyr Lys Gly Met Cys
1               5                   10                  15

Leu Arg Asp His Asn Cys Ala Leu Val Cys Arg Asn Glu Gly Phe Ser
            20                  25                  30

Gly Gly Asp Cys Ile Gly Phe Arg Arg Arg Cys Phe Cys Thr Lys Leu
        35                  40                  45

Cys

<210> SEQ ID NO 449
<211> LENGTH: 49
<212> TYPE: PRT
<213> ORGANISM: Petunia axillaris

<400> SEQUENCE: 449

Glu Ala Arg Ile Cys Glu Ser Gln Ser His Arg Phe His Gly Thr Cys
1               5                   10                  15

Val Arg Glu Ser Asn Cys Ala Ser Val Cys Gln Thr Glu Gly Phe Ile
            20                  25                  30

Gly Gly Asn Cys Arg Gly Phe Arg Arg Arg Cys Phe Cys Thr Arg Asn
        35                  40                  45

Cys

<210> SEQ ID NO 450
<211> LENGTH: 47
<212> TYPE: PRT
<213> ORGANISM: Petunia axillaris

<400> SEQUENCE: 450

Arg Thr Cys Glu Thr Pro Ser Gln Arg Phe Lys Gly Pro Cys Val Ser
1               5                   10                  15

```
Asp Thr Asn Cys Ala Asn Val Cys Gln Thr Glu Gly Phe Pro Gly Gly
            20                  25                  30

Asp Cys Gln Gly Leu Arg Arg Arg Cys Phe Cys Thr Lys Pro Cys
        35                  40                  45


<210> SEQ ID NO 451
<211> LENGTH: 47
<212> TYPE: PRT
<213> ORGANISM: Petunia axillaris

<400> SEQUENCE: 451

Arg Thr Cys Glu Thr Leu Ser His Arg Phe Arg Gly Pro Cys Val Arg
1               5                   10                  15

Glu Lys Asn Cys Ala Ala Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45


<210> SEQ ID NO 452
<211> LENGTH: 47
<212> TYPE: PRT
<213> ORGANISM: Petunia axillaris

<400> SEQUENCE: 452

Arg Val Cys Met Ser Pro Ser His Gly Tyr Arg Gly Pro Cys Ile Arg
1               5                   10                  15

Asp His Asn Cys Ala Leu Val Cys Arg Asp Glu Gly Phe Ser Gly Gly
            20                  25                  30

Asp Cys Val Gly Ile Gln Arg Lys Cys Tyr Cys Thr Lys Leu Cys
        35                  40                  45


<210> SEQ ID NO 453
<211> LENGTH: 50
<212> TYPE: PRT
<213> ORGANISM: Petunia axillaris

<400> SEQUENCE: 453

Arg Thr Cys Glu His Arg Ser Gln His Tyr Tyr Gly Ala Cys Phe Ala
1               5                   10                  15

Asn Asn Ser Asn Met Asn Asn Asn Cys Asp Ser Met Cys Lys Cys Asp
            20                  25                  30

Gly Phe Asp Gly Gly Phe Cys Arg Leu Thr Asn Cys Phe Cys His Val
        35                  40                  45

Lys Cys
    50


<210> SEQ ID NO 454
<211> LENGTH: 47
<212> TYPE: PRT
<213> ORGANISM: Petunia axillaris

<400> SEQUENCE: 454

Lys Leu Cys Gln Tyr Lys Ser Lys Thr Phe His Gly Val Cys Val Thr
1               5                   10                  15

Gly Asn Thr Cys Asn Gln Lys Cys Gln Ser Glu Ala Phe Asp Gly Gly
            20                  25                  30

Arg Cys Gln Gly Val Arg His Arg Cys Tyr Cys Tyr Arg Thr Cys
        35                  40                  45


<210> SEQ ID NO 455
```

```
<211> LENGTH: 51
<212> TYPE: PRT
<213> ORGANISM: Petunia axillaris

<400> SEQUENCE: 455

Arg Val Cys Arg Thr Asn Ser Lys Arg Tyr Ser Gly Pro Cys Phe Asn
1               5                   10                  15

Asn Asn Asn Asn Arg Asn Gln Asn Cys Asp Phe Ile Cys Arg Arg Cys
            20                  25                  30

Glu Gly Phe Glu Gly Gly His Cys Ser Ser Arg Thr Cys Val Cys Thr
        35                  40                  45

Lys Ser Cys
    50


<210> SEQ ID NO 456
<211> LENGTH: 47
<212> TYPE: PRT
<213> ORGANISM: Punica granatum

<400> SEQUENCE: 456

Arg Thr Cys Glu Ser Gln Ser His Lys Phe Arg Gly Thr Cys Val Ser
1               5                   10                  15

Asn Thr Asn Cys Gly Ser Val Cys Gln Thr Glu Gly Phe His Gly Gly
            20                  25                  30

His Cys Arg Gly Phe Arg Arg Arg Cys Phe Cys Thr Lys Gln Cys
        35                  40                  45


<210> SEQ ID NO 457
<211> LENGTH: 47
<212> TYPE: PRT
<213> ORGANISM: Punica granatum

<400> SEQUENCE: 457

Arg Ile Cys Glu Ser Lys Ser His Arg Phe Arg Gly Val Cys Met Ser
1               5                   10                  15

Asn Ser Asn Cys Ala Ser Val Cys His Asn Glu Gly Phe Pro Gly Gly
            20                  25                  30

Arg Cys Arg Gly Val Arg Lys Arg Cys Phe Cys Thr Lys Val Cys
        35                  40                  45


<210> SEQ ID NO 458
<211> LENGTH: 47
<212> TYPE: PRT
<213> ORGANISM: Solanum tuberosum

<400> SEQUENCE: 458

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45


<210> SEQ ID NO 459
<211> LENGTH: 47
<212> TYPE: PRT
<213> ORGANISM: Solanum tuberosum

<400> SEQUENCE: 459

Arg Asn Cys Glu Ser Leu Ser His Arg Phe Lys Gly Pro Cys Thr Arg
1               5                   10                  15
```

```
Asp Ser Asn Cys Ala Ser Val Cys Glu Thr Glu Arg Phe Ser Gly Gly
            20                  25                  30

Asn Cys His Gly Phe Arg Arg Arg Cys Phe Cys Thr Lys Pro Cys
        35                  40                  45


<210> SEQ ID NO 460
<211> LENGTH: 47
<212> TYPE: PRT
<213> ORGANISM: Solanum tuberosum

<400> SEQUENCE: 460

Arg Thr Cys Glu Ser Gln Ser Arg Arg Phe Lys Gly Leu Cys Phe Ser
1               5                   10                  15

Lys Ser Asn Cys Gly Ser Val Cys His Thr Glu Gly Phe Ser Gly Gly
            20                  25                  30

His Cys Arg Gly Phe Arg Arg Arg Cys Phe Cys Thr Arg His Cys
        35                  40                  45


<210> SEQ ID NO 461
<211> LENGTH: 47
<212> TYPE: PRT
<213> ORGANISM: Solanum tuberosum

<400> SEQUENCE: 461

Arg Thr Cys Glu Ser Gln Ser His Lys Tyr Lys Gly Pro Cys Val Arg
1               5                   10                  15

Lys Ser Asn Cys Gly Ala Val Cys Gln Thr Glu Gly Phe Thr Gly Gly
            20                  25                  30

His Cys Arg Gly Val Arg Arg Arg Cys Phe Cys Thr Lys His Cys
        35                  40                  45


<210> SEQ ID NO 462
<211> LENGTH: 47
<212> TYPE: PRT
<213> ORGANISM: Solanum tuberosum

<400> SEQUENCE: 462

Arg Thr Cys Glu Ser Gln Ser His Ser Phe Lys Gly Pro Cys Val Gly
1               5                   10                  15

Asp Thr Asn Cys Ala Ser Val Cys Gln Thr Glu Gly Phe Ile Gly Gly
            20                  25                  30

Asp Cys Arg Gly Leu Arg Arg Gln Cys Phe Cys Thr Arg Asn Cys
        35                  40                  45


<210> SEQ ID NO 463
<211> LENGTH: 47
<212> TYPE: PRT
<213> ORGANISM: Solanum tuberosum

<400> SEQUENCE: 463

Arg Thr Cys Glu Ser Gln Ser Asn Arg Phe Lys Gly Thr Cys Val Arg
1               5                   10                  15

Asp Ser Asn Cys Ala Thr Val Cys Gln Thr Glu Gly Phe Ile Gly Gly
            20                  25                  30

Asn Cys Arg Gly Phe Arg Arg Arg Cys Phe Cys Thr Arg Asn Cys
        35                  40                  45


<210> SEQ ID NO 464
<211> LENGTH: 49
<212> TYPE: PRT
```

```
<213> ORGANISM: Solanum tuberosum

<400> SEQUENCE: 464

Arg Val Cys Ile Ser Gln Ser His Arg Tyr Lys Gly Pro Cys Leu Arg
1               5                   10                  15

Asp His Asn Cys Ala Leu Val Cys Arg Asn Glu Tyr Phe Ser Gly Gly
            20                  25                  30

Asp Cys Ile Gly Phe Gly Phe His Arg Lys Cys Tyr Cys Thr Lys Phe
        35                  40                  45

Cys


<210> SEQ ID NO 465
<211> LENGTH: 46
<212> TYPE: PRT
<213> ORGANISM: Phaseolus vulgaris

<400> SEQUENCE: 465

Lys Thr Cys Phe Thr Lys Lys Glu Gly Trp Gly Arg Cys Ile Ala Asp
1               5                   10                  15

Phe Thr Cys Ala Arg Ser Cys Arg Asn Val Gly Tyr Ile Gly Gly Lys
            20                  25                  30

Cys Gln Gly Leu Thr Arg Arg Cys Phe Cys Val Leu Asn Cys
        35                  40                  45


<210> SEQ ID NO 466
<211> LENGTH: 50
<212> TYPE: PRT
<213> ORGANISM: Phaseolus vulgaris

<400> SEQUENCE: 466

Ala Glu Gly Lys Ile Cys Arg Thr Lys Ser Arg Lys Tyr Thr Gly Ala
1               5                   10                  15

Cys Tyr Ser Asn Asp Ile Cys Ala Asn Tyr Cys Lys Gly Asp Gly Phe
            20                  25                  30

Asp Asp Gly Asp Cys Gly Gly Leu Ser His Ile Cys Phe Cys Thr Lys
        35                  40                  45

Asn Cys
    50


<210> SEQ ID NO 467
<211> LENGTH: 47
<212> TYPE: PRT
<213> ORGANISM: Phaseolus vulgaris

<400> SEQUENCE: 467

Arg Leu Cys Glu Ser Pro Ser His Ser Phe Lys Gly Leu Cys Phe Asn
1               5                   10                  15

Asp Arg Asn Cys Ala Asn Val Cys Leu Thr Glu Gly Phe Thr Gly Gly
            20                  25                  30

Lys Cys Glu Gly Ala Arg His Arg Cys Phe Cys Thr Ile Ile Cys
        35                  40                  45


<210> SEQ ID NO 468
<211> LENGTH: 47
<212> TYPE: PRT
<213> ORGANISM: Phaseolus vulgaris

<400> SEQUENCE: 468

Arg Leu Cys Trp Ser Glu Ser Gln Ala Phe Lys Gly Leu Cys Phe Ser
1               5                   10                  15
```

Asn Asp Asn Cys Ala Thr Val Cys Leu Thr Glu Gly Phe Thr Gly Gly
20 25 30

Lys Cys Glu Gly Leu Arg Arg Arg Cys Phe Cys Ser Lys Asn Cys
35 40 45

<210> SEQ ID NO 469
<211> LENGTH: 47
<212> TYPE: PRT
<213> ORGANISM: Phaseolus vulgaris

<400> SEQUENCE: 469

Arg Gly Cys Glu Ser Arg Ser Arg His Leu Arg Gly Lys Cys Glu Ser
1 5 10 15

Asp Glu Asn Cys Ala Ser Ala Cys Arg Thr Glu Arg Phe Ser Gly Gly
20 25 30

His Cys Arg Gly Phe Arg Cys Arg Cys Phe Cys Asp Lys Arg Ser
35 40 45

<210> SEQ ID NO 470
<211> LENGTH: 47
<212> TYPE: PRT
<213> ORGANISM: Phaseolus vulgaris

<400> SEQUENCE: 470

Arg Thr Cys Glu Ser Gln Ser His Arg Phe Lys Gly Pro Cys Val Ser
1 5 10 15

Asp Thr Asn Cys Ala Ser Val Cys Arg Thr Glu Arg Phe Ser Gly Gly
20 25 30

His Cys Arg Gly Phe Arg Arg Arg Cys Phe Cys Thr Lys His Cys
35 40 45

<210> SEQ ID NO 471
<211> LENGTH: 47
<212> TYPE: PRT
<213> ORGANISM: Phaseolus vulgaris

<400> SEQUENCE: 471

Arg Val Cys Glu Ser Gln Ser His Gly Phe Lys Gly Ala Cys Thr Gly
1 5 10 15

Asp His Asn Cys Ala Leu Val Cys Arg Asn Glu Gly Phe Ser Gly Gly
20 25 30

Asn Cys Arg Gly Phe Arg Arg Arg Cys Phe Cys Thr Lys Ile Cys
35 40 45

<210> SEQ ID NO 472
<211> LENGTH: 47
<212> TYPE: PRT
<213> ORGANISM: Phaseolus vulgaris

<400> SEQUENCE: 472

Arg His Cys Glu Ser Lys Ser His Arg Phe Lys Gly Met Cys Leu Ser
1 5 10 15

Asp Arg Asn Cys Ala Ser Val Cys His Leu Glu Gly Phe Thr Gly Gly
20 25 30

Asn Cys Arg Gly Phe Arg Arg Arg Cys Phe Cys Thr Arg His Cys
35 40 45

<210> SEQ ID NO 473
<211> LENGTH: 47
<212> TYPE: PRT

<213> ORGANISM: Populus trichocarpus

<400> SEQUENCE: 473

Arg Val Cys Leu Ser Gln Ser His His Tyr Lys Gly Pro Cys Leu Arg
1 5 10 15

Gly His Asn Cys Ala Met Val Cys Lys Thr Glu Gly Phe Ala Gly Gly
20 25 30

Glu Cys Lys Gly Phe Ile Ser Arg Cys Phe Cys Ala Lys Leu Cys
35 40 45

<210> SEQ ID NO 474
<211> LENGTH: 47
<212> TYPE: PRT
<213> ORGANISM: Populus trichocarpus

<400> SEQUENCE: 474

Arg Val Cys Leu Ser Gln Ser His Ser Phe Lys Gly Pro Cys Val Arg
1 5 10 15

Gly His Asn Cys Ala Ser Val Cys Lys Thr Glu Gly Phe Pro Gly Gly
20 25 30

Glu Cys Lys Gly Phe Arg Arg Arg Cys Phe Cys Ala Lys Pro Cys
35 40 45

<210> SEQ ID NO 475
<211> LENGTH: 47
<212> TYPE: PRT
<213> ORGANISM: Populus trichocarpus

<400> SEQUENCE: 475

Arg Val Cys Leu Ser Gln Ser His Ser Phe Lys Gly Pro Cys Val Arg
1 5 10 15

Gly His Asn Cys Ala Ser Val Cys Lys Thr Glu Gly Phe Pro Gly Gly
20 25 30

Glu Cys Lys Gly Phe Arg Arg Arg Cys Phe Cys Ala Lys Pro Cys
35 40 45

<210> SEQ ID NO 476
<211> LENGTH: 47
<212> TYPE: PRT
<213> ORGANISM: Populus trichocarpus

<400> SEQUENCE: 476

Arg Val Cys Gln Ser Gln Ser His Tyr Phe Lys Gly Pro Cys Ala Arg
1 5 10 15

Asp His Asn Cys Ala Trp Val Cys Arg Asn Glu Gly Phe Ser Gly Gly
20 25 30

Arg Cys Lys Gly Phe Arg Arg Arg Cys Phe Cys Thr Lys Leu Cys
35 40 45

<210> SEQ ID NO 477
<211> LENGTH: 47
<212> TYPE: PRT
<213> ORGANISM: Populus trichocarpus

<400> SEQUENCE: 477

Arg Val Cys Gln Ser Gln Ser His Tyr Phe Lys Gly Pro Cys Ala Arg
1 5 10 15

Asp His Asn Cys Ala Trp Val Cys Arg Asn Glu Gly Phe Ser Gly Gly
20 25 30

```
Arg Cys Lys Gly Phe Arg Arg Arg Cys Phe Cys Thr Lys Leu Cys
        35                  40                  45


<210> SEQ ID NO 478
<211> LENGTH: 47
<212> TYPE: PRT
<213> ORGANISM: Prunus persica

<400> SEQUENCE: 478

Arg Val Cys Gln Ser Gln Ser His Gly Phe Arg Gly Pro Cys Ile Arg
1               5                   10                  15

His His Asn Cys Ala Leu Val Cys Arg Asn Glu Gly Phe Ser Gly Gly
            20                  25                  30

Arg Cys Arg Gly Phe Arg Arg Arg Cys Phe Cys Thr Arg Leu Cys
        35                  40                  45


<210> SEQ ID NO 479
<211> LENGTH: 47
<212> TYPE: PRT
<213> ORGANISM: Prunus persica

<400> SEQUENCE: 479

Arg Thr Cys Glu Ser Gln Ser Asn Arg Phe Lys Gly Thr Cys Val Ser
1               5                   10                  15

Thr Ser Asn Cys Ala Ser Val Cys Gln Thr Glu Gly Phe Pro Gly Gly
            20                  25                  30

His Cys Arg Gly Phe Arg Arg Arg Cys Phe Cys Thr Lys His Cys
        35                  40                  45


<210> SEQ ID NO 480
<211> LENGTH: 57
<212> TYPE: PRT
<213> ORGANISM: Prunus persica

<400> SEQUENCE: 480

Arg Asp Ala Lys Lys Val Glu Pro Lys Lys Lys Thr Cys Asp Ser Gln
1               5                   10                  15

Ser Gln Lys Phe Lys Gly Met Cys Phe Leu Thr Ser Ser Cys Val Gln
            20                  25                  30

Ser Cys Lys Ser Glu Gly Phe Thr Gly Gly Gln Cys Arg Gly Phe Arg
        35                  40                  45

Arg Arg Cys Phe Cys Ser Lys Asn Cys
    50                  55


<210> SEQ ID NO 481
<211> LENGTH: 57
<212> TYPE: PRT
<213> ORGANISM: Prunus persica

<400> SEQUENCE: 481

Arg Ser Ala Lys Lys Val Glu Pro Lys Lys Arg Thr Cys Glu Ser Gln
1               5                   10                  15

Ser Gln Lys Phe Lys Gly Ile Cys Phe Leu Ser Ser Asn Cys Ala Thr
            20                  25                  30

Ser Cys Thr Thr Glu Gly Phe Asn Gly Gly Gln Cys Arg Gly Phe Arg
        35                  40                  45

Arg Arg Cys Phe Cys Ser Lys Ala Cys
    50                  55
```

```
<210> SEQ ID NO 482
<211> LENGTH: 57
<212> TYPE: PRT
<213> ORGANISM: Prunus persica

<400> SEQUENCE: 482

Lys Ile Cys Glu Val Thr Ser Lys Thr Phe Ile Gly Leu Cys Ile Lys
1               5                   10                  15

Asp Arg Asn Cys Met Val Arg Cys His Ser Glu Gly Tyr Gly Tyr Gly
            20                  25                  30

Lys Cys Ser His Ile Leu Arg Lys Cys Arg Cys Leu Lys Pro Cys Val
        35                  40                  45

Ala Glu Glu Thr Lys Glu Asn Leu Pro
    50                  55


<210> SEQ ID NO 483
<211> LENGTH: 55
<212> TYPE: PRT
<213> ORGANISM: Prunus persica

<400> SEQUENCE: 483

Lys Val Ala Thr Lys Glu Glu Ser Arg Thr Cys Glu Ser Leu Ser Thr
1               5                   10                  15

Lys Phe Lys Gly Phe Cys Leu Arg Ser Ser Arg Cys Ala Glu Ala Cys
            20                  25                  30

Gln Lys Glu Gly Phe Met Gly Gly Lys Cys Pro Gly Phe Arg Leu Arg
        35                  40                  45

Cys Thr Cys Thr Lys Lys Cys
    50                  55


<210> SEQ ID NO 484
<211> LENGTH: 55
<212> TYPE: PRT
<213> ORGANISM: Prunus persica

<400> SEQUENCE: 484

Lys Val Ala Thr Lys Glu Glu Ser Arg Thr Cys Glu Ser Leu Ser Thr
1               5                   10                  15

Lys Phe Lys Gly Phe Cys Leu Arg Ser Ser Arg Cys Ala Glu Ala Cys
            20                  25                  30

Gln Lys Glu Gly Phe Met Gly Gly Lys Cys Pro Gly Phe Arg Leu Arg
        35                  40                  45

Cys Thr Cys Thr Lys Lys Cys
    50                  55


<210> SEQ ID NO 485
<211> LENGTH: 55
<212> TYPE: PRT
<213> ORGANISM: Prunus persica

<400> SEQUENCE: 485

Lys Val Glu Thr Lys Glu Thr Ser Arg Thr Cys Glu Ser Leu Ser Thr
1               5                   10                  15

Lys Phe Lys Gly Pro Cys Ile Arg Ser Ser Asn Cys Ala Asn Ile Cys
            20                  25                  30

Glu Glu Glu Gly Phe Lys Gly Gly Lys Cys Val Gly Phe Arg Leu Arg
        35                  40                  45

Cys Thr Cys Thr Lys Asn Cys
    50                  55
```

<210> SEQ ID NO 486
<211> LENGTH: 55
<212> TYPE: PRT
<213> ORGANISM: Prunus persica

<400> SEQUENCE: 486

```
Lys Val Glu Thr Lys Glu Thr Ser Arg Thr Cys Glu Ser Leu Ser Thr
1               5                   10                  15

Lys Phe Lys Gly Pro Cys Ile Arg Ser Ser Asn Cys Ala Asn Ile Cys
            20                  25                  30

Glu Glu Glu Gly Phe Lys Gly Gly Lys Cys Val Gly Phe Arg Leu Arg
        35                  40                  45

Cys Thr Cys Thr Lys Asn Cys
    50                  55
```

<210> SEQ ID NO 487
<211> LENGTH: 55
<212> TYPE: PRT
<213> ORGANISM: Prunus persica

<400> SEQUENCE: 487

```
Lys Val Glu Thr Lys Glu Thr Ser Arg Thr Cys Glu Ser Leu Ser Thr
1               5                   10                  15

Lys Phe Lys Gly Pro Cys Ile Arg Ser Ser Asn Cys Ala Asn Ile Cys
            20                  25                  30

Glu Glu Glu Gly Phe Lys Gly Gly Lys Cys Val Gly Phe Arg Leu Arg
        35                  40                  45

Cys Thr Cys Thr Lys Asn Cys
    50                  55
```

<210> SEQ ID NO 488
<211> LENGTH: 55
<212> TYPE: PRT
<213> ORGANISM: Prunus persica

<400> SEQUENCE: 488

```
Lys Val Glu Thr Lys Glu Thr Ser Arg Thr Cys Glu Ser Leu Ser Thr
1               5                   10                  15

Lys Phe Lys Gly Pro Cys Ile Arg Ser Ser Asn Cys Ala Asn Ile Cys
            20                  25                  30

Glu Glu Glu Gly Phe Lys Gly Gly Lys Cys Val Gly Phe Arg Leu Arg
        35                  40                  45

Cys Thr Cys Thr Lys Asn Cys
    50                  55
```

<210> SEQ ID NO 489
<211> LENGTH: 55
<212> TYPE: PRT
<213> ORGANISM: Prunus persica

<400> SEQUENCE: 489

```
Lys Val Glu Thr Lys Glu Thr Ser Arg Thr Cys Glu Ser Leu Ser Thr
1               5                   10                  15

Lys Phe Lys Gly Pro Cys Phe Arg Ser Ser Asn Cys Ala Asn Ile Cys
            20                  25                  30

Glu Lys Glu Gly Phe Lys Gly Gly Lys Cys Val Gly Phe Arg Leu Arg
        35                  40                  45

Cys Thr Cys Thr Lys Asn Cys
    50                  55
```

```
<210> SEQ ID NO 490
<211> LENGTH: 55
<212> TYPE: PRT
<213> ORGANISM: Prunus persica

<400> SEQUENCE: 490

Lys Ala Ala Thr Lys Glu Asn Ser Arg Thr Cys Glu Ser Leu Ser Thr
1               5                   10                  15

Lys Phe Lys Gly Leu Cys Phe Arg Ser Ser Asn Cys Ala Asp Ile Cys
            20                  25                  30

Lys Lys Glu Gly Phe Leu Glu Gly Lys Cys Ala Gly Phe Arg Leu Arg
        35                  40                  45

Cys Thr Cys Thr Lys Lys Cys
    50                  55


<210> SEQ ID NO 491
<211> LENGTH: 47
<212> TYPE: PRT
<213> ORGANISM: Pisum sativum

<400> SEQUENCE: 491

Arg Asp Cys Glu Ser Lys Ser His Lys Phe Lys Gly Thr Cys Leu Ser
1               5                   10                  15

Asp Thr Asn Cys Ala Ser Val Cys Gln Thr Glu Arg Phe Thr Gly Gly
            20                  25                  30

His Cys Arg Gly Phe Arg His Arg Cys Tyr Cys Thr Thr His Cys
        35                  40                  45


<210> SEQ ID NO 492
<211> LENGTH: 47
<212> TYPE: PRT
<213> ORGANISM: Pisum sativum

<400> SEQUENCE: 492

Arg Asp Cys Glu Ser Pro Ser Gln Lys Phe Lys Gly Leu Cys Phe Ser
1               5                   10                  15

Asp Thr Asn Cys Ala Ser Val Cys Gln Thr Glu Gly Phe Pro Gly Gly
            20                  25                  30

Lys Cys Glu Gly Leu Arg His Arg Cys Phe Cys Thr Lys Pro Cys
        35                  40                  45


<210> SEQ ID NO 493
<211> LENGTH: 47
<212> TYPE: PRT
<213> ORGANISM: Pisum sativum

<400> SEQUENCE: 493

Arg Asp Cys Glu Ser Pro Ser Gln Lys Phe Lys Gly Val Cys Leu Ser
1               5                   10                  15

Asp Arg Asn Cys Ala Ser Val Cys Gln Thr Glu Gly Phe Thr Gly Gly
            20                  25                  30

Asp Cys Lys Gly Leu Arg Gln Arg Cys Phe Cys Thr Lys Pro Cys
        35                  40                  45


<210> SEQ ID NO 494
<211> LENGTH: 47
<212> TYPE: PRT
<213> ORGANISM: Pisum sativum
```

<400> SEQUENCE: 494

Arg Asp Cys Glu Ser Pro Ser Gln Ile Phe Lys Gly Leu Cys Phe Thr
1 5 10 15

Asp Thr Asn Cys Ala Ser Val Cys His Thr Glu Gly Phe Pro Gly Gly
20 25 30

Lys Cys Lys Gly Leu Pro Lys Arg Cys Ile Cys Thr Lys Pro Cys
35 40 45

<210> SEQ ID NO 495
<211> LENGTH: 46
<212> TYPE: PRT
<213> ORGANISM: Pisum sativum

<400> SEQUENCE: 495

Ala Gly Thr Cys Pro Ser Pro Ser Thr Lys Phe Lys Gly Val Cys Val
1 5 10 15

Ser Asp Phe Asp Cys Met Ile Thr Cys Gln Met Glu Gly Leu Ser Glu
20 25 30

Gly Lys Cys Gln Ser Leu Lys Cys Ile Cys Ala Lys Pro Cys
35 40 45

<210> SEQ ID NO 496
<211> LENGTH: 39
<212> TYPE: PRT
<213> ORGANISM: Pisum sativum

<400> SEQUENCE: 496

Ser Glu Cys Asn Asp Glu Glu Cys Glu Trp Ser Cys Ile Asp Lys Gly
1 5 10 15

Phe Leu Asp Gly Val Cys Ser Pro Ser Ser Asn Gln Cys Phe Cys Val
20 25 30

Ile His Arg Val Ile Ile Arg
35

<210> SEQ ID NO 497
<211> LENGTH: 50
<212> TYPE: PRT
<213> ORGANISM: Pisum sativum

<400> SEQUENCE: 497

Asn Ser Cys Gln Ser Lys Ser Ser Gln Phe Lys Gly Ile Cys Leu Ser
1 5 10 15

Asn Lys Lys Cys Ala Arg Val Cys His Leu Glu Gly Phe Leu Glu Gly
20 25 30

Gly Lys Cys Lys Gly Lys Leu Leu Lys His Cys Ser Cys Lys Lys Ser
35 40 45

Ile Cys
50

<210> SEQ ID NO 498
<211> LENGTH: 45
<212> TYPE: PRT
<213> ORGANISM: Pisum sativum

<400> SEQUENCE: 498

Arg Gly Cys Lys Val Lys Ser Thr Lys Phe Arg Gly Pro Cys Ser Phe
1 5 10 15

Asp Lys Asn Cys Ala Thr Val Cys Arg Gly Glu Gly Tyr Arg Asp Gly
20 25 30

```
Asp Cys His Gly Leu Arg Arg Arg Cys Met Cys Leu Cys
        35                  40                  45


<210> SEQ ID NO 499
<211> LENGTH: 47
<212> TYPE: PRT
<213> ORGANISM: Pisum sativum

<400> SEQUENCE: 499

Arg Lys Cys Val Ser Gln Ser His Arg Phe His Gly Pro Cys Leu Arg
1               5                   10                  15

Asp Ser Asn Cys Ala Thr Val Cys Leu Gly Glu Gly Phe Thr Gly Gly
            20                  25                  30

Asp Cys His Gly Phe Arg Arg Arg Cys Phe Cys Ser Arg Phe Cys
        35                  40                  45


<210> SEQ ID NO 500
<211> LENGTH: 56
<212> TYPE: PRT
<213> ORGANISM: Pisum sativum

<400> SEQUENCE: 500

Arg His Cys Glu Ser Pro Ser His Arg Phe Lys Gly Ile Cys Val Arg
1               5                   10                  15

Lys Ser Asn Cys Ala Ala Ile Cys Gln Thr Glu Gly Phe Ser Ser Gly
            20                  25                  30

Lys Cys Arg Gly Phe Arg Ser Arg Cys Val Cys Ile Lys His Cys His
        35                  40                  45

His His Glu Glu Glu Val Gln Asn
    50                  55


<210> SEQ ID NO 501
<211> LENGTH: 57
<212> TYPE: PRT
<213> ORGANISM: Pisum sativum

<400> SEQUENCE: 501

Arg Leu Cys Glu Ser Ala Ser His Arg Phe Lys Gly Ile Cys Val Arg
1               5                   10                  15

Lys Ser Asn Cys Gly Ala Val Cys Gln Thr Glu Gly Phe Ser Gly Gly
            20                  25                  30

Lys Cys Arg Gly Leu Arg Ala Arg Cys Met Cys Thr Lys His Cys His
        35                  40                  45

Gln Glu Glu Glu Ala Glu Val Lys Asn
    50                  55


<210> SEQ ID NO 502
<211> LENGTH: 57
<212> TYPE: PRT
<213> ORGANISM: Pisum sativum

<400> SEQUENCE: 502

Met Arg Val Asp Gly Ala Arg Thr Asn Arg Met Cys Asp Ser Lys Ser
1               5                   10                  15

His Lys Phe Arg Gly Leu Cys Val Ser Asp Thr Asn Cys Arg Asn Val
            20                  25                  30

Cys Gln Thr Glu Arg Phe Ser Asp Gly His Cys Arg Gly Ala Arg Arg
        35                  40                  45
```

```
Arg Cys Tyr Cys Gln Asn Pro Cys Ile
    50                  55


<210> SEQ ID NO 503
<211> LENGTH: 57
<212> TYPE: PRT
<213> ORGANISM: Pisum sativum

<400> SEQUENCE: 503

Arg Leu Cys Glu Ser Ala Ser His Arg Phe Lys Gly Ile Cys Val Arg
1               5                   10                  15

Lys Ser Asn Cys Gly Ala Val Cys Gln Thr Glu Gly Phe Ser Gly Gly
            20                  25                  30

Lys Cys Arg Gly Leu Arg Ala Arg Cys Met Cys Thr Lys His Cys His
        35                  40                  45

Gln Glu Glu Glu Ala Glu Val Lys Asn
    50                  55


<210> SEQ ID NO 504
<211> LENGTH: 47
<212> TYPE: PRT
<213> ORGANISM: Quercus lobata

<400> SEQUENCE: 504

Arg Thr Cys Glu Ser Gln Ser His Arg Phe Lys Gly Pro Cys Val Arg
1               5                   10                  15

Lys Ser Asn Cys Ala Ser Val Cys Gln Thr Glu Gly Phe His Gly Gly
            20                  25                  30

Gln Cys Arg Gly Phe Arg Arg Arg Cys Phe Cys Thr Lys His Cys
        35                  40                  45


<210> SEQ ID NO 505
<211> LENGTH: 47
<212> TYPE: PRT
<213> ORGANISM: Quercus lobata

<400> SEQUENCE: 505

Arg Val Cys Glu Ser Gln Ser His Lys Phe Lys Gly Ala Cys Met Ser
1               5                   10                  15

Asn His Asn Cys Ala Leu Val Cys Arg Asn Glu Gly Phe Ser Gly Gly
            20                  25                  30

Arg Cys Arg Gly Phe Arg His Arg Cys Phe Cys Thr Arg Ile Cys
        35                  40                  45


<210> SEQ ID NO 506
<211> LENGTH: 50
<212> TYPE: PRT
<213> ORGANISM: Rosa chinensis

<400> SEQUENCE: 506

Glu Asn Leu Arg Thr Cys Asp Ser Pro Ser Gly Lys Phe Lys Gly Pro
1               5                   10                  15

Cys Ile Ile Ser Ser Asn Cys Ala Leu Thr Cys Gln Lys Glu Gly Phe
            20                  25                  30

Ala Gly Gly His Cys Arg Asp Phe Leu Arg Lys Cys Tyr Cys Ala Lys
        35                  40                  45

Pro Cys
    50
```

```
<210> SEQ ID NO 507
<211> LENGTH: 47
<212> TYPE: PRT
<213> ORGANISM: Rosa chinensis

<400> SEQUENCE: 507

Arg Thr Cys Glu Thr Leu Ser His Lys Phe Lys Gly Thr Cys Leu Arg
1               5                   10                  15

Glu Ser Asn Cys Ala Ser Val Cys Gln Thr Glu Gly Phe Ser Gly Gly
            20                  25                  30

Asp Cys Arg Gly Leu Arg Arg Arg Cys Phe Cys Thr Lys His Cys
        35                  40                  45


<210> SEQ ID NO 508
<211> LENGTH: 59
<212> TYPE: PRT
<213> ORGANISM: Rosa chinensis

<400> SEQUENCE: 508

Gly Ile Gly Pro Asn Val Met Val Ala Glu Ala Arg Thr Cys Glu Ser
1               5                   10                  15

Gln Ser Leu Lys Tyr Glu Gly Met Cys Leu Arg Glu Ser His Cys Ala
            20                  25                  30

Ser Val Cys Gln Thr Glu Gly Tyr Ser Gly Gly Asp Cys His Gly Leu
        35                  40                  45

Tyr Ser Ile Cys Val Cys Thr Lys Asp Cys Gln
    50                  55


<210> SEQ ID NO 509
<211> LENGTH: 58
<212> TYPE: PRT
<213> ORGANISM: Rosa chinensis

<400> SEQUENCE: 509

Gly Ile Gly Pro Asn Val Thr Val Ala Glu Ala Arg Lys Cys Glu Ser
1               5                   10                  15

Gln Ser His Lys Phe Ala Gly Ile Cys Leu Ile Glu Ser Asn Cys Ala
            20                  25                  30

Ser Ile Cys Lys Thr Glu Gly Tyr Ser Gly Gly Asn Cys Gly Gly Phe
        35                  40                  45

Arg Arg Arg Cys Phe Cys Thr Lys Asp Cys
    50                  55


<210> SEQ ID NO 510
<211> LENGTH: 47
<212> TYPE: PRT
<213> ORGANISM: Rosa chinensis

<400> SEQUENCE: 510

Arg Lys Cys Glu Ser Gln Ser His Lys Phe Glu Gly Ile Cys Leu Lys
1               5                   10                  15

Gln Ser Asn Cys Ala Ser Ile Cys Lys Thr Glu Gly Tyr Ser Gly Gly
            20                  25                  30

Asn Cys Arg Gly Phe Arg Arg Arg Cys Phe Cys Thr Lys Asp Cys
        35                  40                  45


<210> SEQ ID NO 511
<211> LENGTH: 58
<212> TYPE: PRT
<213> ORGANISM: Rosa chinensis
```

<400> SEQUENCE: 511

Gly Ile Gly Pro Asn Val Met Val Ala Glu Ala Arg Lys Cys Glu Ser
1 5 10 15

Gln Ser His Lys Phe Ala Gly Ile Cys Leu Ile Glu Ser Asn Cys Ala
20 25 30

Ser Ile Cys Lys Thr Glu Gly Tyr Ser Gly Gly Asn Cys Gly Gly Phe
35 40 45

Arg Arg Arg Cys Phe Cys Thr Lys Asp Cys
50 55

<210> SEQ ID NO 512
<211> LENGTH: 47
<212> TYPE: PRT
<213> ORGANISM: Rosa chinensis

<400> SEQUENCE: 512

Arg Val Cys Glu Val Pro Ser Lys Thr Phe Ser Gly Leu Cys Phe Ser
1 5 10 15

Asp Thr His Cys Ile Val Arg Cys His Ser Glu Gly Tyr Gly Tyr Gly
20 25 30

Lys Cys Ser His Ile Leu Arg Arg Cys Arg Cys Leu Lys Ala Cys
35 40 45

<210> SEQ ID NO 513
<211> LENGTH: 48
<212> TYPE: PRT
<213> ORGANISM: Rosa chinensis

<400> SEQUENCE: 513

Lys Ile Cys Glu Val Pro Ser Lys Thr Phe Lys Gly Leu Cys Val Lys
1 5 10 15

Asp Arg Asn Cys Val Val Arg Cys His Ser Glu Gly Tyr Gly Asn Gly
20 25 30

Lys Cys Ser His Val Arg Arg Gln Cys Met Cys Leu Lys Ile Cys Asp
35 40 45

<210> SEQ ID NO 514
<211> LENGTH: 47
<212> TYPE: PRT
<213> ORGANISM: Rosa chinensis

<400> SEQUENCE: 514

Lys Ile Cys Glu Tyr Pro Ser Arg Thr Phe Lys Gly Leu Cys Val Lys
1 5 10 15

Asp Lys Asn Cys Val Val Arg Cys Arg Ser Glu Gly Tyr Asn Tyr Gly
20 25 30

Lys Cys Ser His Val Arg Arg Arg Cys Arg Cys Phe Lys Pro Cys
35 40 45

<210> SEQ ID NO 515
<211> LENGTH: 47
<212> TYPE: PRT
<213> ORGANISM: Rosa chinensis

<400> SEQUENCE: 515

Arg Val Cys Glu Ser Gln Ser His Gly Phe His Gly Thr Cys Ile Arg
1 5 10 15

Ala His Asn Cys Ala Leu Val Cys Arg His Glu Gly Phe Ser Gly Gly
20 25 30

Arg Cys Arg Gly Phe Arg Arg Arg Cys Phe Cys Thr Arg Arg Cys
35 40 45

<210> SEQ ID NO 516
<211> LENGTH: 47
<212> TYPE: PRT
<213> ORGANISM: Rosa chinensis

<400> SEQUENCE: 516

Arg Val Cys Glu Ser Arg Ser His Gly Phe His Gly Thr Cys Ile His
1 5 10 15

His Asn Asn Cys Ala Leu Val Cys Arg Asn Glu Gly Phe Pro Gly Gly
20 25 30

Arg Cys Arg Gly Phe Arg Arg Arg Cys Phe Cys Thr Arg Asn Cys
35 40 45

<210> SEQ ID NO 517
<211> LENGTH: 47
<212> TYPE: PRT
<213> ORGANISM: Salvia bowleyana

<400> SEQUENCE: 517

Arg Thr Cys Glu Ser Lys Ser His Arg Phe Lys Gly Ile Cys Val Arg
1 5 10 15

Lys Ala Asn Cys Ala Ala Val Cys Gln Thr Glu Gly Phe His Ser Gly
20 25 30

His Cys Arg Gly Phe Arg Arg Arg Cys Tyr Cys Thr Arg His Cys
35 40 45

<210> SEQ ID NO 518
<211> LENGTH: 42
<212> TYPE: PRT
<213> ORGANISM: Salvia bowleyana

<400> SEQUENCE: 518

Arg Thr Cys Glu Ser Glu Ser Ser Ser Phe Lys Gly Leu Cys Leu Arg
1 5 10 15

Asn Ala Asp Cys Tyr Ile Val Cys Gln Thr Glu Gly Phe Ser Gly Gly
20 25 30

Lys Cys Ser Cys Phe Cys Thr Lys Pro Cys
35 40

<210> SEQ ID NO 519
<211> LENGTH: 47
<212> TYPE: PRT
<213> ORGANISM: Salvia bowleyana

<400> SEQUENCE: 519

Arg Thr Cys Glu Ser Glu Ser Ser Thr Phe Lys Gly Leu Cys Leu Lys
1 5 10 15

Asn Ala Asp Cys Tyr Ile Val Cys Arg Thr Glu Gly Phe Ser Gly Gly
20 25 30

Lys Cys Ser Ser Phe Leu Arg Arg Cys Phe Cys Thr Lys Pro Cys
35 40 45

<210> SEQ ID NO 520
<211> LENGTH: 74
<212> TYPE: PRT
<213> ORGANISM: Salvia bowleyana

<400> SEQUENCE: 520

Val Val Cys Ser Ala Ala Ser Arg Leu Phe Ser Gly Leu Cys Phe Ser
1               5                   10                  15

Asp Ser Asn Cys Ser Ser Ile Cys Glu Lys Glu Gly Phe Leu Thr Gly
            20                  25                  30

Val Cys Lys Gly Leu Gln Cys Ile Cys Gln Lys Asp Cys Gly Gly Gly
        35                  40                  45

Asp Gly Gly Asp Pro Gly Gln Gly Gly Ala Asp Gln Ser Ala Leu Ile
    50                  55                  60

Asn Arg Lys Leu Leu Asp Gln Leu Leu Val
65                  70

<210> SEQ ID NO 521
<211> LENGTH: 56
<212> TYPE: PRT
<213> ORGANISM: Salvia bowleyana

<400> SEQUENCE: 521

Ala Ala Ala Ser Val Val Glu Glu Lys Arg Ser Cys Gln Ser Gln Ser
1               5                   10                  15

His Lys Phe Lys Gly Lys Cys Phe Ser Asp Lys Asn Cys Gly Ser Val
            20                  25                  30

Cys Gln Thr Glu Gly Phe Pro Ser Gly Lys Cys His Gly Leu Arg Gln
        35                  40                  45

Arg Cys Phe Cys Thr Arg Pro Cys
    50                  55

<210> SEQ ID NO 522
<211> LENGTH: 56
<212> TYPE: PRT
<213> ORGANISM: Salvia bowleyana

<400> SEQUENCE: 522

Ala Met Cys Ser Ala Pro Ser Lys Leu Phe Arg Gly Val Cys Leu Leu
1               5                   10                  15

Arg Ser Asn Cys Ser Ser Ile Cys Ala Thr Glu Gly Phe Leu Tyr Gly
            20                  25                  30

Leu Cys Lys Asp Leu Lys Cys Val Cys Tyr Lys Asp Cys Asn Val Val
        35                  40                  45

Gly Ser Gly Gly Asp Ala Gln His
    50                  55

<210> SEQ ID NO 523
<211> LENGTH: 74
<212> TYPE: PRT
<213> ORGANISM: Salvia bowleyana

<400> SEQUENCE: 523

Val Met Cys Ser Ala Ala Ser Arg Leu Phe Ser Gly Leu Cys Phe Ser
1               5                   10                  15

Asp Asn Asn Cys Ser Ala Ile Cys Glu Lys Glu Gly Phe Leu Ser Gly
            20                  25                  30

Val Cys Lys Gly Leu Lys Cys Val Cys Gln Lys Asp Cys Asn Gly Gly
        35                  40                  45

Gly Gly Gly Gly Gly Asn Gly Gly Gly Asp Gly Gly Asp Gln Asp Gln
    50                  55                  60

```
Gly Pro Pro Ala Gln Gly Gly Gly Asp Gln
65                  70


<210> SEQ ID NO 524
<211> LENGTH: 74
<212> TYPE: PRT
<213> ORGANISM: Salvia bowleyana

<400> SEQUENCE: 524

Val Met Cys Ser Ala Ala Ser Arg Leu Phe Ser Gly Leu Cys Phe Ser
1               5                   10                  15

Asp Asn Asn Cys Ser Ala Ile Cys Glu Lys Glu Gly Phe Leu Ser Gly
            20                  25                  30

Val Cys Lys Gly Leu Lys Cys Val Cys Gln Lys Asp Cys Asn Gly Gly
        35                  40                  45

Gly Gly Gly Asn Gly Gly Gly Asp Gly Gly Asp Gln Asp Gln Gly Pro
    50                  55                  60

Pro Ala Gln Gly Gly Gly Asp Gln Ser Pro
65                  70


<210> SEQ ID NO 525
<211> LENGTH: 73
<212> TYPE: PRT
<213> ORGANISM: Salvia bowleyana

<400> SEQUENCE: 525

Ala Met Cys Ser Ala Pro Ser Arg Leu Phe Arg Gly Leu Cys Phe Arg
1               5                   10                  15

Arg Ser Asn Cys Thr Ser Ile Cys Glu Lys Glu Gly Phe Leu Tyr Gly
            20                  25                  30

Leu Cys Lys Gly Leu Lys Cys Val Cys Tyr Lys Asp Cys Asn Ala Ala
        35                  40                  45

Gly Gly Gly Gly Asn Gly Gly Asp Pro Gly Gln Gly Pro Pro Asp Gln
    50                  55                  60

Gly Gly Asp Asp Gln Pro Pro Pro Leu
65                  70


<210> SEQ ID NO 526
<211> LENGTH: 56
<212> TYPE: PRT
<213> ORGANISM: Salvia bowleyana

<400> SEQUENCE: 526

Ala Ala Ala Ser Val Val Glu Glu Lys Arg Ser Cys Gln Ser Gln Ser
1               5                   10                  15

His Lys Phe Lys Gly Lys Cys Phe Ser Asp Lys Asn Cys Gly Ser Val
            20                  25                  30

Cys Gln Thr Glu Gly Phe Pro Ser Gly Lys Cys His Gly Leu Arg Gln
        35                  40                  45

Arg Cys Phe Cys Thr Arg Pro Cys
    50                  55


<210> SEQ ID NO 527
<211> LENGTH: 61
<212> TYPE: PRT
<213> ORGANISM: Salvia bowleyana
```

<400> SEQUENCE: 527

```
Ala Met Cys Ser Ala Pro Ser Lys Leu Phe Arg Gly Val Cys Leu Leu
1               5                   10                  15

Arg Ser Asn Cys Ser Ser Ile Cys Ala Thr Glu Gly Phe Leu Tyr Gly
            20                  25                  30

Leu Cys Lys Asp Leu Lys Cys Val Cys Tyr Lys Asp Cys Asn Val Val
        35                  40                  45

Gly Ser Gly Ser Gly Gly Ser Gly Gly Asp Ala Gln His
    50                  55                  60
```

<210> SEQ ID NO 528
<211> LENGTH: 48
<212> TYPE: PRT
<213> ORGANISM: Simmondsia chinensis

<400> SEQUENCE: 528

```
Arg Ile Cys Gln Ser Gln Ser His Leu Phe Arg Gly Pro Cys Val Arg
1               5                   10                  15

Asn His Asn Cys Ala Ser Val Cys Gln Asn Glu Gly Phe Ser Asp Gly
            20                  25                  30

Ser Cys Arg Gly Phe Arg Arg Arg Cys Phe Cys Ala Lys Phe Cys Pro
        35                  40                  45
```

<210> SEQ ID NO 529
<211> LENGTH: 42
<212> TYPE: PRT
<213> ORGANISM: Sechium edule

<400> SEQUENCE: 529

```
Gln Ser His Gly Phe His Gly Ala Cys Leu Ser Asp His Asn Cys Ala
1               5                   10                  15

Val Val Cys Arg Asn Glu Gly Phe Ser Gly Gly Asp Cys Lys Gly Phe
            20                  25                  30

Arg Arg Arg Cys Phe Cys Thr Arg His Cys
        35                  40
```

<210> SEQ ID NO 530
<211> LENGTH: 48
<212> TYPE: PRT
<213> ORGANISM: Sechium edule

<400> SEQUENCE: 530

```
Arg Thr Cys Glu Ser Pro Ser Arg His Phe Lys Gly Val Cys Phe Ser
1               5                   10                  15

Arg Asn Asn Cys Gly His Val Cys Lys Thr Glu Gly Phe His Gly Gly
            20                  25                  30

His Cys Arg Gly Phe Arg Arg Arg Cys Phe Cys Thr Lys His Cys Leu
        35                  40                  45
```

<210> SEQ ID NO 531
<211> LENGTH: 48
<212> TYPE: PRT
<213> ORGANISM: Sechium edule

<400> SEQUENCE: 531

```
Arg Thr Cys Glu Ser Gln Ser His His Phe Lys Gly Leu Cys Phe Ser
1               5                   10                  15

Lys Asn Asn Cys Gly His Val Cys Lys Thr Glu Gly Phe His Gly Gly
            20                  25                  30
```

```
His Cys Arg Gly Phe Arg Arg Arg Cys Phe Cys Thr Lys His Cys Ala
        35                  40                  45


<210> SEQ ID NO 532
<211> LENGTH: 50
<212> TYPE: PRT
<213> ORGANISM: Sequoiadendron giganteum

<400> SEQUENCE: 532

Arg Met Cys Lys Ser Gln Ser His Thr Phe Lys Gly Tyr Cys Val Ser
1               5                   10                  15

Asp Ser Asn Cys Lys Asn Val Cys Arg Thr Glu Lys Phe Pro Thr Gly
            20                  25                  30

Gly Cys Asp Phe His Val Ala Ser Arg Lys Cys Tyr Cys Tyr Lys Pro
        35                  40                  45

Cys Ala
    50


<210> SEQ ID NO 533
<211> LENGTH: 47
<212> TYPE: PRT
<213> ORGANISM: Solanum lycopersicum

<400> SEQUENCE: 533

Arg Thr Cys Glu Ser Gln Ser His Arg Tyr Lys Gly Pro Cys Val Arg
1               5                   10                  15

Lys Asn Asn Cys Ala Asn Val Cys Lys Thr Glu Gly Phe Ser Gly Gly
            20                  25                  30

His Cys Arg Gly Phe Arg Arg Arg Cys Phe Cys Ala Lys His Cys
        35                  40                  45


<210> SEQ ID NO 534
<211> LENGTH: 47
<212> TYPE: PRT
<213> ORGANISM: Solanum lycopersicum

<400> SEQUENCE: 534

Arg Thr Cys Glu Ser Gln Ser His His Phe Lys Gly Asn Cys Leu Ser
1               5                   10                  15

Asp Thr Asn Cys Gly Ser Val Cys Arg Thr Glu Gly Phe Thr Gly Gly
            20                  25                  30

Asn Cys Arg Gly Phe Arg Arg Arg Cys Phe Cys Thr Arg Asn Cys
        35                  40                  45


<210> SEQ ID NO 535
<211> LENGTH: 50
<212> TYPE: PRT
<213> ORGANISM: Solanum lycopersicum

<400> SEQUENCE: 535

Ala Glu Ala Arg Thr Cys Glu Ser Gln Ser Asn Ser Phe Lys Gly Thr
1               5                   10                  15

Cys Val Arg Asp Ser Asn Cys Ala Thr Val Cys Gln Thr Glu Gly Phe
            20                  25                  30

Ile Gly Gly Asn Cys Arg Gly Phe Arg Arg Arg Cys Phe Cys Thr Arg
        35                  40                  45

Asn Cys
    50
```

```
<210> SEQ ID NO 536
<211> LENGTH: 47
<212> TYPE: PRT
<213> ORGANISM: Solanum lycopersicum

<400> SEQUENCE: 536

Arg Thr Cys Glu Pro Gln Ser His Ser Phe Lys Gly Pro Cys Ser Arg
1               5                   10                  15

Asp Ser Asn Cys Ala Thr Val Cys Gln Thr Glu Gly Phe Ile Gly Gly
            20                  25                  30

Asp Cys Arg Gly Leu Arg Arg Gln Cys Phe Cys Thr Thr Glu Cys
        35                  40                  45


<210> SEQ ID NO 537
<211> LENGTH: 47
<212> TYPE: PRT
<213> ORGANISM: Solanum lycopersicum

<400> SEQUENCE: 537

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Phe Arg Arg Arg Cys Phe Cys Thr Arg Pro Cys
        35                  40                  45


<210> SEQ ID NO 538
<211> LENGTH: 47
<212> TYPE: PRT
<213> ORGANISM: Solanum lycopersicum

<400> SEQUENCE: 538

Arg Val Cys Met Ser Pro Ser His Ser Tyr His Gly Pro Cys Trp His
1               5                   10                  15

Asp His Asn Cys Ala Ile Val Cys Arg Asn Glu Gly Phe Ser Gly Gly
            20                  25                  30

Asn Cys Val Gly Ile Gln Leu Lys Cys Tyr Cys Thr Lys Leu Cys
        35                  40                  45


<210> SEQ ID NO 539
<211> LENGTH: 47
<212> TYPE: PRT
<213> ORGANISM: Solanum lycopersicum

<400> SEQUENCE: 539

Arg Val Cys Ile Ser Gln Ser His Arg Tyr Arg Gly Pro Cys Val Leu
1               5                   10                  15

Asp His Asn Cys Ala Ile Ile Cys Arg Asn Glu Gly Phe Ser Gly Gly
            20                  25                  30

Asp Cys Ile Gly Trp Arg Arg Arg Cys Phe Cys Thr Lys Leu Cys
        35                  40                  45


<210> SEQ ID NO 540
<211> LENGTH: 47
<212> TYPE: PRT
<213> ORGANISM: Solanum pennellii

<400> SEQUENCE: 540

Arg Thr Cys Glu Thr Gln Ser His Lys Tyr Lys Gly Pro Cys Val Arg
1               5                   10                  15
```

```
Lys Ser Asn Cys Ala Asn Val Cys Lys Thr Glu Gly Phe Arg Gly Gly
            20                  25                  30

His Cys Arg Gly Phe Arg Arg Arg Cys Phe Cys Thr Lys Asn Cys
        35                  40                  45


<210> SEQ ID NO 541
<211> LENGTH: 55
<212> TYPE: PRT
<213> ORGANISM: Solanum pennellii

<400> SEQUENCE: 541

Gly Ile Arg Lys Thr Asp Ala Lys Leu Cys Gln Tyr His Ser Glu Thr
1               5                   10                  15

Phe His Gly Val Cys Val Thr Gly Asn Asn Cys Asn Arg His Cys Gln
            20                  25                  30

Arg Glu Asn Phe Glu Gly Gly Arg Cys His Gly Ile Arg His Tyr Arg
        35                  40                  45

Cys Val Cys Tyr Arg Thr Cys
    50                  55


<210> SEQ ID NO 542
<211> LENGTH: 47
<212> TYPE: PRT
<213> ORGANISM: Solanum pennellii

<400> SEQUENCE: 542

Arg His Cys Glu Ser Leu Ser His Arg Phe Lys Gly Pro Cys Ala Ser
1               5                   10                  15

Asp Lys Asn Cys Ala Ser Ile Cys Glu Thr Glu Arg Phe Ser Gly Gly
            20                  25                  30

Asn Cys Arg Gly Phe Arg Arg Arg Cys Phe Cys Thr Lys Pro Cys
        35                  40                  45


<210> SEQ ID NO 543
<211> LENGTH: 47
<212> TYPE: PRT
<213> ORGANISM: Solanum pennellii

<400> SEQUENCE: 543

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Phe Arg Arg Arg Cys Phe Cys Thr Arg Pro Cys
        35                  40                  45


<210> SEQ ID NO 544
<211> LENGTH: 47
<212> TYPE: PRT
<213> ORGANISM: Solanum pennellii

<400> SEQUENCE: 544

Arg Thr Cys Glu Ser Gln Ser His Ser Phe Lys Gly Pro Cys Ser Arg
1               5                   10                  15

Asp Ser Asn Cys Ala Thr Val Cys Gln Thr Glu Gly Phe Ile Gly Gly
            20                  25                  30

Asp Cys Arg Gly Leu Arg Arg Gln Cys Phe Cys Thr Thr Asp Cys
        35                  40                  45
```

<210> SEQ ID NO 545
<211> LENGTH: 47
<212> TYPE: PRT
<213> ORGANISM: Solanum pennellii

<400> SEQUENCE: 545

```
Arg Thr Cys Glu Ser Gln Ser Asn Ser Phe Lys Gly Thr Cys Val Arg
1               5                   10                  15

Asp Ser Asn Cys Ala Thr Val Cys Gln Thr Glu Gly Phe Ile Gly Gly
            20                  25                  30

Asn Cys Arg Gly Phe Arg Arg Arg Cys Phe Cys Thr Arg Asn Cys
        35                  40                  45
```

<210> SEQ ID NO 546
<211> LENGTH: 47
<212> TYPE: PRT
<213> ORGANISM: Solanum pennellii

<400> SEQUENCE: 546

```
Arg Thr Cys Glu Ser Gln Ser His His Phe Lys Gly Asn Cys Leu Ser
1               5                   10                  15

Asp Thr Asn Cys Gly Ser Val Cys Arg Thr Glu Gly Phe Thr Gly Gly
            20                  25                  30

Asn Cys Arg Gly Phe Arg Arg Arg Cys Phe Cys Thr Arg Asn Cys
        35                  40                  45
```

<210> SEQ ID NO 547
<211> LENGTH: 47
<212> TYPE: PRT
<213> ORGANISM: Solanum pennellii

<400> SEQUENCE: 547

```
Arg Val Cys Met Ser Pro Ser His Ser Tyr His Gly Pro Cys Trp His
1               5                   10                  15

Asp His Asn Cys Ala Ile Val Cys Arg Asn Glu Gly Phe Ser Gly Gly
            20                  25                  30

Asn Cys Val Gly Ile Gln Leu Lys Cys Tyr Cys Thr Lys Leu Cys
        35                  40                  45
```

<210> SEQ ID NO 548
<211> LENGTH: 47
<212> TYPE: PRT
<213> ORGANISM: Solanum pennellii

<400> SEQUENCE: 548

```
Arg Val Cys Ile Ser Gln Ser His Arg Tyr Arg Gly Pro Cys Val Leu
1               5                   10                  15

Asp His Asn Cys Ala Ile Ile Cys Arg Asn Glu Gly Phe Ser Gly Gly
            20                  25                  30

Asp Cys Ile Gly Trp Arg Arg Arg Cys Phe Cys Thr Lys Leu Cys
        35                  40                  45
```

<210> SEQ ID NO 549
<211> LENGTH: 47
<212> TYPE: PRT
<213> ORGANISM: Schrenkiella parvula

<400> SEQUENCE: 549

```
Arg Thr Cys Glu Ser Lys Ser His Arg Phe Arg Gly Val Cys Val Ser
1               5                   10                  15
```

```
Asp Gly Asn Cys Gly Asn Val Cys His Asn Glu Gly Phe Gly Gly Gly
            20                  25                  30

Lys Cys Arg Gly Phe Arg Arg Arg Cys Phe Cys Thr Arg His Cys
        35                  40                  45
```

<210> SEQ ID NO 550
<211> LENGTH: 47
<212> TYPE: PRT
<213> ORGANISM: Schrenkiella parvula

<400> SEQUENCE: 550

```
Arg Thr Cys Glu Ser Gln Ser His Arg Phe Lys Gly Lys Cys Leu Ser
1               5                   10                  15

Asp Gly Asn Cys Gly Asn Val Cys His Asn Glu Gly Phe Gly Gly Gly
            20                  25                  30

Lys Cys Arg Gly Phe Arg Arg Arg Cys Phe Cys Thr Arg Asn Cys
        35                  40                  45
```

<210> SEQ ID NO 551
<211> LENGTH: 45
<212> TYPE: PRT
<213> ORGANISM: Schrenkiella parvula

<400> SEQUENCE: 551

```
Lys Thr Cys Glu Ser Pro Ser Gly Lys Tyr His Gly Val Cys Leu Asn
1               5                   10                  15

Ala Lys Asn Cys Ala Ser Val Cys Pro Ser Glu Gly Phe Thr Gly Gly
            20                  25                  30

His Cys Lys Ser Leu Arg Cys Tyr Cys Ile Lys Thr Cys
        35                  40                  45
```

<210> SEQ ID NO 552
<211> LENGTH: 63
<212> TYPE: PRT
<213> ORGANISM: Schrenkiella parvula

<400> SEQUENCE: 552

```
Thr Glu Met Gly Pro Ala Asp Val Glu Pro Arg Ile Cys Glu Thr Leu
1               5                   10                  15

Ser Lys Val Phe Lys Gly Met Cys Trp Asn Gln Asn Asn Cys Ala Ile
            20                  25                  30

Met Cys Arg Glu Phe Glu His Phe His Ser Gly His Cys Arg Gly Phe
        35                  40                  45

Leu Arg Arg Cys Tyr Cys Thr Lys Arg Cys Asp Gly Gly Pro Ser
    50                  55                  60
```

<210> SEQ ID NO 553
<211> LENGTH: 52
<212> TYPE: PRT
<213> ORGANISM: Tarenaya hassleriana

<400> SEQUENCE: 553

```
Glu Arg Gly Glu Gly Arg Met Cys Gln Ser Lys Ser His His Phe His
1               5                   10                  15

Arg Thr Cys Val Ser Asn His Asn Cys Ala Met Val Cys Arg Thr Glu
            20                  25                  30
```

Gly Phe Ser Gly Gly His Cys Val Gly Phe Arg Arg Arg Cys Phe Cys
35 40 45

Thr Arg Leu Cys
50

<210> SEQ ID NO 554
<211> LENGTH: 47
<212> TYPE: PRT
<213> ORGANISM: Tarenaya hassleriana

<400> SEQUENCE: 554

Arg Thr Cys Glu Ser Pro Ser His Arg Phe Lys Gly Ala Cys Leu Ser
1 5 10 15

Glu Thr Asn Cys Ala Asn Val Cys His Asn Glu Gly Phe Ile Gly Gly
20 25 30

Asn Cys Arg Gly Leu Arg Arg Arg Cys Phe Cys Thr Lys His Cys
35 40 45

<210> SEQ ID NO 555
<211> LENGTH: 47
<212> TYPE: PRT
<213> ORGANISM: Theobroma caccao

<400> SEQUENCE: 555

Arg Thr Cys Gln Ser Gln Ser His Arg Phe Lys Gly Met Cys Met Arg
1 5 10 15

Lys Ser Asn Cys Ala Ala Val Cys Gln Thr Glu Gly Phe His Ser Gly
20 25 30

His Cys Arg Gly Phe His Arg Arg Cys Phe Cys Thr Lys His Cys
35 40 45

<210> SEQ ID NO 556
<211> LENGTH: 47
<212> TYPE: PRT
<213> ORGANISM: Theobroma caccao

<400> SEQUENCE: 556

Arg Thr Cys Glu Ser Lys Ser His Ala Phe Lys Gly Pro Cys Leu Ser
1 5 10 15

Asp His Asn Cys Gly Leu Val Cys Arg Asn Glu Gly Phe Pro Asp Gly
20 25 30

Trp Cys Arg Gly Ile Arg Arg Arg Cys Phe Cys Thr Arg Arg Cys
35 40 45

<210> SEQ ID NO 557
<211> LENGTH: 47
<212> TYPE: PRT
<213> ORGANISM: Theobroma caccao

<400> SEQUENCE: 557

Arg Leu Cys Glu Ser Lys Ser His Gly Phe Lys Gly Ala Cys Leu Ser
1 5 10 15

Asp His Asn Cys Gly Met Val Cys Ser Asn Glu Gly Phe Ser Gly Gly
20 25 30

Arg Cys Arg Gly Phe Arg His Arg Cys Phe Cys Thr Arg Arg Cys
35 40 45

<210> SEQ ID NO 558
<211> LENGTH: 47
<212> TYPE: PRT

<213> ORGANISM: Theobroma caccao

<400> SEQUENCE: 558

```
Arg Val Cys Glu Ser Lys Ser His Lys Phe Lys Gly Pro Cys Leu Gly
1               5                   10                  15

Asp His Asn Cys Ala Leu Val Cys Arg Asn Glu Gly Phe Ser Gly Gly
            20                  25                  30

Arg Cys Arg Gly Phe Arg His Arg Cys Phe Cys Thr Lys Leu Cys
        35                  40                  45
```

<210> SEQ ID NO 559
<211> LENGTH: 47
<212> TYPE: PRT
<213> ORGANISM: Thlaspi arvense

<400> SEQUENCE: 559

```
Arg Thr Cys Glu Ser Lys Ser His Arg Phe Lys Gly Ala Cys Leu Ser
1               5                   10                  15

Glu Thr Asn Cys Lys Asn Val Cys His Asn Glu Gly Phe Arg Gly Gly
            20                  25                  30

Asn Cys Arg Gly Leu Arg Arg Arg Cys Phe Cys Thr Arg Asn Cys
        35                  40                  45
```

<210> SEQ ID NO 560
<211> LENGTH: 47
<212> TYPE: PRT
<213> ORGANISM: Eutrema salsugineum

<400> SEQUENCE: 560

```
Arg Lys Cys Glu Ser Lys Ser His Arg Phe Lys Gly Lys Cys Leu Ser
1               5                   10                  15

Glu Thr Asn Cys Lys Asn Val Cys His Asn Glu Gly Phe Thr Gly Gly
            20                  25                  30

Asn Cys Arg Gly Phe Arg Arg Arg Cys Phe Cys Thr Arg Asn Cys
        35                  40                  45
```

<210> SEQ ID NO 561
<211> LENGTH: 46
<212> TYPE: PRT
<213> ORGANISM: Eutrema salsugineum

<400> SEQUENCE: 561

```
Arg Thr Cys Glu Ser Ala Ser Gly Lys Phe Gln Gly Val Cys Leu Asn
1               5                   10                  15

Ser Lys Ser Cys Ala Ser Val Cys Gln Ser Asn Glu Gly Phe Ser Gly
            20                  25                  30

Gly His Cys Asn Ser Leu Arg Cys Tyr Cys Thr Lys Thr Cys
        35                  40                  45
```

<210> SEQ ID NO 562
<211> LENGTH: 47
<212> TYPE: PRT
<213> ORGANISM: Eutrema salsugineum

<400> SEQUENCE: 562

```
Arg Met Cys Gln Ser Lys Ser His His Phe Lys His Met Cys Trp Ser
1               5                   10                  15

Asp His Asn Cys Ala Ile Ile Cys Arg Asn Glu Gly Phe Ser Gly Gly
            20                  25                  30
```

```
Arg Cys Arg Gly Phe His Arg Arg Cys Tyr Cys Thr Arg Leu Cys
        35                  40                  45


<210> SEQ ID NO 563
<211> LENGTH: 50
<212> TYPE: PRT
<213> ORGANISM: Eutrema salsugineum

<400> SEQUENCE: 563

Gln Gln Ile Cys Lys Ala Arg Ser Ile Asn Phe Thr Ala Leu Cys Leu
1               5                   10                  15

Arg Trp Ser Lys Cys Lys Gln Ala Cys Leu Thr Glu Asn Phe Pro Asp
            20                  25                  30

Gly Arg Cys Ile Ala Arg Arg Cys Phe Cys Met Thr Pro Cys His Phe
        35                  40                  45

Leu Thr
    50


<210> SEQ ID NO 564
<211> LENGTH: 52
<212> TYPE: PRT
<213> ORGANISM: Eutrema salsugineum

<400> SEQUENCE: 564

Gln Gln Ile Cys Glu Ala Arg Ser Ile Asn Phe Arg Gly Met Cys Met
1               5                   10                  15

Lys Trp Arg Asn Cys Gln Arg Val Cys Met Ser Glu Gly Phe Pro Asp
            20                  25                  30

Gly Arg Cys Ala Gly Phe Ile Arg Arg Cys Ile Cys Arg Lys Pro Cys
        35                  40                  45

Pro Ile Leu Ser
    50


<210> SEQ ID NO 565
<211> LENGTH: 100
<212> TYPE: PRT
<213> ORGANISM: Eutrema salsugineum

<400> SEQUENCE: 565

Arg Met Cys Glu Ser Ser Ser Gln Leu Phe Asn Gly Pro Cys Leu Ser
1               5                   10                  15

Thr Thr Asn Cys Ala Asn Ile Cys His Asn Glu Gly Phe Thr Asp Gly
            20                  25                  30

Asp Cys Gln Gly Phe Arg Arg Arg Cys Ile Cys Thr Arg Pro Cys Thr
        35                  40                  45

Pro Arg Gly Met Glu Arg Lys Thr Leu Gly Leu Phe Phe Met Leu Phe
    50                  55                  60

Leu Leu Leu Ser Ala Asp Lys Tyr Tyr Phe Met Asp Ala Asp Val Ala
65                  70                  75                  80

Leu Lys Thr Ala Glu Ala Arg Arg Cys Glu Ser Lys Ser His Lys Phe
                85                  90                  95

Lys Gly Pro Cys
            100


<210> SEQ ID NO 566
<211> LENGTH: 48
<212> TYPE: PRT
<213> ORGANISM: Trifolium pratense
```

<400> SEQUENCE: 566

Arg Thr Cys Glu Ser Gln Ser His Lys Phe Lys Gly Pro Cys Ala Ser
1 5 10 15

Asp His Asn Cys Ala Ser Val Cys Gln Thr Glu Arg Phe Pro Gly Gly
20 25 30

His Cys Arg Gly Phe Arg Arg Arg Cys Phe Cys Thr Thr His Cys Ser
35 40 45

<210> SEQ ID NO 567
<211> LENGTH: 55
<212> TYPE: PRT
<213> ORGANISM: Trifolium pratense

<400> SEQUENCE: 567

Glu Met Val Val Glu Thr Glu Gly Arg His Cys Glu Ser Lys Ser His
1 5 10 15

Arg Phe Lys Gly Met Cys Leu Ser Asp His Asn Cys Ala Ser Val Cys
20 25 30

His Val Glu Gly Phe Pro Gly Gly Asn Cys Arg Gly Phe Arg Arg Arg
35 40 45

Cys Phe Cys Lys Lys Arg Cys
50 55

<210> SEQ ID NO 568
<211> LENGTH: 48
<212> TYPE: PRT
<213> ORGANISM: Trifolium pratense

<400> SEQUENCE: 568

Arg Lys Cys Glu Ser Lys Arg Arg Trp Ile Tyr Gly Asn Cys Leu Ser
1 5 10 15

Asp Glu Lys Cys Ala Ser Asp Cys Leu Val Lys Gly Phe Leu Phe Gly
20 25 30

Lys Cys Arg Gly Tyr Asp Asn Arg Cys Tyr Cys Lys Lys Pro Arg Cys
35 40 45

<210> SEQ ID NO 569
<211> LENGTH: 47
<212> TYPE: PRT
<213> ORGANISM: Tripterygium wilfordii

<400> SEQUENCE: 569

Arg Val Cys Ala Ser Lys Ser His Tyr Tyr Lys Gly Pro Cys Leu His
1 5 10 15

Asn His Asn Cys Ala Met Val Cys Arg Asn Glu Gly Phe Ser Gly Gly
20 25 30

Lys Cys His Gly Leu Gly Arg Arg Cys Phe Cys Thr Lys Leu Cys
35 40 45

<210> SEQ ID NO 570
<211> LENGTH: 47
<212> TYPE: PRT
<213> ORGANISM: Tripterygium wilfordii

<400> SEQUENCE: 570

Arg Val Cys Leu Ser Pro Ser His Lys Phe His Gly Thr Cys Val Arg
1 5 10 15

Gly His Asn Cys Ala Glu Ile Cys Arg Thr Glu Gly Phe Ser Gly Gly
20 25 30

```
Asp Cys His Gly Phe Arg Arg Arg Cys Met Cys Ser Arg Arg Cys
        35                  40                  45


<210> SEQ ID NO 571
<211> LENGTH: 57
<212> TYPE: PRT
<213> ORGANISM: Phtheirospermum japonicum

<400> SEQUENCE: 571

Ala Gly Glu Glu Ala Val Gly Glu Glu Lys Lys Ala Cys Lys Tyr Lys
1               5                   10                  15

Ser Glu Lys Phe Trp Gly Ile Cys Ile Thr Asp Ser Lys Cys Ile Glu
            20                  25                  30

Val Cys Arg Arg Glu Gly Phe Gln Thr Gly Asp Cys Lys Gly Leu Arg
        35                  40                  45

Arg Arg Cys Tyr Cys Val Asn Asn Cys
    50                  55


<210> SEQ ID NO 572
<211> LENGTH: 82
<212> TYPE: PRT
<213> ORGANISM: Vigna mungo

<400> SEQUENCE: 572

Val Ala Ser Gly Gly Lys Asp Lys Thr Lys Lys Pro Gly Arg Tyr Ile
1               5                   10                  15

Ala Thr Glu Leu Glu Asn Ile Glu Thr Asn Tyr Phe Ser Asp Tyr Thr
            20                  25                  30

Gly Phe Glu Ile Gln Ile Asp Ser Thr Asp Val Asp Asp Ala Ile Asp
        35                  40                  45

Thr Leu Ser Glu Val Ala Ser Lys Lys Leu Val Gln Ile Leu Leu Arg
    50                  55                  60

Phe Val Ala Leu Phe Leu Pro Val Ala Pro Ile Pro Pro Leu Pro Ile
65                  70                  75                  80

Pro Ser


<210> SEQ ID NO 573
<211> LENGTH: 48
<212> TYPE: PRT
<213> ORGANISM: Zea mays

<400> SEQUENCE: 573

Arg Thr Cys Gln Ser Gln Ser His Arg Phe Arg Gly Pro Cys Leu Arg
1               5                   10                  15

Arg Ser Asn Cys Ala Asn Val Cys Arg Thr Glu Gly Phe Pro Gly Gly
            20                  25                  30

Arg Cys Arg Gly Phe Arg Arg Arg Cys Phe Cys Thr Thr His Cys His
        35                  40                  45


<210> SEQ ID NO 574
<211> LENGTH: 55
<212> TYPE: PRT
<213> ORGANISM: Zea mays

<400> SEQUENCE: 574

Arg Val Val Val Glu Glu Thr Leu Cys Leu Ser Gln Ser His Ala Phe
1               5                   10                  15

Lys Gly Val Cys Leu Ser Asn Thr Asn Cys Asp Asn Val Cys Lys Thr
            20                  25                  30
```

```
Glu Lys Phe Thr Gly Gly Glu Cys Lys Met Asp Gly Val Met Arg Lys
        35                  40                  45

Cys Tyr Cys Lys Lys Val Cys
    50                  55


<210> SEQ ID NO 575
<211> LENGTH: 49
<212> TYPE: PRT
<213> ORGANISM: Zea mays

<400> SEQUENCE: 575

Arg His Cys Leu Ser Gln Ser His Arg Phe Lys Gly Leu Cys Met Ser
1               5                   10                  15

Ser Asn Asn Cys Ala Asn Val Cys Gln Thr Glu Asn Phe Pro Gly Gly
            20                  25                  30

Glu Cys Lys Ala Glu Gly Ala Thr Arg Lys Cys Phe Cys Lys Lys Ile
        35                  40                  45

Cys


<210> SEQ ID NO 576
<211> LENGTH: 55
<212> TYPE: PRT
<213> ORGANISM: Zea mays

<400> SEQUENCE: 576

Gly Pro Val Thr Met Val Ser Ala Arg Lys Cys Glu Ser Gln Ser Phe
1               5                   10                  15

Arg Phe Lys Gly Pro Cys Ser Arg Asp Ala Asn Cys Ala Asn Val Cys
            20                  25                  30

Leu Thr Glu Gly Phe Thr Gly Gly Val Cys Lys Gly Leu Arg His Arg
        35                  40                  45

Cys Phe Cys Thr Arg Asp Cys
    50                  55


<210> SEQ ID NO 577
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 577

Gly Ala Cys Leu Lys Asn Arg His Ser Lys His Tyr Gly Cys Tyr Cys
1               5                   10                  15

Tyr Tyr Arg His Cys Tyr
            20


<210> SEQ ID NO 578
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION
```

<400> SEQUENCE: 578

Gly Ala Cys Leu Lys Asn Arg His Ser Lys His Tyr Gly Trp Phe Trp
1 5 10 15

Tyr Tyr Arg His Cys Tyr
20

<210> SEQ ID NO 579
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 579

Gly Ala Cys Leu Lys Asn Arg His Ser Lys His Tyr Gly Phe Phe Trp
1 5 10 15

Tyr Tyr Arg His Cys Tyr
20

<210> SEQ ID NO 580
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (16)..(16)
<223> OTHER INFORMATION: AMIDATION

<400> SEQUENCE: 580

Gly Arg Cys Arg Gly Phe Arg Arg Arg Cys Phe Cys Thr Thr His Cys
1 5 10 15

<210> SEQ ID NO 581
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 581

Gly Gly Arg Cys Lys Gly Phe Leu Arg Arg Phe Trp Phe Thr Arg Ile
1 5 10 15

Cys

<210> SEQ ID NO 582
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (17)..(17)
<223> OTHER INFORMATION: AMIDATION

<400> SEQUENCE: 582

Gly Gly Arg Cys Lys Gly Phe Arg Arg Arg Trp Tyr Trp Thr Arg Ile
1               5                   10                  15

Cys

<210> SEQ ID NO 583
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (16)..(16)
<223> OTHER INFORMATION: AMIDATION

<400> SEQUENCE: 583

Ser Gly Arg Cys Arg Ile Leu Phe Arg Cys Phe Cys Thr Lys Asn Cys
1               5                   10                  15

<210> SEQ ID NO 584
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (16)..(16)
<223> OTHER INFORMATION: AMIDATION

<400> SEQUENCE: 584

Ser Gly Arg Cys Arg Ile Leu Phe Arg Trp Phe Trp Thr Lys Asn Cys
1               5                   10                  15

<210> SEQ ID NO 585
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (16)..(16)
<223> OTHER INFORMATION: AMIDATION

<400> SEQUENCE: 585

Ser Gly Arg Cys Arg Ile Leu Phe Arg Trp Tyr Phe Thr Lys Asn Cys
1               5                   10                  15

<210> SEQ ID NO 586
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (18)..(18)
<223> OTHER INFORMATION: AMIDATION

<400> SEQUENCE: 586

Gly Ala Cys His Arg Gln Gly Phe Gly Phe Ala Cys Phe Cys Tyr Lys
1               5                   10                  15

Lys Cys

<210> SEQ ID NO 587
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid other than cysteine
<220> FEATURE:
<221> NAME/KEY: VARIANT
<222> LOCATION: (4)..(13)
<223> OTHER INFORMATION: Xaa is any amino acid other than cysteine, Xaa7 to Xaa13 are optionally present
<220> FEATURE:
<221> NAME/KEY: VARIANT
<222> LOCATION: (14)..(16)
<223> OTHER INFORMATION: Xaa is F, W, or Y

<400> SEQUENCE: 587

```
Gly Xaa Cys Xaa Xaa Xaa Xaa Xaa Xaa Xaa Xaa Xaa Xaa Xaa Xaa Xaa
1               5                   10                  15
```

<210> SEQ ID NO 588
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(15)
<223> OTHER INFORMATION: Xaa is any amino acid, Xaa7 to Xaa15 are optionally present
<220> FEATURE:
<221> NAME/KEY: VARIANT
<222> LOCATION: (16)..(18)
<223> OTHER INFORMATION: Xaa is F, W, or Y

<400> SEQUENCE: 588

```
Gly Xaa Cys Xaa Xaa Xaa Xaa Xaa Xaa Xaa Xaa Xaa Xaa Xaa Xaa Xaa
1               5                   10                  15

Xaa Xaa
```

<210> SEQ ID NO 589
<211> LENGTH: 21
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(18)
<223> OTHER INFORMATION: Xaa is any amino acid, Xaa7 to Xaa18 are optionally present
<220> FEATURE:
<221> NAME/KEY: VARIANT
<222> LOCATION: (19)..(21)
<223> OTHER INFORMATION: Xaa is F, W, or Y

<400> SEQUENCE: 589

```
Gly Xaa Cys Xaa Xaa Xaa Xaa Xaa Xaa Xaa Xaa Xaa Xaa Xaa Xaa Xaa
1               5                   10                  15
```

```
Xaa Xaa Xaa Xaa Xaa
            20


<210> SEQ ID NO 590
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(15)
<223> OTHER INFORMATION: Xaa is any amino acid, Xaa7 to Xaa15 are
      optionally present

<400> SEQUENCE: 590

Gly Xaa Cys Xaa Xaa Xaa Xaa Xaa Xaa Xaa Xaa Xaa Xaa Xaa Xaa Cys
1               5                   10                  15


<210> SEQ ID NO 591
<211> LENGTH: 19
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(18)
<223> OTHER INFORMATION: Xaa is any amino acid, Xaa7 to Xaa18 are
      optionally present

<400> SEQUENCE: 591

Gly Xaa Cys Xaa Xaa Xaa Xaa Xaa Xaa Xaa Xaa Xaa Xaa Xaa Xaa Xaa
1               5                   10                  15

Xaa Xaa Cys


<210> SEQ ID NO 592
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is any amino acid  other than cysteine
<220> FEATURE:
<221> NAME/KEY: VARIANT
<222> LOCATION: (4)..(13)
<223> OTHER INFORMATION: Xaa is any amino acid  other than cysteine,
      wherein Xaa 7 to Xaa 13 are optionally present
<220> FEATURE:
<221> NAME/KEY: VARIANT
<222> LOCATION: (15)..(15)
<223> OTHER INFORMATION: Xaa is any amino acid other than cysteine

<400> SEQUENCE: 592

Gly Xaa Cys Xaa Xaa Xaa Xaa Xaa Xaa Xaa Xaa Xaa Xaa Cys Xaa Cys
1               5                   10                  15
```

MODIFIED ANTIMICROBIAL PEPTIDES

CROSS-REFERENCE TO RELATED APPLICATIONS

This application claims the benefit of U.S. Patent Application Ser. No. 63/365,928, filed Jun. 6, 2022, and U.S. Patent Application Ser. No. 63/202,559, filed Jun. 16, 2021, which are each incorporated herein by reference in their entireties.

GOVERNMENT SUPPORT STATEMENT

This invention was made with government support under National Science Foundation EAGER Award Number 1955461 awarded by the National Science Foundation. The government has certain rights in the invention.

SEQUENCE LISTING

The replacement sequence listing contained in the file named "P13511US02R_ST25", which is 295,533 bytes as measured in the Windows operating system, which was created on Mar. 17, 2025 and electronically filed herewith, is incorporated herein by reference in its entirety. The sequence listing contained in the file named "P13511US02_ST25", which is 294,870 bytes as measured in the Windows operating system, and which was created on Jun. 13, 2022, and electronically filed herewith, is incorporated herein by reference in its entirety.

BACKGROUND

Protection of agriculturally important crops from pathogenic microbes (e.g., fungi or oomycetes) is crucial in improving crop yields. Microbial infections are a particular problem in damp climates and can become a major concern during crop storage, where such infections can result in spoilage and contamination of food or feed products with microbial toxins. Unfortunately, modern growing methods, harvesting and storage systems can promote plant pathogen infections.

Control of plant pathogens is further complicated by the need to simultaneously control multiple microbes of distinct genera. For example, microbes such as *Alternaria; Ascochyta; Aphenomyces; Botrytis; Cercospora; Colletotrichum; Diplodia; Erysiphe; Fusarium; Gaeumanomyces; Helminthosporium; Leptosphaeria, Macrophomina; Magnaporthe; Nectria; Peronospora; Phoma; Phakopsora, Phymatotrichum; Phytophthora; Plasmopara; Podosphaera; Puccinia; Pythium; Pyrenophora; Pyricularia; Rhizoctonia; Sclerotium; Sclerotinia; Septoria; Thielaviopsis; Uncinula; Venturia*; and *Verticillium* species are all recognized plant pathogens.

Certain microbes (e.g., fungi, including mold, yeast and dimorphic fungi, or oomycetes) can also be pathogenic to various vertebrates including humans, livestock, companion animals, fish, and the like. Microbes including dermatophytes, *Aspergillus, Candida, Cryptococcus, Coccidiomyces, Penicillium, Rhizopus, Apophysomyces, Cunninghamella, Saksenaea, Rhizomucor, Syncephalostrum, Cokeromyces, Actinomucor, Pythium, Fusarium, Histoplasmosis*, or *Blastomyces* species are also important vertebrate pathogens.

A group of proteins known as defensins have been shown to inhibit plant pathogens. Defensins have been previously identified as small cysteine-rich peptides of about 45-54 amino acids that constitute an important component of the innate immunity of plants (Thomma et al., 2002; Lay and Anderson, 2005; Vriens et al., 2014). Widely distributed in plants, defensins vary greatly in their amino acid composition. However, they all have a compact shape which is stabilized by either four or five intramolecular disulfide bonds. Plant defensins have previously been characterized as comprising a conserved gamma core peptide comprising a conserved GXCX3-9C (where X is any amino acid) sequence (Sagaram et al., 2011; Lacerda et al., 2014). The three dimensional structure of the previously characterized gamma core peptide consists of two antiparallel β-sheets, with an interpolated turn region (Ibid.). Antimicrobial activity of certain defensins has been correlated with the presence of positively charged amino acid residues in the gamma core peptide (Spelbrink et al, Plant Physiol., 2004; Sagaram et al, 2013).

Plant defensins have been extensively studied for their role in plant defense. Some plant defensins inhibit the growth of a broad range of microbes at micromolar concentrations (Broekaert et al, 1995; Broekaert et al, 1997; da Silva Conceicao and Broekaert, 1999) and, when expressed in transgenic plants, confer strong resistance to microbial pathogens (da Silva Conceicao and Broekaert, 1999; Thomma et al., 2002; Lay and Anderson, 2005). Two small cysteine-rich proteins isolated from radish seed, Rs-AFP1 and Rs-AFP2, inhibited the growth of many pathogenic microbes when the pure protein was added to an in vitro antimicrobial assay medium (U.S. Pat. No. 5,538,525). Transgenic tobacco plants containing the gene encoding Rs-AFP2 protein were found to be more resistant to attack by microbes than non-transformed plants.

Defensin genes have also been identified in the legume *Medicago truncatula* (Hanks et al., 2005). The cloned MtDef2 protein has been demonstrated through in vitro experiments to have little or no antimicrobial activity (Spelbrink et al., 2004). The *Medicago truncatula* defensin proteins MtDef4 (U.S. Pat. No. 7,825,297; incorporated herein by reference in its entirety) and MtDef5 (WO2014179260 and US Patent Appl. Pub. No. 20160208278; both incorporated herein by reference in its entirety) have antimicrobial activity. The C-terminal 16 amino acid GMA4-C peptide of the MtDef4 defensin protein inhibited *Fusarium graminearum* at concentrations as low as 3 μM (Sagaram et al., 2011)

Plant defensins with potent antifungal activity in vitro often fail to confer effective disease resistance in planta. This constrains their commercial development as antifungal agents in transgenic crops. Antifungal plant defensins are generally cationic and cationic residues in their sequences are believed to initiate passage through fungal cell envelope by electrostatic interactions with the anionic fungal cell membrane (Kerenga et al., 2019). Potassium (K+) is an essential macronutrient and is also the most abundant cation in plants. The concentration of K+ in the plant cell cytoplasm is consistently between 100 and 200 mM (Shabala and Pottosin, 2010 and between 10 and 200 mM in the apoplast (White and Karley, 2010). Calcium is an essential secondary micronutrient and its concentrations can range from 0.1% to 6% of the dry weight of plants (Broadley et al., 2003). The concentrations of sodium (Na+) in plants range from 0.001%-8% (Marschner, 1995). Na+ is an essential micronutrient for plants in saline soils.

Many plant defensins that have been characterized to date lose their antifungal activity at elevated concentrations of mono- and bivalent cations such as 100 mM KCl or 2 mM $CaCl_2$). However, the maize plant defensin ZmD32 having a predicted charge of +10.1 at pH 7 exhibits inhibitory activity against *Candida* sp. and *E. coli* in the presence of 100 mM NaCl while the *Nicotiana benthamiana* plant defensin NbD6 having a predicted charge of +7.6 at pH 7 exhibits inhibitory activity against *Candida albicans* in the presence of 100 mM NaCl (Kerenga et al., 2019).

SUMMARY

A peptide comprising SEQ ID NO: 1, wherein said peptide does not comprise the corresponding full-length sequence of the defensin peptide of SEQ ID NO: 8, 16, 20, 23, 26, 29, 37, 38, 39, 40, or 41; optionally wherein said peptide comprises a modified gamma-core consensus sequence GXCX3-8 (F/W/Y)(F/W/Y)(F/W/Y) set forth in SEQ ID NO: 33, GXCX3-9(F/W/Y)(F/W/Y)(F/W/Y) set forth in SEQ ID NO: 34, GXCX3-8 (F/W/Y) (SEQ ID NO: 43), or GXCX3-9(F/W/Y) (SEQ ID NO: 44); and/or optionally wherein the C-terminal cysteine residue or C-terminal amino acid residue is amidated is provided. A peptide having at least 75%, 82%, or 94% sequence identity across the entire length of any one of SEQ ID NO: 3, 4, 5, or 6, wherein the peptide is not identical to SEQ ID NO: 8, optionally wherein any amino acid substitution in said sequence increases or maintains the net positive charge at neutral pH and/or increases or maintains hydrophobicity of the peptide, and optionally wherein the C-terminal cysteine residue is amidated. A peptide having at least 75%, 82%, or 94% sequence identity across the entire length of SEQ ID NO: 7, 12, 13, 14, 15, 17-20, 22, 23, 25, 26, 28, 29, 31, and 32, wherein the peptide is not identical to SEQ ID NO: 8, 16, 20, 23, 26, 29, 37, 38, 39, 40, or 41, optionally wherein the peptide of SEQ ID NO: 5, SEQ ID NO: 13, 14, 15, 18, 19, 20, 22, 23, 26, 28, 29, 31, or 32 comprises a disulfide bond between the two cysteine residues and optionally wherein any substitution increases or maintains the net positive charge at neutral pH and/or increases or maintains hydrophobicity of the peptide, and optionally wherein the C-terminal cysteine residue or C-terminal amino acid residue is amidated, is provided. A defensin C-terminal peptide variant comprising conserved C1 and C4 cysteine residues corresponding to N-terminal and C-terminal cysteines of a reference defensin C-terminal peptide, wherein conserved C2 and C3 cysteine residues of the reference defensin C-terminal peptide are independently substituted with tryptophan, tyrosine, phenylalanine, leucine, valine, isoleucine, or methionine; and optionally wherein the defensin peptide variant has a net positive charge of at least 3, 3.5, 4, 5, or 6 and a hydrophobic amino acid content at least 18% is provided. A C-terminal defensin peptide variant comprising a modified gamma-core consensus sequence GXCX3-8 (F/W/Y)(F/W/Y)(F/W/Y) (SEQ ID NO: 33), GXCX3-9(F/W/Y)(F/W/Y)(F/W/Y) (SEQ ID NO: 34), GXCX3-8 (F/W/Y) (SEQ ID NO: 43), GXCX3-9(F/W/Y) (SEQ ID NO: 44), GXCX3-8(F/W/Y/L/V/I/M) (SEQ ID NO: 45), GXCX3-10 (F/W/Y/L/V/I/M) (SEQ ID NO: 46), GXCX3-8 (L/V/I/M) (F/W/Y) (L/V/I/M) (SEQ ID NO: 47), GXCX3-10 (L/V/I/M)(F/W/Y) (L/V/I/M) (SEQ ID NO: 48), GXCX3-8(F/W/Y/L/V/I/M) (F/W/Y)(F/W/Y/L/V/I/M) (SEQ ID NO: 49), GXCX3-10(F/W/Y/L/V/I/M) (F/W/Y)(F/W/Y/L/V/I/M) (SEQ ID NO: 50), GXCX3-8(F/W/Y/L/V/I/M)(F/W/Y/L/V/I/M)(F/W/Y/L/V/I/M) (SEQ ID NO: 51), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), or GXCX3-10(F/W/Y/L/V/I/M)(F/W/Y/L/V/I/M)(F/W/Y/L/V/I/M) (SEQ ID NO: 52) is provided. In certain embodiments, the aforementioned peptide exhibits antimicrobial activity, wherein the antimicrobial activity is optionally one or more of an anti-fungal or antibacterial activity. Compositions comprising any of the aforementioned peptides and an agriculturally, pharmaceutically, or veterinary-practicably acceptable carrier, diluent, or excipient are also provided. Compositions comprising any of the aforementioned peptides and carriers, diluents, or excipients for use in treating, preventing, or inhibiting microbial infection in a subject in need thereof are also provided.

Methods for: (i) preventing or reducing crop damage by a plant pathogenic microbe or (ii) preventing contamination of plants, plant parts, seeds, feedstuff obtained therefrom, or foodstuff obtained therefrom with an undesirable microbe, comprising the step of contacting a plant, a plant seed, or other part of said plant with an effective amount of any of the aforementioned compositions, where the composition optionally comprises an agriculturally acceptable carrier, diluent, or excipient, are also provided.

Plant parts including seeds which are least partly coated with any of the aforementioned compositions, where the composition optionally comprises an agriculturally acceptable carrier, diluent, or excipient, are also provided.

Medical devices comprising the device and an aforementioned composition, wherein the device comprises at least one surface that is topically coated and/or impregnated with the composition, where the composition optionally comprises a pharmaceutically or veterinary-practicably acceptable carrier, diluent, or excipient are also provided.

Methods for treating, preventing, or inhibiting a microbial infection in a subject in need thereof comprising administering to said subject an effective amount of any of the aforementioned compositions, where the composition optionally comprises a pharmaceutically or veterinary-practicably acceptable carrier, diluent, or excipient are also provided. Use of any of any of the aforementioned compositions in a method of treating, preventing, or inhibiting microbial or yeast infection in a subject in need thereof are provided. Use of any of the aforementioned first antimicrobial peptide or proteins in the manufacture of a medicament or composition for inhibiting microbial or yeast infection in a subject in need thereof are also provided.

Recombinant polynucleotides comprising a polynucleotide peptides comprising any of the aforementioned peptides, wherein the polynucleotide encoding the antimicrobial peptide is operably linked to a polynucleotide comprising a promoter which is heterologous to the polynucleotide encoding the first antimicrobial peptide, optionally wherein any amino acid substitution in said sequence increases or maintains the net positive charge and/or hydrophobicity of the peptide, are provided.

Plant nuclear or plastid genomes comprising a polynucleotide encoding an antimicrobial peptide comprising any of the aforementioned peptides, wherein the polynucleotide is heterologous to the nuclear or plastid genome and wherein the polynucleotide is operably linked to an endogenous promoter of the nuclear or plastid genome, are provided.

Cells, plant, and plant parts including seeds comprising the aforementioned recombinant polynucleotides or genomes are provided.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 shows an alignment of a non-limiting subset of reference defensin C-terminal peptides which include the conserved C1, C2, C3, and C4 cysteines (in bold). The conserved gamma core peptide is underlined.

FIG. 3 shows an alignment of a non-limiting subset of reference defensin C-terminal peptides which include the conserved C1, C2, C3, and C4 cysteines (in bold), the gamma-core consensus, and various modified gamma-core consensus sequences provided herein. The conserved gamma core peptide is underlined and is absent from the modified gamma-core consensus peptides.

FIG. 4 shows a data table with antimicrobial activity of various GMA4C defensin peptide variants.

FIG. 5A, B show results of a drop inoculation assay showing the antifungal activity of GMA4C_V9 (SEQ ID NO: 581) and GMA4C_V10 peptides (SEQ ID NO: 582). GMA4C_V10 completely abrogates gray mold symptoms at 6 μM.

FIG. 6A, B show results of a drop inoculation assay showing the antifungal activity of GMAOe1C_WT (SEQ ID NO: 577), GMAOe1C_V3 (SEQ ID NO: 578), and GMAOe1C_V4 (SEQ ID NO: 579).

DETAILED DESCRIPTION

Definitions

Figure 1A:
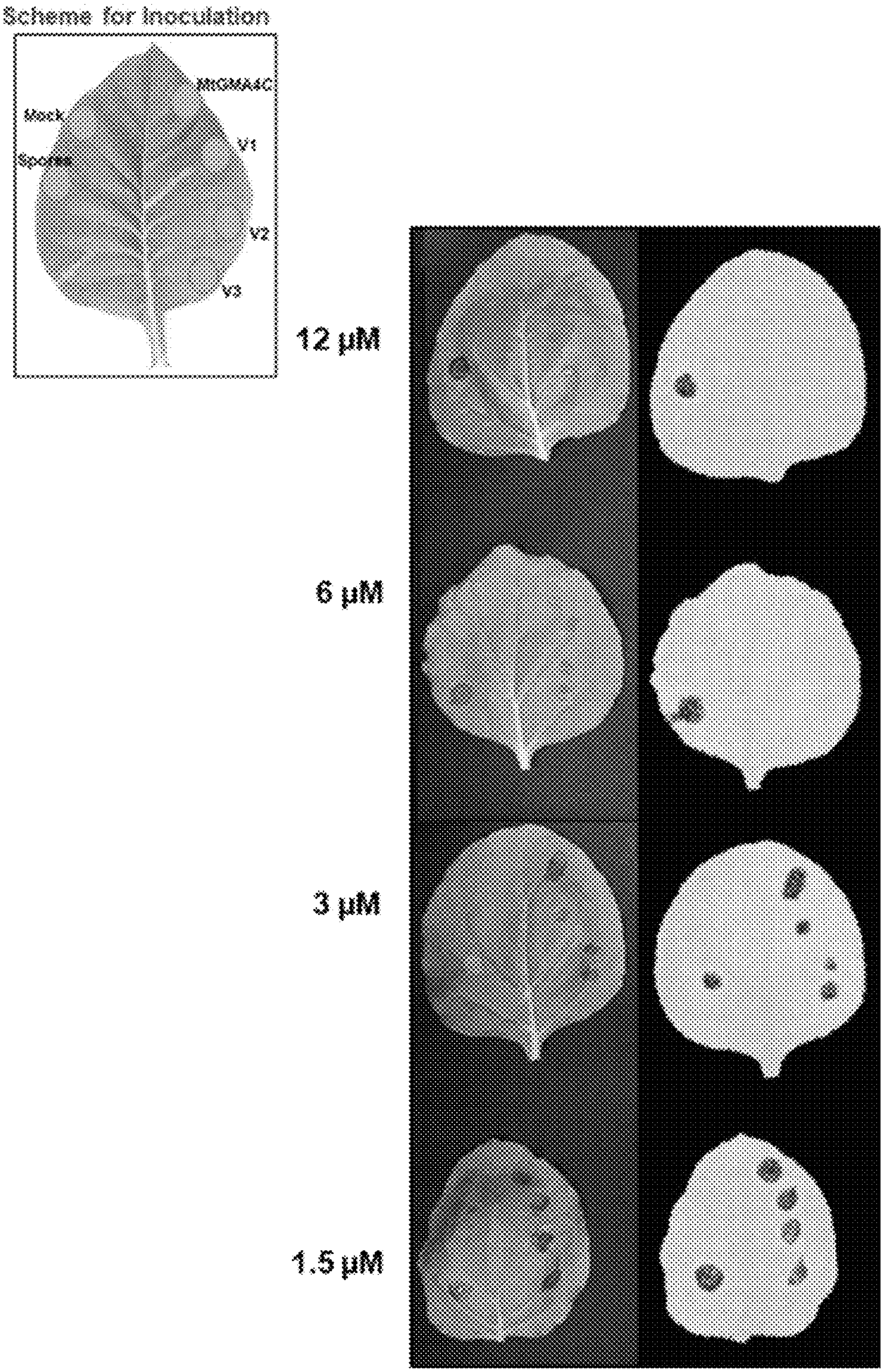
FIGS. 1A and 1B show drop inoculation assays on *Nicotiana benthamiana* leaves. Four-week-old leaves of *N. benthamiana* were used for drop-inoculation assays against *B. cinerea* with different concentration of GMA4C peptides. 1A. Pictorial representation of the drop-inoculation assays and pictures were taken after 48 h of incubation in both white-light and with CropReporter. Damaged area is represented in red color in CropReporter images. Data for GMA4C_AC wild-type control (SEQ ID NO: 2) is in left most panel (labelled "GMA4C"), data for GMA4c_V1A (SEQ ID NO:3) is in panel 2nd from left, data for GMA4c_V2A (SEQ ID NO: 4) is in panel 3rd from left, and data for GMA4c_V3A (SEQ ID NO:5) is in panel 4th from left. 1B, Lesions were measured after 48 h using the ImageJ software and their sizes are shown on the graph.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "correspond," "corresponding," and the like, when used in the context of an amino acid position, mutation, and/or substitution in any given peptide (e.g., a defensin variant peptide) with respect to the reference peptide sequence (e.g., reference defensin C-terminal peptide sequence including SEQ ID NO: 8, 16, 20, 23, 26, 29, 37, 38, 39, 40, 41 or 89-122) all refer to the amino acid residue in the given peptide sequence that has the same location in the given peptide as the residue in the reference amino acid sequence when the given peptide is aligned to the reference sequence. In certain embodiments, the alignment is an alignment of the 4 conserved cysteine residues of a defensin C-terminal peptide of a defensin variant peptide and a reference defensin C-terminal peptide sequence (e.g., as shown in FIGS. 2 and 3).

As used herein, the terms "include," "includes," and "including" are to be construed as at least having the features to which they refer while not excluding any additional unspecified features.

Where a term is provided in the singular, other embodiments described by the plural of that term are also provided.

The phrase "antimicrobial peptide" as used herein refer to peptides which exhibit any one or more of the following characteristics of inhibiting the growth of microbial cells, killing microbial cells, disrupting or retarding stages of the microbial life cycle such as spore germination, sporulation, or mating, and/or disrupting microbial cell infection, penetration or spread within a plant or other susceptible subject, including a human, livestock, poultry, fish, or a companion animal (e.g. dog or cat).

As used herein, the terms "acidic" or "anionic" are used interchangeably to refer to amino acids such as aspartic acid and glutamic acid.

As used herein, the term "amino acid" refers to an organic compound that contains amino (—$NH_3$) and carboxylate (—$CO_2$) functional groups, along with a side chain (R group) specific to each amino acid. Amino acid residues in polypeptides are in certain instance referred to herein by one letter amino acid codes as follows: G—Glycine (Gly); P—Proline (Pro); A—Alanine (Ala); V—Valine (Val); L—Leucine (Leu); I—Isoleucine (Ile); M—Methionine (Met); C—Cysteine (Cys); F—Phenylalanine (Phe); Y—Tyrosine (Tyr); W—Tryptophan (Trp); H—Histidine (His); K—Lysine (Lys); R—Arginine (Arg); Q—Glutamine (Gln); N—Asparagine (Asn); E—Glutamic Acid (Glu); D—Aspartic Acid (Asp); S—Serine (Ser); or T—Threonine (Thr).

As used herein, the terms "basic" and "cationic" are used interchangeably to refer to amino acids such as arginine, histidine, and lysine.

As used herein, the phrase "cation-tolerant" refers to a defensin peptide or defensin peptide variant which exhibits equivalent in vitro antifungal or antimicrobial activity or no more than about a 1.5-, 2-, 3-, or 4-fold decrease in in vitro antifungal or antimicrobial activity in the presence of 100 mM KCl or 100 mM NaCl as compared to the antifungal activity of the defensin peptide or defensin peptide variant in the absence of KCl or NaCl.

As used herein, the phrase "consensus sequence" refers to an amino acid, DNA or RNA sequence created by aligning two or more homologous sequences and deriving a new sequence having either the conserved or set of alternative amino acid, deoxyribonucleic acid, or ribonucleic acid residues of the homologous sequences at each position in the created sequence.

The phrases "combating microbial damage", "combating or controlling microbial damage" or "controlling microbial damage" as used herein refer to reduction in damage to a crop plant or crop plant product due to infection by a microbial pathogen. More generally, these phrases refer to reduction in the adverse effects caused by the presence of a pathogenic microbe in the crop plant. Adverse effects of microbial growth are understood to include any type of plant tissue damage or necrosis, any type of plant yield reduction, any reduction in the value of the crop plant product, and/or production of undesirable microbial metabolites or microbial growth by-products including to mycotoxins.

The phrase "defensin peptide" is used herein to refer to a peptide comprising a conserved gamma core peptide. Plant defensins have been previously characterized as comprising a conserved GXCX3-9C gamma core peptide sequence (SEQ ID NO: 9), where X is any amino acid residue (Lacerda et al.) or a conserved GXCX3-10C variant gamma core peptide sequence (SEQ ID NO: 10), where X is any amino acid residue. In certain embodiments, defensin peptides disclosed herein can also include non-standard defensin gamma core peptides comprising a GXCX3-12C (SEQ ID NO: 590) or GXCX3-15C (SEQ ID NO: 591). Therefore, as used in this disclosure, a plant defensin or defensin or C-terminal peptide comprising fragment thereof can comprise a conserved GXCX3-9C (SEQ ID NO: 9), GXCX3-10C (SEQ ID NO: 10), GXCX3-12C (SEQ ID NO: 590) or GXCX3-15C (SEQ ID NO: 591) gamma core peptide sequence, where X is any amino acid residue. Defensin peptides include proteins that are antimicrobial, that can permeabilize plasma membranes, that can bind phospholipids, that can bind sphingolipids, or that exhibit any combination of those properties. A defensin peptide can be naturally occurring or non-naturally occurring (e.g., synthetic and/or chimeric).

The phrase "defensin peptide variant" is used herein to describe a modified defensin peptide comprising either: (i) a conserved gamma core peptide of SEQ ID NO: 9 or 10 and at least one amino acid substitution in a source defensin peptide; or (ii) a modified gamma core variant sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34), GXCX3-8(F/W/Y) (SEQ ID NO: 43), GXCX3-9(F/W/Y) (SEQ ID NO: 44), GXCX3-8(F/W/Y/L/V/I/M) (SEQ ID NO: 45), GXCX3-10(F/W/Y/L/V/I/M) (SEQ ID NO: 46), GXCX3-8 (L/V/I/M)(F/W/Y) (L/V/I/M) (SEQ ID NO: 47), GXCX3-10 (L/V/I/M)(F/W/Y) (L/V/I/M) (SEQ ID NO: 48), GXCX3-8(F/W/Y/L/V/I/M) (F/W/Y)(F/W/Y/L/V/I/M) (SEQ ID NO: 49), GXCX3-10(F/W/Y/L/V/I/M) (F/W/Y) (F/W/Y/L/V/I/M) (SEQ ID NO: 50), GXCX3-8(F/W/Y/L/V/I/M)(F/W/Y/L/V/I/M)(F/W/Y/L/V/I/M) (SEQ ID NO: 51), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), or GXCX3-10(F/W/Y/L/V/I/M)(F/W/Y/L/V/I/M)(F/W/Y/L/V/I/M) (SEQ ID NO: 52). In certain embodiments, defensin peptide variants provided herein are less than full length defensin peptides (e.g., peptides comprising, consisting essentially of, or consisting of: (i) 30 amino acid residues or less; or (ii) 15, 16, or 17 to 30 amino acid residues).

The phrase "reference defensin C-terminal peptide" is used herein to refer to a less than full length defensin peptide comprising a conserved GXCX3-9C gamma core peptide sequence (SEQ ID NO: 9), a conserved GXCX3-10C variant gamma core peptide sequence (SEQ ID NO: 10), a non-standard GXCX3-12C (SEQ ID NO: 590) gamma core sequence, or a non-standard GXCX3-15C (SEQ ID NO: 591) gamma core sequence, and the two additional conserved cysteine residues located C-terminal to the gamma core peptide sequence, wherein the cysteine located closest to the N-terminus of the reference defensin C-terminal peptide corresponds to the cysteine located closest to the N-terminus of the gamma core sequence of SEQ ID NO: 9 or SEQ ID NO: 10. Examples of reference defensin C-terminal peptides include an MtDef4 C-terminal peptide (SEQ ID NO: 8), an MtDef5A C-terminal peptide (SEQ ID NO: 16), an MtDef5B C-terminal peptide (SEQ ID NO: 41), an MtDef6 peptide (SEQ ID NO: 21), an OeDef1 C-terminal peptide (SEQ ID NO: 24), an OeDef7 C-terminal peptide (SEQ ID NO: 27), an SbDef1 C-terminal peptide (SEQ ID NO: 30), an NaD1 C-terminal peptide (SEQ ID NO: 37), an RsAFP2 C-terminal peptide (SEQ ID NO: 38), a DmAMP1 C-terminal peptide (SEQ ID NO: 39), and an HsAFP1 (SEQ ID NO: 40). Other examples of reference defensin C-terminal peptides include SEQ ID NO: 89 to 122. Reference defensin C-terminal peptides thus include 4 conserved cysteine residues, which are referred to herein as C1 (most N-terminal in both the peptide and in the gamma core peptide sequence), C2 (C-terminal to C1 and located in the gamma core peptide sequence), C3 (C-terminal to C2), and C4 (C-terminal to C3). An alignment of a non-limiting subset of reference defensin C-terminal peptides comprising the conserved gamma core peptide sequence and the C1, C2, C3, and C4 cysteines is shown in FIG. 2. An alignment of a non-limiting subset of reference defensin C-terminal peptides comprising the conserved gamma core peptide sequence and the C1, C2, C3, and C4 cysteines, the gamma core consensus comprising the C1 and C2 cysteines, and certain modified gamma core consensus sequences provided herein is shown in FIG. 3. Other reference defensin C-terminal peptides that include those contained in the full length defensin peptides of SEQ ID NO: 123 to 434 and 436 to 576.

As used herein, the terms "edit," "editing," "edited" and the like refer to processes or products where insertions, deletions, and/or nucleotide substitutions are introduced into a genome. Such processes include methods of inducing homology directed repair and/or non-homologous end joining of one or more sites in the genome.

The phrases "genetically edited plant" or "edited plant" are used herein to refer to a plant comprising one or more nucleotide insertions, deletions, substitutions, or any combination thereof in the genomic DNA of the plant. Such genetically edited plants can be constructed by techniques including CRISPR/Cas endonuclease-mediated editing, meganuclease-mediated editing, engineered zinc finger endonuclease-mediated editing, and the like.

The term "heterologous", as used herein in the context of a second polynucleotide that is operably linked to a first polynucleotide, refers to: (i) a second polynucleotide that is derived from a source distinct from the source of the first polynucleotide; (ii) a second polynucleotide derived the same source as the first polynucleotide, where the first, second, or both polynucleotide sequence(s) is/are modified from its/their original form; (iii) a second polynucleotide arranged in an order and/or orientation or in a genomic position or environment with respect to the first polynucleotide that is different than the order and/or orientation in or genomic position or environment of the first and second polynucleotides in a naturally occurring cell; or (iv) the second polynucleotide does not occur in a naturally occurring cell that contains the first polynucleotide. Heterologous polynucleotides include polynucleotides that promote transcription (e.g., promoters and enhancer elements), transcript abundance (e.g., introns, 5'UTR, and 3'UTR), translation, or a combination thereof as well as polynucleotides encoding defensin peptide variants or defensin peptides, spacer peptides, or localization peptides. In certain embodiments, a nuclear or plastid genome can comprise the first polynucleotide, where the second polynucleotide is heterologous to the nuclear or plastid genome. A "heterologous" polynucleotide that promotes transcription, transcript abundance, translation, or a combination thereof as well as polynucleotides encoding defensin peptide variants or defensin peptides, spacer peptides, or localization peptides can be autologous to the cell but, however, arranged in an order and/or orientation or in a genomic position or environment that is different than the order and/or orientation in or genomic position or environment in a naturally occurring cell. A polynucleotide that promotes transcription, transcript abundance, translation, or a combination thereof as well as polynucleotides encoding defensin peptide variants or defensin peptides, spacer peptides, or localization can be heterologous to another polynucleotide when the polynucleotides are not operably linked to one another in a naturally occurring cell. Heterologous peptides or proteins include peptides or proteins that are not found in a cell or organism as the cell or organism occurs in nature. As such, heterologous peptides or proteins include peptides or proteins that are localized in a subcellular location, extracellular location, or expressed in a tissue that is distinct from the subcellular location, extracellular location, or tissue where the peptide is found in a cell or organism as it occurs in nature. Heterologous polynucleotides include polynucleotides that are not found in a cell or organism as the cell or organism occurs in nature.

The phrases "inhibiting growth of a plant pathogenic microbe," "inhibit microbial growth", and the like as used herein refers to methods that result in any measurable decrease in microbial growth, where microbial growth includes any measurable decrease in the numbers and/or extent of microbial cells, spores, conidia, or mycelia. As used herein, "inhibiting growth of a plant pathogenic microbe" is also understood to include any measurable decrease in the adverse effects cause by microbial growth in a plant. Adverse effects of microbial growth in a plant include any type of plant tissue damage or necrosis, any type of plant yield reduction, any reduction in the value of the crop plant product, and/or production of undesirable microbial metabolites or microbial growth by-products including mycotoxins. As used herein, the phrase "inhibition of microbial growth" and the like, unless otherwise specified, can include inhibition in a plant, human or animal.

The phrases "percent identity" or "sequence identity" as used herein refer to the number of elements (i.e., amino acids or nucleotides) in a sequence that are identical within a defined length of two DNA, RNA segments in an alignment resulting in the maximal number of identical elements, and is calculated by dividing the number of identical elements by the total number of elements in the defined length of the aligned segments and multiplying by 100.

The phrase "transgenic" refers to an organism or progeny thereof wherein the organism's or progeny organism's DNA of the nuclear or organellar genome contains an inserted exogenous DNA molecule of 10 or more nucleotides in length. The phrase "transgenic plant" refers to a plant or progeny thereof wherein the plant's or progeny plant's DNA of the nuclear or plastid genome contains an introduced exogenous DNA molecule of 10 or more nucleotides in length. Such introduced exogenous DNA molecules can be naturally occurring, non-naturally occurring (e.g., synthetic and/or chimeric), from a heterologous source, or from an autologous source.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description

Antimicrobial peptides and proteins referred to as defensin peptide variants are provided herein. The antimicrobial peptides and proteins can be applied directly to a plant, feedstuffs, or foodstuffs; applied to a plant in the form of microorganisms that produce the defensin peptide variant or protein, or the plants can be genetically edited to produce the defensin peptide variant or protein. The present disclosure also relates to recombinant or edited polynucleotides, microorganisms and plants transformed with the recombinant or edited polynucleotides, plants comprising genetically edited nuclear or plastid genomes encoding the defensin peptide variants and proteins and compositions comprising the defensin peptide variants and proteins useful in controlling pathogenic microbes including plant pathogenic microbes. In certain embodiments, the defensin variant protein comprising two defensin peptide variants or a defensin peptide variant and another peptide (including a defensin peptide variant or defensin peptide) can provide for improved inhibition of microbial growth when compared to a protein containing only one of the antimicrobial peptides found in the defensin variant protein. In certain embodiments, the defensin peptide variants and proteins provided herein are cation-tolerant. Such cation-tolerant defensins can be more effective than cation-sensitive defensins in providing effective control of plant pathogenic microbes in transgenic crops. Cation-tolerant defensins provided herein can function (e.g., inhibit plant pathogenic microbes including fungal pathogens) in the normal cation-rich physiological environment of plant tissues. Cation-tolerant defensins provided herein can also function (e.g., inhibit pathogenic microbes including fungal pathogens) in the normal cation-rich physiological environment of a subject (e.g., a human or animal) infected with pathogenic microbes.

Provided herein are recombinant polynucleotides comprising a polynucleotide encoding a first antifungal peptide operably linked to a polynucleotide comprising a promoter that is heterologous to the polynucleotide encoding the first antifungal protein. In certain embodiments, the first antifungal peptide is a defensin peptide variant.

Defensin peptide variants include peptides comprising, consisting essentially of, or consisting of the sequence: Xaa1-G-Xaa3-C-Xaa5-Xaa6-Xaa7-Xaa8-Xaa9-Xaa10-Xaa11-Xaa12-Xaa13-Xaa14-Xaa15-Xaa16-Xaa17-Xaa18-Xaa19-Xaa20-Xaa21-Xaa22-Xaa23, where Xaa1 is F, G, or absent; Xaa3 is A, G, Y, H, S, R or Dab; Xaa5 is H, L, S, N, R, K, or Dab; Xaa6, Xaa7, Xaa8, Xaa9, Xaa10, Xaa11, Xaa12, Xaa13, Xaa14, and Xaa15 are each independently R, K, H, N, D, F, G, Q, P, A, I, L, V, Y, S, or Dab, wherein one or more of Xaa8, Xaa9, Xaa10, Xaa11, Xaa12, Xaa13, Xaa14, and/or Xaa15 may be absent; Xaa16 is C, V, W, Y, or F; Xaa17 is L, I, W, Y, or F; Xaa18 is C, V, W, Y, or F; Xaa19 is K, T, F, W, or Y; Xaa20 is R, K, T, L, F, Q, or Dab, Xaa21 is N, H, K, R, P, Q, I, F, W, or Y; Xaa22 is N, H, K, P, Q, I, F, W, Y, or absent; and Xaa23 is C and is optionally amidated, wherein Dab is diaminobutyric acid (SEQ ID NO: 1). In certain embodiments, peptides comprising SEQ ID NO: 1 can further comprise one or more additional amino acids located C terminal to the C-terminus of SEQ ID NO:1, wherein said C-terminal amino acids are optionally amidated. In certain embodiments, peptides comprising SEQ ID NO: 1 can comprise a modified gamma core variant sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34). GXCX3-8(F/W/Y) (SEQ ID NO: 43), or GXCX3-9(F/W/Y) (SEQ ID NO: 44). Defensin peptide variants also include peptides encompassed by the sequence: Xaa1-GRC-Xaa5-GFRRR(F/W/Y)(F/W/Y)(F/W/Y)XXXC—$(NH_2)$, where Xaa1 is F, G, or absent; Xaa5 is R or K; Xaa14 is T, F, W, or Y; Xaa15 is R, K, or Dab; Xaa16 is I, F, W, or Y; and Xaa1 7 is C and is optionally amidated, wherein Dab is diaminobutyric acid (SEQ ID NO: 14). Defensin peptide variants further include peptides encompassed by the sequence Xaa1-G-Xaa2-C-Xaa5-Xaa6-Xaa7-GF-Xaa10-Xaa11-Xaa12-(F/W/Y)(F/W/Y)(F/W/Y)-Xaa16-Xaa17-Xaa18-C—$(NH_2)$, where Xaa1 is F, G, or absent, Xaa3 is A, F, W, Y, or absent; Xaa5 is H, R, or K; Xaa6 is R or K; Xaa7 is Q, R, or K; Xaa10 is G, R, or K; Xaa 11 is F, W, Y, R, or K; Xaa12 is A, F, W, Y, R, or K; Xaa16 is F, W, Y, R, or K; Xaa17 is R or K; Xaa18 is R or K; and the C-terminal cysteine is optionally amidated (SEQ ID NO: 17). Defensin variant peptides set forth herein do not comprise the corresponding full-length sequence of the wild-type defensin peptide of SEQ ID NO: 8, 16, 20, 23, 26, 29, 37, 38, 39, 40, or 41. Table 1 sets forth defensin peptide variants of SEQ ID NO: 1, 3-7 11, 13, and 14 as well as the GMA4C peptides of SEQ ID NO:2 and SEQ ID NO:8. In certain embodiments, the aforementioned defensin peptide variants comprise, consist essentially of, or consist of: (i) 30 amino acid residues or less; or (ii) 15, 16, or 17 to 30 amino acid residues.

TABLE 1

Defensin peptides and Defensin peptide variants

| SEQ ID NO: | Peptide | Sequence[3] | Net Charge | Hydro-phobicity |
|---|---|---|---|---|
| 1 | Defensin Variant Peptide | $X_1GX_3CX_5X_6X_7X_8X_9X_{10}X_{11}X_{12}X_{13}X_{14}X_{15}X_{16}X_{17}X_{18}X_{19}X_{20}X_{21}X_{22}$ C-$(NH_2)$, wherein $X_1$ is F, G, or absent; $X_3$ is A, G, Y, H, S, R or Dab; $X_5$ is H, L, S, N, R, K, or Dab; $X_6$, $X_7$, $X_8$, $X_9$, $X_{10}$, $X_{11}$, $X_{12}$, $X_{13}$, $X_{14}$, and $X_{15}$ are each independently R, K, H, N, D, F, G, Q, P, A, I, L, V, Y, S, or Dab, wherein one or more of $X_8$, $X_9$, $X_{10}$, $X_{11}$, $X_{12}$, $X_{13}$, $X_{14}$, and/or $X_{15}$ may be absent; $X_{16}$ is C, V, W, Y, or F; $X_{17}$ is L, I, W, Y, or F; $X_{18}$ is C, V, W, Y, or F; $X_{19}$ is K, T, F, W, or Y; $X_{20}$ is R, K, T, L, F, Q, or Dab, $X_{21}$ is N, H, K, R, P, Q, I, F, W, or Y; $X_{22}$ is N, H, K, P, Q, I, F, W, Y, or absent; and $C_{23}$ and is optionally amidated | | |
| 2 | GMA4C_AC | GGRCRGFRRRCFCTTHC-$NH_2$ | 5.5 | 12% |
| 3 | GMA4C_V1A | GGRCKGFRRRCFCTRIC-$NH_2$ | 6 | 18% |
| 4 | GMA4C_V2A | GGRCRGFRRRCFCTRIC-$NH_2$ | 6 | 18% |
| 5 | GMA4C_V3A[1] | GGRCRGFRRRVFVTRIC-$NH_2$ | 6 | 29% |
| 6 | GMA4C_V4A | FGRCRGFRRRCFCWRWC-$NH_2$ | 6 | 29% |
| 7 | GMA4C_V5A[2] | FG(Dab)C(Dab)GF(Dab)(Dab)(Dab)CFCW(Dab)WC-$NH_2$ | 6 | 29% |
| 8 | GMA4AC | GRCRGFRRRCFCTTHC | 5.5 | 12% |
| 9 | Gamma-core consensus 1 | GXCX3-9C | | |
| 10 | Gamma-core consensus 2 | GXCX3-10C | | |
| 11 | GMA4C_V4 | FGRCRGFRRRCFCWRWC | 6 | 29% |
| 12 | GMA4C_V5[2] | FG(Dab)C(Dab)GF(Dab)(Dab)(Dab)CFCW(Dab)WC | | |
| 13 | GMA4C_V6A[1] | GGRCKGFRRRWFWTRIC-NH2 | 6 | 29% |
| 14 | GMA4C_V7 | XGRCKGFRRR(F/W/Y)(F/W/Y)(F/W/Y)XXXC-$(NH_2)$ | | |

TABLE 1-continued

| SEQ ID NO: | Peptide | Sequence[3] | Net Charge | Hydro-phobicity |
|---|---|---|---|---|
| Defensin peptides and Defensin peptide variants | | | | |
| 15 | GMA4C_V8A | GGRCKGFRRRWYWTRIC-$NH_2$ | 6 | 29% |
| 16 | GMA5A | GACHRQGFGFACFCYKKC | 3.5 | 33% |
| 17 | GMA5A_V1 | XGXCXXXGFXXXXFXXXXC-($NH_2$) | | |
| 18 | GMA5A_V2_ | GACHRQGFGFA(F/W/Y)(F/W/Y)(F/W/Y)YKKC-($NH_2$) | 3.5 | 44% |
| 19 | GMA5A_V3 | GACHRQGFGFAWFWYKKC-$NH_2$ | 3.5 | 44% |
| 20 | GMA5A_V4 | GACHRQGFGFAFFFYKKC-$NH_2$ | 3.5 | 44% |
| 21 | GMA6C | GGRCRGFRRRCFCTRPC | +6 | 12% |
| 22 | GMA6C_V1 | GGRCRGFRRR(F/W/Y)(F/W/Y)(F/W/Y) TRPC-($NH_2$) | +6 | 23.5% |
| 23 | GMA6C_V2 | GGRCRGFRRRWFWTRPC-$NH_2$ | +6 | 23.5% |
| 24 | GMAOe1C | GACLKNRHSKHYGCYCYYRHCY | 5.5 | 32% |
| 25 | GMAOe1C_V1 | GACLKNRHSKHYG(F/W/Y)(F/W/Y)(F/W/Y)YYRHCY-($NH_2$) | 5.5 | 41% |
| 26 | GMAOe1C_V2 | GACLKNRHSKHYGWFWYYRHCY-$NH_2$ | 5.5 | 41% |
| 27 | GMAOe7C | GGLCRGFRRRCFCTKHC | 5.5 | 18% |
| 28 | GMAOe7C_V1 | GGLCRGFRRR(F/W/Y)(F/W/Y)(F/W/Y)TKHC-($NH_2$) | 5.5 | 29% |
| 29 | GMAOe7C_V2 | GGLCRGFRRRWFWTKHC-$NH_2$ | 5.5 | 29% |
| 30 | GMASb1C | GGYCSSRRQICKCTLQC | 3 | 18% |
| 31 | GMASb1C_V1 | GGYCSSRRQI(F/W/Y)(F/W/Y)(F/W/Y)TLQC-($NH_2$) | 2 | 35% |
| 32 | GMASb1C_V2 | GGYCSSRRQIWFWTLQC-$NH_2$ | 2 | 35% |
| 33 | Modified Gamma-core consensus 1 | GXCX3-8 (F/W/Y)(F/W/Y)(F/W/Y) | | |
| 34 | Modified Gamma-core consensus 2 | GXCX3-9(F/W/Y)(F/W/Y)(F/W/Y) | | |
| 35 | GMA1C | GRCRDDFRCWCTKNC | +2 | 13% |
| 36 | GMA1C_V1 | GRCRILFRCFCTKNC | +4 | 27% |
| 37 | GMANaD1C | GHCSKILRRCLCTKPC | +4.5 | 19% |
| 38 | GMARsAFP2C | GSCNYVFPAHKCICYFPC | +1.5 | 39% |
| 39 | GMADmAMP1C | GACHVRNGKHMCFCYFNC | +3 | 33% |
| 40 | GMAHsAFP1 | GACHYQFPSVKCFCTQNC | +1.5 | 28% |
| 41 | GMA5B | GACHRQGIGFACFCKKKC | +4.5 | 28% |
| 42 | GMAOe1_V3 | GACLKNRHSKHYGFFWYYRHCY | +5.5 | 36% |

TABLE 1-continued

| Defensin peptides and Defensin peptide variants | | | | |
|---|---|---|---|---|
| SEQ ID NO: | Peptide | Sequence[3] | Net Charge | Hydro-phobicity |
| 43 | Modified Gamma-core consensus 3 | GXCX3-8 (F/W/Y) | | |
| 44 | Modified Gamma-core consensus 4 | GXCX3-9(F/W/Y) | | |
| 45 | Modified Gamma-core consensus 5 | GXCX3-8(F/W/Y/L/V/I/M) | | |
| 46 | Modified Gamma-core consensus 6 | GXCX3-10(F/W/Y/L/V/I/M) | | |
| 47 | Modified Gamma-core consensus 7 | GXCX3-8(L/V/I/M) (F/W/Y)(L/V/I/M) | | |
| 48 | Modified Gamma-core consensus 8 | GXCX3-10(L/V/I/M) (F/W/Y)(L/V/I/M) | | |
| 49 | Modified Gamma-core consensus 9 | GXCX3-8(F/W/Y/L/V/I/M) (F/W/Y)(F/W/Y/L/V/I/M) | | |
| 50 | Modified Gamma-core consensus 10 | GXCX3-10(F/W/Y/L/V/I/M) (F/W/Y)(F/W/Y/L/V/I/M) | | |
| 51 | Modified Gamma-core consensus 11 | GXCX3-8(F/W/Y/L/V/I/M)(F/W/Y/L/V/I/M)(F/W/Y/L/V/I/M) | | |
| 52 | Modified Gamma-core consensus 12 | GXCX3-10(F/W/Y/L/V/I/M)(F/W/Y/L/V/I/M)(F/W/Y/L/V/I/M) | | |
| 587 | Modified Gamma-core consensus 13 | GXCX3-10(F/W/Y)(F/W/Y)(F/W/Y) | | |
| 588 | Modified Gamma-core consensus 14 | GXCX3-12(F/W/Y)(F/W/Y)(F/W/Y) | | |
| 589 | Modified Gamma-core consensus 15 | GXCX3-15(F/W/Y)(F/W/Y)(F/W/Y) | | |
| 590 | Non-standard Defensin gamma core 1 | GXCX3-12C | | |
| 591 | Non-standard Defensin gamma core 2 | GXCX3-15C | | |

[1]Substitution of cysteine at Xaa11 and Xaa13 with valine (GMA4C_V3A; SEQ ID NO: 5) or with tryptophan (GMA4CV6; SEQ ID NO: 13) can provide a cyclic peptide with a disulfide bond between the residue 4 cysteine and residue 17 cysteine.

[2]Dab = diaminobutyric acid

[3]Amidation status: $-NH_2$ is a C-terminal amidated peptide and -(NH2) is an optionally amidated C-terminal peptide In certain embodiments, defensin peptide variants of this disclosure are characterized as containing a defensin gamma-core peptide that is involved in the antifungal activity of plant defensins. A gamma-core peptide typically contains a net positive charge and has at least one hydrophobic amino acid. In certain embodiments, a defensin peptide variant can comprise the gamma-core consensus sequence of GXCX3-9C where X is any amino acid (SEQ ID NO: 9). In certain embodiments, a defensin peptide variant comprises a gamma-core peptide having a variant gamma-core consensus sequence of GXCX3-10C where X is any amino acid (SEQ ID NO: 10). In certain embodiments, a defensin peptide variant comprises the gamma-core consensus sequence of GXCX3-9C (SEQ ID NO: 9) or GXCX3-10C (SEQ ID NO:10); wherein X is preferentially selected from cationic and/or hydrophobic amino acids. In certain embodiments, a defensin peptide variant comprises SEQ ID NO: 1, comprises the gamma-core consensus sequence of GXCX3-9C (SEQ ID NO: 9) or GXCX3-10C (SEQ ID NO: 10); wherein X is preferentially selected from cationic and/or hydrophobic amino acids, wherein any of the variable (Xaa) amino acid residues of SEQ ID NO: 1 comprise amino acid residues that maintains or increases the number of cationic and/or hydrophobic amino acids found in SEQ ID NO: 3-7. It is believed that the gamma-core peptide is involved in phospholipid- and/or sphingolipid-binding while specific amino acids outside the gamma-core motif are also involved in phospholipid- and sphingolipid-binding. With respect to SEQ ID NO: 1, the sequence between the first cysteine (C1) and the second cysteine (C2) from the amino terminus (or in certain embodiments a corresponding region in a defensin peptide variant) also contributes to antimicrobial activity.

Defensin peptide variants comprising variant defensin C-terminal peptides provided herein can also comprise substitutions of one or more of the conserved cysteine residues of a wild-type defensin C-terminal peptide sequence. Conserved cysteine residues which can be substituted can correspond to C1, C2, C3, or C4 in a defensin C-terminal peptide, C1 is the most N-terminal cysteine, C2 is the $2^{nd}$ most N-terminal cysteine, C3 is the $3^{rd}$ most N-terminal cysteine, and C4 is the most C-terminal cysteine; see FIG. 2). A non-limiting subset of reference defensin C-terminal peptides which comprise the C1, C2, C3, and C4 conserved cysteines include the GMA4C peptide of SEQ ID NO: 8, MtDef5A peptide of SEQ ID NO: 16, MtDef5A peptide of SEQ ID NO: 41, MtDef6 peptide of SEQ ID NO: 20, OeDef1 peptide of SEQ ID NO: 23, OeDef7 peptide of SEQ ID NO: 26, SbDef1 peptide of sequence ID NO: 29, an NaD1 C-terminal peptide (SEQ ID NO: 37), an RsAFP2 C-terminal peptide (SEQ ID NO: 38), a DmAMP1 C-terminal peptide (SEQ ID NO: 39), and an HsAFP1 (SEQ ID NO: 40) and can be substituted in at least the C2 and/or C3 positions to obtain a defensin peptide variant. Additional non-limiting reference defensin C-terminal peptides which comprise the C1, C2, C3, and C4 conserved cysteines include the defensin C-terminal peptides set forth in SEQ ID NO: 89 to 122. Additional non-limiting reference defensin C-terminal peptides which comprise the C1, C2, C3, and C4 conserved cysteines include defensin C-terminal peptides contained in the full length defensin peptides of SEQ ID NO: 123 to 434 and 436 to 576.

In certain embodiments, defensin peptide variants provided herein will lack a canonical gamma-core consensus sequence of GXCX3-9C (SEQ ID NO: 9) or GXCX3-10C (SEQ ID NO: 10). In certain embodiments, defensin peptide variants provided herein will comprise a substitution of tryptophan, tyrosine, or phenylalanine for the C-terminal cysteine residue of the gamma core consensus sequence of SEQ ID NO: 9 or 10 (e.g., C2 in a reference SEQ ID NO: 8, 16, 20, 23, 26, 29, 37, 38, 39, 40, 41, or 89 to 122). In certain embodiments, defensin peptide variants provided herein comprise a substitution of both the C2 and C3 residues corresponding to the C2 and C3 residues in a reference C-terminal defensin peptide (e.g., SEQ ID NO: 8, 16, 20, 23, 26, 29, 37, 38, 39, 40, 41, or 89 to 122). A GMA4C variant having a valine substitution of C2 and C3 is set forth in SEQ ID NO: 5. A GMA4C variant having a tryptophan substitution of C2 and C3 is set forth in SEQ ID NO: 13. In certain embodiments, defensin peptide variants provided herein comprise a tryptophan, tyrosine or phenylalanine substitution of the C2 and C3 residues corresponding to the C2 and C3 residues in a reference C-terminal defensin peptide (e.g., SEQ ID NO: 8, 16, 20, 23, 26, 29, 37, 38, 39, 40, 41, or 89 to 122). In certain embodiments, defensin peptide variants set for the herein can further comprise a tryptophan, tyrosine, or phenylalanine residue in the amino acid position located between the C2 and C3 residues in a reference C-terminal defensin peptide (e.g., SEQ ID NO: 8, 16, 20, 23, 26, 29, 37, 38, 39, 40, 41, 89 to 122). Defensin peptide variants set forth herein comprising tryptophan, tyrosine or phenylalanine substitution of the C2 and C3 residues corresponding to the C2 and C3 residues in a reference C-terminal defensin peptide can comprise a modified gamma core variant sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), GXCX3-8(F/W/Y) (SEQ ID NO: 43), or GXCX3-9(F/W/Y) (SEQ ID NO: 44). In certain embodiments, the aforementioned defensin peptide variants comprise, consist essentially of, or consist of: (i) 30 amino acid residues or less; or (ii) 15, 16, or 17 to 30 amino acid residues. In certain embodiments, the aforementioned defensin peptide variants comprise, consist essentially of, or consist of a peptide corresponding to the C-terminal end of a defensin peptide comprising the C1, C2, C3, and C4 conserved cysteines (e.g. SEQ ID NO: 8, 16, 20, 23, 26, 29, 37, 38, 39, 40, 41, 89-122 or contained in the full length defensin peptides of SEQ ID NO: 123 to 434 and 436 to 576) wherein a tryptophan, tyrosine or phenylalanine substitution of the C2 and C3 residues corresponding to the C2 and C3 residues in a reference C-terminal defensin peptide can result in a defensin variant peptide comprising a modified gamma core variant sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), GXCX3-8(F/W/Y) (SEQ ID NO: 43), or GXCX3-9(F/W/Y) (SEQ ID NO: 44) and optionally comprise a peptide having just two (2) cysteine residues corresponding to the conserved C1 and C4 cysteines of a reference defensin C-terminal peptide.

In certain embodiments, additional defensin peptide variants lacking a canonical gamma-core consensus sequence of GXCX3-9C (SEQ ID NO: 9) or GXCX3-10C (SEQ ID NO:10) are provided. In certain embodiments, defensin peptide variants provided herein will comprise a substitution of tryptophan, tyrosine, phenylalanine, leucine, isoleucine, valine, or methionine for the C-terminal cysteine residue of the gamma core consensus sequence of SEQ ID NO: 9 or 10 (e.g., C2 in a reference SEQ ID NO: 8, 16, 20, 23, 26, 29, 37, 38, 39, 40, 41, or 89 to 122 or contained in the full length defensin peptides of SEQ ID NO: 123 to 434 and 436 to 576). In certain embodiments, defensin peptide variants provided herein comprise an independent substitution of both the C2 and C3 residues corresponding to the C2 and C3 residues in a reference C-terminal defensin peptide (e.g., SEQ ID NO: 8, 16, 20, 23, 26, 29, 37, 38, 39, 40, 41, or 89 to 122 or contained within the full length defensin peptides of SEQ ID NO: 123 to 434 and 436 to 576) with a tryptophan, tyrosine, phenylalanine, leucine, isoleucine, valine, or methionine residue. In certain embodiments, defensin peptide variants provided herein comprise substitutions of the C2 and C3 residues corresponding to the C2 and C3 residues in a reference C-terminal defensin peptide (e.g., SEQ ID NO: 8, 16, 20, 23, 26, 29, 37, 38, 39, 40, 41, or 89 to 122 or contained within the full length defensin peptides of SEQ ID NO: 123 to 434 and 436 to 576) with a tryptophan, tyrosine, phenylalanine, leucine, isoleucine, valine, or methionine residue. In certain embodiments, defensin peptide variants set for the herein can further comprise a tryptophan, tyrosine, phenylalanine, leucine, isoleucine, valine, or methionine residue in the amino acid position located between the C2 and C3 residues in a reference C-terminal defensin peptide (e.g., SEQ ID NO: 8, 16, 20, 23, 26, 29, 37, 38, 39, 40, 41, 89 to 122 or contained within the full length defensin peptides of SEQ ID NO: 123 to 434 and 436 to 576). Defensin peptide variants set forth herein comprising independent tryptophan, tyrosine, phenylalanine, leucine, isoleucine, valine, or methionine substitutions of the C2 and C3 residues corresponding to the C2 and C3 residues in a reference C-terminal defensin peptide can result in a defensin variant peptide comprising a modified gamma core variant sequence GXCX3-10 (L/V/I/M)(F/W/Y) (L/V/I/M) (SEQ ID NO: 48), GXCX3-8(F/W/Y/L/V/I/M) (F/W/Y)(F/W/Y/L/V/I/M) (SEQ ID NO: 49), GXCX3-10(F/W/Y/L/V/I/M) (F/W/Y)(F/W/Y/L/V/I/M) (SEQ ID NO: 50), GXCX3-8(F/W/Y/L/V/I/M)(F/W/Y/L/V/I/M)(F/W/Y/L/V/I/M) (SEQ ID NO: 51), or GXCX3-10(F/W/Y/L/V/I/M)(F/W/Y/L/V/I/M)(F/W/Y/L/V/I/M) (SEQ ID NO: 52). In certain embodiments, the aforementioned defensin peptide variants comprise, consist essentially of, or consist of: (i) 30 amino acid residues or less; or (ii) 15, 16, or 17 to 30 amino acid residues. In certain embodiments, the aforementioned defensin peptide variants comprise, consist essentially of, or consist of a peptide corresponding to the C-terminal end of a defensin peptide comprising the C1, C2, C3, and C4 conserved cysteines (e.g. SEQ ID NO: 8, 16, 20, 23, 26, 29, 37, 38, 39, 40, 41, 89-122 or contained in the full length defensin peptides of SEQ ID NO: 123 to 434 and 436 to 576) wherein an independent tryptophan, tyrosine, phenylalanine, leucine, valine, isoleucine or methionine substitution of the C2 and C3 residues corresponding to the C2 and C3 residues in a reference C-terminal defensin peptide can result in a defensin variant peptide comprising a modified gamma core variant sequence of SEQ ID NO: 48, 49, 50, 51, or 52 and optionally comprise a peptide having just two (2) cysteine residues corresponding to the conserved C1 and C4 cysteines of a reference defensin C-terminal peptide.

In certain embodiments, a defensin peptide variant comprises an amino acid sequence having at least 70%, 75%, 80%, 82%, 85%, 90%, 92%, 94%, 95%, or 100% sequence identity across the entire length of SEQ ID NO: 3-7, 12-15, 17-20, 22, 23, 25, 26, 28, 29, 31, 32, 42, 578, 579, 581, 582, 584, or 585 wherein said peptide does not comprise the corresponding full-length or C-terminal sequence of the defensin peptide of SEQ ID NO: 8, 16, 20, 23, 26, 29, 37, 38, 39, 40, 41, 123 to 434, or 436 to 576. In certain embodiments, such defensin peptide variants will having at least 70%, 75%, 80%, 82%, 85%, 90%, 92%, 94%, 95%, or 100% sequence identity across the entire length of SEQ ID NO: 3-7, 12-15, 17-20, 22, 23, 25, 26, 28, 29, 31, 32, 42, 578, 579, 581, 582, 584, or 585 further comprise the gamma-core consensus sequence of GXCX3-9C (SEQ ID NO: 9) or GXCX3-10C (SEQ ID NO:10); wherein X is any amino acid or wherein X is selected from cationic and/or hydrophobic amino acids. In certain embodiments, such defensin peptide variants will having at least 70%, 75%, 80%, 82%, 85%, 90%, 92%, 94%, 95%, or 100% sequence identity across the entire length of SEQ ID NO: 3-7, 12-15, 17-20, 22, 23, 25, 26, 28, 29, 31, 32, 42, 578, 579, 581, 582, 584, or 585 further comprise a modified gamma core variant sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), GXCX3-8(F/W/Y) (SEQ ID NO: 43), GXCX3-9(F/W/Y) (SEQ ID NO: 44), GXCX3-8(F/W/Y/L/V/I/M) (SEQ ID NO: 45), GXCX3-10(F/W/Y/L/V/I/M) (SEQ ID NO: 46), GXCX3-8 (L/V/I/M)(F/W/Y) (L/V/I/M) (SEQ ID NO: 47), GXCX3-10 (L/V/I/M)(F/W/Y) (L/V/I/M) (SEQ ID NO: 48), GXCX3-8(F/W/Y/L/V/I/M) (F/W/Y)(F/W/Y/L/V/I/M) (SEQ ID NO: 49), GXCX3-10(F/W/Y/L/V/I/M) 50), GXCX3-(F/W/Y)(F/W/Y/L/V/I/M) (SEQ ID NO: 8(F/W/Y/L/V/I/M)(F/W/Y/L/V/I/M)(F/W/Y/L/V/I/M) (SEQ ID NO: 51), or GXCX3-10(F/W/Y/L/V/I/M)(F/W/Y/L/V/I/M)(F/W/Y/L/V/I/M) (SEQ ID NO: 52). In certain embodiments, such defensin peptide variants will have at least 70%, 75%, 80%, 82%, 85%, 90%, 92%, 94%, 95%, or 100% sequence identity across the entire length of SEQ ID NO: 3-7, 2-15, 17-20, 22, 23, 25, 26, 28, 29, 31, 32, 42, 578, 579, 581, 582, 584, or 585 have a net positive charge of at least about 5.8 at neutral pH and/or a hydrophobicity percentage of at least about 15%. In certain embodiments, a first structural feature of the defensin peptide variants is a net positive charge at neutral pH. In certain embodiments, the defensin peptide variants will have a net positive charge at neutral pH of at least +2, +3, +3.5, +4, +5, +6, +7, +8, +9, or +10. In certain embodiments, the defensin peptide variants will have a net positive charge at neutral pH of at least +3, +3.5, +4, +5, +6, or +7 to about +8, +9, or +10. In certain embodiments, the hydrophobicity percentage of such defensin peptide variants is at least about 15% to 30%, about 16% to 19%, or about 28% to 30%. In certain embodiments, the aforementioned defensin peptide variants comprise, consist essentially of, or consist of: (i) 30 amino acid residues or less; or (ii) 15, 16, or 17 to 30 amino acid residues. In certain embodiments, any of the aforementioned defensin peptide variants comprise a peptide having just two (2) cysteine residues and optionally comprise the two cysteine residues corresponding to the conserved C1 and C4 cysteines of a reference defensin C-terminal peptide.

In certain embodiments, defensin peptide variants comprise amino acid substitutions which increase or maintain the net positive charge of the peptide at neutral pH and/or increase or maintain the hydrophobicity of the peptide. Amino acid substitutions in SEQ ID NO: 3-7, 12-15, 17-20, 22, 23, 25, 26, 28, 29, 31, 32, 42, 578, 579, 581, 582, 584, or 585 which can maintain net positive charge of the peptide at neutral pH include substitution of a lysine, arginine, or Dab (diaminobutyric acid) residue in SEQ ID NO: 3-7, 12-15, 17-20, 22, 23, 25, 26, 28, 29, 31, 32, 42, 578, 579, 581, 582, 584, or 585 with a different amino acid residue selected from the group consisting of lysine, arginine, Dab (diaminobutyric acid), or other non-naturally occurring amino acid which is positively charged at neutral pH. Amino acid substitutions in SEQ ID NO: 3-7, 12-15, 17-20, 22, 23, 25, 26, 28, 29, 31, 32, 42, 578, 579, 581, 582, 584, or 585 which can increase net positive charge at neutral pH include substitution of a polar (e.g. cysteine or threonine) or non-polar (e.g., glycine) residue in SEQ ID NO: 3-7, 12, 12-15, 17-20, 22, 23, 25, 26, 28, 29, 31, 32, 42, 578, 579, 581, 582, 584, or 585 with a different amino acid residue selected from the group consisting of lysine, arginine, Dab (diaminobutyric acid), or other non-naturally occurring amino acid residue which is positively charged at neutral pH. Amino acid substitutions in SEQ ID NO: 3-7, 12-15, 17-20, 22, 23, 25, 26, 28, 29, 31, 32, 42, 578, 579, 581, 582, 584, or 585 which can maintain hydrophobicity of the peptide include substitution of a glycine, valine, phenylalanine, or isoleucine residue in SEQ ID NO: 3-7, 12-15, 17-20, 22, 23, 25, 26, 28, 29, 31, 32, 42, 578, 579, 581, 582, 584, or 585 with a different amino acid residue selected from the group consisting of glycine, alanine, valine, leucine, phenylalanine, isoleucine, or methionine. Amino acid substitutions in SEQ ID NO: 3-7, 12-15, 17-20, 22, 23, 25, 26, 28, 29, 31, 32, 42, 578, 579, 581, 582, 584, or 585 which can increase hydrophobicity of the peptide include substitution of a polar (e.g. cysteine or threonine) residue in SEQ ID NO: 3-7, 12-15, 17-20, 22, 23, 25, 26, 28, 29, 31, 32, 42, 578, 579, 581, 582, 584, or 585 with a different amino acid residue selected from the group consisting of glycine, alanine, valine, leucine, phenylalanine, or isoleucine. In certain embodiments, such substitutions which increase or maintain net positive charge or hydrophobicity of the peptide will comprise a defensin peptide variant having the gamma-core consensus sequence of GXCX3-9C (SEQ ID NO: 9) or GXCX3-10C (SEQ ID NO:10). In certain embodiments, such substitutions which increase or maintain net positive charge or hydrophobicity of the peptide will comprise a defensin peptide variant having the modified gamma core variant sequence GXCX3-8 (F/W/Y)(F/W/Y)(F/W/Y) (SEQ ID NO: 33) or GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589) GXCX3-8(F/W/Y)(F/W/Y)(F/W/Y) (SEQ ID NO: 33), GXCX3-8(F/W/Y) (SEQ ID NO: 43), or GXCX3-9(F/W/Y) (SEQ ID NO: 44). In certain embodiments, such substitutions which increase or maintain net positive charge or hydrophobicity of the peptide will comprise a defensin peptide variant having the modified gamma core variant sequence can comprise a modified gamma core variant sequence of SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52. In certain embodiments, the aforementioned defensin peptide variants comprise, consist essentially of, or consist of: (i) 30 amino acid residues or less; or (ii) 15, 16, or 17 to 22, 24, 16, 28 or 30 amino acid residues. In certain embodiments, any of the aforementioned defensin peptide variants comprise a peptide having just two (2) cysteine residues and optionally comprise the two cysteine residues corresponding to the conserved C1 and C4 cysteines of a reference defensin C-terminal peptide.

In certain embodiments, one or more amino acids in any of the aforementioned or other variant defensin peptide variant sequences are substituted with another amino acid(s), the charge and polarity of which is similar to that of the original amino acid, i.e., a conservative amino acid substitution. Substitutes for an amino acid within the defensin peptide variant or protein, or defensin peptide sequence can be selected from other members of the class to which the originally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include: (1) acidic (anionic, negatively charged) amino acids such as aspartic acid and glutamic acid; (2) basic (cationic, positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes within defensin peptide sequences can be made by substituting one amino acid within one of these groups with another amino acid within the same group. Biologically functional equivalents of defensin peptide variants can have 10 or fewer conservative amino acid changes, seven or fewer conservative amino acid changes, or five, four, three, two, or one conservative amino acid changes. The encoding nucleotide sequence (e.g., gene, plasmid DNA, cDNA, or synthetic DNA) will thus have corresponding base substitutions, permitting it to encode biologically functional equivalent forms of the defensin peptide variants. Certain semi-conservative substitutions in defensin peptide variants including: (i) the substitution of a neutral polar amino acid residue with a neutral nonpolar (hydrophobic) amino acid residue; or (ii) the substitution of a neutral nonpolar (hydrophobic) amino acid residue with a neutral polar amino acid residue are also provided. In particular, semi-conservative substitutions of a neutral polar tyrosine residue with a hydrophobic amino acid residue are provided. Biologically functional equivalents of defensin peptide variants can have 10 or fewer semi conservative amino acid changes, seven or fewer semi-conservative amino acid changes, or five, four, three, two, or one semi-conservative amino acid changes.

Nucleic acid molecules encoding any of the aforementioned defensin peptide variants are also provided herein. Recombinant DNA molecules comprising the aforementioned nucleic acid molecules are also provided herein and in particular recombinant DNA molecules comprising a heterologous promoter that is operably linked to the aforementioned nucleic acid molecules are also provided herein.

A defensin peptide variant provided herein can be operably linked to another defensin peptide variant, defensin, or antimicrobial peptide via a spacer peptide sequence that is not susceptible to cleavage by an endoproteinase, including a plant endoproteinase. Such peptide linker sequences that join peptides in multimeric or multi-domain proteins have been disclosed (Argos, 1990; George R A, Heringa (2002)). Examples of suitable peptide sequences from multimeric or multi-domain proteins that can be used as spacer domains include immunoglobulin hinge regions from immunoglobulins, a linker between the lipoyl and E3 binding domain in pyruvate dehydrogenase (Turner et ah, 1993), a linker between the central and C-terminal domains in cysteine proteinase (P9; Mottram et ah, 1989), and functional variants thereof. Spacer peptides for use in the defensin variant proteins can also be wholly or partially synthetic peptide sequences. Such synthetic spacer peptides are designed to provide for a flexible linkage between the at least one defensin peptide variant and another peptide (including a defensin peptide variant or defensin peptide) and to be resistant to cleavage by endogenous plant or other endoproteinases. In certain embodiments, the length of the synthetic spacer peptide can be between about 3, 4, 8, 10, 12, or 16 and about 20, 24, 28, 30, 40, or 50 amino acid residues in length. In certain embodiments, the synthetic spacer peptide can comprise a glycine-rich or glycine/serine containing peptide sequence. The composition and design of peptides suitable for flexible linkage of protein domains described in the literature (Chen et al., 2013) can be adapted for use as spacer peptides in the defensin variant proteins provided herein. Spacer peptides useful for joining defensin monomers described in US Patent Appln. Publications US20190194268 and US20190185877, which are each incorporated herein by reference in their entireties, can also be used to join defensin peptide variants disclosed herein to other defensin peptide variants, defensins, antimicrobial peptides, or other peptides.

A defensin peptide variant provided herein can be operably linked to another defensin peptide variant, defensin, or antimicrobial peptide via a linker peptide sequence that is susceptible to cleavage by an endoproteinase, including a plant endoproteinase. In certain embodiments, the resultant defensin variant protein can be expressed in a cell such that the endoproteinase cleaves the defensin variant protein to provide at least one defensin peptide variant and another peptide (including a defensin peptide variant or defensin peptide). Such defensin variant proteins can be provided in a cellular compartment (e.g., cytoplasm, mitochondria, plastid, vacuole, or endoplasmic reticulum) or extracellular space (i.e., to the apoplast) having an endoproteinase that cleaves the linker peptide. Cleavable linker peptides are disclosed in WO2014078900, Vasivarama and Kirti, 2013a, Frangois et al, Vasivarama and Kirti, 2013b, and WO2017127558 can be used in the defensin variant proteins provided herein.

Expression cassettes that provide for expression of the defensin peptide variant in monocotyledonous plants, dicotyledonous plants, or both can be constructed. Such defensin peptide variant expression cassette construction can be effected either in a plant expression vector or in the genome of a plant. Expression cassettes are DNA constructs wherein various promoter, coding (e.g. defensin peptide variant encoding), and polyadenylation sequences are operably linked. In general, expression cassettes typically comprise a promoter that is operably linked to a sequence of interest, which is operably linked to a polyadenylation or terminator region. In certain instances including the expression of recombinant or edited polynucleotides in monocot plants, it can also be useful to include an intron sequence. When an intron sequence is included it is typically placed in the 5' untranslated leader region of the recombinant or edited polynucleotide. In certain instances, it can also be useful to incorporate specific 5' untranslated sequences in a recombinant or edited polynucleotide to enhance transcript stability or to promote efficient translation of the transcript. Expression cassettes and vectors for expression of other defensin peptides or proteins in plants, including those disclosed in U.S. Pat. No. 10,253,328 which is incorporated herein by reference in its entirety, can be adapted for expression of the defensin peptide variants in transgenic plants. Any of the defensin peptide variant expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. The aforementioned methods of introducing transgenes are described in US Patent Appl. Pub. No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety.

In certain embodiments, a plant comprising a recombinant or edited polynucleotide encoding a defensin peptide variant can be obtained by using techniques that provide for site specific insertion of heterologous DNA into the genome of a plant (e.g., by CRISPR, TALEN, or Zinc finger nuclease-mediated gene editing). In certain embodiments, a DNA fragment encoding at least a defensin peptide variant is site specifically integrated into the genome to a plant cell, tissue, part, or whole plant to create a sequence within that genome that encodes a defensin peptide variant. Examples of methods for inserting foreign DNA at specific sites in the plant genome with site-specific nucleases such as meganucleases or zinc-finger nucleases are at least disclosed in Voytas, 2013. Examples of methods for inserting foreign DNA into the plant genome with clustered regularly interspaced short palindromic repeats (CRISPR)-associated (Cas)-guide RNA technology and a Cas endonuclease are at least disclosed by Svitashev et al., 2015; Murovec et al., 2017; Kumar and Jain, 2015; and in US Patent Appl. Pub. No. 20150082478, which is specifically incorporated herein by reference in its entirety.

Expression of defensin peptide variants in yeast is also specifically contemplated herein. The construction of expression vectors for production of heterologous proteins in various yeast genera is well established. In general, such expression vectors typically comprise a promoter that is operably linked to a sequence of interest which is operably linked to a polyadenylation or terminator region. Examples of yeast genera that have been used to successfully express heterologous genes include *Candida, Kluveromyces, Hansuela, Pichia, Saccharomyces, Schizosaccharomyces*, and *Yarrowia*. A general description of expression vectors and transformation systems for *Saccharomyces* is found in Kingsman et al (1985). Expression vectors and transformation systems useful for yeasts other than *Saccharomyces* are described in Reiser et al (1990). Expression cassettes and vectors for expression of other defensin peptides or proteins in yeast, including those disclosed in U.S. Pat. No. 10,253,328, which is incorporated herein by reference in its entirety, can be adapted for expression of the defensin peptide variants in yeast.

Expression of defensin peptide variants in bacteria is also specifically contemplated herein. The construction of expression vectors for production of heterologous proteins in various bacterial systems have been described. In general, such expression vectors typically comprise a promoter that is operably linked to a sequence encoding peptide sequence(s) of interest (e.g., a signal transit peptide region at the n-terminus of a defensin variant peptide) which is operably linked to a procaryotic terminator region. Examples of bacterial genera that have been used to successfully express heterologous genes include *Acinetobacter, Alcaligenes, Azotobacter, Bacillus, Escherichia, Lactobacillus, Lactococcus, Streptomyces*, and *Pseudomonas. E. coli* expression systems useful for production of proteins comprising disulfide bonds and that can be adapted for use in expression of the defensin variant peptides provided herein include those described in are described in Kuddus et al. (2017) Biotechnol Prog 233:1520-1528. doi: 10.1002/btpr.Protein Science 2508, Kiedzierska et al. (2008) Protein Expr Purif 60, 82-88, Chang et al. (2015) *Amino Acids* 47, 579-587, Buchko et al. (2018) Protein Science 27, 1611-1623, Marques et al. (2008) J Appl Microbiol 106, 1640-1648, and Pazgier et al. (2006) Protein Expr Pur 49, 1-8. Systems for expressing proteins which comprise disulfide bonds can be adapted for expression of the Defensin peptides in *E. coli* include those disclosed in U.S. Patent Publication No. US 2020/0172915, which is incorporated herein by reference in its entirety, and in Berkmen, M. Protein Expr Purif. 2012; 82 (1): 240-51. doi: 10.1016/j.pep.2011.10.009.

Other bacterial expression systems for expression of the useful for production of proteins comprising disulfide bonds and that can be adapted for use in expression of the defensin variant peptides provided herein include those described in U.S. Pat. No. 10,604,761, which is incorporated herein by reference in its entirety.

Also provided are antimicrobial compositions for agricultural, pharmaceutical, or veterinary use comprising either an antimicrobial plant, or antimicrobial human or veterinary, pathogenic microbe inhibitory amount ("antimicrobial effective amount") of one or more the present isolated, purified antimicrobial defensin peptide variants, or biologically functional equivalents thereof. Such compositions can comprise one, or any combination of, defensin peptide variants or proteins disclosed herein, and an agriculturally, pharmaceutically, or veterinary-practicably acceptable carrier, diluent, or excipient. As indicated below, other components relevant in agricultural and therapeutic contexts can be included in such compositions as well. The antimicrobial compositions can be used for inhibiting the growth of, or killing, defensin peptide variant-susceptible pathogenic microbes associated with plant, human or animal microbial infections. Such antimicrobial compositions can be formulated for topical administration, and applied topically to either plants, the plant environment (including soil), or humans or animals. Such antimicrobial compositions can be formulated for enteral, parenteral, and/or intravenous administration of the composition, and administered to a subject in need thereof; such subject can be a human, livestock, poultry, fish, or a companion animal. The defensin peptide variants can be formulated alone, in any combination with one another, and either of these can additionally be formulated in combination with other conventional antimicrobial therapeutic compounds such as, by way of non-limiting example, polyene antimicrobials; imidazole, triazole, and thiazole antimicrobials; allylamines; and echinocandins that are routinely used in human and veterinary medicine. Administration of the compositions that comprise defensin peptide variants to a human or animal subject in need thereof can be accomplished via a variety of routes that include topical application, enteral administration, parenteral administration, and/or intravenous administration. The antimicrobial peptides and compositions can be used to control microbial pathogens or contaminants including: (i) a bacterial pathogen of plants or animals, wherein the bacterial pathogen is optionally a member of the group Enterobacteriaceae and optionally wherein the bacterial pathogen is a *Salmonella* sp., *Escherichia* sp., or *Listeria* sp.; (ii) is a *Fusarium* sp., *Alternaria* sp., *Aphenomyces* sp., *Verticillium* sp., *Phytophthora* sp., *Colletotrichum* sp., *Botrytis* sp., *Cercospora* sp., *Phakopsora* sp. *Rhizoctonia* sp., *Sclerotinia* sp., *Pythium* sp., *Phoma* sp., *Leptosphaeria* sp., *Gaeumannomyces* sp., *Puccinia* sp. *Septoria* sp., *Penicillium* sp., *Lasiodiplodia* sp., *Phomopsis* sp., *Mycosphaerella* sp., *Golovinomyces* sp., *Erisyphe* sp., *Albugo* sp., *Setosphaeria* sp., *Cochliobolus* sp., *Helminthosporium* sp., *Diplodia* sp., or *Stenocarpella* sp.; (iii) an *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis, Coccidiomyces* or *Blastomyces* species; (iv) a *Candida* species and wherein the *Candida* species is *Candida albicans* (*C. albicans*), *C. auris, C. glabrata, C parapsilosis, C. tropicalis*, or *C. krusei*; or (v) dermatophyte is optionally selected from the group consisting of *Trichophyton rubrum, Trichophyton interdigitale, Trichophyton violaceum, Trichophyton tonsurans, Trichophyton soudanense, Trichophyton mentagrophytes, Microsporum flavum, Epidermophyton floccosum*, and *Microsporum gypseum*.

Agricultural compositions comprising any of the present defensin peptide variant molecules alone, or in any combination, can be formulated as described in, for example, Winnacker-Kuchler (1986) Chemical Technology, Fourth Edition, Volume 7, Hanser Verlag, Munich; van Falkenberg (1972-1973) Pesticide Formulations, Second Edition, Marcel Dekker, N.Y.; and K. Martens (1979) Spray Drying Handbook, Third Edition, G. Goodwin, Ltd., London. Formulation aids, such as carriers, inert materials, surfactants, solvents, and other additives are also well known in the art, and are described, for example, in Watkins, Handbook of Insecticide Dust Diluents and Carriers, Second Edition, Darland Books, Caldwell, N.J., and Winnacker-Kuchler (1986) Chemical Technology, Fourth Edition, Volume 7, Hanser Verlag, Munich. Using these formulations, it is also possible to prepare mixtures of the present defensin peptide variants and proteins with other pesticidally active substances, fertilizers, and/or growth regulators, etc., in the form of finished formulations or tank mixes.

Whether alone or in combination with other active agents, the present antimicrobial defensin peptide variants can be applied to subjects or plants at a concentration in the range of from about 0.1 pg/ml to about 100 mg/ml, or from about 5 μg/ml to about 5 mg/ml, at a pH in the range of from about 3.0 to about 9.0. Such compositions can be buffered using, for example, phosphate buffers between about 1 mM and 1 M, about 10 mM to about 100 mM, or about 15 mM to about 50 mM. In the case of low buffer concentrations, a salt can be added to increase the ionic strength. In certain embodiments, a sodium salt, including NaCl, in the range of from about 1 mM to about 1 M, about 1 mM, 5 mM, or 10 mM to about 20 mM, 50 mM, 100 mM, 150 mM, or 200 mM, or about 10 mM to about 100 mM, can be added or provided in compositions comprising defensin peptide variants and proteins. In certain embodiments, a potassium salt, including KCl, in the range of about 1 mM, 5 mM, or 10 mM to about 20 mM, 50 mM, 100 mM, 150 mM, or 200 mM can be added or provided in compositions comprising defensin peptide variants and proteins. In certain embodiments, a calcium salt, including $CaCl_2$), in the range of about 0.1 mM, 0.5 mM, or 1 mM to about 2 mM, 5 mM, 10 mM, or 20 mM can be added or provided in compositions comprising defensin peptide variants.

Numerous conventional microbial antibiotics and chemical antimicrobial agents (e.g., fungicides) with which the present defensin peptide variants and proteins can be combined are described in Worthington and Walker (1983) The Pesticide Manual, Seventh Edition, British Crop Protection Council. These include, for example, polyoxins, nikkomycins, carboxy amides, aromatic carbohydrates, carboxines, morpholines, inhibitors of sterol biosynthesis, and organophosphorous compounds. In addition, azoles, triazoles and echinocandins fungicides can also be used. Other active ingredients which can be formulated in combination with the present antimicrobial peptides and proteins include, for example, insecticides, attractants, sterilizing agents, acaricides, nematicides, and herbicides. U.S. Pat. No. 5,421,839, which is incorporated herein by reference in its entirety, contains a comprehensive summary of the many active agents with which substances such as the present antimicrobial defensin peptide variants and proteins can be formulated.

Agriculturally useful antimicrobial compositions encompassed herein also include those in the form of host cells, such as bacterial and microbial cells, capable of producing the defensin peptide variants and proteins, and which can colonize plants, including roots, shoots, leaves, or other parts of plants. The term "plant-colonizing microorganism" is used herein to refer to a microorganism that is capable of colonizing the any part of the plant itself and/or the plant environment, including, and which can express the present defensin variant antimicrobial peptides and proteins in the plant and/or the plant environment. A plant colonizing micro-organism is one that can exist in symbiotic or non-detrimental relationship with a plant in the plant environment. U.S. Pat. No. 5,229,112, which is incorporated herein by reference in its entirety, discloses a variety of plant-colonizing microorganisms that can be engineered to express antimicrobial peptides and proteins, and methods of use thereof, applicable to the defensin variant antimicrobial peptides and proteins disclosed herein. Plant-colonizing microorganisms expressing the presently disclosed defensin variant antimicrobial peptides and proteins useful in inhibiting microbial growth in plants include bacteria selected from the group consisting of *Bacillus* spp. including *Bacillus thuringiensis, Bacillus israelensis*, and *Bacillus subtilis, Candidatus Liberibacter asiaticus; Pseudomonas* spp.; *Arthrobacter* spp., *Azospyrillum* spp., *Clavibacter* spp., *Escherichia* spp.; *Agrobacterium* spp., for example *A. radiobacter, Rhizobium* spp., *Erwinia* spp. *Azotobacter* spp., *Azospirillum* spp., *Klebsiella* spp., *Alcaligenes* spp., *Rhizobacterium* spp., *Xanthomonas* spp., *Ralstonia* spp. and *Flavobacterium* spp. In certain embodiments, the microorganism is a yeast selected from the group consisting of *Saccharomyces cerevisiae, Pichia pastoris*, and *Pichia methanolica*. In certain embodiments, the plant colonizing microorganism can be an endophytic bacteria or microbe. When applying the present defensin peptide variant molecules to the rhizosphere, rhizosphere-colonizing bacteria from the genus *Pseudomonas* are particularly useful, especially the fluorescent pseudomonads, e.g., *Pseudomonas fluorescens*, which is especially competitive in the plant rhizosphere and in colonizing the surface of the plant roots in large numbers. Examples of suitable phylloplane (leaf) colonizing bacteria are *P. putida, P. syringae*, and *Erwinia* species.

Embodiments

The following numbered embodiments form part of the disclosure:

1a. A peptide comprising the sequence SEQ ID NO: 1, wherein said peptide does not comprise the corresponding full-length sequence of the defensin peptide of SEQ ID NO: 8, 16, 20, 23, 26, 29, 37, 38, 39, 40, or 41; optionally wherein said peptide comprises a modified gamma-core consensus sequence GXCX3-8(F/W/Y)(F/W/Y)(F/W/Y) set forth in SEQ ID NO: 33, GXCX3-9(F/W/Y)(F/W/Y)(F/W/Y) set forth in SEQ ID NO: 34, GXCX3-8(F/W/Y) (SEQ ID NO: 43), or GXCX3-9(F/W/Y) (SEQ ID NO: 44); and/or optionally wherein the C-terminal cysteine residue or C-terminal amino acid residue is amidated.

1b. A peptide having at least 50%, 55%, 60%, 68%, 75%, 82%, or 94% sequence identity across the entire length of any one of SEQ ID NO: 3, 4, 5, or 6, wherein the peptide is not identical to SEQ ID NO: 8, optionally wherein any amino acid substitution in said sequence increases or maintains the net positive charge at neutral pH and/or increases or maintains hydrophobicity of the peptide, and optionally wherein the C-terminal cysteine residue is amidated.

1c. A peptide having at least 50%, 55%, 60%, 68%, 75%, 82%, 94%, 95%, or 100% sequence identity across the entire length of SEQ ID NO:7, 12, 13, 14, 15, 17-20, 22, 23, 25, 26, 28, 29, 31, 32, 42, 578, 579, 581, 582, 584, or 585, wherein the peptide is not identical to SEQ ID NO: 8, 16, 20, 23, 26, 29, 37, 38, 39, 40, or 41, optionally wherein the peptide of SEQ ID NO:5, SEQ ID NO: 13, 14, 15, 18, 19, 20, 22, 23, 26, 28, 29, 31, 32, 42, 42, 578, 579, 581, 582, 584, or 585 comprises a disulfide bond between the two cysteine residues and optionally wherein any substitution increases or maintains the net positive charge at neutral pH and/or increases or maintains hydrophobicity of the peptide, and optionally wherein the C-terminal cysteine residue or C-terminal amino acid residue is amidated.

1d. A defensin C-terminal peptide variant comprising conserved C1 and C4 cysteine residues corresponding to N-terminal and C-terminal cysteines of a reference defensin C-terminal peptide, wherein conserved C2 and C3 cysteine residues of the reference defensin C-terminal peptide are independently substituted with tryptophan, tyrosine, phenylalanine, leucine, valine, isoleucine, or methionine; and optionally wherein the defensin peptide variant has a net positive charge of at least 3, 3.5, 4, 5, or 6 and a hydrophobic amino acid content at least 18%.

1e. A C-terminal defensin peptide variant comprising a modified gamma-core consensus sequence GXCX3-8(F/W/Y)(F/W/Y)(F/W/Y) (SEQ ID NO: 33), GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), GXCX3-8(F/W/Y) (SEQ ID NO: 43), GXCX3-9(F/W/Y) (SEQ ID NO: 44), GXCX3-8(F/W/Y/L/V/I/M) (SEQ ID NO: 45), GXCX3-10(F/W/Y/L/V/I/M) (SEQ ID NO: 46), GXCX3-8 (L/V/I/M)(F/W/Y) (L/V/I/M) (SEQ ID NO: 47), GXCX3-10 (L/V/I/M)(F/W/Y) (L/V/I/M) (SEQ ID NO: 48), GXCX3-8 (F/W/Y/L/V/I/M)(F/W/Y)(F/W/Y/L/V/I/M) (SEQ ID NO: 49), GXCX3-10(F/W/Y/L/V/I/M)(F/W/Y)(F/W/Y/L/V/I/M) (SEQ ID NO: 50), GXCX3-8(F/W/Y/L/V/I/M)(F/W/Y/L/V/I/M)(F/W/Y/L/V/I/M) (SEQ ID NO: 51), or GXCX3-10(F/W/Y/L/V/I/M)(F/W/Y/L/V/I/M)(F/W/Y/L/V/I/M) (SEQ ID NO: 52), optionally wherein the peptide further comprises a conserved C4 cysteine residue, optionally wherein the cysteine residue in the modified gamma-core consensus sequence forms a disulfide bond with the conserved C4 cysteine residue, and/or optionally wherein the defensin peptide variant has a net positive charge of at least 3, 3.5, 4, 5, or 6 and a hydrophobic amino acid content at least 18%.

1f. A peptide comprising a modified gamma-core consensus sequence GXCX3-8 (F/W/Y)(F/W/Y)(F/W/Y) (SEQ ID NO:33), GXCX3-9(F/W/Y)(F/W/Y)(F/W/Y) (SEQ ID NO: 34), GXCX3-10(F/W/Y)(F/W/Y)(F/W/Y) (SEQ ID NO: 587), GXCX3-12(F/W/Y)(F/W/Y)(F/W/Y) (SEQ ID NO: 588), GXCX3-15(F/W/Y)(F/W/Y)(F/W/Y) ((SEQ ID NO: 589), GXCX3-8(F/W/Y) (SEQ ID NO: 43), or GXCX3-9(F/W/Y) (SEQ ID NO: 44), GXCX3-8(F/W/Y/L/V/I/M) (SEQ ID NO: 45), GXCX3-10(F/W/Y/L/V/I/M) (SEQ ID NO: 46), GXCX3-8 (L/V/I/M)(F/W/Y) (L/V/I/M) (SEQ ID NO: 47), GXCX3-10 (L/V/I/M)(F/W/Y) (L/V/I/M) (SEQ ID NO: 48), GXCX3-8(F/W/Y/L/V/I/M) (F/W/Y)(F/W/Y/L/V/I/M) (SEQ ID NO: 49), GXCX3-10(F/W/Y/L/V/I/M) (F/W/Y)(F/W/Y/L/V/I/M) (SEQ ID NO: 50), GXCX3-8(F/W/Y/L/V/I/M)(F/W/Y/L/V/I/M)(F/W/Y/

L/V/I/M) (SEQ ID NO: 51), or GXCX3-10(F/W/Y/L/V/I/M)(F/W/Y/L/V/I/M)(F/W/Y/L/V/I/M) (SEQ ID NO: 52), wherein the peptide further comprises a second C-terminal cysteine residue located C-terminal to the cysteine residue in the modified gamma-core consensus sequence, and wherein the peptide has a net positive charge of at least 3, 3.5, 4, 5, or 6 and a hydrophobic amino acid content at least 18%, optionally wherein the peptide comprises a disulfide bond between the two cysteine residues.

2. The peptide of embodiment 1a, 1b, 1c, 1d, 1d, or 1f, wherein said peptide comprises; (i) an amino acid sequence selected from the group consisting of SEQ ID NO:3, SEQ ID NO:4, SEQ ID NO:5, SEQ ID NO:6, SEQ ID NO:7, SEQ ID NO: 12, SEQ ID NO: 13, SEQ ID NO: 14, SEQ ID NO: 15, 17-20, 22, 23, 25, 26, 28, 29, 31, 32, 42, 578, 579, 581, 582, 584, or 585; optionally wherein the peptide of SEQ ID NO:5, SEQ ID NO: 13, SEQ ID NO: 14, 15, 18, 19, 20, 22, 23, 26, 28, 29, 32, 42, 578, 579, 581, 582, 584, or 585 comprises a disulfide bond between the two cysteine residues; (ii) an amino acid sequence having at least 50%, 55%, 60%, 68%, 75%, 82%, 94%, 95%, or 100% sequence identity across the entire length of SEQ ID NO:7, SEQ ID NO: 12, SEQ ID NO: 13, SEQ ID NO: 14, 15, 17-20, 22, 23, 25, 26, 28, 29, 31, 32, 18, 19, 20, 22, 23, 26, 28, 29, 32, 42, 578, 579, 581, 582, 584, or 585, wherein said peptide does not comprise the corresponding full-length sequence of the defensin peptide of SEQ ID NO: 8, 16, 20, 23, 26, 29, 37, 38, 39, 40, or 41; and optionally wherein the peptide comprises a disulfide bond between the two cysteine residues; or (iii) wherein said peptide exhibits antimicrobial activity.

3. The peptide of embodiment 1a, 1b, 1c, 1d, 1d, 1f, or 2, wherein the peptide comprises, consists essentially of, or consists of: (i) 30 amino acid residues or less; (ii) 15, 16, or 17 to 30 amino acid residues; or (iii) 15, 16, or 17 to 30 amino acid residues and contains two cysteine residues.

4. A composition comprising the peptide of any of one embodiments 1a, 1b, 1c, 1d, 1e, or 1f to 3 and an agriculturally, pharmaceutically, or veterinary-practicably acceptable carrier, diluent, or excipient.

5. The composition of embodiment 4, wherein the peptide is provided at a concentration of about 0.1, 0.5, 1.0, or 5 μg/ml to about 1, 5, 20, 50, or 100 mg/ml or at a concentration of about 0.1, 0.5, 1.0, or 5 pg/gram to about 1, 5, 20, 50, or 100 mg/gram and optionally wherein the composition comprises a sodium salt at a concentration of at least 100 mM and/or a calcium salt at a concentration of at least 2 mM.

6. A method for: (i) preventing or reducing crop damage by a plant pathogenic microbe; or (ii) preventing contamination of plants, plant parts, seeds, feedstuff obtained therefrom, or foodstuff obtained therefrom with an undesirable microbe, comprising the step of contacting a plant, a plant seed, other part of said plant, feedstuff obtained therefrom, or foodstuff obtained therefrom with an effective amount of the composition of embodiment 4 or embodiment 5.

7. The method of embodiment 6, wherein the plant pathogenic microbe or undesirable microbe is: (i) a bacterial pathogen of plants or animals, wherein the bacterial pathogen is optionally a member of the group Enterobacteriaceae and optionally wherein the bacterial pathogen is a *Salmonella* sp., *Escherichia* sp., or *Listeria* sp.; or (ii) is a *Fusarium* sp., *Alternaria* sp., *Aphenomyces* sp., *Verticillium* sp., *Phytophthora* sp., *Colletotrichum* sp., *Botrytis* sp., *Cercospora* sp., *Phakopsora* sp. *Rhizoctonia* sp., *Sclerotinia* sp., *Pythium* sp., *Phoma* sp., *Leptosphaeria* sp., *Gaeumannomyces* sp., *Puccinia* sp. *Septoria* sp., *Penicillium* sp., *Lasiodiplodia* sp., *Phomopsis* sp., *Mycosphaerella* sp., *Golovinomyces* sp., *Erisyphe* sp., *Albugo* sp., *Setosphaeria* sp., *Cochliobolus* sp., *Helminthosporium* sp., *Diplodia* sp., or *Stenocarpella* sp.

8. A medical device comprising the device and the composition of embodiment 4 or 5, wherein the device comprises at least one surface that is topically coated and/or impregnated with the composition.

9 The medical device of embodiment 8, wherein said device is a stent, a catheter, a contact lens, a condom, a patch, or a diaphragm.

10. A method for treating, preventing, or inhibiting a microbial infection in a subject in need thereof comprising administering to said subject an effective amount of the composition of embodiment 4 or 5.

11. The method of embodiment 10, wherein said administration comprises topical, enteral, parenteral, and/or intravenous introduction of the composition.

12. The method of embodiment 10 or 11, wherein the subject is a human, livestock, poultry, fish, or a companion animal.

13. The method of embodiment 12, wherein the microbial infection is of a mucosal membrane, eye, skin, and/or a nail and the composition is applied to the mucosal membrane, eye, skin, and/or nail.

14. The method of any one of embodiments 10 to 13, wherein the microbial infection is by a dermatophyte, and wherein the dermatophyte is optionally selected from the group consisting of *Trichophyton rubrum, Trichophyton interdigitale, Trichophyton violaceum, Trichophyton tonsurans, Trichophyton soudanense, Trichophyton mentagrophytes, Microsporum flavum, Epidermophyton floccosum*, and *Microsporum gypseum.*

15. The method of any one of embodiments 10 to 13, wherein the microbial infection is by: (i) a bacterial pathogen of animals, wherein the bacterial pathogen is optionally a member of the group Enterobacteriaceae and optionally wherein the bacterial pathogen is a *Salmonella* sp., *Escherichia* sp., or *Listeria* sp.; or (ii) an *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis, Coccidiomyces* or *Blastomyces* species.

16. The method of any one of embodiments 10 to 13, wherein the microbial infection is by a *Candida* species and wherein the *Candida* species is *Candida albicans* (*C. albicans*), *C. auris, C. glabrata, C parapsilosis, C. tropicalis*, or *C. krusei.*

17. The composition of embodiment 4 or 5 for use in a method of treating, preventing, or inhibiting microbial infection in a subject in need thereof.

18. The composition of embodiment 17, wherein the subject is a human, livestock, poultry, fish, or a companion animal.

19. A plant part that is at least partly coated with the composition of embodiment 4 or 5.

20. The plant part of embodiment 19, wherein the part is a seed and the seed is optionally a corn, soybean, wheat, rice, cotton, *Brassica* sp., or tomato seed.

21. The plant part of embodiment 19, wherein the plant part is a fruit, vegetable, or flower.
22. A recombinant polynucleotide comprising a polynucleotide encoding an antimicrobial peptide of embodiment 1a, 1b, 1c, 1d, 1e, 1f, 2, or 3, wherein the polynucleotide encoding the first antimicrobial peptide is operably linked to a polynucleotide comprising a promoter which is heterologous to the polynucleotide encoding the first antimicrobial peptide, optionally wherein any amino acid substitution in said sequence increases or maintains the net positive charge and/or increases or maintains hydrophobicity of the peptide.
23. The recombinant polynucleotide of embodiment 22, wherein the recombinant polynucleotide further comprises a polynucleotide encoding: (i) a transit peptide, a vacuolar targeting peptide, and/or an endoplasmic reticulum targeting peptide; (ii) a plastid targeting peptide; and/or (iii) a polyadenylation or transcriptional termination signal, wherein the polynucleotides of (i), (ii), and/or (iii) are operably linked to the polynucleotide encoding the antimicrobial peptide.
24. The recombinant polynucleotide of embodiment 22 or 23, wherein the polynucleotide encoding the first antimicrobial peptide is inserted into a heterologous nuclear or plastid genome of a cell and operably linked to an endogenous promoter located in the heterologous nuclear or plastid genome.
25. A plant nuclear or plastid genome comprising a polynucleotide encoding an antimicrobial peptide of embodiment 1a, 1b, 1c, 1d, 1e, 1f, 2, or 3, and wherein the polynucleotide is heterologous to the nuclear or plastid genome and wherein the polynucleotide is operably linked to an endogenous promoter of the nuclear or plastid genome.
26. A cell comprising the recombinant polynucleotide of embodiment 22 or the genome of embodiment 25, wherein the cell is optionally a bacterial, yeast, or plant cell.
27. A plant comprising the recombinant polynucleotide of embodiment 22 or the genome of embodiment 25.
28. A plant part of the plant of embodiment 26, wherein the plant part comprises the recombinant polynucleotide or genome, optionally wherein the plant part is a seed, stem, leaf, root, tuber, flower, or fruit.
29. A method for producing plant seed that provides plants resistant to infection by a plant pathogenic microbe that comprises the steps of: (i) selfing or crossing the plant of embodiment 22; and (ii) harvesting seed that comprises the recombinant polynucleotide of the plant from the self or cross, thereby producing plant seed that provide plants resistant to infection by a plant pathogenic microbe.

PUBLICATIONS CITED

Argos, (1990) J Mol Biol. February 20; 211 (4): 943-58.
Broadley, M. R., Bowen, H. C., Cotterill, H. L., Hammond, J. P., Meacham, M. C., Mead, A., and White, P. J. (2003). Journal of Experimental Botany 54, 1431-1446
Buchko et al. (2018) Protein Science 27, 1611-1623.
Chang et al. (2015) *Amino Acids* 47, 579-587.
Chen et al., (2013) Adv Drug Deliv Rev.; 65 (10): 1357-1369.
da Silva Conceicao, A., and Broekaert, W. F. (1999). Plant Defensins. In Pathogenesis-related proteins in plants, S. Muthukrishnan, ed (New York: CRC Press), pp. 247-260.
Frangois et al., Plant Physiology (2002) 128:1346-1358.
George R A, and Heringa (2002) J Protein Eng. 15 (11): 871-879.
Hanks, J. N., et al., (2005). Plant Mol Biol 58, 385-399.
Kerenga B K, et al., (2019) Front. Microbiol. 10:795. doi: 10.3389/fmicb.2019.00795
Kiedzierska, et al. (2008) Protein Expr Purif 60, 82-8.
Kingsman S M, et al., (1985) Biotechnol Genet Eng Rev. 3:377-416.
Kuddus et al. (2017). Biotechnol Prog 233:1520-1528. doi: 10.1002/btpr.Protein Science 2508.
Kumar, V. and Jain, M. (2015) J Exp Bot 66:47-57.
Lacerda et ah, Frontiers in Microbio. (2014) 5 (116): 1-10.
Lay, F. T., and Anderson, M. A. (2005) Curr Protein Pept Sci 6, 85-101.
Marques et al. (2008) J Appl Microbiol 106, 1640-1648.
Mottram et al., FEBS Lett. (1989) 258 (2): 211-215.
Murovec et al., Plant Biotechnol J. 2017 August; 15 (8): 917-926.
Pazgier et al. (2006) Protein Expr Pur 49, 1-8.
Reiser J, et al., (1990) Adv Biochem Eng Biotechnol.; 43: 75-102.
Sagaram et al., (2011) PLOS ONE 6: el8550.
Sagaram et al., (2013) PLOS ONE, 8 (12): e82485.
Shabala, S., and Pottosin, I. I. (2010) Signal. Commun. Plants 87-110.
Svitashev et al., (2015) Plant Physiology, 169 (2): 931-945.
Spelbrink, R. G., et al., (2004). Plant Physiol 135, 2055-2067.
Terras, F. R., et al., (1992). J Biol Chem 267, 15301-15309.
Thomma, B. P. H. J., Cammue, B. P. A., and Thevissen, K. (2002). Planta 216, 193-202.
Turner et al., (1993) Protein Eng. 6 (1): 101-108.
Voytas, D. Annual Review of Plant Biology, Vol. 64:327-350, 2013.
Vasivarama and Kirti (2013a) Plant Cell Tiss Organ Cult, 115:309-319.
Vasivarama and Kirti (2013b) Funct Integr Genomics 13:435-443.
Vriens, K., et al. Molecules 2014, 19, 12280-12303; doi: 10.3390/molecules190812280.
White, P., and Karley, A. (2010). Potassium. In Cell Biology of Metals and Nutrients; Hell, R., Mendel, R. R., Eds.; Springer: Berlin/Heidelberg, Germany., 199-224

EXAMPLES

Example 1

Crude peptides (GMA4C-AC, GMA4C_V1, GMA4C_V2 and GMA4C_V3) were synthesized chemically by Biomatik Inc, Canada, and GMA4C_V4 and GMA4C_V5 by Alan Scientific Inc. (USA) and were further purified, using a linear gradient of acetonitrile/water mixture, in a C-18 reverse phase HPLC (Agilent Technologies, USA). HPLC fractions were lyophilized and resuspended in nuclease-free water. Concentration of each peptide was determined using the BCA assay performed according to the manufacturer's protocol (Thermo-Fisher Scientific, USA). Antifungal activity was determined in assays in SFM culture media. The SFM culture media comprises $K_2HPO_4$ (2.5 mM), $MgSO_4$ (50 μM), $CaCl_2$) (50 μM), $FeSO_4$ (5 M), $CoCl_2$ (0.1 μM), $CuSO_4$ ((0.1 μM), $Na_2MoO_4$ (2 μM), $H_3BO_3$ (0.5 μM), KI (0.1 μM), $ZnSO_4$ (0.5 μM), $MnSO_4$ (0.1 μM), glucose (10 g/liter), asparagine (1 g/liter), methionine (20 mg/liter), myo-inositol (2 mg/liter), biotin (0.2 mg/liter), thiamine-HCL (1 mg/liter), and pyridoxine-HCL (0.2 mg/liter), pH 7.0.)

Antifungal activity in vitro in low cationic conditions: The GMA4C variants GMA4C_V1A (SEQ ID NO: 3), GMA4C_V3A (SEQ ID NO: 5), and GMA4C_V4A (SEQ ID NO: 6), exhibit antifungal activity equivalent to the wild-type GMA4C_AC control (SEQ ID NO: 2) in vitro against *B. cinerea*. The GMA4C variant GMA4C_V2A (SEQ ID NO: 4) exhibited a reduction in antifungal activity relative to the wild-type GMA4C_AC control in vitro against *B. cinerea*. GMA4C_V6A (SEQ ID NO: 13) exhibits an increase in antifungal activity relative to the wild-type GMA4C_AC control in vitro against *B. cinerea*.

Figure 1B:
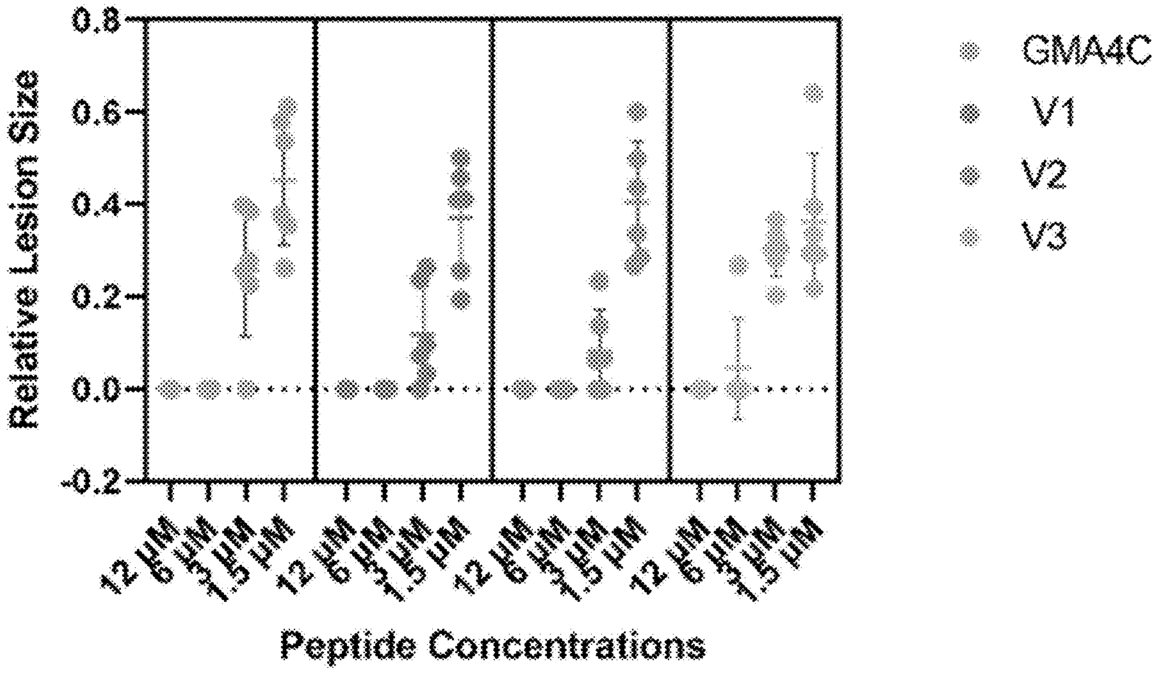

Antifungal activity in planta. When applied on detached *Nicotiana benthamiana* leaves, GMA4C_V1A and GMA4C_V3A are more potent than GMA4C_AC or GMA4C_V2A in reducing gray mold disease symptoms caused by *B. cinerea* as shown in FIGS. 1A and 1B. When applied on tomato leaves, GMA4C_V1A is more effective in reducing disease symptoms caused by *P. capsici* than GMA4C_AC.

Antifungal activity in vitro in presence of cations. When tested for antifungal activity against *B. cinerea* in the presence of 100 mM NaCl, 100 mM KCl, or 2 mM $CaCl_2$), all of the peptides including GMA4C_AC retain their antifungal activity in presence of 100 mM NaCl or 100 mM KCl. However, GMA4C_V1A and GMA4C_V4A have 2-fold more potent activity than GMA4C_AC. In presence of 2 mM $CaCl_2$), only GMA4C_V1A and GMA4C_V4A inhibit fungal growth at 6 µM, whereas other peptides such as plant defensins MtDef4 or OeDef1 show little or no activity at this concentration.

TABLE 2

GMA4C and its variants retain antifungal activity against *B. cinerea* in presence of salts.

| Peptide | SEQ ID NO: | SFM MIC (µM) [1] | SFM + 100 mM NaCl MIC (µM) [1] | SFM + 100 mM KCl MIC (µM) [1] | SFM + 2 mM $CaCl_2$ MIC (µM) [1] |
|---|---|---|---|---|---|
| GMA4C_AC [1] | 2 | 3 | 3 | 6 | >6 (a few germinated at 6) |
| GMA4C_V1A | 3 | 3 | 1.5 | 3 | 6 |
| GMA4C _V2A | 4 | 6 | 3 | 6 | >6 |
| GMA4C_V3A | 5 | 3 | 1.5-3 | >6 | >6 |
| GMA4C_V4A | 6 | 1.5-3 | 1.5 | 1.5 | 3-6 |
| GMA4C_V4 Non-amidated | 11 | 3 | 3 | 3 | 6 |
| GMA4C_V5A | 7 | 6 | 6 | >6 | >6 |
| GMA4C_V5 Non-amidated | 12 | 6 | 6 | >6 | >6 (very sensitive) |
| GMA4C_V6A | 13 | 1.5 | 0.75-1.5 | 1.5-3 | 3-6 |

[1] The Minimal Inhibitory Concentration (MIC) is the concentration of the peptide at which there is no significant growth of the microorganism relative to the growth of the microorganism in growth medium lacking the compound, protein, or peptide.

Antifungal activity against human fungal pathogens: GMA4C_V1A and GMA4C_V3A show antifungal activity against *C. auris*, and *C. glabrata* in the RPMI medium rich in cations, but the parental MtDef4 defensin does not show activity.

TABLE 3

Composition of Roswell Park Memorial Institute 1640 culture medium (RPMI media; with glutamine and phenol red but without bicarbonate)

| Constituent | Water, g/L |
|---|---|
| L-arginine (free base) | 0.2 |
| L-asparagine (anhydrous) | 0.05 |
| L-aspartic acid | 0.02 |
| L-cystine * 2HC1 | 0.0652 |
| L-glutamic acid | 0.02 |
| L-glutamine | 0.3 |
| Glycine | 0.01 |
| L-histidine (free base) | 0.015 |
| L-hydroxyproline | 0.02 |
| L-isoleucine | 0.05 |
| L-leucine | 0.05 |
| L-lysine * HCI | 0.04 |
| L-methionine | 0.015 |
| L-phenylalanine | 0.015 |
| L-proline | 0.02 |
| L-serine | 0.03 |
| L-threonine | 0.02 |
| L-tryptophan | 0.005 |
| L-tyrosine * 2Na | 0.02883 |
| L-valine | 0.02 |
| Biotin | 0.0002 |
| D-pantothenic acid | 0.00025 |
| Choline chloride | 0.003 |
| Folic acid | 0.001 |
| Myo-inositol | 0.035 |
| Niacinamide | 0.001 |
| PABA | 0.001 |
| Pyridoxine HCI | 0.001 |
| Riboflavin | 0.0002 |
| Thiamine HCI | 0.001 |
| Vitamin $B_{12}$ | 0.000005 |
| Calcium Nitrate $H_2O$ | 0.01 |
| Potassium chloride | 0.4 |
| Magnesium sulfate (anhydrous) | 0.04884 |
| Sodium chloride | 6 |
| Sodium phosphate, dibasic (anhydrous) | 0.8 |
| D-glucose | 2 |
| Glutathione, reduced | 0.001 |
| Phenol red, Na | 0.0053 |

TABLE 4

GMA4C_V1A and GMA4C_V3A exhibit antifungal activity in vitro in the RPMI medium against *Candida auris* and *C. glabrata*.

| Peptide | *Candida albicans* MIC (µg/ml) [1] | *Candida auris* MIC (µg/ml) [1] | Candida glabrata MIC (µg/ml) [1] |
|---|---|---|---|
| MtDef4 | >46.9 | 46.9 | >46.9 |
| GMA4C_V1A | 46.9 | 11.9 | 11.9 |
| GMA4C_V3A | >46.9 | 23.9 | 23.9 |

[1] The Minimal Inhibitory Concentration (MIC) is the concentration of the protein or peptide at which there is no significant growth of the microorganism relative to the growth of the microorganism in growth medium lacking the compound, protein, or peptide.

Example 2. Activity of GMA4C-Variants Against Pathogenic Microbes

Testing for antifungal activity used half-strength potato dextrose broth for peptides and RPMI for comparator antifungals fluconazole and voriconazole. CLSI M27 and M38 methodologies used for to measure MICs. Minimal Inhibitory Concentration (MIC) is the concentration of the compound, protein, or peptide at which there is no significant growth of the microorganism relative to the growth of the microorganism in growth medium lacking the compound, protein, or peptide.

All testing was performed in RPMI buffered with 0.165M MOPS. The concentration range for peptides in potato dextrose broth was 0.06-2 mcg/ml, the concentration range for fluconazole was 0.125-64 mcg/ml, and the concentration range for voriconazole was 0.03-16 mcg/ml. MICs were determined at 24-72 hours.

TABLE 5

Formula for Potato Dextrose Broth
Potato Dextrose Broth

| Value | Ingredients and conditions |
|---|---|
| 1000 ml | water |
| 4 g (from 200 g infused potato) | Potatoes (sliced, unpeeled, washed) |
| 20 g | Glucose |
| pH 5.6 | Final pH |
| 25 C. | Temperature |

TABLE 6

MIC values for GMA4C variants. The complete table with data for fluconazole and Voriconazole are provided in FIG. 4.

| Species (isolate) | Isolate No. | GMA4C_V1A 100% | GMA4C_V2A 100% | GMA4C_V4A 100% | GMA4C_V5A 100% |
|---|---|---|---|---|---|
| *C. parapsilosis* | ATCC 22019 | 4 | 8 | 8 | 8 |
| *C. krusei* | ATCC 6258 | 8 | 16 | 8 | 8 |
| *P. variotii* | MYA-363 | 4 | 8 | 8 | 4 |
| *Candida albicans* | SC5314 | 8 | 16 | 8 | 16 |
| | ATCC 90028 | 8 | 16 | 8 | 16 |
| | CA3 | 8 | 16 | 8 | 8 |
| *Candida auris* | DI17-47 | 8 | 16 | 8 | 16 |
| | DI17-48 | 8 | 16 | 8 | 16 |
| | DI17-46 | 8 | 16 | 8 | 16 |
| *Aspergillus fumigatus* | AF293 | 32 | 32 | 16 | 32 |
| | DI15-106 | >32 | >32 | 16 | >32 |
| | DI15-116 | >32 | >32 | 32 | >32 |
| *Fusarium* | F1 (*F. oxysporum*) | 4 | 8 | 8 | 8 |
| | F2 (*F. oxysporum*) | 4 | 16 | 8 | 16 |
| | F4 (*F. solani*) | 4 | 8 | 8 | 8 |
| *Coccidioides* sp. | Cocci1 | 8 | 8 | 4 | 2 |
| | Cocci2 | 4 | 16 | 16 | 16 |
| | DI17-143 | 8 | 16 | 16 | 16 |

TABLE 7

Antifungal activity of peptides against human yeast pathogens in half-strength potato dextrose broth

| Peptide | *Candida albicans* (33795) MIC (μM) | *Candida auris* (38883) MIC (μM) | *Candida glabrata* (38827) MIC (μM) |
|---|---|---|---|
| MtDef4 [1] | 1.1 | 1.1 | 0.55 |
| GMA4C_V1A (SEQ ID NO: 3) | 11.2 | 11.2 | 11.2 |
| GMA4C_V3A (SEQ ID NO: 5) | 2.8 | 5.6 | 2.8 |

[1] Full Length MtDef4 protein is described in US. Pat. No. 7,825,297.

All pathogen isolates used in this assay are resistant to an antifungal drug Fluconazole. Antifungal assays were conducted in half-strength potato dextrose broth.

TABLE 8

Synergistic (or Additive) Effects of GMA4C_v3 or MtDef4/Fluconazole Combination

| | GMA4C_V3A (SEQ ID NO: 5 )/Fluconazole | | | |
|---|---|---|---|---|
| | MIC alone μg/ml (μM) | MIC in combination μg/ml (μM) | FICI[1] | Interpretation |
| *C. albicans* | 11.7/64 (4.2/206) | 2.9/8 (1.4/25.8) | 0.375 | Synergistic |

TABLE 8-continued

| Synergistic (or Additive) Effects of GMA4C_v3 or MtDef4/Fluconazole Combination | | | | |
|---|---|---|---|---|
| C. glabrata | 11.7/64 (4.2/206) | 5.9/8 (2.8/25.8) | 0.625 | Additive |
| Full Length MtDef4[2] Protein/Fluconazole | | | | |
| | MIC alone μg/ml (μM) | MIC in combination μg/ml (μM) | FICI[1] | Interpretation |
| *C. albicans* | 5.9/64 (1.1/206) | 2.9/2 (0.55/6.45) | 0.53 | Additive |

TABLE 8-continued

| Synergistic (or Additive) Effects of GMA4C_v3 or MtDef4/Fluconazole Combination | | | | |
|---|---|---|---|---|
| C. glabrata | 2.9/64 (1.1/206) | 1.5/64 (0.28/206) | 1.5 | No difference |

Conclusion: GMA4C_v3 shows synergistic enhancement of antifungal activity against drug resistant *C. albicans* in combination with Fluconazole

[1]FICI is Fractional Inhibitory Concentration Index. It is calculated as $MIC_A$ combination/MIC alone + $MIC_B$ combination/$MIC_B$ alone where $MIC_A$ combination is the MIC of agent A in combination and $MIC_A$ alone is the MIC of agent A alone). Agent A is peptide (GMAC_V3A) and Agent B is Fluconazole in top table. Agent A is full length MtDef4 protein and Agent B is Fluconazole in fluconazole in bottom table.

[2]Full Length MtDef4 protein is described in US. Pat. No. 7,825,297, incorporated herein by reference in its entirety.

TABLE 9

Antifungal activity of peptides (MIC in μM) against human nail pathogens (*Tricophyton* spp.) and Aspergillosis (*Aspergillus fumigatus*).

| Peptide (SEQ ID NO: ) | *Tricophyton rubrum* (23014) | *Tricophyton metagrophytes* (26103) | *Aspergillus fumigatus* (36843) |
|---|---|---|---|
| MtDef4 [1] | 2.2 | 1.1 | >8.9 |
| GMA4C_V1A (SEQ ID NO: 3) | 11.2 | 11.2 | 22.4 |
| GMA4C_V3A (SEQ ID NO: 5) | 5.6 | 5.6 | 11.2 |
| OeDef1 [2] | 3.8 | 3.8 | >7.6 |
| OeDef1 _V3 (SEQ ID NO: 42) | 4.0 | 4.0 | >7.9 |

[1] Full Length MtDef4 protein is described in US. Pat. No. 7,825,297.
[2] Full length OeDef1 defensin protein is described in WO 2020/146373.

TABLE 10

Antifungal activity of GMA4C variants (MIC in μM) against *Candida* spp. and Aspergillosis (*Aspergillus fumigatus*).

| Species | Isolate | GMA4C_V1A (SEQ ID NO: 3) | GMA4C_V2A (SEQ ID NO: 4) | GMA4C_V4 (SEQ ID NO: 11) | GMA4C_V5 (SEQ ID NO: 12) |
|---|---|---|---|---|---|
| *Candida albicans* | SC5314 | 3.8 | 7.6 | 3.8 | 7.6 |
| | ATCC 90028 | 3.8 | 7.6 | 3.8 | 7.6 |
| | CA3 | 3.8 | 7.6 | 3.8 | 3.8 |
| *Candida parapsilosis* | ATCC 22019 | 1.9 | 3.8 | 3.8 | 3.8 |
| *Candida auris* | DI17-47 | 3.8 | 7.6 | 3.8 | 7.6 |
| | DI17-48 | 3.8 | 7.6 | 3.8 | 7.6 |
| | DI17-46 | 3.8 | 7.6 | 3.8 | 7.6 |
| *Aspergillus fumigatus* | AF293 | 15.2 | 15.2 | 7.6 | 15.2 |
| | DI15-106 | >15.2 | >15.2 | 7.6 | >15.2 |
| | DI15-116 | >15.2 | >15.2 | 15.2 | >15.2 |
| *Fusarium* | F1 (*F. oxysporum*) | 3.8 | 3.8 | 3.8 | 3.8 |
| | F2 (*F. oxysporum*) | 3.8 | 7.6 | 3.8 | 7.6 |
| | F4 (*F. solani*) | 3.8 | 3.8 | 3.8 | 3.8 |
| *Coccidioides* sp. | Cocci1 | 3.8 | 3.8 | 1.9 | 0.9 |
| | Cocci2 | 1.9 | 7.6 | 7.6 | 7.6 |
| | DI17-143 | 1.9 | 7.6 | 7.6 | 7.6 |

Example 3. Antibacterial Activity of GMA4C_V1A Against Human Bacterial Pathogens

*Salmonella Typhimurium* var. Copenhagen, Enterotoxigenic *E. coli*-F4 and *Listeria monocytogens* (F5244) strains were grown overnight on an LB agar plate at 37_C. A small number of bacteria was scraped from the plate and added to Mueller-Hinton (MH) growth media and grown to log phase. Cells were diluted to $1\text{-}3\times10^6$ CFU/mL and 50 ul were added to each well in a polypropylene 96-well plate. Synthesized peptide GMA4C_V1A was diluted into 0.2% BSA, 0.01% acetic acid solution and added to the concentration of 0.2, 0.4, 0.80, 1.6, 3.25, 7.5, 15, 30 and 60 and 120 μM. Then, 50 ul of each peptide solution was added to 50 ul of bacterial cells. Plates were parafilmed and incubated at 37° C. overnight. The concentrations at which bacterial growth inhibition was determined based on the $OD_{600}$ nm value at each concentration relative to the $OD_{600}$ nm value of MH medium alone and that of bacterial growth in MH medium without any peptide. The Minimal Inhibitory Concentration (MIC) is the concentration of the peptide at which there is no significant growth of the microorganism relative to the growth of the microorganism in growth medium lacking the peptide.

TABLE 11

Antibacterial activity of GMA4C_V1A (SEQ ID NO: 3) Concentrations of GMA4C_V1A (in μM) at which growth inhibition of each bacterial pathogen was observed

| Peptide | *S. Typhimurium* var. Copenhagen | Enterotoxigenic *E. coli*-F4 | *L. monocytogenes* F5244 |
|---|---|---|---|
| GMA4C_V1 | 15-60 | 7.5-60 | 15-30 |

Example 4. Antimicrobial Activity of Defensin Peptide Fragments

Crude chemically synthesized defensin-derived peptides with 80-85% purity were obtained from Biomatik Inc, Canada or from Alan Scientific Inc., USA. Each peptide was further purified using a C-18 reverse phase HPLC (Agilent, Singapore). HPLC fractions containing the peptide were lyophilized and resuspended in nuclease-free water. Concentrations were determined using BCA assays using manufacturer's protocol (Thermo-Fisher Scientific) for their accurate quantification.

The fungal strains of *Botrytis cinerea* T-4, *Alternaria alternata, Cercospora* sojina and, *Colletotrichum gloeosporioides* were each cultured in their respective normal growth medium shown in Table 12. Fungal spores were harvested by flooding the fungal growth plates with sterile water. The spore suspension was filtered through two layers of Miracloth, centrifuged at 13,600 rpm for 1 min, washed, and re-suspended in low-salt Synthetic Fungal Medium (SFM) (U.S. Pat. No. 6,316,407). The spore suspension was adjusted to the desired spore count using a hemocytometer.

TABLE 12

| Strains | Medium for spore production | Culture conditions |
|---|---|---|
| *B. cinerea* | 20% V8 | 7-25 days, 25° C. |
| *Alternaria alternata* | 10% Potato-Dextrose Agar | 7-15 days, 25° C. |
| *Cercospora sojina* | 20% V8 | 12 hr light/12 hr dark at 25° C. |
| *Colletotrichum ploeosporioides* | 10% Potato-Dextrose Agar | 7-15 days, 25° C. |

The antifungal activity of truncated defensin-derived peptides and their variants against *B. cinerea, A. alternata, C. sojina* and *C. gloeosporioides* fungal pathogens was determined spectrophotometrically using a 96-well plate assay (Sagaram et al., (2011) PLOS ONE 6: e18550. doi: 10.1371/journal.pone.0018550). Forty-five microliter of peptide at concentrations of 0.375, 0.75, 1.5, 3, 12 μM was added to each well of the microtiter plate containing 45 μL of (~105 *B. cinerea* spores/ml) spore suspension. The quantitative fungal growth inhibition was determined by measuring the absorbance at 595 nm using a (Tecan Infinite M200 ProTecan Systems Inc., San Jose, CA) microplate reader after 48 h. Fungal cell viability was determined using the resazurin cell viability assay (Chadha and Kale, (2015) *Lett Appl Microbiol* 61, 238-244, Li et al., (2019) Mol Plant Microbe Interact 32, 1649-1664). After incubation of the pathogen/peptide mixture for 48 h, 10 ul of 0.1% resazurin solution was added to each well and re-incubated overnight. A change in color of the resazurin from blue to pink or colorless indicated the presence of live fungal cells. The MIC value of each peptide was determined as the minimal concentration of peptide at which no change in blue color was observed. MIC values of defensin-derived peptides and their variants were also determined in SFM and SFM supplemented with 100 mM NaCl, 100 mM or 2 mM $CaCl_2$) as described above.

The semi-in planta antifungal activity of each defensin-derived peptide and its variants against *B. cinerea* was determined using the detached leaves of *N. benthamiana* Nb1 as described previously (Li et al., (2019) Mol Plant Microbe Interact 32, 1649-1664; Velivelli et al., (2020) Proceedings of the National Academy of Sciences. 117, 16043-16054). Each peptide was tested at concentrations of 1.5 μM, 3 μM and 6 μM. Following incubation of each peptide/fungal spore mixture at room temperature for 48 h, leaves were photographed in white-light. High-resolution fluorescence images were also taken using CropReporter (Pheno Vation, Wageningen, Netherlands). These images depicted the calculated Fv/FM (maximum quantum yield of photosystem II) values of diseased area affected by *B. cinerea* infection. Colors in the images show five different classes ranging from class I to class V (0.000 to 0.700) depicting varying degrees of tissue damage. Green color in each image represents class V in 0.600 to ≥0.700 range depicting healthy area on leaf surface. In contrast, red color represents class I in the 0.000 to 0.160 range and depicts severely damaged or diseased leaf surface.

The primary amino acid sequences, length, net charge and percentage of hydrophobic amino acids of defensin-derived peptides are shown in Table 13. These peptides are derived from plant defensins OeDef1, MtDef4, MsDefl and MtDef5A. Amino acid substitutions in the wild-type sequence of each peptide were made to increase the net charge and hydrophobicity. In addition, a disulfide bond was introduced into specific variants to make them pseudo-cyclic. Peptides that can form a single disulfide bond and a pseudo-cyclic peptide are shown as "+" in the "Disulfide Bond" column of Table 13. All peptides also carry a carboxy-terminal amide group.

TABLE 13

Amino acid sequences, length, net charge and % hydrophobic amino acids of defensin-derived peptides. The presence of a disulfide bond is indicated where necessary.

| Peptide | Sequence (disulfide presence) | SEQ ID NO | Length | Net Charge | % Hydrophob. amino acids |
|---|---|---|---|---|---|
| GMAOe1C (WT) | GACLKNRHSKHYGCYCYYRHCY-$NH_2$ | 577 | 22 | 4.5 | 32 |

TABLE 13-continued

Amino acid sequences, length, net charge and % hydrophobic amino acids of defensin-derived peptides. The presence of a disulfide bond is indicated where necessary.

| Peptide | Sequence (disulfide presence) | SEQ ID NO | Length | Net Charge | % Hydrophob. amino acids |
|---|---|---|---|---|---|
| GMAOe1C_V3 | GACLKNRHSKHYGWFWYYRHCY-$NH_2$ (disulfide +) | 578 | 22 | 4.5 | 41 |
| GMAOe1C_V4 | GACLKNRHSKHYGFFWYYRHCY-$NH_2$ (disulfide +) | 579 | 22 | 4.5 | 41 |
| GMA4AC | GRCRGFRRRCFCTTHC-$NH_2$ | 580 | | | |
| GMA4C_V9 | GGRCKGFLRRFWFTRIC-$NH_2$ (disulfide +) | 581 | 17 | 5 | 35 |
| GMA4C_V10 | GGRCKGFRRRWYWTRIC-$NH_2$ (disulfide +) | 582 | 17 | 6 | 29 |
| GMA1C_V1 | SGRCRILFRCFCTKNC-$NH_2$ | 583 | 16 | 4 | 25 |
| GMA1C_V2 | SGRCRILFRWFWTKNC-$NH_2$ (disulfide +) | 584 | 16 | 4 | 37 |
| GMA1C_V3 | SGRCRILFRWYFTKNC-$NH_2$ (disulfide +) | 585 | 16 | 4 | 37 |
| GMA5CA_WT | GACHRQGFGFACFCYKKC-$NH_2$ | 586 | 18 | 3.5 | 28 |
| GMA5CA_V3 | GACHRQGFGFAWFWYKKC-$NH_2$ (disulfide +) | 19 | 18 | 3.5 | 39 |
| GMA5CA_V4 | GACHRQGFGFAFFFYKKC-$NH_2$ (disulfide +) | 20 | 18 | 3.5 | 39 |

The minimal inhibitory concentration (MIC) value of each defensin-derived peptide and its variants was determined (Table 14). It has been hypothesized that the presence of cations significantly weakens the electrostatic interactions between a positively charged defensin and negatively charged fungal membranes (Chu et al., (2013) Antimicrobial Agents and Chemotherapy 57:4050-4052). We therefore determined the antifungal activity of each peptide against *B. cinerea* in SFM supplemented with 100 mM NaCl, 100 mM KCl or 2 mM $CaCl_2$) (Table 14).

TABLE 14

MIC values of defensin-derived peptides against *Botrytis cinerea*

| Peptide | SEQ ID NO | MIC (μM) SFM | MIC (μM) (SFM + 100 mM NaCl) | MIC (μM) (SFM + 100 mM KCl) | MIC (μM) (SFM + 2 mM $CaCl_2$) |
|---|---|---|---|---|---|
| GMAOe1C_WT | 577 | 3 | 3-6 | 6-12 | >12 |
| GMAOe1C_V3 | 578 | 1.5 | 2-3 | 6-12 | 3-6 |
| GMAOe1C_V4 | 579 | 1.5 | 6 | 6-12 | 6-12 |
| GMA4AC | 580 | 3 | ND[1] | ND | ND |
| GMA4C_V9 | 581 | 3 | 3 | 6-12 | 12 |
| GMA4C_V10 | 582 | 3 | 3 | 3-6 | 3 |
| GMA1C | 35 | >12 | >12 | >12 | >12 |
| GMA1C_V1 | 583 | >6 | >6 | >12 | — |
| GMA1C_V2 | 584 | 1.5-3 | 3 | >12 | 3 |
| GMA1C_V3 | 585 | 1.5 | 3 | >12 | 6 |
| GMA5CA_WT | 586 | 6 | >12 | >12 | >12 |
| GMA5CA_V3 | 19 | 3 | >12 | >12 | >12 |
| GMA5CA_V4 | 20 | 3 | >12 | >12 | >12 |

[1]ND is not determined.

MIC values of defensin-derived peptides were also tested against *Alternaria alternata, Cercospora sojina*, and *Colletotrichum gloeosporioides* (Table 15).

TABLE 15

In vitro antifungal activity of antifungal peptides against *Alternaria alternata, Cercospora sojina* and *Colletotrichum gloeosporioides*

| Peptide | SEQ ID NO | *Alternaria alternata* | *Cercospora sojina* | *Colletotrichum gloeosporioides* |
|---|---|---|---|---|
| GMA4AC_WT | 580 | >12 | >12 | >12 |
| GMA4C_V9 | 581 | >12 | 6 | >12 |
| GMA4C_V10 | 582 | >12 | 6 | >12 |
| GMA5CA_WT | 586 | 6 | 12 | >12 |
| GMA5CA_V3 | 19 | 3 | 6 | >12 |
| GMA5CA_V4 | 20 | 3 | 6 | >12 |

Figure 5A:
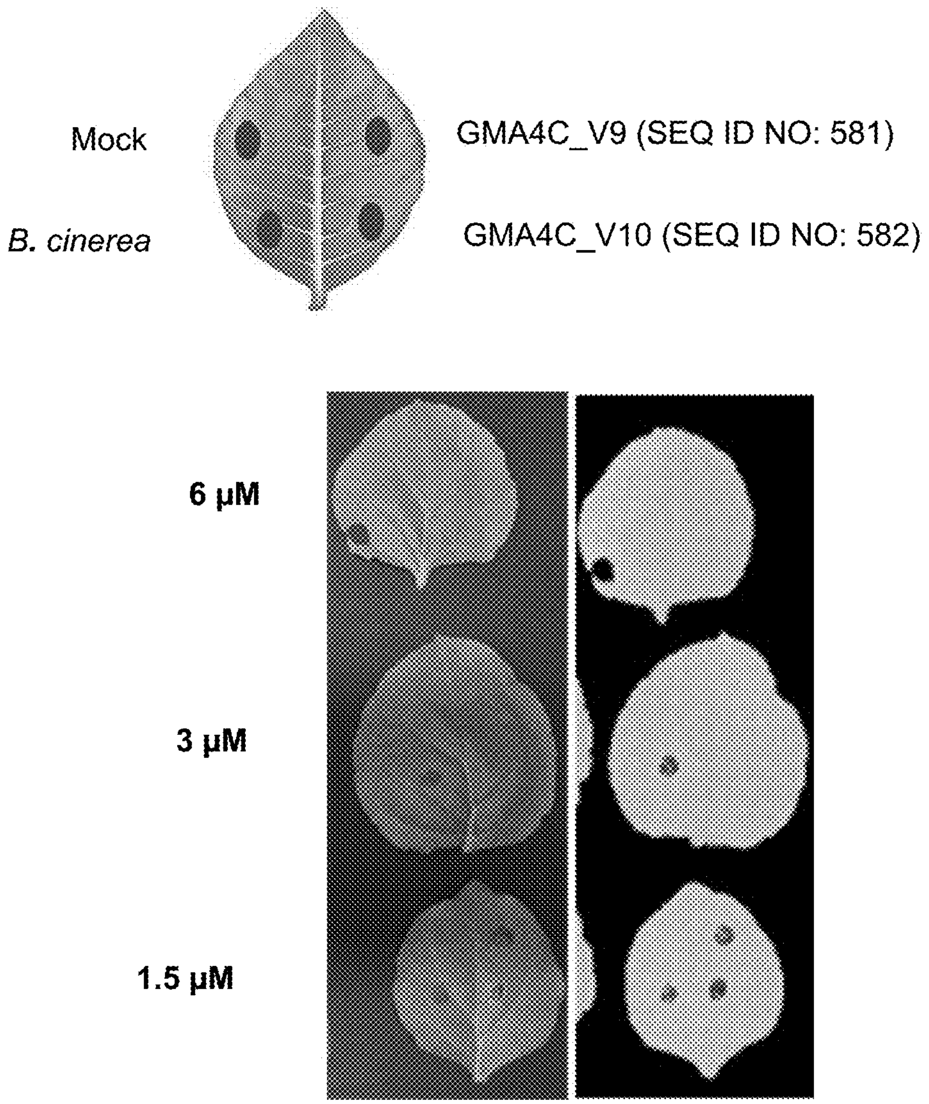
FIG. 5A, B.
Figure 5B:
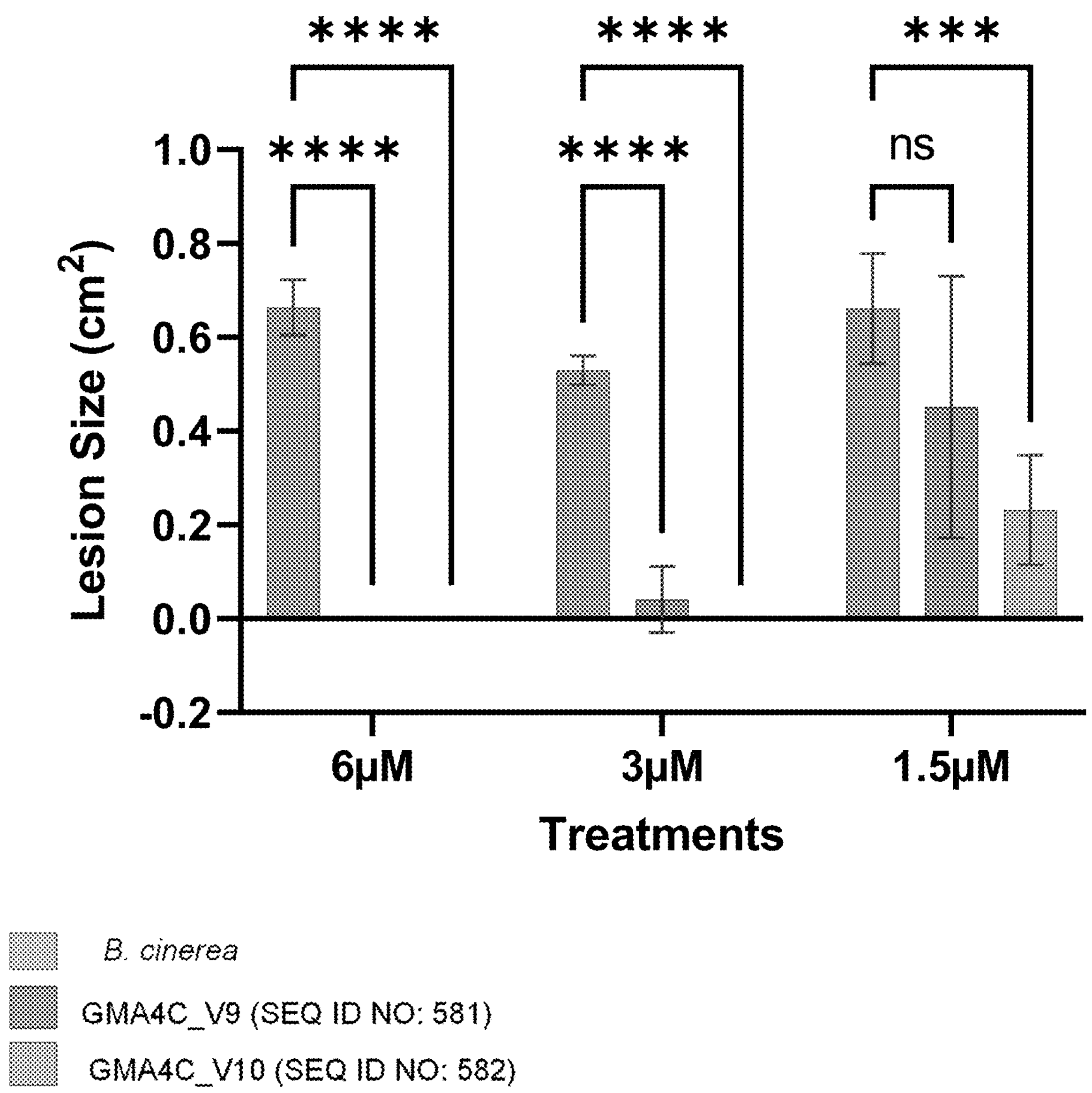
In FIG. 5B, the left-most bars are for the no treatment control ("*B. cinerea*"), middle bars are GMA4C_V9 (SEQ ID NO: 581) treatment, and rightmost bars are GMA4C_V10 (SEQ ID NO: 582) treatment. At 3 μM and 1.5 μM, GMA4C_V10 is more effective in reducing the symptoms of gray mold than GMA4C_V9.

Semi-in planta antifungal activity of GMA4C_V9, GMA4C_V10, GMAOe1C_WT, GMAOe1C_V3, GMAOe1C_V4, GMA1C_V1 and GMA1C_V2 peptides against *B. cinerea* was determined by using the detached leaves of *N. benthamiana*. Each peptide at concentrations of 1.5 μM, 3 μM and 6 μM was applied on leaf as drops and freshly prepared conidial inoculum was applied immediately to each drop of the peptide. Leaves were assessed for attenuation of gray mold symptoms after 48 h of inoculation relative to no peptide controls by measuring lesion sizes. GMA4C_V9 and GMA4C_V10 peptides are both effective in reducing gray mold disease symptoms. However, at low concentrations of 1.5 μM and 3 μM, GMA4C_V10 is more effective in reducing the symptoms of gray mold than GMA4C_V9 (FIG. 5).

Figure 6B:
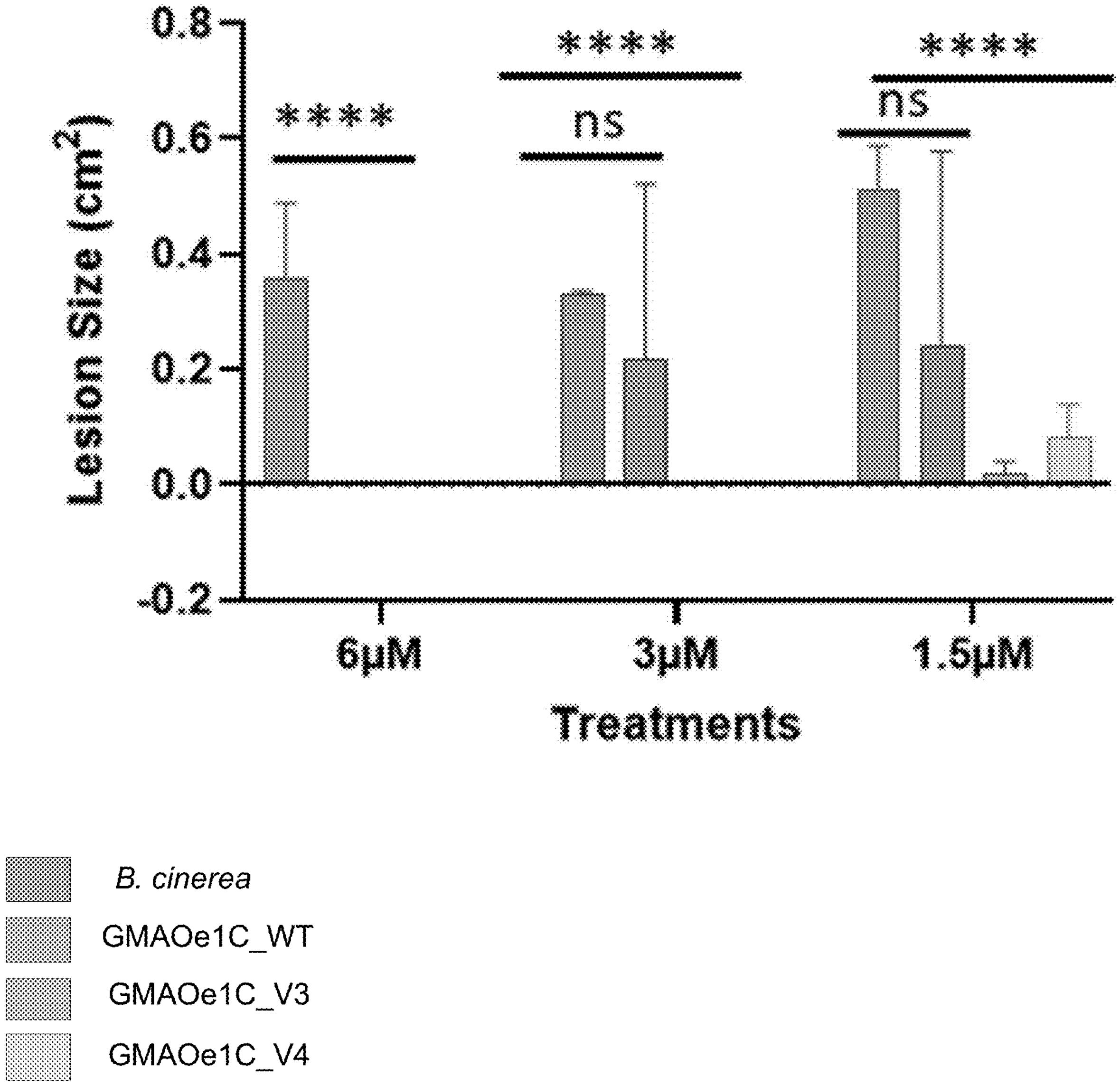
In FIG. 6B, the left-most bars are for the no treatment control ("*B. cinerea*"), 2nd from left bars are GMAOe1C_WT treatment, 3rd from left bars are GMAOe1C_V3 treatment, and 4th from left bars are GMAOe1C_V4 treatment. GMAOe1C_V3 and GMAOe1C_V4 at 3 μM and 6 μM completely abrogated gray mold symptoms but GMAOe1C_WT is only effective at 6 μM. At a concentration of 1.5 μM, GMAOe1C_V3 is more effective than GMAOe1C_V4 or GMAOe1C_WT.

A drop inoculation assay was also performed to test the antifungal activity of GMAOe1C_WT, GMAOe1C_V3, GMAOe1C_V4. The results revealed that GMAOe1C_V3 and GMAOe1C_V4 at concentration of 3 and 6 μM completely abrogated gray mold symptoms, but GMAOe1C_WT was only effective at 6 μM. At a concentration of 1.5 μM, GMAOe1C_V3 is more effective than GMAOe1C_V4 or GMAOe1C_WT (FIGS. 6A and 6B).

Figure 7A:
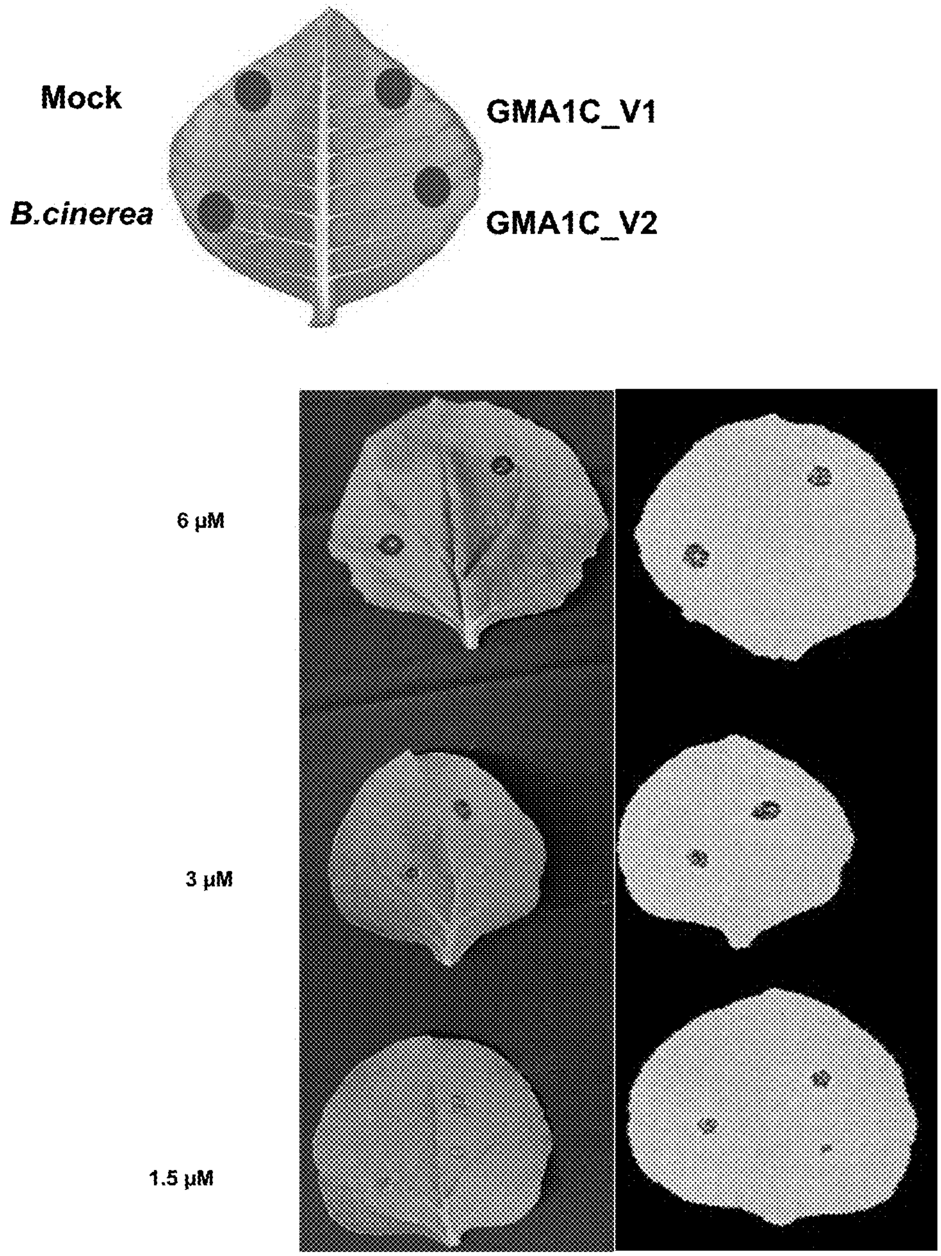
FIG. 7A, B show results of a drop inoculation assay showing the antifungal activity of GMA1C_V1 (SEQ ID NO: 583) and GMA1C_V2 (SEQ ID NO: 584) against *B. cinerea*.
Figure 7B:
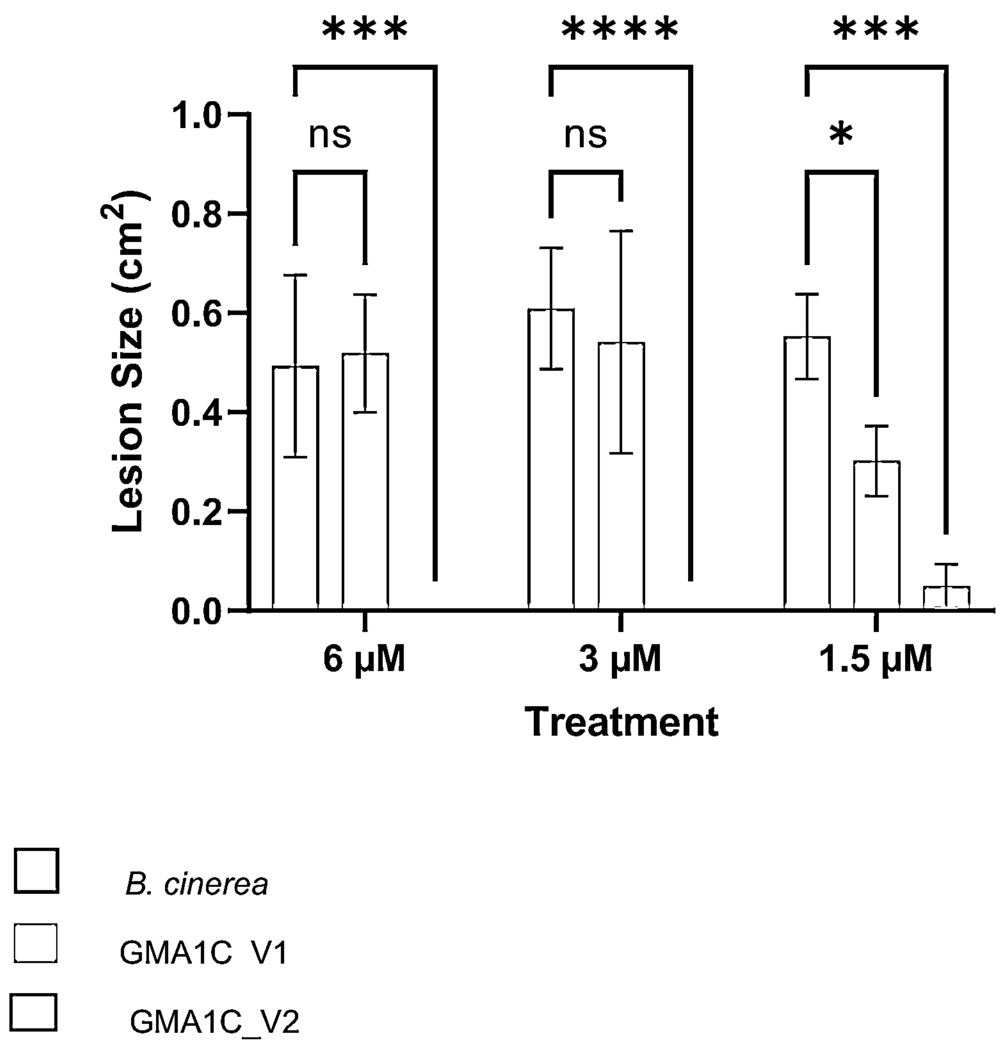
In FIG. 7B, the left-most bars are for the no treatment control ("*B. cinerea*"), middle bars are GMA1C_V1 (SEQ ID NO: 583) treatment, and rightmost bars are GMA1C_V2 (SEQ ID NO: 584) treatment.

A drop inoculation assay was also performed to test the antifungal activity of GMA1C_V1 and GMA1C_V2. (FIGS. 7A and 7B). GMA1C_V2 at 3 μM and 6 μM completely abrogated gray mold symptoms. GMA1C_V1 failed to reduce disease symptoms at these concentrations. At a concentration of 1.5 μM, GMA1C_V2 was more effective than GMA1C_V1 (FIGS. 7A and 7B).

The results above indicate that the panel of modifications (e.g., amino acid substitutions) introduced into these truncated defensin-derived peptides confer greater antifungal activity than the wild-type truncated peptides.

The breadth and scope of the present disclosure should not be limited by any of the above-described examples.

What is claimed is:

1. An antifungal peptide comprising a modified C-terminal plant defensin peptide wherein:

(i) the unmodified C terminal plant defensin peptide comprises from N-terminus to C-terminus the conserved amino acid sequence GXCX3-10(C)(X)(C) (SEQ ID NO: 592) and a conserved cysteine residue located at the C-terminus of the unmodified C terminal plant defensin peptide;

(ii) the conserved amino acid sequence GXCX3-10(C)(X)(C) (SEQ ID NO: 592) of the unmodified C terminal plant defensin peptide is replaced with a modified gamma-core consensus sequence GXCX3-10(F/W/Y)(F/W/Y)(F/W/Y) (SEQ ID NO: 587) in the modified C-terminal plant defensin peptide;

(iii) the modified C-terminal plant defensin peptide retains the conserved cysteine residue located at the C-terminus of the unmodified C terminal plant defensin peptide;

(iv) the modified C-terminal plant defensin peptide has a net positive charge of at least 3 at neutral pH and a hydrophobic amino acid content at least 18%, wherein the hydrophobic amino acids are alanine, leucine, isoleucine, valine, proline, phenylalanine, tryptophan, and methionine; and (v) the modified C-terminal plant defensin peptide exhibits antifungal activity.

2. The antifungal peptide of claim 1, wherein the modified C-terminal plant defensin peptide comprises a disulfide bond between the cysteine residue in the modified gamma-core consensus sequence and the conserved cysteine residue located at the C-terminus of the modified C-terminal defensin peptide.

3. The antifungal peptide of claim 1, wherein the modified C-terminal plant defensin peptide consists of 15 to 30 amino acid residues.

4. A composition comprising the antifungal peptide of claim 1 and an agriculturally, pharmaceutically, or veterinary-practicably acceptable carrier, diluent, or excipient.

5. The composition of claim 4, wherein the antifungal peptide is provided at a concentration of about 0.1 pg/ml to about 100 mg/ml or at a concentration of about 0.1 pg/gram to about 100 mg/gram and optionally wherein the composition comprises a sodium salt at a concentration of at least 100 mM and/or a calcium salt at a concentration of at least 2 mM.

6. A method for preventing or reducing crop damage by a plant pathogenic microbe comprising the step of contacting a plant, a plant seed, or other part of said plant with an effective amount of the composition of claim 4.

7. The method of claim 6, wherein the plant pathogenic microbe is a *Fusarium* sp., *Alternaria* sp., *Verticillium* sp., *Phytophthora* sp., *Colletotrichum* sp., *Botrytis* sp., *Cercospora* sp., *Phakopsora* sp., *Rhizoctonia* sp., *Sclerotinia* sp., *Pythium* sp., *Phoma* sp., *Leptosphaeria* sp., *Gaeumannomyces* sp., *Puccinia* sp., *Septoria* sp., *Penicillium* sp., *Lasiodiplodia* sp., *Phomopsis* sp., *Mycosphaerella* sp., *Golovinomyces* sp., *Erisyphe* sp., Albugo sp., *Setosphaeria* sp., *Cochliobolus* sp., *Helminthosporium* sp., *Diplodia* sp., or *Stenocarpella* sp.

8. A medical device comprising the device and the composition of claim 4, wherein the device comprises at least one surface that is topically coated and/or impregnated with the composition.

9. The medical device of claim 8, wherein said device is a stent, a catheter, a contact lens, a condom, a patch, or a diaphragm.

10. A method for treating, preventing, or inhibiting a fungal *Candida* species infection in a subject in need thereof comprising administering to said subject an effective amount of the composition of claim 4.

11. The method of claim 10, wherein said administration comprises topical, enteral, parenteral, and/or intravenous introduction of the composition.

12. The method of claim 10, wherein the subject is a human, livestock, poultry, fish, or a companion animal.

13. The method of claim 10, wherein the fungal or *Candida* species infection is of a mucosal membrane, eye, skin, and/or a nail and the composition is applied to the mucosal membrane, eye, skin, and/or nail.

14. The method of claim 10, wherein the fungal infection is by a dermatophyte, and wherein the dermatophyte is optionally selected from the group consisting of *Trichophyton rubrum, Trichophyton interdigitale, Trichophyton violaceum, Trichophyton tonsurans, Trichophyton soudanense, Trichophyton mentagrophytes, Microsporum flavum, Epidermophyton floccosum*, and *Microsporum gypseum.*

15. The method of claim 10, wherein the microbial infection is by an *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis*, or *Blastomyces* species.

16. The method of claim 10, wherein the microbial infection is by a *Candida* species and wherein the *Candida* species is *Candida albicans* (*C. albicans*), *C. auris, C. glabrata, C. parasilosis, C. tropicalis*, or *C. krusei.*

17. A plant part that is at least partly coated with the composition of claim 4.

18. The plant part of claim 17, wherein the part is a seed and the seed is optionally a corn, soybean, wheat, rice, cotton, *Brassica* sp., or tomato seed.

19. The plant part of claim 17, wherein the plant part is a fruit, vegetable, or flower.

20. A recombinant polynucleotide comprising a polynucleotide encoding a peptide comprising the antifungal peptide of claim 1, wherein the polynucleotide encoding the antifungal peptide is operably linked to a polynucleotide comprising a promoter which is heterologous to the polynucleotide encoding the antifungal peptide.

21. The peptide of claim 1, wherein the conserved cysteine residue located at the C-terminus of the modified C-terminal defensin peptide is amidated.

* * * * *